United States Patent
Mazur et al.

(10) Patent No.: US 9,944,624 B2
(45) Date of Patent: Apr. 17, 2018

(54) SUBSTITUTED AMINO TRIAZOLES USEFUL AS HUMAN CHITINASE INHIBITORS

(71) Applicant: OncoArendi Therapeutics S.A., Warsaw (PL)

(72) Inventors: Marzena Mazur, Łódź (PL); Robert Koralewski, Łódź (PL); Bartlomiej Borek, Łódź (PL); Sylwia Olejniczak, Łódź (PL); Wojciech J. Czestkowski, Pabianice (PL); Michał C. Piotrowicz, Łódź (PL); Jacek P. Olczak, Łódź (PL); Adam A. Golebiowski, Warsaw (PL); Agnieszka Bartoszewicz, Warsaw (PL); Elżbieta Maziarz, Kamień (PL); Michał Łukasz Kowalski, Godziszka (PL)

(73) Assignee: OncoArendi Therapeutics S.A., Warsaw (PL)

( * ) Notice: Subject to any disclaimer, the term of this patent is extended or adjusted under 35 U.S.C. 154(b) by 0 days.

(21) Appl. No.: 15/255,226

(22) Filed: Sep. 2, 2016

(65) Prior Publication Data

US 2017/0066743 A1   Mar. 9, 2017

Related U.S. Application Data

(60) Provisional application No. 62/214,299, filed on Sep. 4, 2015.

(51) Int. Cl.
*C07D 401/14* (2006.01)
*C07D 413/14* (2006.01)
*C07D 417/14* (2006.01)
*C07D 498/04* (2006.01)

(52) U.S. Cl.
CPC .......... *C07D 401/14* (2013.01); *C07D 413/14* (2013.01); *C07D 417/14* (2013.01); *C07D 498/04* (2013.01)

(58) Field of Classification Search
CPC .. C07D 401/14; C07D 413/14; C07D 417/14; C07D 498/04
See application file for complete search history.

(56) References Cited

FOREIGN PATENT DOCUMENTS

WO    WO-2015/095701 A1    6/2015

OTHER PUBLICATIONS

Cole et al., "Identification and Characterization of Acidic Mammalian Chitinase Inhibitors," J Med Chem, 53(16): 6122-6126 (2010).
International Search Report and Written Opinion for International Application No. PCT/IB/2016/055269 dated Oct. 21, 2016.
Polish Search Report for Polish Application No. PL415076 dated Mar. 23, 2016.
Sutherland et al., "Analyzing Airway Inflammation with Chemical Biology: Dissection of Acidic Mammalian Chitinase Function with a Selective Drug-like Inhibitor," Chem Biol, 16(5): 569-579 (2011).

*Primary Examiner* — Rebecca L Anderson
(74) *Attorney, Agent, or Firm* — Foley Hoag LLP

(57) ABSTRACT

Disclosed are amino triazole compounds substituted with a piperidinyl ring that is itself substituted with a heterocyclic ring. These compounds are inhibitors of acidic mammalian chitinase and chitotriosidase. Also disclosed are methods of using the compounds to treat asthma reactions caused by allergens, as well as acute and chronic inflammatory diseases, autoimmune diseases, dental diseases, neurologic diseases, metabolic diseases, liver diseases, polycystic ovary syndrome, endometriosis, and cancer.

27 Claims, No Drawings

SUBSTITUTED AMINO TRIAZOLES USEFUL AS HUMAN CHITINASE INHIBITORS

RELATED APPLICATIONS

This application claims the benefit of priority to U.S. Provisional Patent Application Ser. No. 62/214,299, filed Sep. 4, 2015, the contents of which are hereby incorporated by reference.

BACKGROUND OF THE INVENTION

Acidic mammalian chitinase (AMCase; $M_r=\sim 52.2$ kD) is a secreted enzyme, typically found in the stomach, salivary gland, and lungs. Unique among mammalian enzymes in that it has an acidic pH optimum, the enzyme catalyzes the hydrolysis of artificial chitin-like substrates. It is induced during Th2 inflammation through an IL-13-dependent mechanism. Chitinases are believed to play a key role in the innate immunity to parasites and other infectious agents. When produced in a dysregulated fashion, the enzymes may also play an important role in the pathogenesis of allergy and/or asthma.

Asthma is a chronic inflammatory disease of the airways characterized by recurrent episodes of reversible airway obstruction and airway hyperresponsiveness (AHR). Typical clinical manifestations include shortness of breath, wheezing, coughing and chest tightness that can become life threatening or fatal. While existing therapies focus on reducing the symptomatic bronchospasm and pulmonary inflammation, there is a growing awareness of the role of long-term airway remodeling in the accelerated lung deterioration in asthmatics. Airway remodeling refers to a number of pathological features, including epithelial smooth muscle and myofibroblast hyperplasia and/or metaplasia, subepithelial fibrosis and matric deposition.

It is generally accepted that allergic asthma is initiated by an inappropriate inflammatory reaction to airborne allergens. The lungs of asthmatics demonstrate an intense infiltration of lymphocytes, mast cells and, especially, eosinophils. AMCase is prominently expressed in lungs from antigen-sensitized and challenged and IL-13-transgenic mice. AMCase mRNA is not readily detected in lung tissues from patients without known lung disease, but has been detected, histologically and morphometrically, in the epithelial cells and subepithelial cells in tissues from patients with asthma.

Preliminary published studies (Zhu Z, Zheng T, Homer R J, Kim Y K, Chen N Y, Cohn L, Hamid Q, and Elias J A. Acidic mammalian chitinase in asthmatic Th2 inflammation and IL-13 pathway activation. Science 304: 1678-1682, 2004; Matsumoto T, et al. Demethylallosamidin, a chitinase inhibitor, suppresses airway inflammation and hyperresponsiveness. Biochem Biophys Res Commun 390: 103-108, 2009) suggest that AMCase plays a role in the Th-2 driven inflammatory response in a murine model of allergic asthma. Th-1 responses do not seem to be involved. No therapeutic effect was observed in a mouse model that expresses Th-1, but not Th-2 (Fitz L J, et al. Acidic mammalian chitinase is not a critical target for allergic airway disease. Am J Respir Cell Mol Biol 46: 71-9, 2011). This result would be expected since Th-1 cells are primarily involved in host defense against pathogens.

Chitotriosidase 1 (CHIT1, $M_r=\sim 52$ kD or $\sim 39$ kDa) is a chitinase expressed predominantly in the myeloid cells and lung epithelial cells as an innate immune mediator that digests the cell walls of chitin-containing eukaryotic pathogens. CHIT1 is a circulating enzyme, with both endochitinolytic and tranglycosylating activity. Besides its role in chitin recognition and innate immune response, CHIT1 is implicated in pathogenesis of fibrotic lung diseases. Lung fibrosis was significantly reduced in CHIT1 knockout mice in bleomycin-induced lung fibrosis animal model and it was suggested that this chitinase plays a role in tissue remodeling and fibrogenesis in the lung.

Idiopathic pulmonary fibrosis (IPF) is a progressive fibroproliferative disorder refractory to current pharmacological therapies with a median survival of only 3-5 years following diagnosis. IPF is a devastating disease characterized by excessive matrix deposition that disrupts the normal architecture of the lung parenchyma. The key pathological features of IPF include fibroblastic foci, areas of epithelial cysts associated with the honeycombing appearance of the lung, and mild lymphoplasmacytic interstitial inflammation that is associated with areas of type II cell hyperplasia. The pathogenesis of each form of lung fibrosis remains poorly understood. They each result in a progressive loss of lung function with increasing dyspnea, and most forms ultimately result in mortality.

Poor prognosis of IPF patients generates a great need for novel targets that can be used as a therapeutic strategy to improve clinical outcomes in IPF, with CHIT1 among them. CHIT1 overexpression was shown in fibrotic Interstitial Lung Disease (ILD), including IPF (Bargagli W et al. Chitotriosidase activity in patients with interstitial lung diseases. Respir Med. 101(10):2176-81, 2007) and chronic obstructive pulmonary disease (COPD) (Letuve S et al. Lung chitinolytic activity and chitotriosidase are elevated in chronic obstructive pulmonary disease and contribute to lung inflammation. Am J Pathol. 176(2):638-49, 2010) characterized by inflammation and tissue remodeling and was interestingly shown to be potent amplifier of TGFβ signaling (Lee C G et al. Chitinase 1 is a biomarker for and therapeutic target in scleroderma-associated interstitial lung disease that augments TGF-β1 signaling. J Immunol. 189(5):2635-44, 2012). A study showed that CHIT1 activity was elevated in the BAL of IPF patients compare to controls suggesting it might be responsible for remodeling and tissue damage seen in the lung from IPF patients. As such, it is conceivable that CHIT1 could be involved in fibrogenesis of other ILD, such as systemic sclerosis (SSc), where patient group with lung involvement show high levels of circulating CHIT1 activity that correlate with disease severity.

Diseases, disorders, and conditions mediated by AMCase and CHIT1 are discussed in more detail below.

Substituted amino triazoles that inhibit AMCase and CHIT1 been described (see international patent application publication No. WO 2015/095701, and U.S. provisional patent application No. 62/094,446).

There is an ongoing need to investigate the inhibition of AMCase and CHIT1, and to discover treatments for conditions associated with elevated expression of AMCase or CHIT1, such as asthma and allergic responses or COPD and fibroproliferative disorders. In particular, there is a need for new molecular scaffolds that effectively inhibit AMCase and CHIT1, therefore, can act as therapeutic agents for the treatment of these conditions.

SUMMARY OF THE INVENTION

In one aspect, the invention provides a compound represented by formula (I),

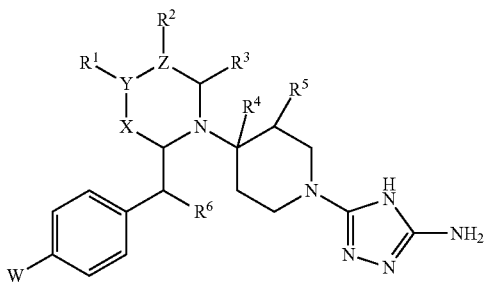

(I)

wherein:

W is halo, (C₁-C₃)alkyl, (C₁-C₃)alkoxy-, or (C₁-C₃)alkyl-thio-;

X is a single bond, —CH₂—, —CH₂CH₂—, —CH═CH—, —C((C₁-C₃)alkyl)₂-, or —C(O)—;

Y is a single bond, —CH—, —CHCH₂—, —CH₂CH—, —C═CH—, —CH═C—, —N—, —O—, —OCH₂—, —S(O)—, or —S(O)₂—;

if Y is a single bond, —O—, —OCH₂—, —S(O)—, or —S(O)₂—, then R¹ is absent;

R¹ is H, OH, (C₁-C₆)alkyl, (C₁-C₆)haloalkyl, (C₁-C₆)alkoxy, (C₁-C₆)hydroxyalkyl, (C₁-C₆)alkoxy(C₁-C₆)alkyl, aryl(C₁-C₆)alkyl, heteroaryl(C₁-C₆)alkyl, —C(O)(C₁-C₆)alkyl, —C(O)aryl, —C(O)heteroaryl, —C(O)aryl(C₁-C₆)alkyl, —C(O)heteroaryl(C₁-C₆)alkyl, —S(O)₂(C₁-C₆)alkyl, —S(O)₂aryl, —S(O)₂heteroaryl, —S(O)₂aryl(C₁-C₆)alkyl, —S(O)₂heteroaryl(C₁-C₆)alkyl, —CO₂H, —C(O)O(C₁-C₆)alkyl, —C(O)O(aryl), —C(O)O(heteroaryl), —C(O)O(aryl(C₁-C₆)alkyl), —C(O)O(heteroaryl(C₁-C₆)alkyl), —C(O)NH₂, —C(O)NHOH, —C(O)NHCN, —C(O)NH((C₁-C₆)alkyl), —C(O)N((C₁-C₆)alkyl)₂, —C(O)NH(aryl(C₁-C₆)alkyl), —C(O)N(aryl(C₁-C₆)alkyl)₂, —C(O)NH(aryl), —C(O)N(aryl)((C₁-C₆)alkyl), —C(O)N(aryl)₂, —C(O)N(C₁-C₆)alkyl)(aryl(C₁-C₆)alkyl), —C(O)N(aryl)(aryl(C₁-C₆)alkyl), —C(O)NH((C₁-C₆)haloalkyl), —C(O)N((C₁-C₆)haloalkyl)₂, —S(O)₂ NH₂, —S(O)₂NH((C₁-C₆)alkyl), —S(O)₂NH((C₁-C₆)haloalkyl), —S(O)₂NH(aryl), —S(O)₂NH(heteroaryl(C₁-C₆)alkyl), —S(O)₂NH(heteroaryl), —S(O)₂N((C₁-C₆)alkyl)₂, —S(O)₂NHC(O)(C₁-C₆)alkyl, —S(O)₂NHC(O)(C₁-C₆)haloalkyl, —S(O)₂NHC(O)aryl, —S(O)₂NHC(O)aryl(C₁-C₆)alkyl, —S(O)₂NHC(O)heteroaryl, —S(O)₂NHC(O)heteroaryl(C₁-C₆)alkyl, —NHS(O)₂(C₁-C₆)alkyl, —NHS(O)₂aryl, —NHS(O)₂(C₁-C₆)haloalkyl, —NHS(O)₂aryl(C₁-C₆)alkyl, —NHS(O)₂heteroaryl, —NHS(O)₂heteroaryl(C₁-C₆)alkyl, —NHC(O)((C₁-C₆)alkyl), —NHC(O)((C₁-C₆)haloalkyl), —NHC(O)(aryl), —NHC(O)(aryl(C₁-C₆)alkyl), —NHC(O)(heteroaryl), —NHC(O)(heteroaryl(C₁-C₆)alkyl), —NHC(O)NH(C₁-C₆)alkyl), —NHC(O)NHaryl, —NHC(O)NH(aryl(C₁-C₆)alkyl), —NHC(O)NH(heteroaryl), —NHC(O)NH(heteroaryl(C₁-C₆)alkyl), —C(O)NHS(O)₂(C₁-C₆)alkyl, —C(O)NHS(O)₂aryl, C(O)NHS(O)₂((C₁-C₆)haloalkyl), —C(O)NHS(O)₂(aryl(C₁-C₆)alkyl), —C(O)NHS(O)₂heteroaryl, —C(O)NHS(O)₂(heteroaryl(C₁-C₆)alkyl), —P(O)(OH)₂, —((C₁-C₆)alkylene)C(O)OH, —((C₁-C₆)alkylene)C(O)O(C₁-C₆)alkyl, —NH₂, —NH(C₁-C₆)alkyl, —N((C₁-C₆)alkyl)₂, —NC, —CN, —C(S)NH₂, —NHC(O)NH₂, —C≡CH, (C₁-C₆)alkylthio-, (C₁-C₆)mercaptoalkyl-, or —C(O)heterocyclyl;

Z is —CH—, —C(O)—, —C((C₁-C₃)alkyl)-, or —C(═CH₂)—;

if Z is —C(O)—, then R² is absent,

R² is H, OH, halo, (C₁-C₆)alkyl, (C₁-C₆)alkoxy, (C₁-C₆)hydroxyalkyl, (C₁-C₆)alkoxy(C₁-C₆)alkyl, —CO₂H, —C(O)O(C₁-C₆)alkyl, —C(O)O(aryl), —C(O)O(heteroaryl), —C(O)O(aryl(C₁-C₆)alkyl), —C(O)O(heteroaryl(C₁-C₆)alkyl), —C(O)NHOH, —C(O)NHCN, —C(O)NH₂, —C(O)NH((C₁-C₆)alkyl), —C(O)N((C₁-C₆)alkyl)₂, —C(O)NH(aryl(C₁-C₆)alkyl), —C(O)N(aryl(C₁-C₆)alkyl)₂, —C(O)NH(aryl), —C(O)N(aryl)((C₁-C₆)alkyl), —C(O)N(aryl)₂, —C(O)N(C₁-C₆)alkyl)(aryl(C₁-C₆)alkyl), —C(O)N(aryl)(aryl(C₁-C₆)alkyl), —C(O)NH((C₁-C₆)haloalkyl), —C(O)N((C₁-C₆)haloalkyl)₂, —S(O)₂ NH₂, —S(O)₂NH((C₁-C₆)alkyl), —S(O)₂NH((C₁-C₆)haloalkyl), —S(O)₂NH(aryl), —S(O)₂NH(heteroaryl(C₁-C₆)alkyl), —S(O)₂NH(heteroaryl), —S(O)₂NH(heteroaryl(C₁-C₆) alkyl), —S(O)₂N((C₁-C₆)alkyl)₂, —S(O)₂NHC(O)(C₁-C₆)alkyl, —S(O)₂NHC(O)(C₁-C₆)haloalkyl, —S(O)₂NHC(O)aryl, —S(O)₂NHC(O)aryl(C₁-C₆)alkyl, —S(O)₂NHC(O)heteroaryl, —S(O)₂NHC(O)heteroaryl(C₁-C₆)alkyl, —NHS(O)₂(C₁-C₆)alkyl, —NHS(O)₂aryl, NHS(O)₂(C₁-C₆)haloalkyl, —NHS(O)₂aryl(C₁-C₆)alkyl, —NHS(O)₂heteroaryl, —NHS(O)₂heteroaryl(C₁-C₆)alkyl, —NHC(O)((C₁-C₆)alkyl), —NHC(O)((C₁-C₆)haloalkyl), —NHC(O)(aryl), —NHC(O)(aryl(C₁-C₆)alkyl), —NHC(O)(heteroaryl), —NHC(O)(heteroaryl(C₁-C₆)alkyl), —NHC(O)NH(C₁-C₆)alkyl, —NHC(O)NHaryl, —NHC(O)NH(aryl(C₁-C₆)alkyl), —NHC(O)NH(heteroaryl), —NHC(O)NH(heteroaryl(C₁-C₆)alkyl), —C(O)NHS(O)₂(C₁-C₆)alkyl, —C(O)NHS(O)₂aryl, C(O)NHS(O)₂((C₁-C₆)haloalkyl), —C(O)NHS(O)₂(aryl(C₁-C₆)alkyl), —C(O)NHS(O)₂heteroaryl, —C(O)NHS(O)₂(heteroaryl(C₁-C₆)alkyl), —P(O)(OH)₂, aryl(C₁-C₆)alkyl, (C₃-C₇)cycloalkyl(C₁-C₆)alkyl-, —NC, —CN, —C(S)NH₂, —NHC(O)NH₂, —C≡CH, (C₁-C₆)alkylthio-, (C₁-C₆)mercaptoalkyl-, or —C(O)heterocyclyl;

or R¹ and R², taken together with the intervening atoms, form a carbocyclic or heterocyclic ring;

R³ is H, (C₁-C₃)alkyl, (C₁-C₃)alkoxy(C₁-C₃)alkyl, (C₁-C₃)alkylthio(C₁-C₃)alkyl, (C₁-C₆)haloalkyl, —NC, —CN, —C(S)NH₂, —NHC(O)NH₂, or —C≡CH;

R⁴ is H, (C₁-C₃)alkyl, (C₁-C₃)alkylthio(C₁-C₃)alkyl, (C₁-C₆)haloalkyl, (C₁-C₃)alkoxy(C₁-C₃)alkyl-, or (C₁-C₄)hydroxyalkyl;

R⁵ is H, halo, —NO₂, —CN, (C₁-C₆)alkyl, (C₁-C₆)haloalkyl, —NH₂, —NH((C₁-C₆)alkyl), —N((C₁-C₆)alkyl)₂, —OH, (C₁-C₆)alkoxy, hydroxy(C₁-C₆)alkyl, (C₁-C₆)alkoxy(C₁-C₆)alkyl, (C₁-C₆)haloalkoxy, —SH, (C₁-C₃)alkylthio(C₁-C₃)alkyl, —NC, —C(S)NH₂, —NHC(O)NH₂, or —C≡CH; and R⁶ is H, halo, —OH, —NH₂, or —SH; or R⁶, taken together with the carbon atom bearing it, represents —C(O)—;

wherein:

any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of —OH, halo, —NH₂, —NH((C₁-C₆)alkyl), —N((C₁-C₆)alkyl)₂, —CN, —NO₂, (C₁-C₆)alkyl, (C₁-C₆)haloalkyl, (C₁-C₆)alkoxy, aryl, heteroaryl, aryl(C₁-C₆)alkyl, heteroaryl(C₁-C₆)alkyl, (C₃-C₇)cycloalkyl, heterocyclyl, —C(O)OH, —C(O)O(C₁-C₆)alkyl, —C(O)NH₂, —C(O)NH(C₁-C₆)alkyl, and —C(O)N((C₁-C₆)alkyl)₂;

or a pharmaceutically acceptable salt, solvate, tautomer, stereoisomer, or polymorph thereof.

In certain embodiments, the invention provides a compound represented by formula (II),

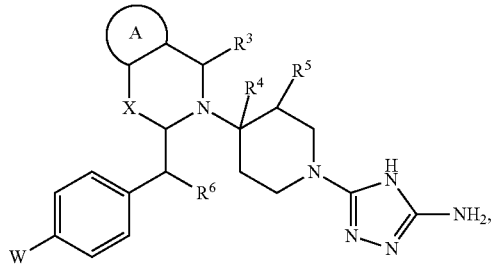

(II)

wherein:
W is halo, $(C_1\text{-}C_3)$alkyl, $(C_1\text{-}C_3)$alkoxy-, or $(C_1\text{-}C_3)$alkylthio-;
X is a single bond, —$CH_2$—, —$CH_2CH_2$—, —CH=CH—, —$C((C_1\text{-}C_3)$alkyl$)_2$-, —C(O)—, —$CH_2O$—, —$CH_2NH$—, or —$CH_2N((C_1\text{-}C_3)$alkyl)-, wherein when X is —$CH_2O$—, —$CH_2NH$—, or —$CH_2N((C_1\text{-}C_3)$alkyl)-, then the O or N atom is covalently bonded to Ring A;
Ring A represents an optionally substituted aryl or heteroaryl ring;
$R^3$ is H, $(C_1\text{-}C_3)$alkyl, $(C_1\text{-}C_3)$alkoxy$(C_1\text{-}C_3)$alkyl, $(C_1\text{-}C_3)$alkylthio$(C_1\text{-}C_3)$alkyl, $(C_1\text{-}C_6)$haloalkyl, —NC, —CN, —$C(S)NH_2$, —$NHC(O)NH_2$, or —C≡CH;
$R^4$ is H, $(C_1\text{-}C_3)$alkyl, $(C_1\text{-}C_3)$alkylthio$(C_1\text{-}C_3)$alkyl, $(C_1\text{-}C_6)$haloalkyl, $(C_1\text{-}C_3)$alkoxy$(C_1\text{-}C_3)$alkyl-, or $(C_1\text{-}C_4)$hydroxyalkyl;
$R^5$ is H, halo, —$NO_2$, —CN, $(C_1\text{-}C_6)$alkyl, $(C_1\text{-}C_6)$haloalkyl, —$NH_2$, —NH$((C_1\text{-}C_6)$alkyl), —N$((C_1\text{-}C_6)$alkyl$)_2$, —OH, $(C_1\text{-}C_6)$alkoxy, hydroxy$(C_1\text{-}C_6)$alkyl, $(C_1\text{-}C_6)$alkoxy$(C_1\text{-}C_6)$alkyl, $(C_1\text{-}C_6)$haloalkoxy, —SH, $(C_1\text{-}C_3)$alkylthio$(C_1\text{-}C_3)$alkyl, —NC, —$C(S)NH_2$, —$NHC(O)NH_2$, or —C≡CH; and
$R^6$ is H, halo, —OH, —$NH_2$, or —SH; or
$R^6$, taken together with the carbon atom bearing it, represents —C(O)—;
wherein:
any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of —OH, halo, —$NH_2$, —NH$((C_1\text{-}C_6)$alkyl), —N$((C_1\text{-}C_6)$alkyl$)_2$, —CN, —$NO_2$, $(C_1\text{-}C_6)$alkyl, $(C_1\text{-}C_6)$haloalkyl, $(C_1\text{-}C_6)$alkoxy, aryl, heteroaryl, aryl$(C_1\text{-}C_6)$alkyl, heteroaryl$(C_1\text{-}C_6)$alkyl, $(C_3\text{-}C_7)$cycloalkyl, heterocyclyl, —C(O)OH, —C(O)O$(C_1\text{-}C_6)$alkyl, —C(O)$NH_2$, —C(O)NH$(C_1\text{-}C_6)$alkyl, and —C(O)N$((C_1\text{-}C_6)$alkyl$)_2$;
or a pharmaceutically acceptable salt, solvate, tautomer, stereoisomer, or polymorph thereof.

Also provided herein are pharmaceutical compositions comprising a therapeutically effective amount of a compound of the invention, and a pharmaceutically acceptable carrier.

In certain aspects, the pharmaceutical composition also includes one or more second therapeutic agents selected from the group consisting of steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, acetylosalicylic acid, COX inhibitors, methotrexate, anti-TNF drugs, rituxin, PD4 inhibitors, p38 inhibitors, PDE4 inhibitors, and antihistamines.

In another aspect, the invention provides methods for inhibiting acidic mammalian chitinase in a cell or a tissue, comprising contacting the cell or the tissue with at least one compound of the invention, or with a pharmaceutical composition of the invention.

In another aspect, the invention provides methods for inhibiting chitotriosidase 1 (CHIT1) in a cell or a tissue, comprising contacting the cell or the tissue with at least one compound of the invention, or with a pharmaceutical composition of the invention.

Also provided herein are methods for treatment or prevention of a disease, disorder, or condition associated with aberrant expression or activity of acidic mammalian chitinase, comprising administering to a subject in need thereof a therapeutically effective amount of at least one compound of the invention, or a pharmaceutical composition of the invention.

The present invention also provides methods for treatment or prevention of a disease, disorder, or condition associated with aberrant expression or activity of CHIT1, comprising administering to a subject in need thereof a therapeutically effective amount of at least one compound of the invention, or a pharmaceutical composition of the invention.

Also provided herein are methods for treatment or prevention of a disease, disorder, or condition selected from the group consisting of allergic diseases, acute and chronic inflammatory diseases, autoimmune diseases, dental diseases, neurologic diseases, metabolic diseases, liver diseases, kidney diseases, skin diseases, polycystic ovary syndrome, endometriosis, fibrotic disorders, storage diseases, and cancer, comprising administering to a subject in need thereof a therapeutically effective amount of at least one compound of the invention, or a pharmaceutical composition of the invention.

The invention further provides methods for inhibiting chitotriosidase and acidic mammalian chitinase in a cell or a tissue, comprising contacting a cell or a tissue with at least one compound of the invention, or with a pharmaceutical composition of the invention.

DETAILED DESCRIPTION

The present invention is based on the unexpected discovery that chemical modification of amino triazole 4-amino piperidine small molecule compounds with a heterocyclic ring (e.g., a substituted morpholine or piperazine) increases the rigidity of the molecule, thus fixing its molecular geometry. This geometrical rigidity beneficially changes numerous molecular properties, and yields unexpected inhibitory efficacy toward acidic mammalian chitinase.

The amino triazole compounds according to the invention are thus useful in the treatment of disorders associated with upregulated and dysregulated AMCase activity, such as asthma and allergic reactions, as well as those disorders associated with upregulated and dysregulated CHIT1 activity.

Definitions

The articles "a" and "an" are used herein to refer to one or to more than one (i.e., to at least one) of the grammatical object of the article. By way of example, "an element" means one element or more than one element.

The terms "group" and "radical" are used interchangeably herein and denote a portion of a molecule in question which is bound to the rest of the molecule by a covalent bond (or bonds, as results from the previous paragraph).

The terms used herein may be preceded and/or followed by a single dash "—", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, $(C_1-C_6)$-alkoxycarbonyloxy and —OC(O)($C_1-C_6$)alkyl indicate the same functionality; similarly, arylalkyl and -alkylaryl indicate the same functionality.

The term "single bond" as used herein, denotes a single covalent bond between two atoms, such as C—C, C—H, or C—O.

The term "alkyl" as used herein is a term of art and refers to saturated aliphatic groups, including straight-chain alkyl groups and branched-chain alkyl groups. The subscripts following C indicate the number (or range of numbers) of carbon atoms in the straight-chain or branched-chain alkyl. In certain embodiments, a straight-chain or branched-chain alkyl has about 30 or fewer carbon atoms in its backbone (e.g., $C_1-C_{30}$ for straight chain, $C_3-C_{30}$ for branched chain), and alternatively, about 20 or fewer, 10 or fewer, or preferably 1-6 carbons. Representative examples of ($C_1-C_6$ alkyl) include, but are not limited to, methyl, ethyl, n-propyl, isopropyl, n-butyl, sec-butyl, isobutyl, tert-butyl, n-pentyl, isopentyl, neopentyl, and n-hexyl. Examples of $C_1-C_3$ alkyl include methyl, ethyl, n-propyl, and isopropyl. Alkyl may represent a group, as already defined, or a portion of a larger moiety, such as ($C_1-C_3$)alkoxy($C_1-C_3$)alkyl. A ($C_1-C_3$) alkoxy($C_1-C_3$)alkyl is bound to the rest of the molecule through the ($C_1-C_3$)alkyl moiety.

The term "cycloalkyl" means mono- or bicyclic or bridged saturated or partially saturated carbocyclic rings, each having from 3 to 12 carbon atoms. Certain cycloalkyls have from 3-8, or from 3-6 carbon atoms in their ring structure. Certain cycloalkyls have from 5-12 carbon atoms in their ring structure, and may have 6-10 carbons in the ring structure. Preferably, cycloalkyl is ($C_3-C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "cycloalkylalkyl" as used herein refers to an alkyl group substituted with one or more cycloalkyl groups. An example of cycloalkylalkyl is cyclohexylmethyl group.

The term "heterocyclyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 14, or 3 to 12 atoms including at least one heteroatom, such as nitrogen, oxygen, or sulfur. More preferred heterocycloalkyl groups have from 5-10 ring members where from 1-4 of the ring members are hetero atoms selected from the group consisting of O, N, and S, the remaining ring atoms being C. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group is optionally substituted by one or more substituents as described below.

As used herein, the term "heterocyclylene" refers to a bivalent heterocyclyl (heterocycloalkyl) group, i.e., a cyclic alkylene group, having from 3-10 members and from 1-4 hetero atoms selected from S, O, and N. An example is piperidine-2,3-dicarboxylic acid, i.e., in that compound, the piperidine ring is a heterocyclylene group.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Preferably, alkenyl contains from 2 to 6 carbons. Representative examples of alkenyl include, but are not limited to, ethenyl, 2-propenyl, 2-methyl-2-propenyl, 3-butenyl, 4-pentenyl, and 5-hexenyl. The unsaturated bond(s) of the alkenyl group can be located anywhere in the moiety and can have either the (Z) or the (E) configuration about the double bond(s). The molecules differing only in their configuration about the double bond are called geometrical isomers.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

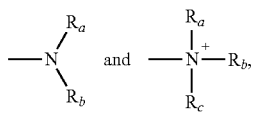

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$. In certain embodiments, the term "amino" refers to —$NH_2$.

The term "amido", as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "azide" or "azido", as used herein, means an —$N_3$ group.

The term "carbonyl" as used herein refers to —C(=O)—.
The term "thiocarbonyl" as used herein refers to —C(=S)—.

The term "alkylthio" as used herein refers to alkyl-S—. Representative examples of $(C_1-C_6)$alkylthio include methylthio, ethylthio, n-propylthio, and tert-butylthio. Representative examples of $(C_1-C_3)$alkylthio include methylthio, ethylthio, and n-propylthio.

The term "mercaptoalkyl" as used herein refers to an alkyl group substituted by an —SH moeity. Representative examples of $(C_1-C_6)$mercaptoalkyl include mercaptomethyl, mercaptoethyl, and mercapto-n-propyl.

The term "carboxy", as used herein, means a —$CO_2H$ group. This group can form a portion of another substituent, such as carboxymethyl, i.e., $HO_2C$—$CH_2$—.

The term "aryl" is a term of art and as used herein refers to include monocyclic, bicyclic, and polycyclic aromatic hydrocarbon groups, for example, benzene, naphthalene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. Representative examples of the polcyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to a phenyl group.

The term "heteroaryl" is a term of art and as used herein refers to a monocyclic or bicyclic aromatic group having 3 to 14, 5 to 14, 3 to 12, or 3 to 10 total atoms including one or more heteroatoms such as nitrogen, oxygen, or sulfur in the ring structure. More preferred heteroaryl groups have from 5-10 ring members where from 1-4 of the ring members are heteroatoms selected from the group consisting of O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. Any heteroaryl can be optionally substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Any heteroaryl or bicyclic heteroaryl can be optionally substituted as detailed below.

The term "aralkyl", "arylalkyl", or "aryl($C_1$-$C_6$)alkyl" is a term of art and as used herein refers to an alkyl group, for example a $C_1$-$C_6$ alkyl group, substituted with an aryl group, wherein the moiety is appended to the parent molecule through the alkyl group. An example of aralkyl is the benzyl group, i.e., the phenyl-methyl-group.

The term "arylene" is art-recognized, and as used herein pertains to a diradical obtained by removing two hydrogen atoms of an aryl group, as defined above. An exemplary arylene group is 1,4-phenylene.

The term "heteroaralkyl", "heteroarylalkyl", or "heteroaryl($C_1$-$C_6$)alkyl" is a term of art and as used herein refers to an alkyl group, for example a $C_1$-$C_6$ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Preferably, the alkoxy group is ($C_1$-$C_6$)alkoxy. Representative examples include, but are not limited to, methoxy, ethoxy, propoxy, 2-propoxy, butoxy, tert-butoxy, pentyloxy, and hexyloxy. Representative examples of ($C_1$-$C_3$)alkoxy include methoxy, ethoxy, and propoxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl. Alkoxycarbonyl can form a portion of another moiety, e.g., methoxycarbonylmethyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2$=CH—$CH_2$—O—) and vinyloxy (i.e., $CH_2$=CH—O—).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The terms "cyano" and "nitrile" is a term of art and as used herein refers to —CN.

The term "nitro", as used herein, means —$NO_2$.

The term "halo" or "halogen" is a term of art and as used herein refers to —F, —Cl, —Br, or —I.

The term "haloalkyl" as used herein refers to an alkyl group, as defined herein, wherein some or all of the hydrogens are replaced with halogen atoms. The term "haloalkoxyl" refers to an alkoxy group, as defined herein, wherein some or all of the hydrogens are replaced with halogen atoms. An exemplary ($C_1$-$C_6$)haloalkyl group is trifluoromethyl.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of ($C_1$-$C_6$)hydroxyalkyl include, but are not limited to, hydroxymethyl, 2-hydroxyethyl, 3-hydroxypropyl, and 2,3-dihydroxypentyl.

The term "sulfonyl", as used herein, refers to the group —$S(O)_2$— that may form a portion of larger moieties, such as methanesulfonyl or p-toluenesulfonyl.

The term "silyl", as used herein, includes hydrocarbyl derivatives of the silyl ($H_3Si$—) group (i.e., (hydrocarbyl)$_3$Si—), wherein a hydrocarbon radicals are univalent groups formed by removing a hydrogen atom from a hydrocarbon, e.g., ethyl, phenyl. The hydrocarbon radicals can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The term "racemic mixture" refers to a mixture containing equal proportions of the first enantiomer of the molecule and of the second enantiomer of this molecule, wherein the second enantiomer is the mirror image of the first one.

The term "scalemic mixture" refers to any non-racemic mixture of stereoisomers of the molecule.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Organic compounds frequently occur in more than one crystalline form, that can differ in their physical and biological properties, such as melting point, stability, solubility, bioavailability. Such crystalline forms are termed polymorphs. All polymorphs of the inventive compounds of formula (I) and of their salts are intended to be within the scope of this invention.

Since many chemical elements can occur as isotopes, their abundance in the molecule of the inventive compound of formula (I) may be identical as in the nature or altered. Some isotopes exhibit different spectral or biological properties, and this phenomenon may be used for analysis of distribution and metabolism of drugs in the body of the recipient. All forms of the compounds of formula (I), both having a natural or unnatural abundance of isotopes of any of their constituent elements are intended to be within the scope of this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or other substitutents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

A "unsaturated" or "partially saturated" compound means that the referenced chemical structure may contain one or more multiple carbon-carbon bonds, but is not aromatic. For example, a unsaturated cycloalkyl group as defined herein includes cyclohexenyl, cyclopentenyl, cyclohexadienyl, and the like.

For purposes of the invention, the chemical elements are identified in accordance with the Periodic Chart of the Elements, IUPAC version, The Merck Index, Twelfth Edition, 1996, inside cover.

Other chemistry terms herein are used according to conventional usage in the art, as exemplified by The McGraw-Hill Dictionary of Chemical Terms (ed. Parker, S., 1985), McGraw-Hill, San Francisco). Unless otherwise defined, all technical and scientific terms used herein have the same meaning as commonly understood by one of ordinary skill in the art to which this invention pertains.

It will be apparent to one skilled in the art that the compounds of this disclosure may exist in tautomeric forms. For example, the following structures illustrate some tautomeric forms of the triazole group.

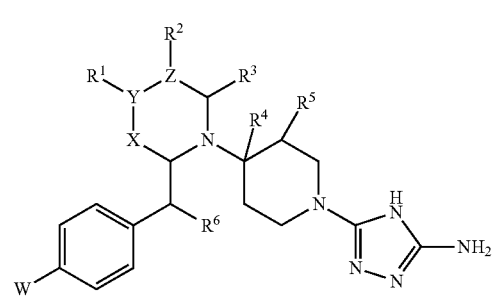

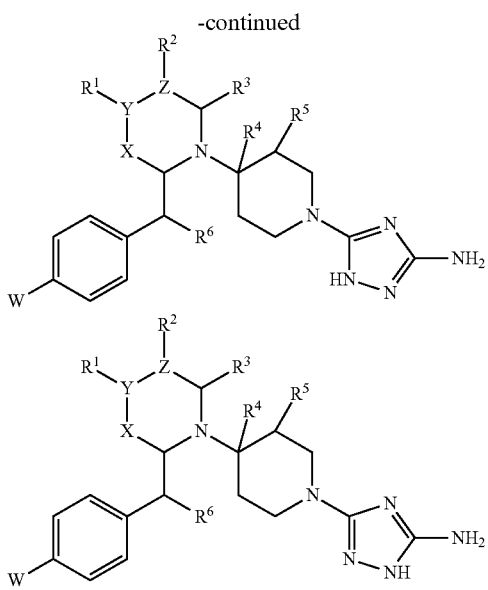

In this specification only one tautomeric form is depicted for each compound, but all such tautomeric forms of the compounds are within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

As used herein, a protic solvent is a solvent that has a hydrogen atom bound to an oxygen (as in a hydroxyl group) or a nitrogen (as in an amine group). In general terms, any solvent that contains labile H$^+$ is called a protic solvent. The molecules of such solvents readily donate protons (H$^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, "subject" refers to a warm blooded animal such as a mammal, preferably a human, or a human child, which is afflicted with, or has the potential to be afflicted with one or more diseases and disorders described herein.

"EC$_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Compounds of the Invention

In certain embodiments, the invention relates to a compound represented by formula (I), wherein:
W is halo, $(C_1-C_3)$alkyl, $(C_1-C_3)$alkoxy-, or $(C_1-C_3)$alkylthio-;
X is a single bond, —$CH_2$—, —$CH_2CH_2$—, —CH=CH—, —C$((C_1-C_3)$alkyl$)_2$-, or —C(O)—;
Y is a single bond, —CH—, —$CHCH_2$—, —$CH_2CH$—, —C=CH—, —CH=C—, —N—, —O—, —$OCH_2$—, —S(O)—, or —S(O)$_2$—;
if Y is a single bond, —O—, —$OCH_2$—, —S(O)—, or —S(O)$_2$—, then $R^1$ is absent;
$R^1$ is H, OH, $(C_1-C_6)$alkyl, $(C_1-C_6)$haloalkyl, $(C_1-C_6)$alkoxy, $(C_1-C_6)$hydroxyalkyl, $(C_1-C_6)$alkoxy$(C_1-C_6)$alkyl, aryl$(C_1-C_6)$alkyl, heteroaryl$(C_1-C_6)$alkyl, —C(O)$(C_1-C_6)$alkyl, —C(O)aryl, —C(O)heteroaryl, —C(O)aryl$(C_1-C_6)$alkyl, —C(O)heteroaryl$(C_1-C_6)$alkyl, —S(O)$_2(C_1-C_6)$alkyl, —S(O)$_2$aryl, —S(O)$_2$heteroaryl, —S(O)$_2$aryl$(C_1-C_6)$alkyl, —S(O)$_2$heteroaryl$(C_1-C_6)$alkyl, —$CO_2$H, —C(O)O$(C_1-C_6)$alkyl, —C(O)O(aryl), —C(O)O(heteroaryl), —C(O)O(aryl$(C_1-C_6)$alkyl), —C(O)O(heteroaryl$(C_1-C_6)$alkyl), —C(O)$NH_2$, —C(O)NHOH, —C(O)NHCN, —C(O)NH$((C_1-C_6)$alkyl), —C(O)N$((C_1-C_6)$alkyl$)_2$, —C(O)NH(aryl$(C_1-C_6)$alkyl), —C(O)N(aryl$(C_1-C_6)$alkyl$)_2$, —C(O)NH(aryl), —C(O)N(aryl)$((C_1-C_6)$alkyl), —C(O)N(aryl)$_2$, —C(O)N$(C_1-C_6)$alkyl)(aryl$(C_1-C_6)$alkyl), —C(O)N(aryl)(aryl$(C_1-C_6)$alkyl), —C(O)NH$((C_1-C_6)$haloalkyl), —C(O)N$((C_1-C_6)$haloalkyl$)_2$, —S(O)$_2$ $NH_2$, —S(O)$_2$NH$((C_1-C_6)$alkyl), —S(O)$_2$NH$((C_1-C_6)$haloalkyl), —S(O)$_2$NH(aryl), —S(O)$_2$NH(heteroaryl$(C_1-C_6)$alkyl), —S(O)$_2$NH(heteroaryl), —S(O)$_2$N$((C_1-C_6)$alkyl$)_2$, —S(O)$_2$NHC(O)$(C_1-C_6)$alkyl, —S(O)$_2$NHC(O)$(C_1-C_6)$haloalkyl, —S(O)$_2$NHC(O)aryl, —S(O)$_2$NHC(O)aryl$(C_1-C_6)$alkyl, —S(O)$_2$NHC(O)heteroaryl, —S(O)$_2$ NHC(O)heteroaryl$(C_1-C_6)$alkyl, —NHS(O)$_2(C_1-C_6)$alkyl, —NHS(O)$_2$aryl, —NHS(O)$_2(C_1-C_6)$haloalkyl, —NHS(O)$_2$aryl$(C_1-C_6)$alkyl, —NHS(O)$_2$heteroaryl, —NHS(O)$_2$heteroaryl$(C_1-C_6)$alkyl, —NHC(O)$((C_1-C_6)$alkyl), —NHC(O)$((C_1-C_6)$haloalkyl), —NHC(O)(aryl), —NHC(O)(aryl$(C_1-C_6)$alkyl), —NHC(O)(heteroaryl), —NHC(O)(heteroaryl$(C_1-C_6)$alkyl), —NHC(O)NH$(C_1-C_6)$alkyl, —NHC(O)NHaryl, —NHC(O)NH(aryl$(C_1-C_6)$alkyl), —NHC(O)NH(heteroaryl), —NHC(O)NH(heteroaryl$(C_1-C_6)$alkyl), —C(O)NHS(O)$_2(C_1-C_6)$alkyl, —C(O)NHS(O)$_2$aryl, C(O)NHS(O)$_2((C_1-C_6)$haloalkyl), —C(O)NHS(O)$_2$(aryl$(C_1-C_6)$alkyl), —C(O)NHS(O)$_2$heteroaryl, —C(O)NHS(O)$_2$(heteroaryl$(C_1-C_6)$alkyl), —P(O)(OH)$_2$, —$((C_1-C_6)$alkylene)C(O)OH, —$((C_1-C_6)$alkylene)C(O)O$(C_1-C_6)$alkyl, —$NH_2$, —NH$(C_1-C_6)$alkyl, —N$((C_1-C_6)$alkyl$)_2$, —NC, —CN, —C(S)$NH_2$, —NHC(O)$NH_2$, —C≡CH, $(C_1-C_6)$alkylthio-, $(C_1-C_6)$mercaptoalkyl-, or —C(O)heterocyclyl;

Z is —CH—, —C(O)—, —C$((C_1-C_3)$alkyl)-, or —C(=$CH_2$)—;
if Z is —C(O)—, then $R^2$ is absent,
$R^2$ is H, OH, halo, $(C_1-C_6)$alkyl, $(C_1-C_6)$alkoxy, $(C_1-C_6)$hydroxyalkyl, $(C_1-C_6)$alkoxy$(C_1-C_6)$alkyl, —$CO_2$H, —C(O)O$(C_1-C_6)$alkyl, —C(O)O(aryl), —C(O)O(heteroaryl), —C(O)O(aryl$(C_1-C_6)$alkyl), —C(O)O(heteroaryl$(C_1-C_6)$alkyl), —C(O)NHOH, —C(O)NHCN, —C(O)$NH_2$, —C(O)NH$((C_1-C_6)$alkyl), —C(O)N$((C_1-C_6)$alkyl$)_2$, —C(O)NH(aryl$(C_1-C_6)$alkyl), —C(O)N(aryl$(C_1-C_6)$alkyl$)_2$, —C(O)NH(aryl), —C(O)N(aryl)$((C_1-C_6)$alkyl), —C(O)N(aryl)$_2$, —C(O)N$(C_1-C_6)$alkyl)(aryl$(C_1-C_6)$alkyl), —C(O)N(aryl)(aryl$(C_1-C_6)$alkyl), —C(O)NH$((C_1-C_6)$haloalkyl), —C(O)N$((C_1-C_6)$haloalkyl$)_2$, —S(O)$_2$ $NH_2$, —S(O)$_2$NH$((C_1-C_6)$alkyl), —S(O)$_2$NH$((C_1-C_6)$haloalkyl), —S(O)$_2$NH(aryl), —S(O)$_2$NH(heteroaryl$(C_1-C_6)$alkyl), —S(O)$_2$NH(heteroaryl), —S(O)$_2$NH(heteroaryl$(C_1-C_6)$ alkyl), —S(O)$_2$N$((C_1-C_6)$alkyl$)_2$, —S(O)$_2$NHC(O)$(C_1-C_6)$alkyl, —S(O)$_2$NHC(O)$(C_1-C_6)$haloalkyl, —S(O)$_2$NHC(O)aryl, —S(O)$_2$NHC(O)aryl$(C_1-C_6)$alkyl, —S(O)$_2$NHC(O)heteroaryl, —S(O)$_2$NHC(O)heteroaryl$(C_1-C_6)$alkyl, —NHS(O)$_2(C_1-C_6)$alkyl, —NHS(O)$_2$aryl, NHS(O)$_2(C_1-C_6)$haloalkyl, —NHS(O)$_2$aryl$(C_1-C_6)$alkyl, —NHS(O)$_2$heteroaryl, —NHS(O)$_2$heteroaryl$(C_1-C_6)$alkyl, —NHC(O)$((C_1-C_6)$alkyl), —NHC(O)$((C_1-C_6)$haloalkyl), —NHC(O)(aryl), —NHC(O)(aryl$(C_1-C_6)$alkyl), —NHC(O)(heteroaryl), —NHC(O)(heteroaryl$(C_1-C_6)$alkyl), —NHC(O)NH$(C_1-C_6)$alkyl, —NHC(O)NHaryl, —NHC(O)NH(aryl$(C_1-C_6)$alkyl), —NHC(O)NH(heteroaryl), —NHC(O)NH(heteroaryl$(C_1-C_6)$alkyl), —C(O)NHS(O)$_2(C_1-C_6)$alkyl, —C(O)NHS(O)$_2$aryl, C(O)NHS(O)$_2((C_1-C_6)$haloalkyl), —C(O)NHS(O)$_2$(aryl$(C_1-C_6)$alkyl), —C(O)NHS(O)$_2$heteroaryl, —C(O)NHS(O)$_2$(heteroaryl$(C_1-C_6)$alkyl), —P(O)(OH)$_2$, aryl$(C_1-C_6)$alkyl, $(C_3-C_7)$cycloalkyl$(C_1-C_6)$alkyl-, —NC, —CN, —C(S)$NH_2$, —NHC(O)$NH_2$, —C≡CH, $(C_1-C_6)$alkylthio-, $(C_1-C_6)$mercaptoalkyl-, or —C(O)heterocyclyl;

or $R^1$ and $R^2$, taken together with the intervening atoms, form a carbocyclic or heterocyclic ring;
$R^3$ is H, $(C_1-C_3)$alkyl, $(C_1-C_3)$alkoxy$(C_1-C_3)$alkyl, $(C_1-C_3)$alkylthio$(C_1-C_3)$alkyl, $(C_1-C_6)$haloalkyl, —NC, —CN, —C(S)$NH_2$, —NHC(O)$NH_2$, or —C≡CH;
$R^4$ is H, $(C_1-C_3)$alkyl, $(C_1-C_3)$alkylthio$(C_1-C_3)$alkyl, $(C_1-C_6)$haloalkyl, $(C_1-C_3)$alkoxy$(C_1-C_3)$alkyl-, or $(C_1-C_4)$hydroxyalkyl;
$R^5$ is H, halo, —$NO_2$, —CN, $(C_1-C_6)$alkyl, $(C_1-C_6)$haloalkyl, —$NH_2$, —NH$((C_1-C_6)$alkyl), —N$((C_1-C_6)$alkyl$)_2$, —OH, $(C_1-C_6)$alkoxy, hydroxy$(C_1-C_6)$alkyl, $(C_1-C_6)$alkoxy$(C_1-C_6)$alkyl, $(C_1-C_6)$haloalkoxy, —SH, $(C_1-C_3)$alkylthio$(C_1-C_3)$alkyl, —NC, —C(S)$NH_2$, —NHC(O)$NH_2$, or —C≡CH; and
$R^6$ is H, halo, —OH, —$NH_2$, or —SH; or
$R^6$, taken together with the carbon atom bearing it, represents —C(O)—;
wherein:
any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of —OH, halo, —NH$_2$, —NH(($C_1$-$C_6$)alkyl), —N(($C_1$-$C_6$)alkyl)$_2$, —CN, —NO$_2$, ($C_1$-$C_6$)alkyl, ($C_1$-$C_6$)haloalkyl, ($C_1$-$C_6$)alkoxy, aryl, heteroaryl, aryl($C_1$-$C_6$)alkyl, heteroaryl($C_1$-$C_6$)alkyl, ($C_3$-$C_7$)cycloalkyl, heterocyclyl, —C(O)OH, —C(O)O($C_1$-$C_6$)alkyl, —C(O)NH$_2$, —C(O)NH($C_1$-$C_6$)alkyl, and —C(O)N(($C_1$-$C_6$)alkyl)$_2$; or a pharmaceutically acceptable salt, solvate, tautomer, stereoisomer, or polymorph thereof.

In further embodiments, the invention is directed to a compound of formula (I), wherein:

W is halo, ($C_1$-$C_3$)alkyl, ($C_1$-$C_3$)alkoxy-, or ($C_1$-$C_3$)alkylthio-;

X is a single bond, —CH$_2$—, —CH$_2$CH$_2$—, —CH=CH—, or —C(O)—;

Y is a single bond, —CH—, —CHCH$_2$—, —CH$_2$CH—, —C=CH—, —CH=C—, —N—, —O—, —S(O)—, or —S(O)$_2$—;

if Y is a single bond, —O—, —S(O)—, or —S(O)$_2$—, then $R^1$ is absent;

$R^1$ is H, ($C_1$-$C_6$)alkyl, ($C_1$-$C_6$)haloalkyl, ($C_1$-$C_6$)alkoxy, ($C_1$-$C_6$)hydroxyalkyl, ($C_1$-$C_6$)alkoxy($C_1$-$C_6$)alkyl, aryl($C_1$-$C_6$)alkyl, heteroaryl($C_1$-$C_6$)alkyl, —C(O)($C_1$-$C_6$)alkyl, —C(O)aryl, —C(O)heteroaryl, —C(O)aryl($C_1$-$C_6$)alkyl, —C(O)heteroaryl($C_1$-$C_6$)alkyl, —S(O)$_2$($C_1$-$C_6$)alkyl, —S(O)$_2$aryl, —S(O)$_2$heteroaryl, —S(O)$_2$aryl($C_1$-$C_6$)alkyl, —S(O)$_2$heteroaryl($C_1$-$C_6$)alkyl, —CO$_2$H, —C(O)O($C_1$-$C_6$)alkyl, —C(O)O(aryl), —C(O)O(heteroaryl), —C(O)O(aryl($C_1$-$C_6$)alkyl), —C(O)O(heteroaryl($C_1$-$C_6$)alkyl), —C(O)NH$_2$, —C(O)NHOH, —C(O)NHCN, —C(O)NH(($C_1$-$C_6$)alkyl), —C(O)N(($C_1$-$C_6$)alkyl)$_2$, —C(O)NH(aryl($C_1$-$C_6$)alkyl), —C(O)N(aryl($C_1$-$C_6$)alkyl)$_2$, —C(O)NH(aryl), —C(O)N(aryl)(($C_1$-$C_6$)alkyl), —C(O)N(aryl)$_2$, —C(O)N($C_1$-$C_6$)alkyl)(aryl($C_1$-$C_6$)alkyl), —C(O)N(aryl)(aryl($C_1$-$C_6$)alkyl), —C(O)NH(($C_1$-$C_6$)haloalkyl), —C(O)N(($C_1$-$C_6$)haloalkyl)$_2$, —S(O)$_2$NH$_2$, —S(O)$_2$NH(($C_1$-$C_6$)alkyl), —S(O)$_2$NH(($C_1$-$C_6$)haloalkyl), —S(O)$_2$NH(aryl), —S(O)$_2$NH(heteroaryl($C_1$-$C_6$)alkyl), —S(O)$_2$NH(heteroaryl), —S(O)$_2$N(($C_1$-$C_6$)alkyl)$_2$, —S(O)$_2$NHC(O)($C_1$-$C_6$)alkyl, —S(O)$_2$NHC(O)($C_1$-$C_6$)haloalkyl, —S(O)$_2$NHC(O)aryl, —S(O)$_2$NHC(O)aryl($C_1$-$C_6$)alkyl, —S(O)$_2$NHC(O)heteroaryl, —S(O)$_2$NHC(O)heteroaryl($C_1$-$C_6$)alkyl, —NHS(O)$_2$($C_1$-$C_6$)alkyl, —NHS(O)$_2$aryl, —NHS(O)$_2$($C_1$-$C_6$)haloalkyl, —NHS(O)$_2$aryl($C_1$-$C_6$)alkyl, —NHS(O)$_2$heteroaryl, —NHS(O)$_2$heteroaryl($C_1$-$C_6$)alkyl, —NHC(O)(($C_1$-$C_6$)alkyl), —NHC(O)(($C_1$-$C_6$)haloalkyl), —NHC(O)(aryl), —NHC(O)(aryl($C_1$-$C_6$)alkyl), —NHC(O)(heteroaryl), —NHC(O)(heteroaryl($C_1$-$C_6$)alkyl), —NHC(O)NH($C_1$-$C_6$)alkyl, —NHC(O)NH(aryl), —NHC(O)NH(aryl($C_1$-$C_6$)alkyl), —NHC(O)NH(heteroaryl), —NHC(O)NH(heteroaryl($C_1$-$C_6$)alkyl), —C(O)NHS(O)$_2$($C_1$-$C_6$)alkyl, —C(O)NHS(O)$_2$aryl, C(O)NHS(O)$_2$(($C_1$-$C_6$)haloalkyl), —C(O)NHS(O)$_2$(aryl($C_1$-$C_6$)alkyl), —C(O)NHS(O)$_2$heteroaryl, —C(O)NHS(O)$_2$(heteroaryl($C_1$-$C_6$)alkyl), —P(O)(OH)$_2$, —(($C_1$-$C_6$)alkylene)C(O)OH, (($C_1$-$C_6$)alkylene)C(O)O($C_1$-$C_6$)alkyl, —NH$_2$, —NH($C_1$-$C_6$)alkyl, —N(($C_1$-$C_6$)alkyl)$_2$, —NC, —CN, —C(S)NH$_2$, —NHC(O)NH$_2$, —C≡CH, ($C_1$-$C_6$)alkylthio-, ($C_1$-$C_6$)mercaptoalkyl-, or —C(O)heterocyclyl;

Z is —CH—, —C(O)—, or —C(($C_1$-$C_3$)alkyl)-;

if Z is —C(O)—, then $R^2$ is absent, $R^2$ is H, halo, ($C_1$-$C_6$)alkyl, ($C_1$-$C_6$)alkoxy, ($C_1$-$C_6$)hydroxyalkyl, ($C_1$-$C_6$)alkoxy($C_1$-$C_6$)alkyl, —CO$_2$H, —C(O)O($C_1$-$C_6$)alkyl, —C(O)O(aryl), —C(O)O(heteroaryl), —C(O)O(aryl($C_1$-$C_6$)alkyl), —C(O)O(heteroaryl($C_1$-$C_6$)alkyl), —C(O)NHOH, —C(O)NHCN, —C(O)NH$_2$, —C(O)NH(($C_1$-$C_6$)alkyl), —C(O)N(($C_1$-$C_6$)alkyl)$_2$, —C(O)NH(aryl($C_1$-$C_6$)alkyl), —C(O)N(aryl($C_1$-$C_6$)alkyl)$_2$, —C(O)NH(aryl), —C(O)N(aryl)(($C_1$-$C_6$)alkyl), —C(O)N(aryl)$_2$, —C(O)N($C_1$-$C_6$)alkyl)(aryl($C_1$-$C_6$)alkyl), —C(O)N(aryl)(aryl($C_1$-$C_6$)alkyl), —C(O)NH(($C_1$-$C_6$)haloalkyl), —C(O)N(($C_1$-$C_6$)haloalkyl)$_2$, —S(O)$_2$NH$_2$, —S(O)$_2$NH(($C_1$-$C_6$)alkyl), —S(O)$_2$NH(($C_1$-$C_6$)haloalkyl), —S(O)$_2$NH(aryl), —S(O)$_2$NH(heteroaryl($C_1$-$C_6$)alkyl), —S(O)$_2$NH(heteroaryl), —S(O)$_2$NH(heteroaryl($C_1$-$C_6$)alkyl), —S(O)$_2$N(($C_1$-$C_6$)alkyl)$_2$, —S(O)$_2$NHC(O)($C_1$-$C_6$)alkyl, —S(O)$_2$NHC(O)($C_1$-$C_6$)haloalkyl, —S(O)$_2$NHC(O)aryl, —S(O)$_2$NHC(O)aryl($C_1$-$C_6$)alkyl, —S(O)$_2$NHC(O)heteroaryl, —S(O)$_2$NHC(O)heteroaryl($C_1$-$C_6$)alkyl, —NHS(O)$_2$($C_1$-$C_6$)alkyl, —NHS(O)$_2$aryl, NHS(O)$_2$($C_1$-$C_6$)haloalkyl, —NHS(O)$_2$aryl($C_1$-$C_6$)alkyl, —NHS(O)$_2$heteroaryl, —NHS(O)$_2$heteroaryl($C_1$-$C_6$)alkyl, —NHC(O)(($C_1$-$C_6$)alkyl), —NHC(O)(($C_1$-$C_6$)haloalkyl), —NHC(O)(aryl), —NHC(O)(aryl($C_1$-$C_6$)alkyl), —NHC(O)(heteroaryl), —NHC(O)(heteroaryl($C_1$-$C_6$)alkyl), —NHC(O)NH($C_1$-$C_6$)alkyl, —NHC(O)NHaryl, —NHC(O)NH(aryl($C_1$-$C_6$)alkyl), —NHC(O)NH(heteroaryl), —NHC(O)NH(heteroaryl($C_1$-$C_6$)alkyl), —C(O)NHS(O)$_2$($C_1$-$C_6$)alkyl, —C(O)NHS(O)$_2$aryl, C(O)NHS(O)$_2$(($C_1$-$C_6$)haloalkyl), —C(O)NHS(O)$_2$(aryl($C_1$-$C_6$)alkyl), —C(O)NHS(O)$_2$heteroaryl, —C(O)NHS(O)$_2$(heteroaryl($C_1$-$C_6$)alkyl), —P(O)(OH)$_2$, aryl($C_1$-$C_6$)alkyl, ($C_3$-$C_7$)cycloalkyl($C_1$-$C_6$)alkyl-, —NC, —CN, —C(S)NH$_2$, —NHC(O)NH$_2$, —C≡CH, ($C_1$-$C_6$)alkylthio-, ($C_1$-$C_6$)mercaptoalkyl-, or —C(O)heterocyclyl;

$R^3$ is H, ($C_1$-$C_3$)alkyl, ($C_1$-$C_3$)alkoxy($C_1$-$C_3$)alkyl, ($C_1$-$C_3$)alkylthio($C_1$-$C_3$)alkyl, ($C_1$-$C_6$)haloalkyl, —NC, —CN, —C(S)NH$_2$, —NHC(O)NH$_2$, or —C≡CH;

$R^4$ is H, ($C_1$-$C_3$)alkyl, ($C_1$-$C_3$)alkylthio($C_1$-$C_3$)alkyl, ($C_1$-$C_6$)haloalkyl, ($C_1$-$C_3$)alkoxy($C_1$-$C_3$)alkyl-, or ($C_1$-$C_4$)hydroxyalkyl;

$R^5$ is H, halo, —NO$_2$, —CN, ($C_1$-$C_6$)alkyl, ($C_1$-$C_6$)haloalkyl, —NH$_2$, —NH(($C_1$-$C_6$)alkyl), —N(($C_1$-$C_6$)alkyl)$_2$, —OH, ($C_1$-$C_6$)alkoxy, hydroxy($C_1$-$C_6$)alkyl, ($C_1$-$C_6$)alkoxy($C_1$-$C_6$)alkyl, ($C_1$-$C_6$)haloalkoxy, —SH, ($C_1$-$C_3$)alkylthio($C_1$-$C_3$)alkyl, —NC, —C(S)NH$_2$, —NHC(O)NH$_2$, or —C≡CH; and $R^6$ is H, halo, —OH, —NH$_2$, or —SH; or $R^6$, taken together with the carbon atom bearing it, represents —C(O)—;

wherein:

any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of —OH, halo, —NH$_2$, —NH(($C_1$-$C_6$)alkyl), —N(($C_1$-$C_6$)alkyl)$_2$, —CN, —NO$_2$, ($C_1$-$C_6$)alkyl, ($C_1$-$C_6$)haloalkyl, ($C_1$-$C_6$)alkoxy, aryl, heteroaryl, aryl($C_1$-$C_6$)alkyl, heteroaryl($C_1$-$C_6$)alkyl, ($C_3$-$C_7$)cycloalkyl, heterocyclyl, —C(O)OH, —C(O)O($C_1$-$C_6$)alkyl, —C(O)NH$_2$, —C(O)NH($C_1$-$C_6$)alkyl, and —C(O)N(($C_1$-$C_6$)alkyl)$_2$. In certain embodiments, W is fluoro, chloro, bromo, methyl, or methoxy.

In certain embodiments, W is chloro or bromo.

In certain embodiments, W is chloro.

In certain embodiments, $R^6$ is H or —OH.

In certain embodiments, $R^6$ is H.

In certain embodiments, X is a single bond, —CH$_2$—, or —C(O)—.

In certain embodiments, X is —CH$_2$—.

In certain embodiments, Y is a single bond, —CH—, —N—, —O—, or —S(O)$_2$—.

In certain embodiments, Y is a single bond, —O—, or —S(O)$_2$—.
In certain embodiments, Y is a single bond.
In certain embodiments, Y is —O—.
In certain embodiments, Y is —CH— or —N—.
In certain embodiments, Y is —CH—.
In certain embodiments, Y is —N—.
In certain embodiments, R$^1$ is H, (C$_1$-C$_6$)alkyl, (C$_1$-C$_6$)haloalkyl, (C$_1$-C$_6$)alkoxy, (C$_1$-C$_6$)hydroxyalkyl, (C$_1$-C$_6$)alkoxy(C$_1$-C$_6$)alkyl, aryl(C$_1$-C$_6$)alkyl, heteroaryl(C$_1$-C$_6$)alkyl, —C(O)(C$_1$-C$_6$)alkyl, —C(O)aryl, —C(O)heteroaryl, —C(O)aryl(C$_1$-C$_6$)alkyl, —C(O)heteroaryl(C$_1$-C$_6$)alkyl, —S(O)$_2$(C$_1$-C$_6$)alkyl, —S(O)$_2$aryl, —S(O)$_2$heteroaryl, —S(O)$_2$aryl(C$_1$-C$_6$)alkyl, —S(O)$_2$heteroaryl(C$_1$-C$_6$)alkyl, —CO$_2$H, —C(O)O(C$_1$-C$_6$)alkyl, —C(O)O(aryl), —C(O)O(heteroaryl), —C(O)O(aryl(C$_1$-C$_6$)alkyl), —C(O)O(heteroaryl(C$_1$-C$_6$)alkyl), —C(O)NH$_2$, —C(O)NHOH, —C(O)NHCN, —C(O)NH((C$_1$-C$_6$)alkyl), —C(O)N((C$_1$-C$_6$)alkyl)$_2$, —C(O)NH(aryl(C$_1$-C$_6$)alkyl), —C(O)N(aryl(C$_1$-C$_6$)alkyl)$_2$, —C(O)NH(aryl), —C(O)N(aryl)((C$_1$-C$_6$)alkyl), —C(O)N(aryl)$_2$, —C(O)N(C$_1$-C$_6$)alkyl)(aryl(C$_1$-C$_6$)alkyl), —C(O)N(aryl)(aryl(C$_1$-C$_6$)alkyl), —((C$_1$-C$_6$)alkylene)C(O)OH, —((C$_1$-C$_6$)alkylene)C(O)O(C$_1$-C$_6$)alkyl, —NH$_2$, —NH(C$_1$-C$_6$)alkyl, —N((C$_1$-C$_6$)alkyl)$_2$, or —C(O)heterocyclyl.

In certain embodiments, R$^1$ is H, (C$_1$-C$_6$)alkyl, (C$_1$-C$_6$)alkoxy, (C$_1$-C$_6$)hydroxyalkyl, (C$_1$-C$_6$)alkoxy(C$_1$-C$_6$)alkyl, —C(O)(C$_1$-C$_6$)alkyl, —C(O)aryl, —C(O)heteroaryl, —C(O)aryl(C$_1$-C$_6$)alkyl, —C(O)heteroaryl(C$_1$-C$_6$)alkyl, —S(O)$_2$(C$_1$-C$_6$)alkyl, —S(O)$_2$aryl, —C(O)O(C$_1$-C$_6$)alkyl, —C(O)O(aryl), —C(O)O(heteroaryl), —C(O)O(aryl(C$_1$-C$_6$)alkyl), —C(O)O(heteroaryl(C$_1$-C$_6$)alkyl), —((C$_1$-C$_6$)alkylene)C(O)OH, —((C$_1$-C$_6$)alkylene)C(O)O(C$_1$-C$_6$)alkyl, or —C(O)heterocyclyl.

In certain embodiments, R$^1$ is H, (C$_1$-C$_6$)alkyl, (C$_1$-C$_6$)alkoxy, —C(O)(C$_1$-C$_6$)alkyl, —S(O)$_2$(C$_1$-C$_6$)alkyl, —S(O)$_2$aryl, —C(O)O(C$_1$-C$_6$)alkyl, —((C$_1$-C$_6$)alkylene)C(O)OH, or —((C$_1$-C$_6$)alkylene)C(O)O(C$_1$-C$_6$)alkyl.

In certain embodiments, R$^1$ is H or (C$_1$-C$_6$)alkyl.
In certain embodiments, R$^1$ is (C$_1$-C$_4$)alkyl.
In certain embodiments, R$^1$ is —C(O)heterocyclyl selected from the group consisting of

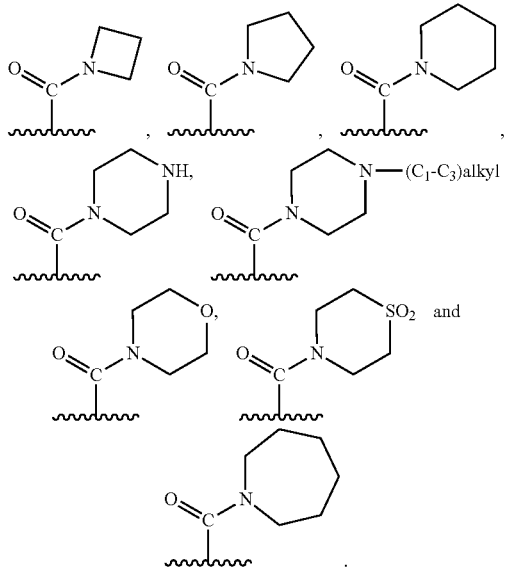

In certain embodiments, R$^1$ is —CH$_2$CO$_2$H or —CH$_2$C(O)O(C$_1$-C$_6$)alkyl.
In certain embodiments, Z is —C(O)—.
In certain embodiments, Z is —C((C$_1$-C$_3$)alkyl)-.
In certain embodiments, Z is —CH—.
In certain embodiments, R$^2$ is H, halo, (C$_1$-C$_6$)alkyl, (C$_1$-C$_6$)alkoxy, (C$_1$-C$_6$)hydroxyalkyl, (C$_1$-C$_6$)alkoxy(C$_1$-C$_6$)alkyl, —CO$_2$H, —C(O)O(C$_1$-C$_6$)alkyl, —C(O)O(aryl), —C(O)O(heteroaryl), —C(O)O(aryl(C$_1$-C$_6$)alkyl), —C(O)O(heteroaryl(C$_1$-C$_6$)alkyl), —C(O)NH$_2$, —C(O)NH((C$_1$-C$_6$)alkyl), —C(O)N((C$_1$-C$_6$)alkyl)$_2$, —C(O)NH(aryl(C$_1$-C$_6$)alkyl), —C(O)N(aryl(C$_1$-C$_6$)alkyl)$_2$, —C(O)NH(aryl), —C(O)N(aryl)((C$_1$-C$_6$)alkyl), —C(O)N(aryl)$_2$, —C(O)N(C$_1$-C$_6$)alkyl)(aryl(C$_1$-C$_6$)alkyl), —C(O)N(aryl)(aryl(C$_1$-C$_6$)alkyl), —C(O)NH((C$_1$-C$_6$)haloalkyl), —C(O)N((C$_1$-C$_6$)haloalkyl)$_2$, aryl(C$_1$-C$_6$)alkyl, (C$_3$-C$_7$)cycloalkyl(C$_1$-C$_6$)alkyl-, or —C(O)heterocyclyl.

In certain embodiments, R$^2$ is H, halo, (C$_1$-C$_6$)alkyl, (C$_1$-C$_6$)alkoxy, (C$_1$-C$_6$)hydroxyalkyl, (C$_1$-C$_6$)alkoxy(C$_1$-C$_6$)alkyl, —CO$_2$H, —C(O)O(C$_1$-C$_6$)alkyl, —C(O)NH$_2$, —C(O)NH((C$_1$-C$_6$)alkyl), aryl(C$_1$-C$_6$)alkyl, or (C$_3$-C$_7$)cycloalkyl(C$_1$-C$_6$)alkyl-.

In certain embodiments, R$^2$ is aryl(C$_1$-C$_6$)alkyl or (C$_3$-C$_7$)cycloalkyl(C$_1$-C$_6$)alkyl-, optionally substituted at any position by —OH, halo, —NH$_2$, (C$_1$-C$_6$)alkyl, (C$_1$-C$_6$)haloalkyl, or (C$_1$-C$_6$)alkoxy.

In certain embodiments, R$^2$ is H, (C$_1$-C$_6$)alkyl, or (C$_1$-C$_6$)alkoxy(C$_1$-C$_6$)alkyl.

In certain embodiments, R$^2$ is H, (C$_1$-C$_4$)alkyl, (C$_1$-C$_3$)alkoxy(C$_1$-C$_3$)alkyl, carboxy, (C$_1$-C$_3$)alkoxycarbonyl, carboxymethyl, or (C$_1$-C$_3$)alkoxycarbonylmethyl.

In certain embodiments, R$^2$ is —C(O)heterocyclyl selected from the group consisting of

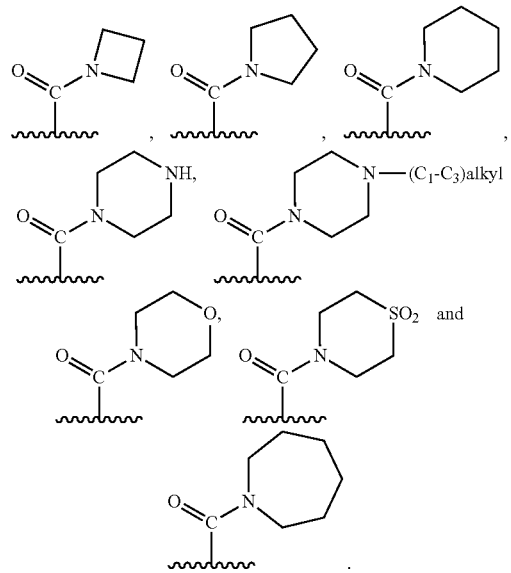

In certain embodiments, R$^2$ is halo(1,4-phenylene)methyl.
In certain embodiments, R$^3$ is H or (C$_1$-C$_3$)alkyl.
In certain embodiments, R$^3$ is H.
In certain embodiments, R$^4$ is H or (C$_1$-C$_3$)alkyl.
In certain embodiments, R$^4$ is H.
In certain embodiments, R$^5$ is H or (C$_1$-C$_3$)alkyl.
In certain embodiments, R$^5$ is H.

In certain embodiments, the compound is represented by formula (I'):

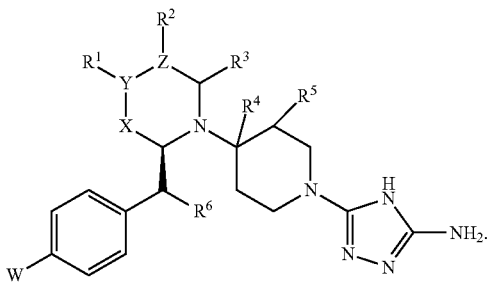

(I')

In certain embodiments of the compound of formula (I):
W is bromo or chloro;
X is a single bond, —CH$_2$—, or —C(O)—;
Y is a single bond, —CH—, —N—, —O—, or —S(O)$_2$—;
  if Y is a single bond, —O—, or —S(O)$_2$—, then R$^1$ is absent,
R$^1$ is H, methyl, isobutyl, methoxy, acetyl, methoxycarbonyl, methanesulfonyl, p-toluenesulfonyl, methoxycarbonylmethyl, or carboxymethyl;
Z is —CH—, —C(O)—, or —C(CH$_3$)—;
  if Z is —C(O)—, then R$^2$ is absent,
R$^2$ is H, methyl, ethyl, isopropyl, isobutyl, —C(O)NH$_2$, —C(O)NHMe, —CH$_2$OH, —CH$_2$OCH$_3$, —CH$_2$OCH$_2$CH$_3$, —C(CH$_3$)$_2$OH, —C(CH$_3$)$_2$OCH$_3$, —CO$_2$H, —CO$_2$CH$_2$CH$_3$, —OCH$_3$, —F, —CH$_2$-(p-chlorophenyl), or —CH$_2$-cyclohexyl;
R$^3$, R$^4$, and R$^5$ are each H; and
R$^6$ is H or OH.

In certain embodiments, the invention provides a compound represented by formula (II),

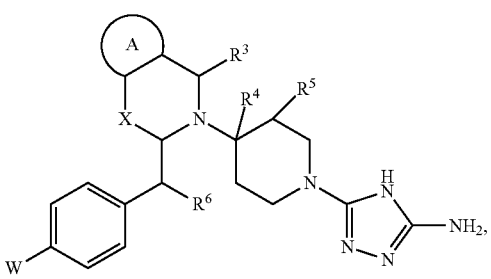

(II)

wherein:
W is halo, (C$_1$-C$_3$)alkyl, (C$_1$-C$_3$)alkoxy-, or (C$_1$-C$_3$)alkylthio-;
X is a single bond, —CH$_2$—, —CH$_2$CH$_2$—, —CH=CH—, —C((C$_1$-C$_3$)alkyl)$_2$-, —C(O)—, —CH$_2$O—, —CH$_2$NH—, or —CH$_2$N((C$_1$-C$_3$)alkyl)-, wherein when X is —CH$_2$O—, —CH$_2$NH—, or —CH$_2$N((C$_1$-C$_3$)alkyl)-, then the O or N atom is covalently bonded to Ring A;
Ring A represents an optionally substituted aryl or heteroaryl ring;
R$^3$ is H, (C$_1$-C$_3$)alkyl, (C$_1$-C$_3$)alkoxy(C$_1$-C$_3$)alkyl, (C$_1$-C$_3$)alkylthio(C$_1$-C$_3$)alkyl, (C$_1$-C$_6$)haloalkyl, —NC, —CN, —C(S)NH$_2$, —NHC(O)NH$_2$, or —C≡CH;

R$^4$ is H, (C$_1$-C$_3$)alkyl, (C$_1$-C$_3$)alkylthio(C$_1$-C$_3$)alkyl, (C$_1$-C$_6$)haloalkyl, (C$_1$-C$_3$)alkoxy(C$_1$-C$_3$)alkyl-, or (C$_1$-C$_4$)hydroxyalkyl;
R$^5$ is H, halo, —NO$_2$, —CN, (C$_1$-C$_6$)alkyl, (C$_1$-C$_6$)haloalkyl, —NH$_2$, —NH((C$_1$-C$_6$)alkyl), —N((C$_1$-C$_6$)alkyl)$_2$, —OH, (C$_1$-C$_6$)alkoxy, hydroxy(C$_1$-C$_6$)alkyl, (C$_1$-C$_6$)alkoxy(C$_1$-C$_6$)alkyl, (C$_1$-C$_6$)haloalkoxy, —SH, (C$_1$-C$_3$)alkylthio(C$_1$-C$_3$)alkyl, —NC, —C(S)NH$_2$, —NHC(O)NH$_2$, or —C≡CH; and
R$^6$ is H, halo, —OH, —NH$_2$, or —SH; or
R$^6$, taken together with the carbon atom bearing it, represents —C(O)—;
wherein:
  any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of —OH, halo, —NH$_2$, —NH((C$_1$-C$_6$)alkyl), —N((C$_1$-C$_6$)alkyl)$_2$, —CN, —NO$_2$, (C$_1$-C$_6$)alkyl, (C$_1$-C$_6$)haloalkyl, (C$_1$-C$_6$)alkoxy, aryl, heteroaryl, aryl(C$_1$-C$_6$)alkyl, heteroaryl(C$_1$-C$_6$)alkyl, (C$_3$-C$_7$)cycloalkyl, heterocyclyl, —C(O)OH, —C(O)O(C$_1$-C$_6$)alkyl, —C(O)NH$_2$, —C(O)NH(C$_1$-C$_6$)alkyl, and —C(O)N((C$_1$-C$_6$)alkyl)$_2$;
or a pharmaceutically acceptable salt, solvate, tautomer, stereoisomer, or polymorph thereof.

In certain embodiments of the compound of formula (II), W is fluoro, chloro, bromo, methyl, or methoxy, preferably chloro.

In certain embodiments of the compound of formula (II), R$^6$ is H.

In certain embodiments, X is —CH$_2$O—, —CH$_2$NH—, or —CH$_2$N((C$_1$-C$_3$)alkyl)-, preferably —CH$_2$O— or —CH$_2$N(CH$_3$)—.

In certain embodiments, R$^3$ is H.
In certain embodiments, R$^4$ is H.
In certain embodiments, R$^5$ is H.

In certain embodiments, Ring A represents a heteroaryl ring, such as a pyridyl ring.

In certain embodiments, Ring A represents an optionally substituted phenyl ring. For example, Ring A may represent a phenyl ring substituted by one or more occurrences of halo, such as chloro.

In certain embodiments, the invention relates to a compound of any one of the following structural formulae:

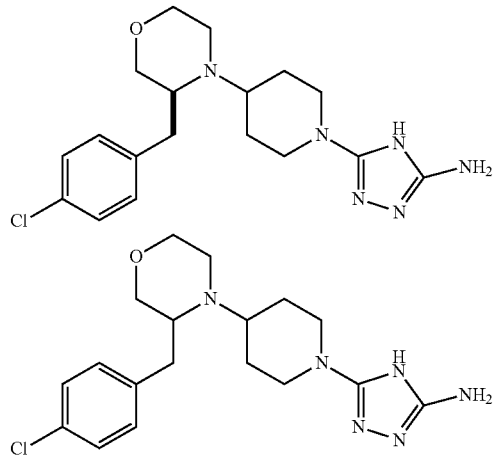

25
-continued
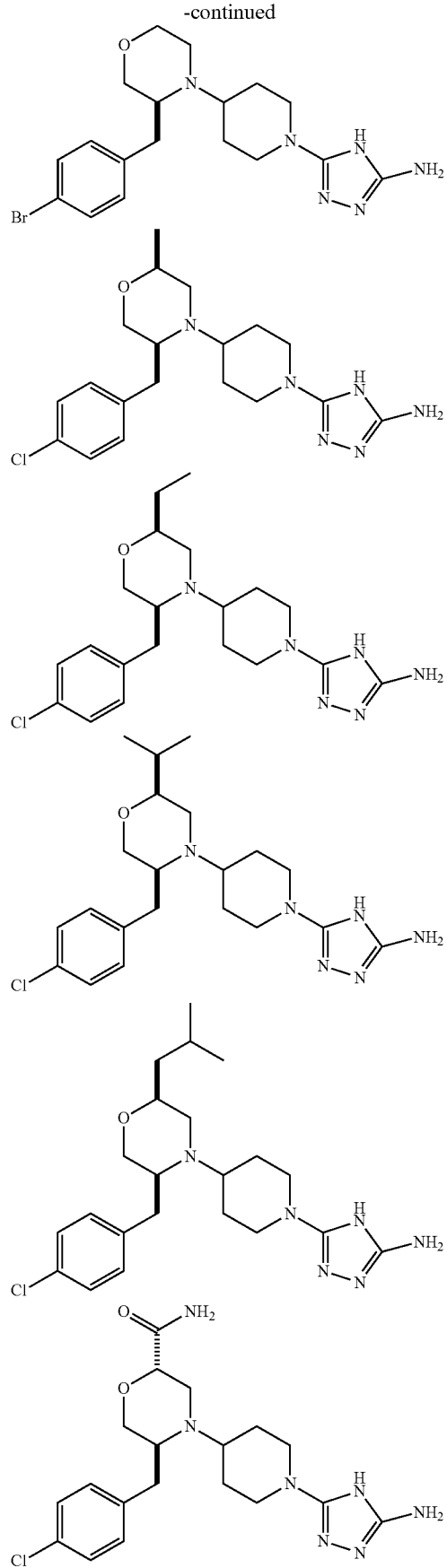
26
-continued
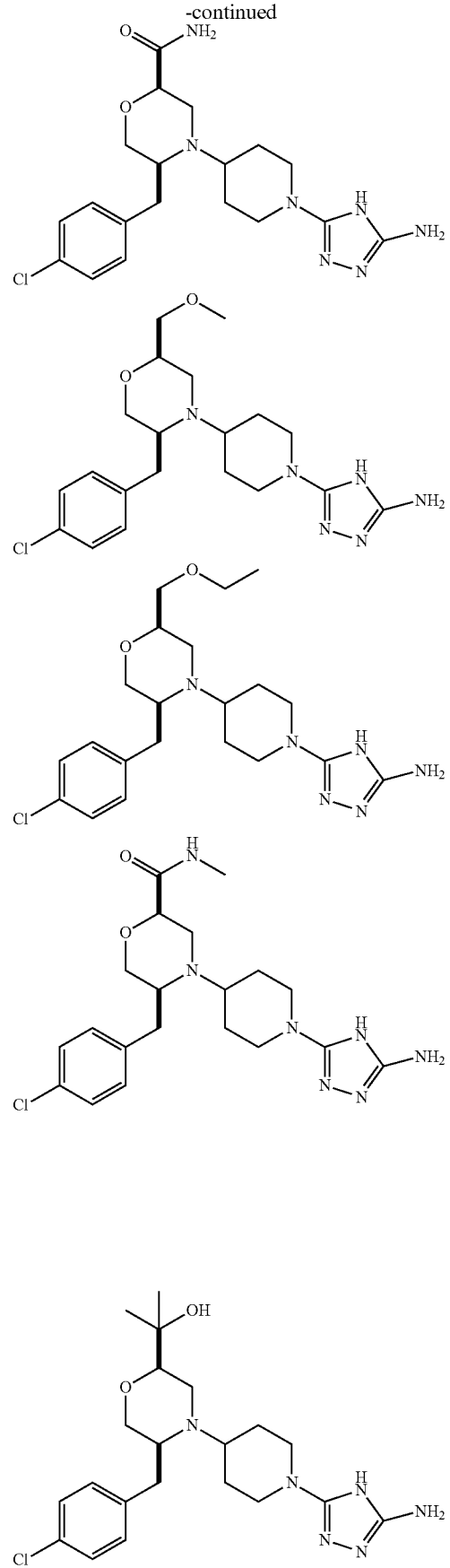

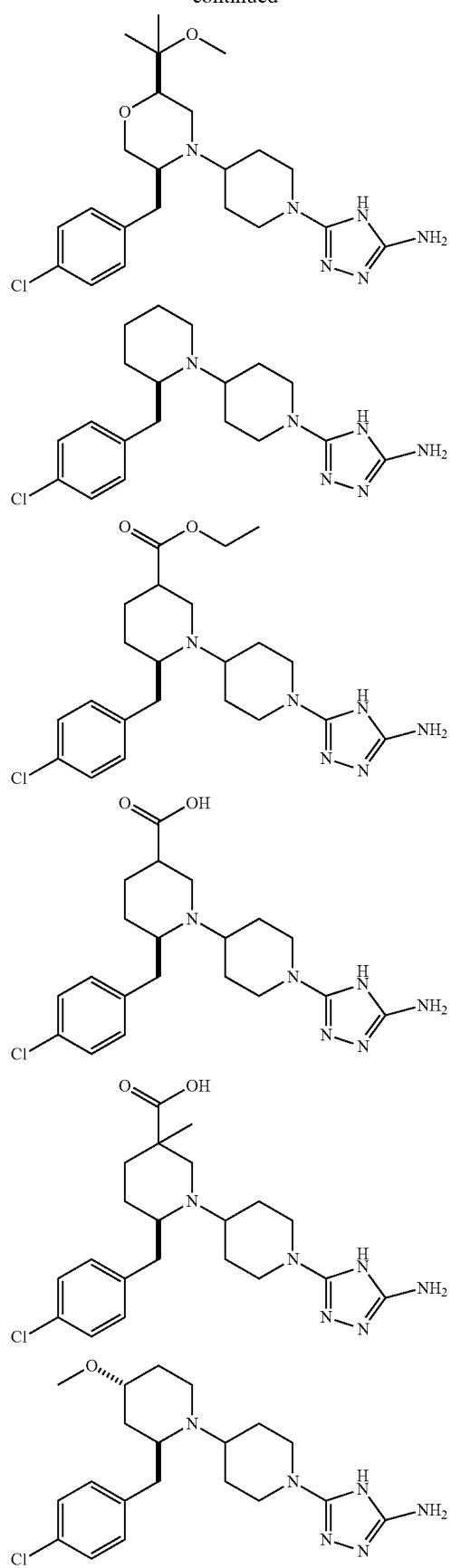
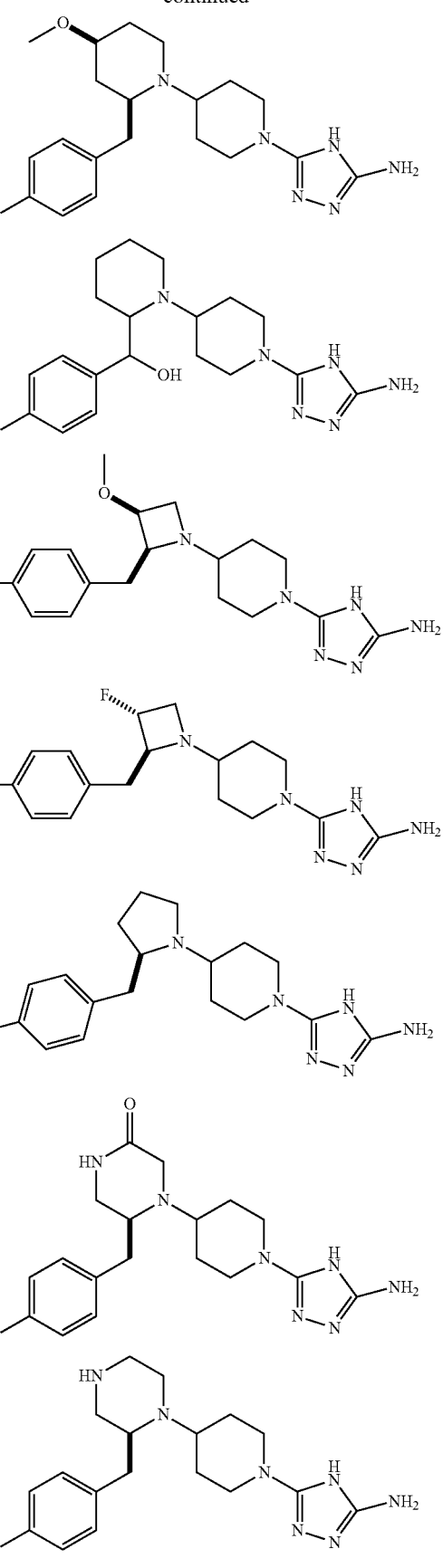

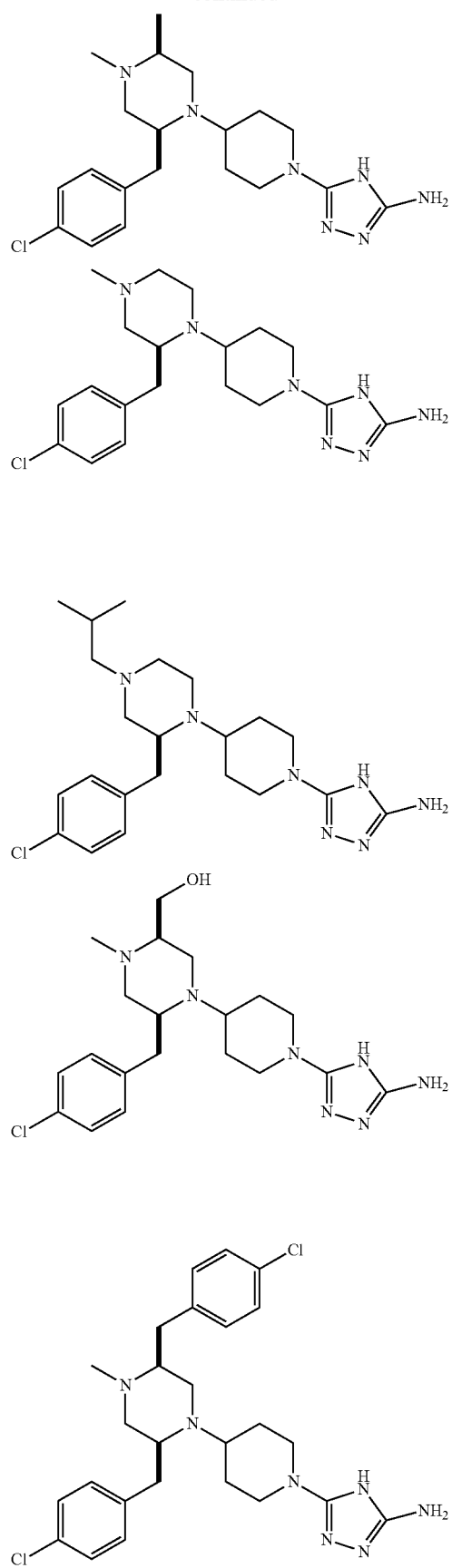
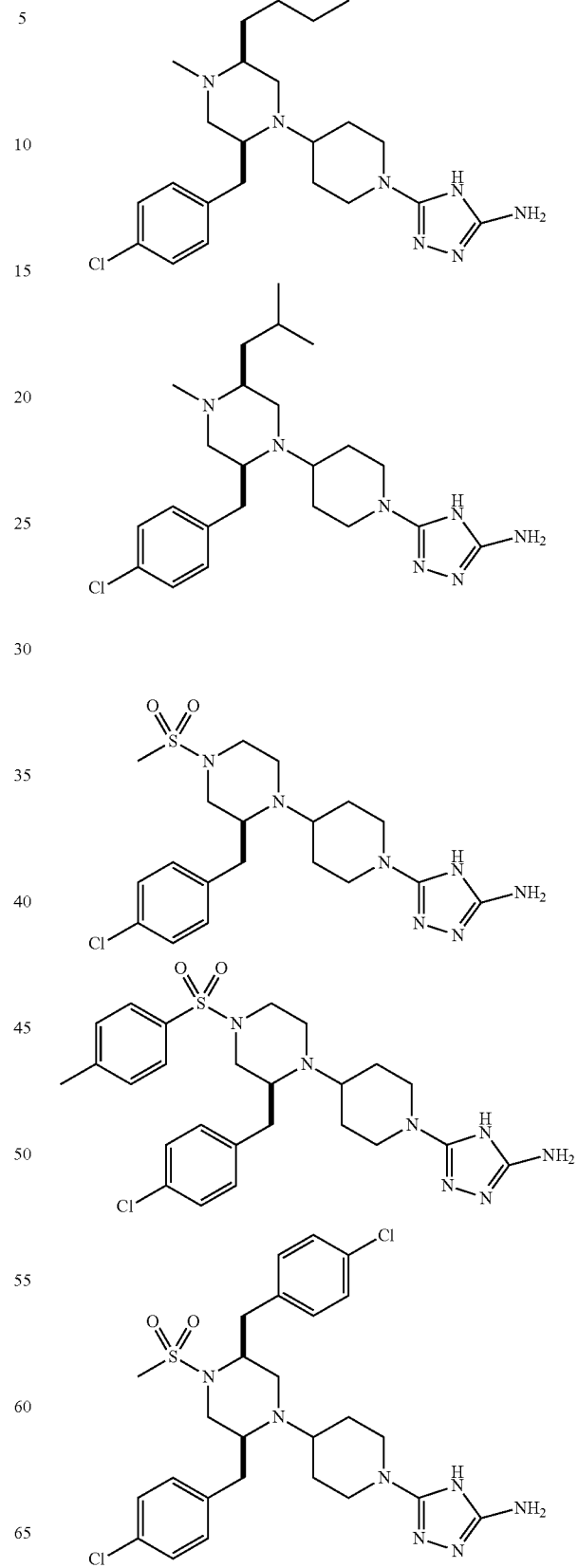

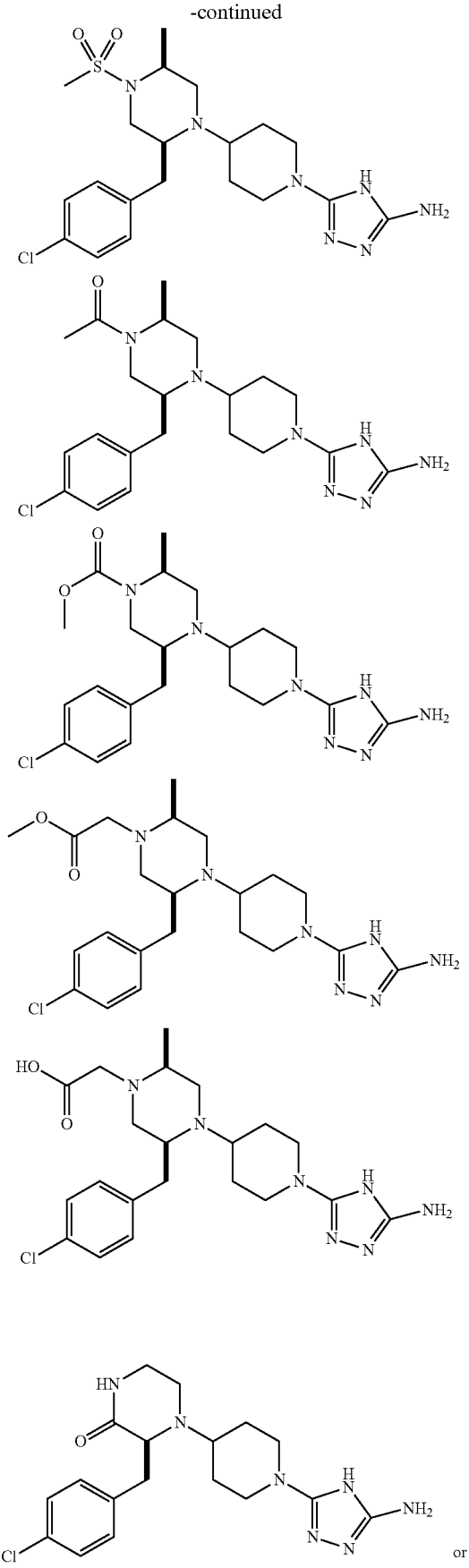
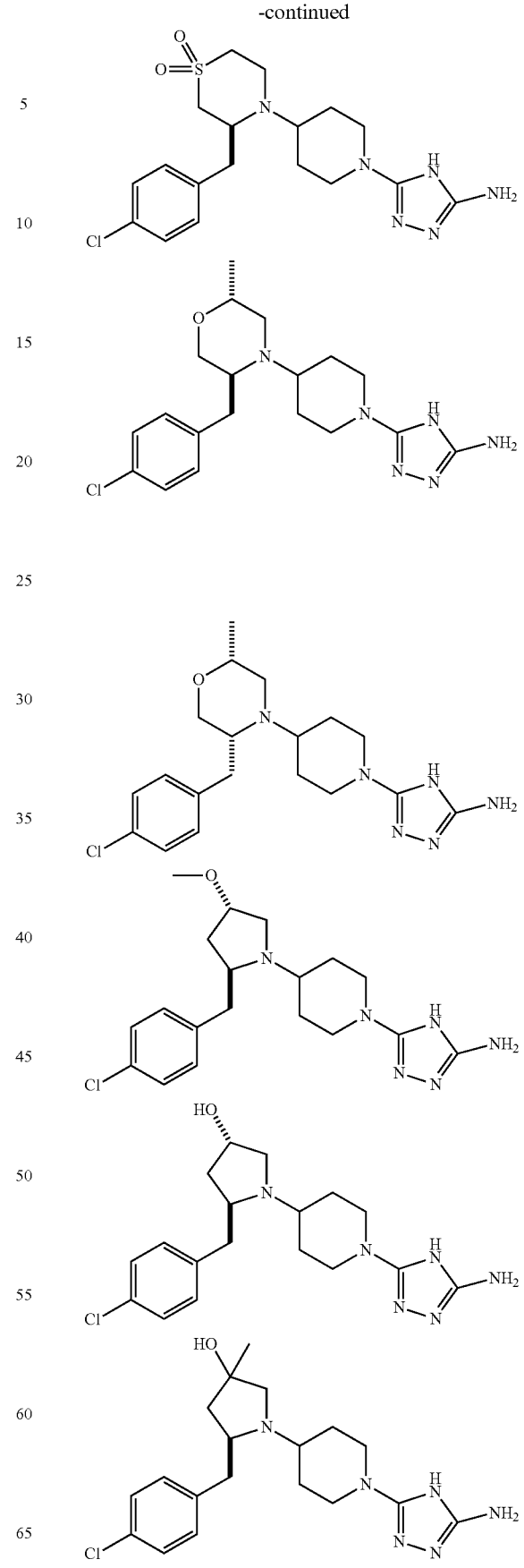

33
-continued
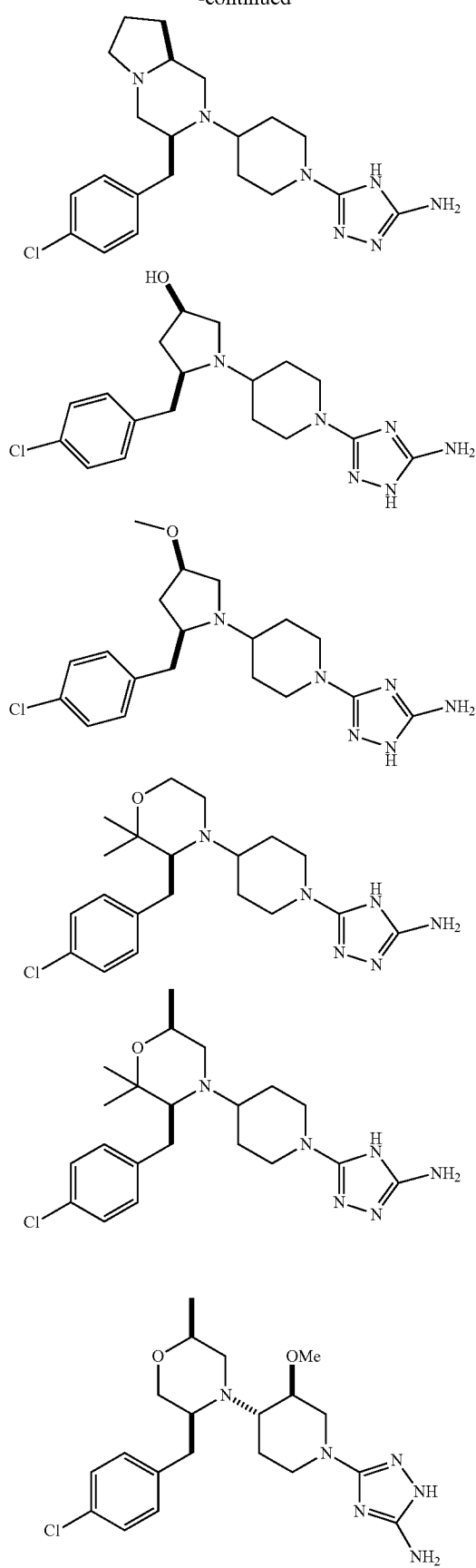
34
-continued
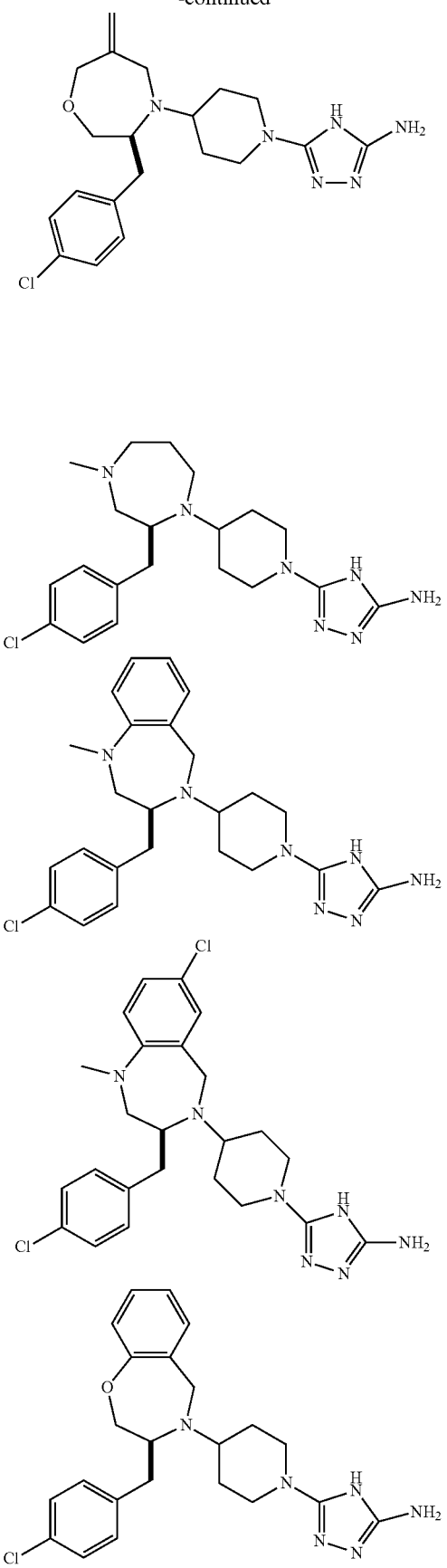

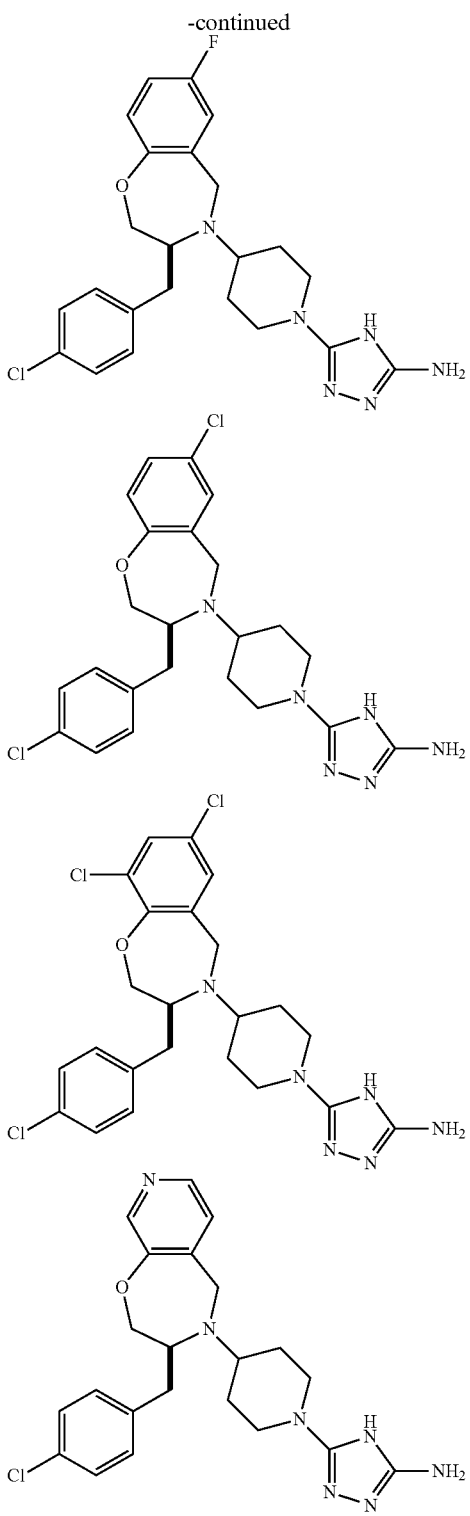

The salts, hydrates, and solvates of the compounds of the invention are preferably pharmaceutically acceptable salts, hydrates, and solvates. The solvates may contain a stoichiometric or non-stoichiometric amount of one or more solvents, such as water, ethanol, or ethyl acetate, in addition to the molecule of the compound of the invention. The solvates formed with water are called hydrates.

The compounds described herein are useful in treating inflammatory diseases, such as esophageal eosinophilic inflammation, keratoconjunctivitis, seasonal allergic conjunctivitis, dry eye syndrome, or chronic rhinosinusitis with or without nasal polyps. The compounds can be used in treating diseases caused by infectious agents, such as fungi, worms and parasites. The compounds can be used in treating chronic obstructive pulmonary disease (COPD) or autoimmune diseases including but not restricted to inflammatory bowel disease or rheumatoid arthritis.

Pharmaceutical Compositions of the Invention

Another aspect of the invention provides a pharmaceutical composition comprising a therapeutically effective amount of a compound of the invention (e.g., a compound of formula (I)), and a pharmaceutically acceptable carrier.

The exact nature of the carrier, or, for example excipient or diluent, will depend upon the desired use for the composition, and may be suitable or acceptable for veterinary use and/or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, rituxin, PD4 inhibitors, p38 inhibitors, PDE4 inhibitors, and antihistamines.

Thus, another aspect of the invention provides a pharmaceutical composition comprising a therapeutically effective amount of a compound of the invention and a second therapeutic agent selected from the group consisting of steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, acetylosalicylic acid, COX inhibitors, methotrexate, anti-TNF drugs, rituxin and other B-cell targeting agents, TNF-targeting agents, PD4 inhibitors, p38 inhibitors, PDE4 inhibitors, and antihistamines.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 20 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, intrathecal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl*

*Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) ($\alpha$1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; the Spinhaler powder inhaler, manufactured by Fisons Corp., Bedford, Mass.; and the Respimat Soft Mist Inhaler, manufactured by Boehringer Ingelheim, Germany. Other hand-driven or human-powered inhaler devices are also applicable.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet, ultrasonic, or soft mist type, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas, e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Methods and Uses

As shown herein, the compounds of the invention are useful for inhibiting the enzymatic and biological activity of Acidic Mammalian Chitinase ("AMCase") and chitotriosidase 1 ("CHIT1").

Accordingly, the invention provides methods for inhibiting acidic mammalian chitinase in a cell or a tissue, comprising contacting a cell or a tissue with at least one compound according to the invention, or with a pharmaceutical composition according to the invention.

Similarly, the invention provides methods for inhibiting chitotriosidase 1 in a cell or a tissue, comprising contacting a cell or a tissue with at least one compound according to the invention, or with a pharmaceutical composition according to the invention.

In other aspects, the invention provides methods for the treatment or prevention of a disease, disorder, or condition associated with aberrant expression or activity of acidic mammalian chitinase, comprising administering to a subject in need thereof a therapeutically effective amount of at least one compound according to the invention, or with a pharmaceutical composition according to the invention.

Similarly, the invention provides methods for the treatment or prevention of a disease, disorder, or condition associated with aberrant expression or activity of chitotriosidase 1, comprising administering to a subject in need thereof a therapeutically effective amount of at least one compound according to the invention, or with a pharmaceutical composition according to the invention.

In certain embodiments, the diseases, disorders, or conditions associated with aberrant expression or activity of acidic mammalian chitinase include allergic diseases, acute and chronic inflammatory diseases, autoimmune diseases, dental diseases, neurologic diseases, metabolic diseases, liver diseases, polycystic ovary syndrome, endometriosis, and cancer.

In further embodiments, the diseases, disorders, or conditions associated with aberrant expression or activity of chitotriosidase 1 include asthma or fibrotic disorders such as idiopathic pulmonary fibrosis (IPF). In other embodiments, such diseases and disorders include fibrotic interstitial lung diseases such as IPF or chronic obstructive pulmonary disease (COPD).

Moreover, the invention provides methods of treating diseases caused by infectious agents, such as fungi, worms, and parasites, the method comprising administering to a subject in need of such treatment an effective amount of one or more compounds of the invention.

In one embodiment, the invention provides methods of treating allergies, comprising administering to a subject in need of such treatment an effective amount of one or more compounds of the invention. In certain embodiments, such allergies are caused by any of a variety of antigens including biological sources such as dust mites, mold, cockroaches and other insects, dander from pets or other mammals, pollens, spores, mold, other fungal sources, and other plant antigens, or non-biological sources such as chemicals (e.g., isocyanates).

In other embodiments, the invention provides a method of screening for therapeutic agents useful for treating asthma in a mammal, comprising: (a) contacting an acidic mammalian chitinase protein with a compound (e.g., a compound of the invention) and a substrate of said chitinase; and (b) determining if the compound inhibits the activity of the chitinase; wherein if the compound inhibits the activity of the chitinase, then the compound is a therapeutic agent useful for treating asthma.

In other aspects, the invention provides methods for monitoring the efficacy of a treatment for asthma, comprising (a) administering a compound of the invention to a mammal, and (b) monitoring the expression of acidic mammalian chitinase in the mammal after administration of the compound, wherein a decrease in the expression of acidic mammalian chitinase indicates that the compound is useful in treating asthma, allergic diseases such as hay fever, allergic rhinitis, atopic dermatitis or other Th-2 mediated or associated diseases.

In other embodiments, the invention provides a method of screening for therapeutic agents useful for treating asthma in a mammal, comprising: (a) contacting a chitotriosidase 1 protein with a compound (e.g., a compound of the invention) and a substrate of said protein; and (b) determining if the compound inhibits the activity of the chitotriosidase 1; wherein if the compound inhibits the activity of the chitotriosidase 1, then the compound is a therapeutic agent useful for treating asthma.

In other aspects, the invention provides methods for monitoring the efficacy of a treatment for asthma and other allergic diseases, comprising (a) administering a compound of the invention to a mammal, and (b) monitoring the expression of inflammatory mediators such as IL-13, IL-5, IL-4, eotaxin, or IgE or inflammatory cells such as eosinophils, neutrophils, or lymphocytes in broncho-alveolar washings, sputum, or tissues obtained from the mammal after administration of the compound; wherein a decrease in expression indicates that the compound is useful in treating asthma or allergic diseases such as hay fever, allergic rhinitis, atopic dermatitis or other Th-2 mediated or associated diseases.

In another aspect, the invention provides methods for assessing the efficacy of an agent for treating asthma in a subject, comprising the steps of:

a) detecting in a subject sample collected at a first point in time the expression level of acidic mammalian chitinase protein;

b) repeating step a) at one or more subsequent points in time after administration of the agent; and c) comparing expression level of acidic mammalian chitinase protein detected in step a) with the expression level(s) detected in step b), wherein a higher expression level of acidic mammalian chitinase protein at the first point in time relative to at least one subsequent point in time indicates that the agent is efficacious in treating asthma.

In certain embodiments, an agent identified by such a method is efficacious in treating asthma, hay fever, allergic rhinitis, atopic dermatitis, allergic reactions, or a disorder associated with Th-2.

Alternatively, the efficacy of an agent for treating asthma or an allergic reaction can be assessed via measuring the expression level of an inflammatory mediator such as IL-13, IL-5, IL-4, eotaxin, IgE, or measuring the amount of inflammatory cells such as eosinophils, neutrophils, or lymphocytes in brocho-alveolar washings, sputum, or tissues obtained from a mammal. In certain such embodiments, the expression level can be measured prior to and after administration of an agent. When the expression level of the inflammatory mediator or the level of inflammatory cells decreases after administration of an agent, such an agent is efficacious in treating asthma, hay fever, allergic rhinitis, atopic dermatitis, allergic reactions, or a disorder associated with Th-2.

Another aspect of the invention provides methods of identifying an agent for treating asthma, comprising:

a) contacting a sample comprising acidic mammalian chitinase protein with the agent; and b) determining the ability of the agent to inhibit activity of acidic mammalian chitinase protein, wherein decreased activity of acidic mammalian chitinase protein identifies an agent for treating asthma.

In certain embodiments, the activity of acidic mammalian chitinase protein is assessed by fluorescence assay using a reagent that is hydrolyzed by acidic mammalian chitinase protein. In certain embodiments, the reagent is 4-methylumbelliferyl B-D-N,N'-diacetylchitobioside hydrate.

Therapeutic Applications

The inventive compounds are useful for inhibiting the enzymatic and biological activity of Acidic Mammalian Chitinase (AMCase) and chitotriosidase 1 (CHIT1). AMCase has been shown to be induced in animal models of asthma and in humans that have died from asthma, while inhibition of AMCase with anti-sera to AMCase or by allosamidin (Zhu et al. Science 304:1678-1682, 2004) or desmethylallosamidin (Matsumoto et al., Biochemical and Biophysical Research Communications 390:103-108, 2009) reduces inflammation in mice. Furthermore, these studies clearly established a link between IL-13 and the induction of AMCase, and that allergic inflammation was dependent on AMCase enzymatic activity. Overexpression of CHIT1 has been linked to fibrotic interstitial lung disease, including idiopathic pulmonary fibrosis and chronic obstructive pulmonary disease (COPD).

More specifically, the invention provides methods for inhibiting AMCase in a cell, comprising contacting a cell with at least one compound according to the present invention, or a composition thereof as described herein.

In some embodiments, the invention provides methods for treatment or prevention of a disease or condition associated with expression or activity of AMCase in a subject. For instance, the disease, disorder, or condition is selected from the group consisting of allergic diseases, acute and chronic inflammatory diseases, autoimmune diseases, dental diseases, neurologic diseases, metabolic diseases, liver diseases, polycystic ovary syndrome, endometriosis, and cancer.

According to certain embodiments, the compounds of the invention are useful for treating allergic diseases, such as asthma, allergic rhinitis, seasonal allergic rhinitis, chronic rhinosinusitis with or without nasal polyps, conjunctivitis, keratoconjunctivitis, seasonal allergic conjunctivitis, dry eye syndrome, eosinophilic esophagitis, celiac disease, food allergies, irritable bowel syndrome, irritable bowel disease, atopic eczema, atopic dermatitis, allergic contact dermatitis, eosinophilic otitis media, eosinophilic pneumonia, and IgG4 mediated disease.

In certain embodiments, the reaction caused by an allergen is allergic rhinitis or atopic dermatitis.

In certain embodiments, the reaction caused by an allergen is characterized by the occurrence of one or more symptoms, which can include red eyes, itchiness, runny nose, eczema, impaired hearing, hives, an asthma attack, increased mucus production in the lungs, coughing, wheezing, and shortness of breath.

Exemplary acute and chronic inflammatory disorders that can be treated using the compounds of the invention include fungal diseases, parasitic infection, celiac disease, microscopic colitis, chronic obstructive pulmonary disease (COPD), idiopathic pulmonary fibrosis, interstitial lung diseases, Cystic Fibrosis (CF), Hermansky-Pudlak and Alzheimer's disease (AD).

In certain embodiments, the disease or condition treated by the methods of the invention is an autoimmune disorder selected from the group consisting of inflammatory bowel disease, ulcerative colitis (UC), Crohn's disease (CD), rheumatoid arthritis (RA), osteoarthritis, psoriasis, scleroderma, multiple sclerosis (MS), Sjögren's syndrome, atherosclerosis, and sarcoidosis.

Compounds in accordance with the present invention are also useful for treating dental diseases such as periodontitis and metabolic diseases such as insulin-dependent diabetes mellitus (IDDM) and non-insulin-dependent diabetes mellitus (NIDDM).

In certain embodiments, the invention provides methods of treating a liver disease selected from group consisting of non-alcoholic fatty liver disease, non-alcoholic steatohepatitis, hepatitis-C virus-induced fibrosis and cirrhosis, and alcoholic fibrosis.

In some embodiments, the methods of the invention are used in the treatment of cancer, wherein the cancer is selected from the group consisting of glioblastoma, breast cancer, colon cancer, primary and metastatic lung cancer, mesothelioma, osteosarcoma, malignant melanoma, ovarian cancer, cervical cancer, prostate cancer, liver cancer, gastric cancer, metastatic renal cancer, leukemia, and lymphoma.

In some embodiments, the subject receiving treatment is a mammal. For instance, the methods and uses described herein are suitable for medical use in humans. Alternatively, the methods and uses are also suitable in a veterinary context, wherein the invention may be administered to warm-blooded animals, birds and reptiles. Warm-blooded animals include, for example, all non-human primates (e.g. chimpanzee and ape), ruminants (e.g. cow, sheep and goat), porcines (e.g. pig), equines (e.g. horse, mule and donkey), camelines (e.g camel and dromedary), canines (e.g. dog), felines (e.g. cat), leporine (e.g. rabbit), murines (e.g. mouse and rat) cavines (e.g. guinea pig), gerbiline (e.g gerbil), cricetine (e.g hamster), mustelines (e.g ferret and weasel) and chinchilines (e.g. chinchilla). Birds include animals of the avian class, for example, all phasianines (e.g. chicken and quail), anserines (e.g. goose), anatines (e.g. ducks), meleagridines (e.g turkey), daruduelines (e.g. canary), psittacines (e.g. parrot, macaw, parakeet and lovebird), cacatuines (e.g. cockatoo) and columbines (e.g. pigeon and turtle dove).

In certain embodiments, the invention is preferably administered to domesticated companion animals and to productive and breeding animals.

Asthma

As described above, AMCase protein has been shown to be induced in the lungs of animal models of asthma and in humans that have died from asthma (Zhu et al. Science 304:1678-1682, 2004, Matsumoto et al., Biochemical and Biophysical Research Communications 390:103-108, 2009, Sutherland et al. Chemistry and Biology 18:569-579, 2011). Further, these investigators also demonstrated that inhibition of AMCase with anti-sera to AMCase, or by inhibitors of AMCase enzymatic activity, reduces inflammation and airway hyper-responsiveness in mice. These studies also clearly established a link between the well described Th-2 interleukin IL-13, and the induction of AMCase protein expression. These studies also demonstrated that IL-13 mediated allergic inflammation can be reduced or eliminated by inhibiting the enzymatic activity of AMCase establishing proof that allergic inflammation is partially or wholly dependent on AMCase enzymatic activity. In one embodiment of the invention, compounds that inhibit enzymatic activity of AMCase or biologic activity of AMCase can be administered to subjects with asthma and or asthmatic symptoms to inhibit related inflammation and alleviate disease symptoms.

Rhinitis

In another embodiment, compounds of the invention can be administered to subjects with allergic rhinits, seasonal allergic rhinitis, or chronic rhinosinusitis to treat the disease since these syndromes are linked to IL-13 (Akdis et al., J. Allergy and Clinical Immunology 131:1479-1490, 2013) and AMCase is known to be produced by epithelial cells from chronic rhinosinusitis with nasal polyps (Ramanathan et al., Am. J. Rhinol. 20: 330-335, 2006, Lalaker et al., Am. J. Rhinol. Allergy 23(1):8-14, 2009, Gu et al. J. Otolaryngol. Head Neck Surg. 40(1):64-69, 2011).

Occular Diseases

AMCase has been clearly demonstrated as an inflammatory mediator in conjunctivitis, keratoconjunctivitis, seasonal allergic conjunctivitis, and dry eye syndrome (Bucolo et al., Frontiers in Pharmacology 2(43):1-4, 2011; Musumeci et al., Cornea 28(6):667-672, 2009.) In addition, inhibition of AMCase in an animal model of inflammatory eye diseases has been shown to alleviate inflammation (Bucolo et al. Pharmacol Res. 3:247-252, 2008). Chitinase proteins have also been shown to be increased in eye tissue of patients with macular degeneration (Rakic et al., Invest. Opthalmol. Vis. Sci. 44(4)1740-1746, 2003). Therefore an aspect of this invention is to treat inflammatory and other eye diseases using a preparation of one or more of the compounds described herein.

Other Allergic Diseases

Eosinophilic Otitis Media is known to involve the AMCase inducing cytokine IL-13 (Ohta et al., Allergology International 63:171-180, 2014) and that AMCase mediates aspects of IL-13 inflammation and pathology. Atopic eczema is another allergic disease where clinical severity has been correlated with levels of IL-13 in lesional skin (Szeqedi et al., J. Eur. Acad. Dermatol. Venereol., epub 2015).

Allergic contact dermatitis also involves IL-13 which is also proposed as a complementary test for the disease (Martins and Reis, J. Eur. Acad. Dermatol. Venereol., 27(3): 390-393, 2013).

Given that these conditions are all associated with IL-13, a potent stimulant for AMCase upregulation and that inhibition of AMCase has been shown to reduce IL-13 mediated inflammation, treatment of subjects with one or more compounds described herein is expected to lead to improvement in these diseases.

Esophageal Eosinophilic Inflammation (EoE)

EoE is a condition mediated by Th-2 inflammation including the presence of eosinophils, CD8+ lymphocytes, FcepsilonRI, mast cells, collagen deposition, and eotaxin-3 (CCL26) mRNA. EoE is associated with other allergic disease where the antigens are often food but also pollen. Existing treatments have low efficacy (attempt to eliminate antigen exposure) and side effects (topical steroids followed by oral steroids then mechanical dilatation). In a mouse model of EoE, AMCase levels are increased in esophageal tissue. Importantly, the AMCase inhibitor allosamidin inhibits eosinophilic inflammation including number of eosinophils, esophageal remodeling, and eotaxin-1 protein (Cho et al., Int. Immunopharmacol. 18(1):35-42, 2014). Treatment of subjects with EoE by one or more compounds described herein is expected to reduce or cure disease symptoms.

Celiac Disease, Food Allergy, Irritable Bowel Syndrome, Inflammatory Bowel Disease A form of Celiac disease is often associated with EoE and also has hallmarks of allergic disease including elevated tissue eosinophils (Mehta and Furuta, Immunol. Allergy Clin. North Am. 35(3):413-437, 2015). Celiac disease has also been defined as an autoimmune disorder distinct from wheat allergy and has some overlap with irritable bowel syndrome (Elli et al., World J. Gastroenterology 21(27): 8221-8226, 2015). Mehta and Furuta also include inflammatory bowel diseases as involving eosinophils in the disease pathogenesis. Therefore, because AMCase is constitutively expressed in the gastrointestinal tract (Boot et al., J. Histochem. Cytochem. 53:1283-1292, 2005) and there is at least partial involvement of allergic inflammation in these diseases, inhibition of AMCase in subjects with these or similar diseases can be treated by the AMCase inhibitors described.

Autoimmune Diseases

For autoimmune diseases including Inflammatory Bowel Disease (IBD), Rheumatoid Arthritis (RA), Multiple Sclerosis (MS) and Insulin-Dependent Diabetes Mellitus (IDDM) or type I diabetes there is evidence of up regulation of AMCase and other proteins in the 18 glycosyl hydrolase family. There is also evidence that these proteins can activate autoimmunity (Sekine et al., Ann. Rheum. Dis., 60(1) 49-54, 2001, Tsuruha et al., J. Rheumatol., 29(7):1459-1466, 2002, Du et al., Rheumatol. Int., 26(1):35-41, 2005)

Inflammatory Bowel Disease (Ulcerative Colitis and Crohn's Disease)

Chitinases have been shown to play a role in the pathogenesis of inflammatory bowel disease (IBD) and models of IBD. There is a growing body of evidence that IBD symptoms can be modified by altering the gut biome (Strober et al., J. Clin. Invest. 117:514-521, 2007, Zatorski and Fichna, 1:15-16, 2014). It has also been established that pathogenic strains of bacteria bind to colonic epithelial cells via bacterial chitin binding protein and chitinase-like molecules (Kawanda et al., Lab. Invest. 88:883-895, 2008) particularly in Crohn's disease (Chassing et al., Gastroenterology 140: 1720-1728, 2011). Pathogenic strains of bacteria in CD invade the intestinal mucosa via binding to epithelial cells and studies in a mouse model of IBD showed enhanced colitis when the mice were infected with bacteria with enhanced binding capability to colonic epithelial cells via chitinase proteins (Low et al. Gastroenterology 145(3):602-612, 2013). Treatment of mammals with intestinal inflammation (UC, CD, irritable bowel disease, microscopic colitis, and or other intestinal diseases) with a preparation of one or more compounds of this invention can be used to treat disease and disease symptoms.

Rheumatoid Arthritis (RA) and Osteoarthritis (OA)

Chitinase-like proteins are over expressed in articular chondrocytes and synovial fibroblasts and serum from RA and OA patients (Hakala et al., J. Biol. Chem., 268(34): 25803-25810, 1993, Hu et al., J. Biol. Chem., 271(32): 19415-19420, 1996, Volck et al., Scand. J. Rheumatol. 28(3):171-179, 1999, Connor et al., Osteoarthritis Cartilage 8(2):87-95, 2000). Serum concentrations of chitinase-like proteins correlates with joint inflammation and destruction in RA and OA (Kzyshkowska et al., Biomarker Insights 2:128-146, 2007). IL-6, a prominent cytokine and target for treatment of RA is known to up-regulate expression of at least one of the chitinase-like proteins (Johansen et al. Can. Epidemiol. Biomarkers Prev. 15(2)194-202, 2006). Furthermore the chitinase proteins have been shown to induce Th1 immune response in RA leukocytes and stimulates growth of synovial cells (Kzyshkowska et al., Biomarker Insights 2:128-146, 2007) and thus can augment and perpetuate chronic inflammation in RA Multiple Sclerosis (MS)

Chitinase proteins are elevated in central spinal fluid in patients with relapsing remitting MS and neuromyelitis optica. These chitinases increased inflammatory mediator release and stimulated migration of inflammatory cells across an in vitro blood brain barrier (Correale and Fiol, Mult. Scler. 17(5):521-31, 2011). Compounds described herein can be used to treat multiple sclerosis and related neurologic diseases.

Diabetes Mellitus

In patients with proliferative diabetic retinopathy, there is increased IL-13 in the vitreous compared to the healthy individuals and especially elevated levels in areas that have developed fibrovascular membranes and contributes to retinopathy (Yoshida et al., Br. J. Opthalmol., 99(5):629-634, 2014). Application of compounds of this invention inhibits AMCase, a downstream mediator of IL-13 effects and can be expected to interfere with diabetic retinopathy. In type II diabetes, also known as non-insulin-dependent diabetes mellitus (NIDDM), plasma concentration of chitinase-like molecules is associated with insulin resistance (Rathcke et al., Inflamm. Res., 55(2):53-59, 2006) and children at risk for diabetes demonstrate increased levels of chitinase proteins vs. normal children (Kyrgios et al., Metabolism 61(4)562-568, 2012). It can reasonably be expected that treatment of subjects with diabetes or pre-diabetes with one or more compounds of this invention can treat or prevent diabetes.

Sjögren's Syndrome (SS)

Chitinase expression is increased in SS patients and levels correlate with disease severity (Greenwell-Wild et al., Arthritis Rheum. 63(10):3103-3115, 2011) indicating that subjects with this syndrome can be treated by compounds herein.

Atherosclerosis

Chitinases and associated family proteins are indicators of activated macrophages in atherosclerotic plaque and enzyme level is increased up to 55 fold in atherosclerotic plaque (Boot et al., J. Biol. Chem., 273(40):25680-25685, 1998, Artieda et al., Arterioscler. Thromb. Vasc. Biol., 23(9):1645-1652, 2003) and causes vascular smooth muscle cell migration. With chitinases involved in the pathogenesis of atherosclerosis, inhibitors of chitinases described in this invention can reasonably be predicted to treat, prevent or resolve atherosclerosis in affected subjects.

Sarcoidosis

Chitinases are also elevated in the serum of patients with sarcoidosis (Grosso et al., Scand. J. Clin. Lab. Invest., 64(1):57-62, 2004) and are produced in sarcoid granuloma in the lung (Johansen et al., Resp. Med. 99(4):396-402, 2005). Chitinase inhibitors described herein can be used to treat subjects with sarcoidosis.

Liver Diseases

Increased chitinase is synthesized in Kupffer cells of non-alcoholic fatty liver steatohepatitis (NASH) patients and stimulates activation of hepatic stellate cells suggesting a role of chitinase proteins in progression of liver fibrosis (Malaguarnera et al., Gut 55(9):1313-1320, 2006, Malaguarnera et al., Am. J. Gastroenterol., 10(9):2060-2069, 2006). Chitinase family proteins are also associated with hepatitis C virus (HCV) induced fibrosis and cirrhosis and in alcoholic and non-alcoholic liver fibrosis (Shakel et al., Hepatology 38(3):577-588, 2003, Tran et al., Eur. J. Gastroenterol. Hepatol. 12(9):989-993, 2000). Also alcoholic steatohepatitis; non-alcoholic steatohepatitis and non-alcoholic fatty-acid liver disease, which occur on a background of metabolic and cardiovascular disease; virally induced hepatic fibrosis; and primary biliary cirrhosis, which has an autoimmune basis are associated with chronic inflammation and fibrosis, and as a result, the compounds described in this invention can be used to treat various liver diseases.

Kidney Diseases

Inflammation and fibrosis are accompanying many kidney diseases such as nephoropathy, including diabetic nephropathy, focal segmental glomerulosclerosis, tubulointerstitial fibrosis, postransplant fibrosis, as well as retroperitoneal fibrosis/Ormond's disease, Compounds described herein may be used to treat subjects with these disorders to alleviate symptoms and reduce exacerbations and disease progression.

Skin Diseases

Increased fibrosis is associated with dermal injury and chronic inflammation accompanying formation of excessive or hypertrophic scars, keloids, autoimmune diseases such as scleroderma, systemic lupus erythematosus (SLE). The compounds described in this invention are reasonably expected to be effective in preventing or treatment of these diseases.

Chronic Obstructive Pulmonary Disease (COPD)

Proteins of the chitinase family are increased by exposure to cigarette smoke and are present at very high levels in patients with COPD (Nikota et al., Resp. Res., 12:39-50, 2011; Letuve et al., Am. J. Pathol., 176:638-649, 2010) and chitinases stimulate release of other pro-inflammatory mediators that mediate lung tissue destruction. Genetic association has also been made between lung function and chitinase expression (Aminuddin et al., Hum. Genet. 131 (7):1105-1114, 2012). Compounds described herein may be used to treat subjects with COPD to alleviate symptoms and reduce exacerbations and disease progression.

Interstitial Lung Diseases, Scleroderma and Hermansky-Pudlak Syndrome

Idiopathic pulmonary fibrosis (IPF) and other interstitial lung diseases are associated with increased chitinases in lung tissue and plasma, and augments TGFbeta pro-fibrotic activity (Cho et al., Allergy Asthma Immunol. Res. 7(1):14-21, 2015; Lee et al. J Immunol. 189(5):2635-44, 2012) and chitinase proteins contribute to injury (Zhou et al. J Clin Invest. 125(8):3178-3192, 2015; Zhou et al., Sci. Transl. Med., 6(240): 240ra76, 2014) such that inhibitors of chitinases can reasonably be expected to treat subjects with lung fibrotic changes.

Cystic Fibrosis (CF)

Chitinase-like proteins are elevated in CF and correlate with disease severity (Hector et al., Plos One, 6(9):e24399-24405, 2011). Therefore treatment of CF patients with one or more compounds of this invention can be expected to improve symptoms and disease severity or progression.

Alzheimer's Disease (AD)

In Alzheimer's disease, chitinase family mRNA and proteins are highly elevated in brain of patients and these proteins are also associated with pathogenic alternatively activated microglial cells in mouse AD models (Colton et al. J. Neuroimflamm. 3:27-38 2006). Chitinase expression was also elevated in ischemic cerebrovascular dementia (CvD) (DiRosa et al., Eur. J. Neurosci., 23(10)2648-2656, 2006) Treatment of subjects with AD or CvD by one or more compounds described herein is expected to reduce disease pathology and progression.

Polycystic Ovary Syndrome (POCS) and Endometriosis

Polycystic ovary syndrome (PCOS) is a low-grade chronic inflammatory state with significantly increased serum chitinase activity (Alanbay et al. Arch Gynecol Obstet. 2012; 286:1065; Aydogdu et al. Exp Clin Endocrinol Diabetes. 2012; 120:261). Chitinase activity in plasma of patients with endometriosis is also significantly increased (Alanbay et al. Gynecol Endocrinol. 2012; 28:220). Treatment of subjects with POCS or endometriosis by one or more compounds described herein is expected to reduce disease pathology and progression.

Other Diseases and Applications

Because chitin is needed for growth of most fungi and insects and chitin remodeling is needed during growth of these organisms which includes chitinase activity to degrade chitin as well as chitin synthesis, inhibitors of chitinase activity and thus the ability of these organisms to remodel, shed ectoskeleton etc., the compounds described in this invention can also have use in medical, agricultural, food processing and production, or other applications where chitinase inhibition would result in reduced survival of chitin containing organisms. These include but are not limited to fungal diseases of mammals such as aspergillosis, cryptococcosis and plant diseases caused by fungal infection or insect damage, tropical diseases including but not limited to malaria and other parasitic diseases. In fact, chitinase activity is increased in malaria (Barone et al., Clin. Chim. Acta. 331(1-2):79-85, 2003) and thus inhibition of chitinase may be useful in inactivating or otherwise rendering the parasite ineffectual.

Storage Diseases

Chitinases are strongly upregulated in Gaucher disease (Bussink et al. Int Rev Cytol. 2006; 252:71-128). Thus inhibition of chitinases with compounds described herein is expected to reduce progression of storage diseases such as Gaucher disease, Fabry disease, lysosomal storage disorders, Niemann-Pick disease, nephropatic cysteinosis, X-linked globotiaosylceramidosis.

Cancer

Chitinase and chitinase-like proteins are over expressed in many cancers including brain tumors such as glioblastoma (Francescone et al. J Biol Chem 2011; 286:15332-43; Ku et al. Int J Cancer 2011; 128:1316-26) or astrocytoma (Zhang et al. Cancer. 2010; 116:2688), breast cancer (Johansen et al. Breast Cancer Res Treat 2003; 80:15-21), colon cancer (Nutt et al., 2005, Pelloski et al., 2005; Fijneman et al. Clin Cancer Res. 2012; 18:2613; Chen et al. Am J Pathol. 2011; 179: 1494), primary and metastatic lung cancer (Wang et al. Tumour Biol 2015; 36:901-7; Johansen et al. Lung Cancer 2004; 46:333-40), mesothelioma (Corradi et al. Anticancer Res. 2013 December; 33(12):5517), osteosarcoma, malignant melanoma (Ma et al. Cancer Res 2015; 75:487-96), ovarian cancer (Hogdall et al. BMC Cancer 2009; 9:8; Dupont et al. J Clin Oncol. 2004; 22:3330), cervical cancer (Ngernyuang et al. Int J Biochem Cell Biol 2014; 51:45-52), prostate cancer (Jeet et al. Endocr Relat Cancer. 2014; 21:723), liver cancer (Pan et al. J Cancer Res Clin Oncol 2013; 139:1043-54), gastric cancer (Li et al. Chin Med J 2012; 125:1777), metastatic renal cancer (Zhangg et al. Tumour Biol 2014; 35:12131-7), hematologic malignancies such as leukemia or lymphoma (Mactier et al. J Proteome Res. 2011; 10:1030; Marchesi et al. Vet Pathol. 2006; 43:773-6; Marchesi et al. J Vet Med A Physiol Pathol Clin Med. 2003; 50:103) and other types of cancers with inflammatory background (Quershi et al. Genes Cancer. 2011; 2:74; Eurich et al. World J Gastroenterol. 2009; 15:5249; Roslind and Johansen, Methods of Mol Biol. 2009; 511: 159). In fact, higher plasma levels indicate poor prognosis and increased metastatic potential for several cancers (Johansen et al., Cancer Epidemiol. Biomarkers Prev., 15(2): 194-202, 2006). Inhibition of chitinase and chitinase-like protein biological function with one or more compounds described in this invention is anticipated to have therapeutic utility in subjects with cancer.

EXAMPLES

The present invention is further illustrated by the following examples, which in no way should be construed as limiting the scope of the claimed invention.

Materials and Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "*Protective Groups in Organic Chemistry,*" Plenum Press, London and New York 1973, in T. W. Greene and P. G. M. Wuts, "*Protective Groups in Organic Synthesis,*" Third edition, Wiley, New York 1999, in "*The Peptides*;" Volume 3 (editors: E. Gross and J. Meienhofer), Academic Press, London and New York 1981, in "*Methoden der organischen Chemie,*" Houben-Weyl, 4th edition, Vol. 15/1, Georg Thieme Verlag, Stuttgart 1974, in H.-D. Jakubke and H. Jescheit, "*Aminosauren, Peptide, Proteine,*" Verlag Chemie, Weinheim, Deerfield Beach, and Basel 1982, and/or in Jochen Lehmann, "*Chemie der Kohlenhydrate: Monosaccharide and Derivate,*" Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Representative synthetic procedures for the preparation of compounds of the invention are outlined below. Substituents carry the same meaning as defined above, unless otherwise noted.

Starting materials can be obtained from commercial sources or prepared by well-established literature methods known to those skilled in the art.

All solvents, substrates and reagents that were commercially available were used without further purification. TLC analysis was performed using pre-coated glass plates (0.2±0.03 mm thickness, GF-254, particle size 0.01-0.04 mm) from Fluorochem Ltd, UK. Column chromatography was performed using high-purity grade silica gel (pore size 60 Å, 220-440 mesh particle size, 35-75 μm particle size) from Fluka.

$^1$H NMR spectra were recorded on Agilent Mercury 400 MHz spectrometer and Bruker Avance 500, 600, and 700 MHz spectrometers (DRX400, DXR500, DRX600, and DXR700, respectively).

All spectra were recorded in appropriate deuterated solvents (CDCl$_3$, DMSO-d$_6$, D$_2$O, CD$_3$OD, etc.) that were commercially available.

Resonances are given in parts per million relative to tetramethylsilane. Data are reported as follows: chemical shift (δ), multiplicity (s=singlet, d=doublet, t=triplet, m=multiplet, bs=broad singlet), coupling constants (J in Hz) and integration.

ESI-MS spectra were obtained on a Waters Alliance 2695 separation module with a PDA 1996 UV detector and Waters Micromass ZQ 2000 mass detector equipped with Kinetex 2.1/50 mm, 2.6 μm C18 column eluted with 0.3 mL/min flow of 3-100% gradient (over 6 min) of acetonitrile in water, and aShimadzu Prominence LC-20AD separation module with a SPD-M20A PDA detector and Shimadzu LCMS-2020 mass detector equipped with Luna, C18, 2 um, 100A, 150×3 mm column eluted with 0.5 mL/min flow of 15-90% gradient (over 13 min) of acetonitrile in water.

Human AMCase Activity Assay

An enzymatic assay with recombinant human AMCase was used in order to establish inhibitory activity of the compounds (Boot et al., 2001, *JBC*: 276). The assay was run in the 96-well plate format, each reaction in the total volume of 100 μL. 4-Methylumbelliferyl B-D-N,N'-diacetylchitobioside hydrate was used as a substrate for the enzyme. Upon hydrolysis by AMCase, the substrate releases 4-methylumbelliferyl (4MU) that, when ionized in basic pH, emits fluorescence at 460 nm.

Briefly, 40 μL of a substrate was added to each well, followed by 10 μL of compound dilution and 50 μL of hAMCase recombinant enzyme solution. The reaction was carried out in citrate buffer, pH 5.2, in the dark, at 37° C. for 60 minutes with shaking. After that time the reaction was stopped by adding 195 μL of Stop Buffer (pH 10.5) to each well. The fluorescence of the reaction product was measured in Perkin Elmer Envision fluorescent plate reader at an excitation wavelength of 355 nm. The IC$_{50}$ values were calculated using GraphPad Prism.

HumanCHIT1 Activity Assay

An enzymatic assay with recombinant human CHIT1 was used in order to establish inhibitory activity of the compounds (Boot et al., 2001, *JBC*: 276). The assay was run in the 96-well plate format, each reaction in the total volume of 100 μL. 4-methylumbelliferyl β-D-N,N',N"-triacetylchitotriose was used as a substrate for the enzyme. Upon hydrolysis by CHIT1, the substrate releases 4-methylumbelliferyl (4MU) that, when ionized in basic pH, emits fluorescence at 460 nm.

Briefly, 40 μL of a substrate was added to each well, followed by 10 μL of compound dilution and 50 μL of CHIT1 recombinant enzyme solution. The reaction was carried out in citrate buffer, pH 5.2, in the dark, at 37° C. for 60 minutes with shaking. After that time the reaction was stopped by adding 195 μL of Stop Solution (pH 10.5) to each well. The fluorescence of the reaction product was measured in Perkin Elmer Envision fluorescent plate reader at an excitation wavelength of 355 nm. The IC$_{50}$ values were calculated using GraphPad Prism.

The compounds disclosed in Table 1 have the IC$_{50}$ values generally ranging from about 0.01 μM to about 100 μM. Their ranges of activity have been assigned as follows:

A: <0.1 μM;
B: 0.1-1 μM;
C: 1-10 μM; and
D: 10-100 μM.

TABLE 1

| Ex. | Structure | Activity on hAMCase, IC$_{50}$ | Activity on hCHIT1, IC$_{50}$ | IUPAC Name |
|---|---|---|---|---|
| 1 | 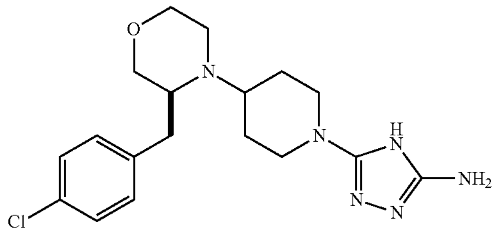 | A | A | (S)-5-(4-(3-(4-chlorobenzyl)morpholino)piperidin-1-yl)-4H-1,2,4-triazol-3-amine |
| 2 | 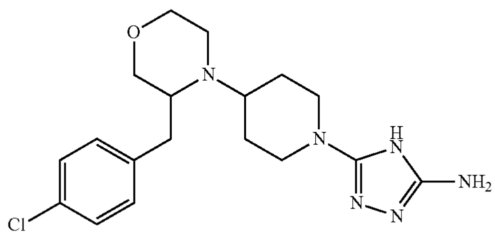 [SMILES: Nc1nnc(N2CCC(N3CCOCC3Cc3ccc(Cl)cc3)CC2)[nH]1] | A | B | 5-(4-(3-(4-chlorobenzyl)morpholino)piperidin-1-yl)-4H-1,2,4-triazol-3-amine |
| 3 | 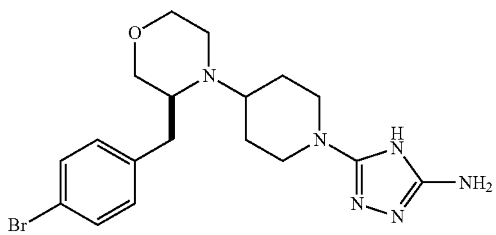 | A | A | (S)-5-(4-(3-(4-bromobenzyl)morpholino)piperidin-1-yl)-4H-1,2,4-triazol-3-amine |
| 4 | 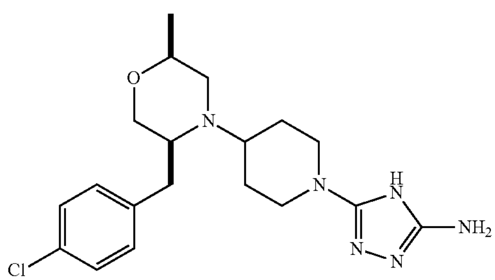 | A | A | 5-(4-((2S,5S)-5-(4-chlorobenzyl)-2-methylmorpholino)piperidin-1-yl)-4H-1,2,4-triazol-3-amine |
| 5 | 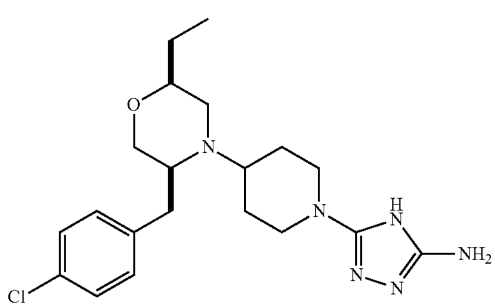 | A | A | 5-(4-((2S,5S)-5-(4-chlorobenzyl)-2-ethylmorpholino)piperidin-1-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
| --- | --- | --- | --- | --- |
| 6 | 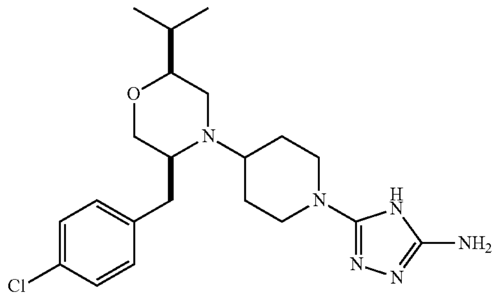 | A | A | 5-(4-((2S,5S)-5-(4-chlorobenzyl)-2-isopropylmorpholino)piperidin-1-yl)-4H-1,2,4-triazol-3-amine |
| 7 | 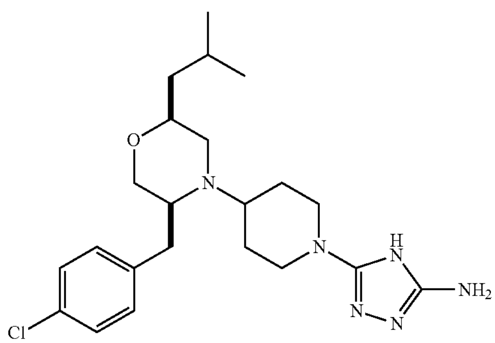 | A | A | 5-(4-((2S,5S)-5-(4-chlorobenzyl)-2-isobutylmorpholino)piperidin-1-yl)-4H-1,2,4-triazol-3-amine |
| 8 | 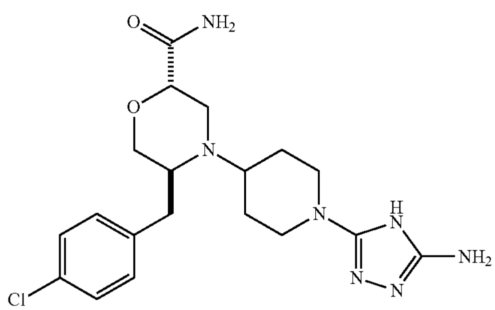 | B | C | (2S,5S)-4-(1-(5-amino-4H-1,2,4-triazol-3-yl)piperidin-4-yl)-5-(4-chlorobenzyl)morpholine-2-carboxamide |
| 9 | 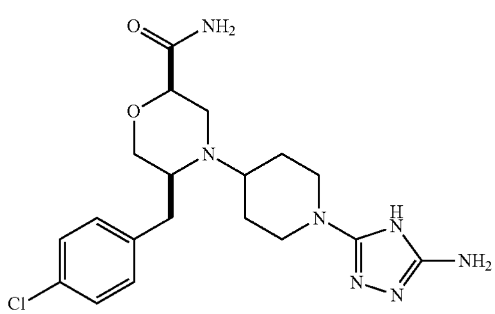 | A | A | (2R,5S)-4-(1-(5-amino-4H-1,2,4-triazol-3-yl)piperidin-4-yl)-5-(4-chlorobenzyl)morpholine-2-carboxamide |
| 10 | 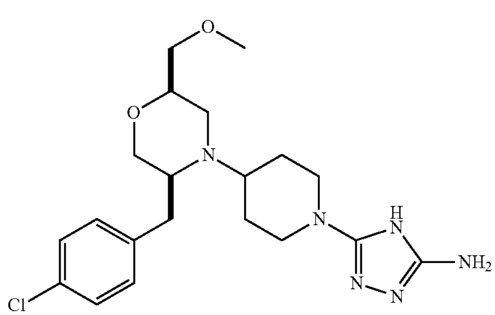 | A | A | 5-(4-((2R,5S)-5-(4-chlorobenzyl)-2-(methoxymethyl)morpholino)piperidin-1-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 11 | 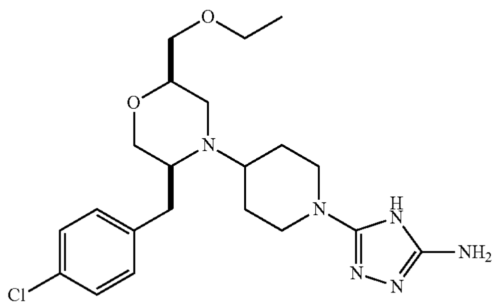 | A | A | 5-(4-((2R,5S)-5-(4-chlorobenzyl)-2-(ethoxymethyl)morpholino)piperidin-1-yl)-4H-1,2,4-triazol-3-amine |
| 12 | 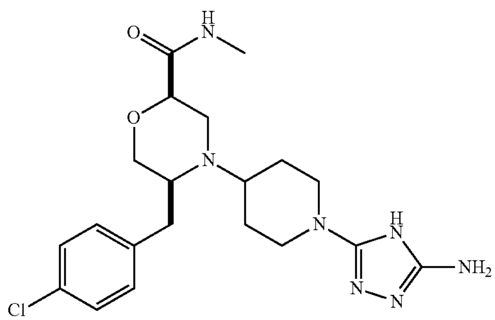 | A | A | (2R,5S)-4-(1-(5-amino-4H-1,2,4-triazol-3-yl)piperidin-4-yl)-5-(4-chlorobenzyl)-N-methylmorpholine-2-carboxamide |
| 13 | 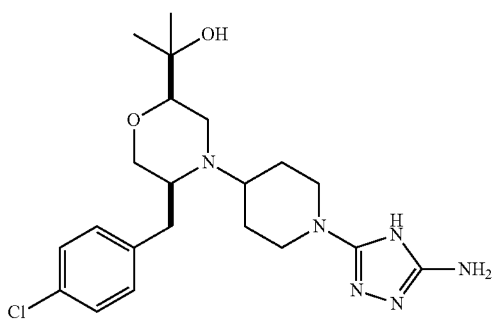 | A | A | 2-((2R,5S)-4-(1-(5-amino-4H-1,2,4-triazol-3-yl)piperidin-4-yl)-5-(4-chlorobenzyl)morpholin-2-yl)propan-2-ol |
| 14 | 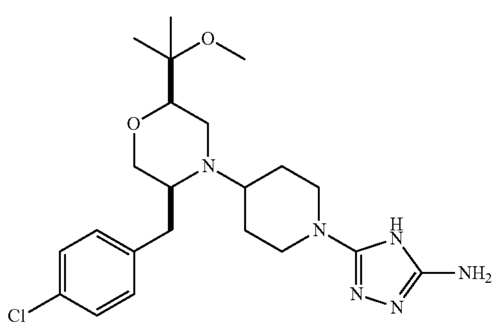 | A | A | 5-(4-((2R,5S)-5-(4-chlorobenzyl)-2-(2-methoxypropan-2-yl)morpholino)piperidin-1-yl)-4H-1,2,4-triazol-3-amine |
| 15 | 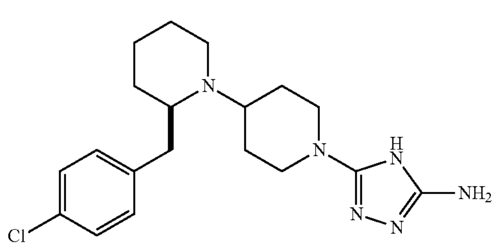 | A | A | (R)-5-(2-(4-chlorobenzyl)-[1,4'-bipiperidin]-1'-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 16 | 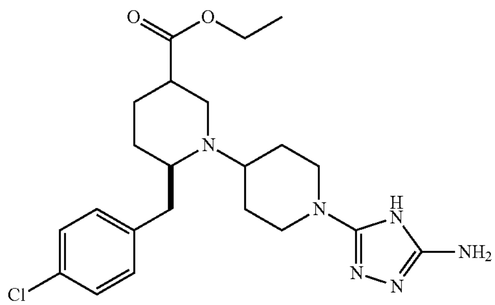 | A | A | (6R)-ethyl 1'-(5-amino-4H-1,2,4-triazol-3-yl)-6-(4-chlorobenzyl)-[1,4'-bipiperidine]-3-carboxylate |
| 17 | 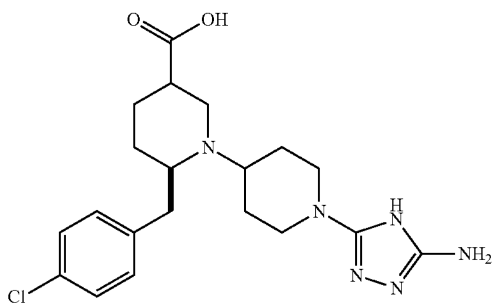 | A | B | (6R)-1'-(5-amino-4H-1,2,4-triazol-3-yl)-6-(4-chlorobenzyl)-[1,4'-bipiperidine]-3-carboxylic acid |
| 18 | 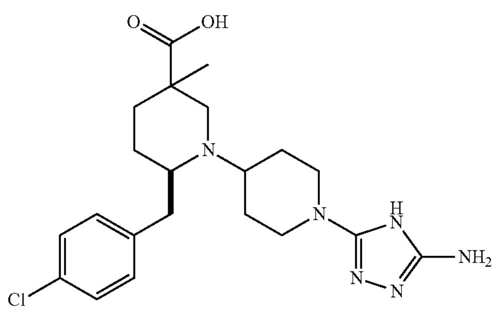 | A | C | (6R)-1'-(5-amino-4H-1,2,4-triazol-3-yl)-6-(4-chlorobenzyl)-3-methyl-[1,4'-bipiperidine]-3-carboxylic acid |
| 19 | 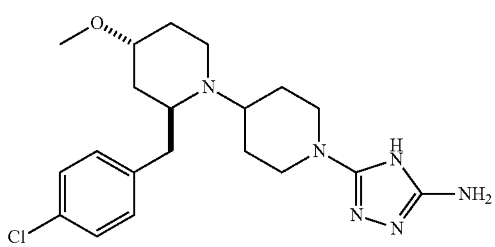 | A | C | 5-((2S,4R)-2-(4-chlorobenzyl)-4-methoxy-[1,4'-bipiperidin]-1'-yl)-4H-1,2,4-triazol-3-amine |
| 20 | 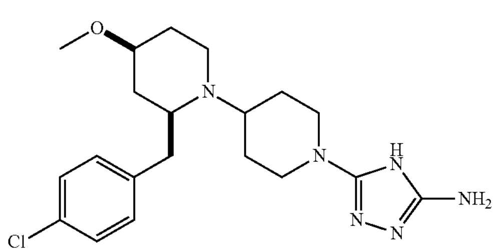 | A | B | 5-((2S,4S)-2-(4-chlorobenzyl)-4-methoxy-[1,4'-bipiperidin]-1'-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 21 | 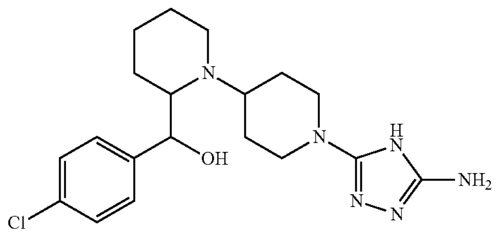 [SMILES: Nc1nnc(N2CCC(N3CCCCC3C(O)c3ccc(Cl)cc3)CC2)[nH]1] | C | D | (1'-(5-amino-4H-1,2,4-triazol-3-yl)-[1,4'-bipiperidin]-2-yl)(4-chlorophenyl)methanol |
| 22 | 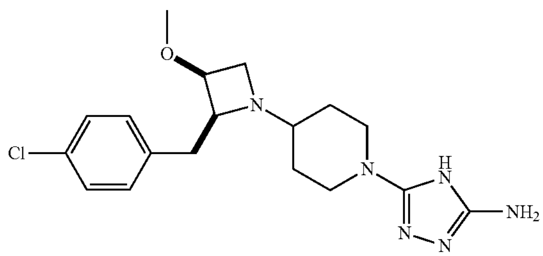 [SMILES: CO[C@H]1CN(C2CCN(c3nnc(N)[nH]3)CC2)[C@H]1Cc1ccc(Cl)cc1] | C | B | 5-(4-((2S,3S)-2-(4-chlorobenzyl)-3-methoxyazetidin-1-yl)piperidin-1-yl)-4H-1,2,4-triazol-3-amine |
| 23 | 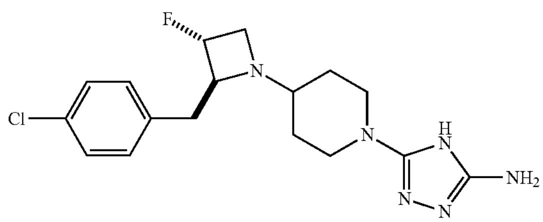 [SMILES: Nc1nnc(N2CCC(N3C[C@@H](F)[C@@H]3Cc3ccc(Cl)cc3)CC2)[nH]1] | C | D | 5-(4-((2S,3R)-2-(4-chlorobenzyl)-3-fluoroazetidin-1-yl)piperidin-1-yl)-4H-1,2,4-triazol-3-amine |
| 24 | 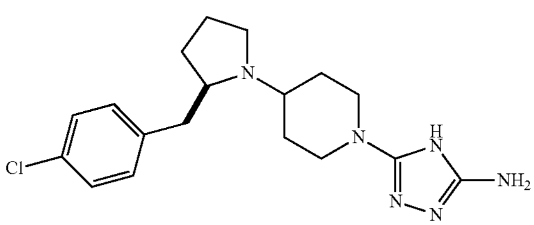 [SMILES: Nc1nnc(N2CCC(N3CCC[C@@H]3Cc3ccc(Cl)cc3)CC2)[nH]1] | A | A | (R)-5-(4-(2-(4-chlorobenzyl)pyrrolidin-1-yl)piperidin-1-yl)-4H-1,2,4-triazol-3-amine |
| 25 | 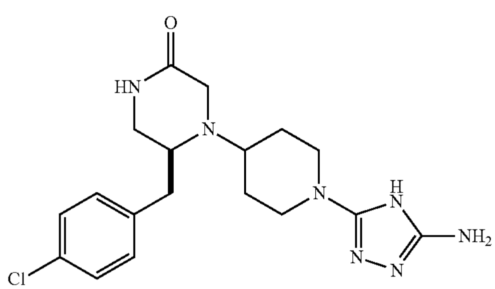 | C | C | (S)-4-(1-(5-amino-4H-1,2,4-triazol-3-yl)piperidin-4-yl)-5-(4-chlorobenzyl)piperazin-2-one |
| 26 | 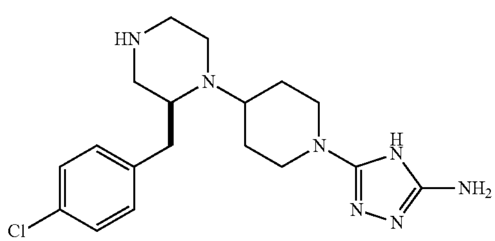 | B | C | (S)-5-(4-(2-(4-chlorobenzyl)piperazin-1-yl)piperidin-1-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 27 | 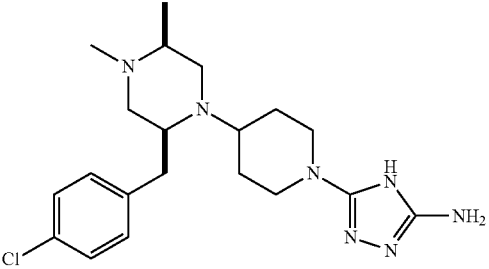 | A | C | 5-(4-((2S,5S)-2-(4-chlorobenzyl)-4,5-dimethylpiperazin-1-yl)piperidin-1-yl)-4H-1,2,4-triazol-3-amine |
| 28 | 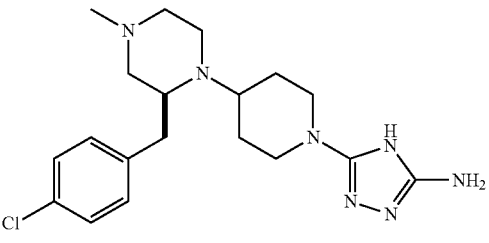 | B | D | (S)-5-(4-(2-(4-chlorobenzyl)-4-methylpiperazin-1-yl)piperidin-1-yl)-4H-1,2,4-triazol-3-amine |
| 29 | 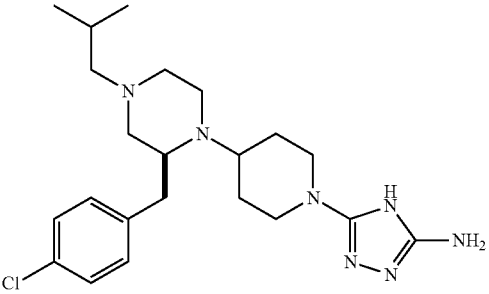 | B | D | (S)-5-(4-(2-(4-chlorobenzyl)-4-isobutylpiperazin-1-yl)piperidin-1-yl)-4H-1,2,4-triazol-3-amine |
| 30 | 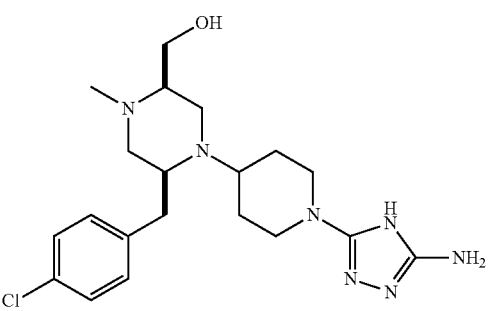 | B | C | ((2R,5S)-4-(1-(5-amino-4H-1,2,4-triazol-3-yl)piperidin-4-yl)-5-(4-chlorobenzyl)-1-methylpiperazin-2-yl)methanol |
| 31 | 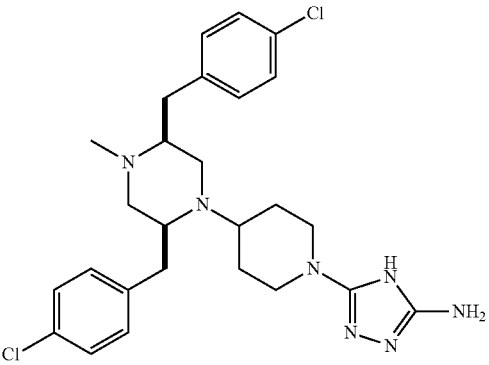 | A | C | 5-(4-((2S,5S)-2,5-bis(4-chlorobenzyl)-4-methylpiperazin-1-yl)piperidin-1-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 32 | 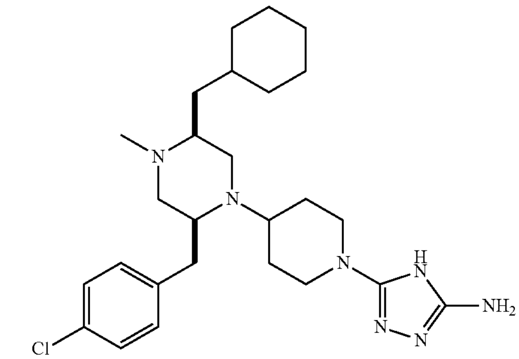 | A | C | 5-(4-((2S,5S)-2-(4-chlorobenzyl)-5-(cyclohexylmethyl)-4-methylpiperazin-1-yl)piperidin-1-yl)-4H-1,2,4-triazol-3-amine |
| 33 | 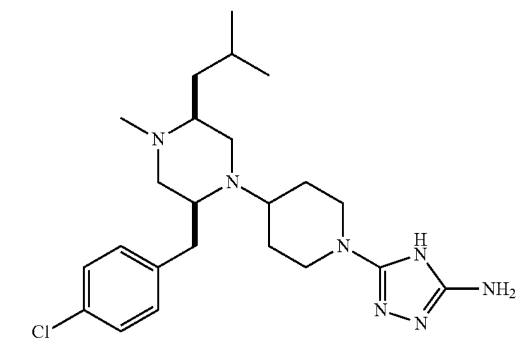 | A | C | 5-(4-((2S,5S)-2-(4-chlorobenzyl)-5-isobutyl-4-methylpiperazin-1-yl)piperidin-1-yl)-4H-1,2,4-triazol-3-amine |
| 34 | 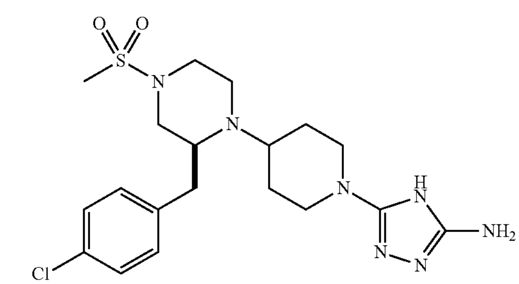 | C | D | (S)-5-(4-(2-(4-chlorobenzyl)-4-(methylsulfonyl)piperazin-1-yl)piperidin-1-yl)-4H-1,2,4-triazol-3-amine |
| 35 | 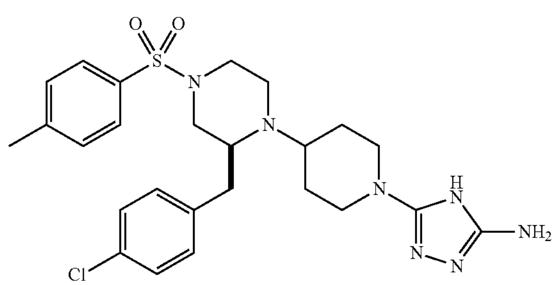 | C | D | (S)-5-(4-(2-(4-chlorobenzyl)-4-tosylpiperazin-1-yl)piperidin-1-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 36 | 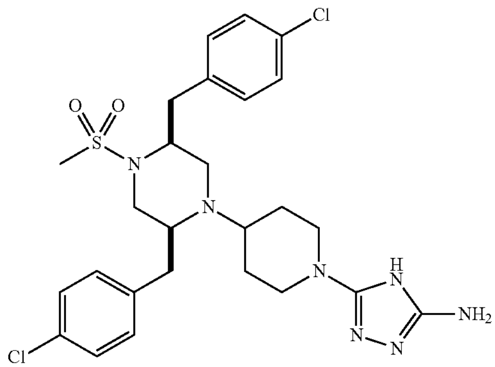 | D | D | 5-(4-((2S,5S)-2,5-bis(4-chlorobenzyl)-4-(methylsulfonyl)piperazin-1-yl)piperidin-1-yl)-4H-1,2,4-triazol-3-amine |
| 37 | 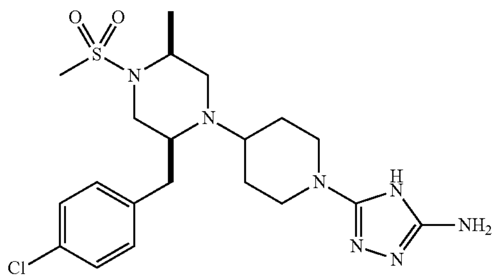 | C | D | 5-(4-((2S,5S)-2-(4-chlorobenzyl)-5-methyl-4-(methylsulfonyl)piperazin-1-yl)piperidin-1-yl)-4H-1,2,4-triazol-3-amine |
| 38 | 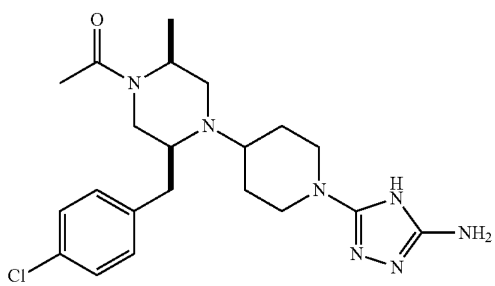 | D | E | 1-((2S,5S)-4-(1-(5-amino-4H-1,2,4-triazol-3-yl)piperidin-4-yl)-5-(4-chlorobenzyl)-2-methylpiperazin-1-yl)ethanone |
| 39 | 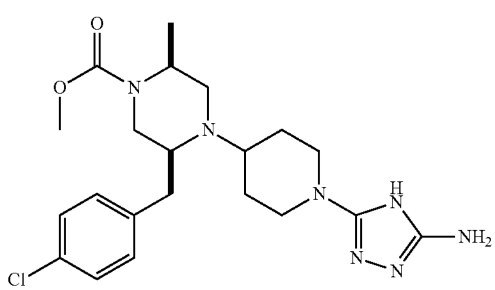 | C | D | (2S,5S)-methyl 4-(1-(5-amino-4H-1,2,4-triazol-3-yl)piperidin-4-yl)-5-(4-chlorobenzyl)-2-methylpiperazine-1-carboxylate |
| 40 | 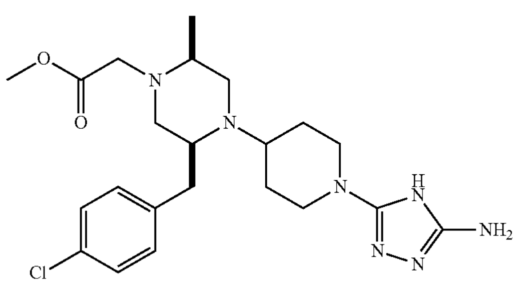 | A | B | methyl 2-((2S,5S)-4-(1-(5-amino-4H-1,2,4-triazol-3-yl)piperidin-4-yl)-5-(4-chlorobenzyl)-2-methylpiperazin-1-yl)acetate |

TABLE 1-continued

| Ex. | Structure | Activity on hAMCase, IC$_{50}$ | Activity on hCHIT1, IC$_{50}$ | IUPAC Name |
|---|---|---|---|---|
| 41 | 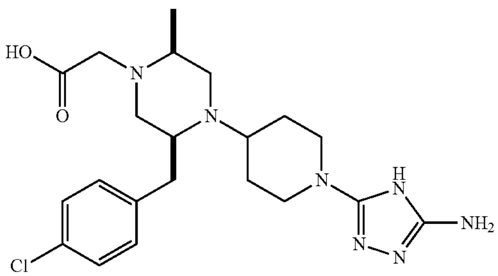 | A | B | 2-((2S,5S)-4-(1-(5-amino-4H-1,2,4-triazol-3-yl)piperidin-4-yl)-5-(4-chlorobenzyl)-2-methylpiperazin-1-yl)acetic acid |
| 42 | 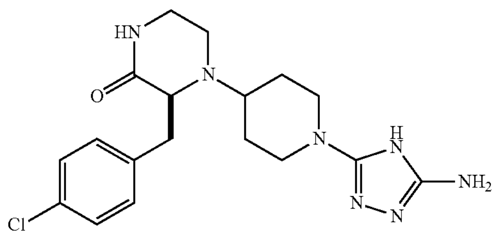 | C | E | (S)-4-(1-(5-amino-4H-1,2,4-triazol-3-yl)piperidin-4-yl)-3-(4-chlorobenzyl)piperazin-2-one |
| 43 | 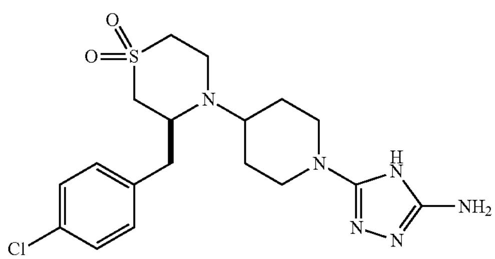 | B | C | (S)-4-(1-(5-amino-4H-1,2,4-triazol-3-yl)piperidin-4-yl)-3-(4-chlorobenzyl)thiomorpholine 1,1-dioxide |
| 44 | 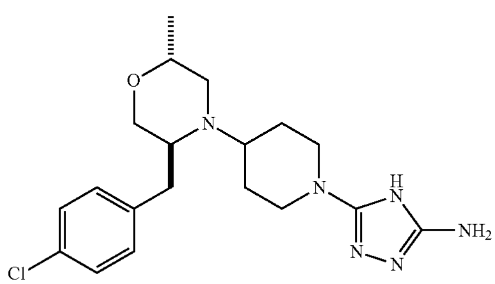 | B | C | 5-(4-((2R,5S)-5-(4-chlorobenzyl)-2-methylmorpholino)piperidin-1-yl)-4H-1,2,4-triazol-3-amine |
| 45 | 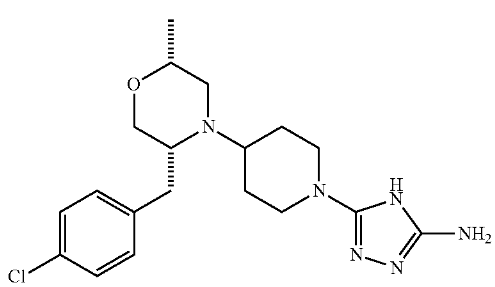 | E | D | 5-(4-((2R,5R)-5-(4-chlorobenzyl)-2-methylmorpholino)piperidin-1-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 46 | 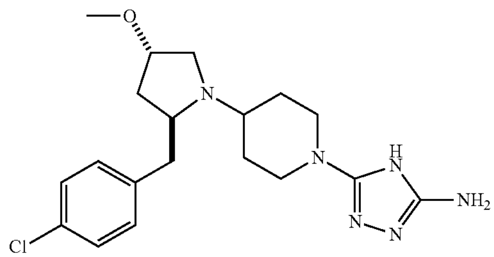 [SMILES: CO[C@H]1C[C@H](Cc2ccc(Cl)cc2)N(C2CCN(c3nnc(N)[nH]3)CC2)C1] | A | A | 5-(4-((2S,4S)-2-(4-chlorobenzyl)-4-methoxypyrrolidin-1-yl)piperidin-1-yl)-4H-1,2,4-triazol-3-amine |
| 47 | 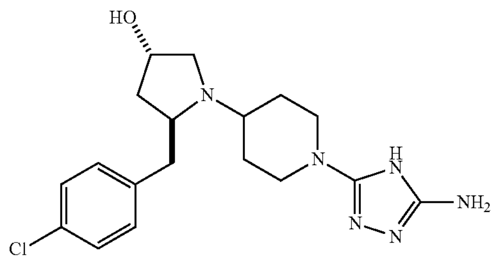 [SMILES: Nc1nnc(N2CCC(N3C[C@@H](O)C[C@@H]3Cc3ccc(Cl)cc3)CC2)[nH]1] | A | A | (3S,5S)-1-(1-(5-amino-4H-1,2,4-triazol-3-yl)piperidin-4-yl)-5-(4-chlorobenzyl)pyrrolidin-3-ol |
| 48 | 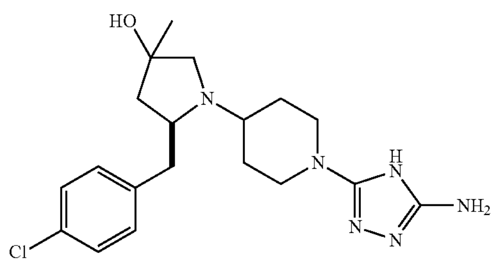 [SMILES: CC1(O)C[C@H](Cc2ccc(Cl)cc2)N(C2CCN(c3nnc(N)[nH]3)CC2)C1] | A | B | (5S)-1-(1-(5-amino-4H-1,2,4-triazol-3-yl)piperidin-4-yl)-5-(4-chlorobenzyl)-3-methylpyrrolidin-3-ol |
| 49 | 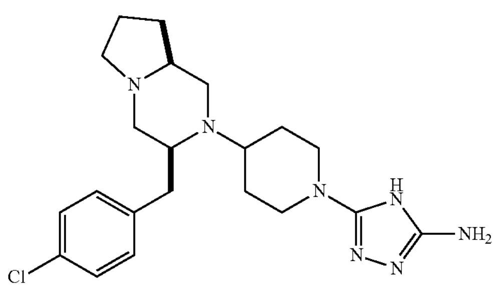 | A | C | 5-(4-((3S,8aS)-3-(4-chlorobenzyl)hexahydro-pyrrolo[1,2-a]pyrazin-2(1H)-yl)piperidin-1-yl)-4H-1,2,4-triazol-3-amine |
| 50 | 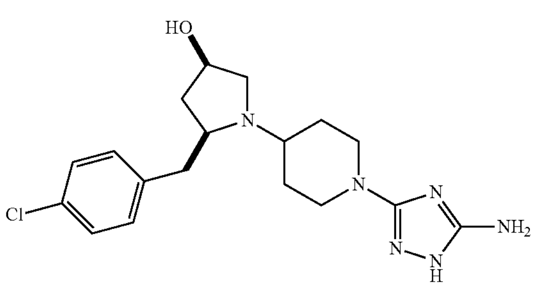 [SMILES: Nc1nc(N2CCC(N3C[C@H](O)C[C@@H]3Cc3ccc(Cl)cc3)CC2)n[nH]1] | A | A | (3R,5S)-1-(1-(5-amino-1H-1,2,4-triazol-3-yl)piperidin-4-yl)-5-(4-chlorobenzyl)pyrrolidin-3-ol |

TABLE 1-continued

| Ex. | Structure | Activity on hAMCase, IC$_{50}$ | Activity on hCHIT1, IC$_{50}$ | IUPAC Name |
|---|---|---|---|---|
| 51 | 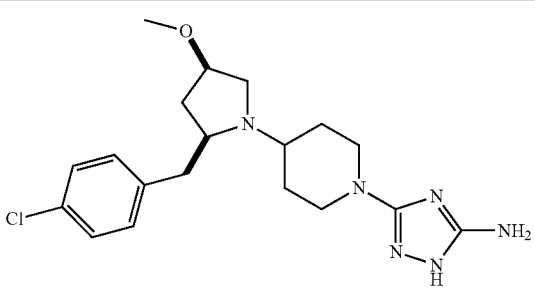 [SMILES: CO[C@@H]1C[C@H](Cc2ccc(Cl)cc2)N(C2CCN(c3n[nH]c(N)n3)CC2)C1] | A | A | 3-(4-((2S,4R)-2-(4-chlorobenzyl)-4-methoxypyrrolidin-1-yl)piperidin-1-yl)-1H-1,2,4-triazol-5-amine |
| 52 | 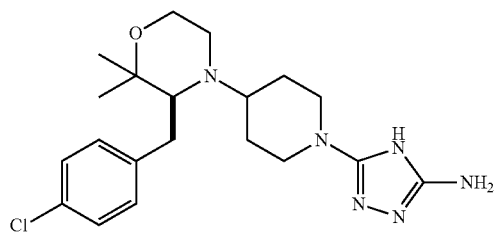 | D | E | (S)-5-(4-(3-(4-chlorobenzyl)-2,2-dimethylmorpholino)piperidin-1-yl)-4H-1,2,4-triazol-3-amine |
| 53 | 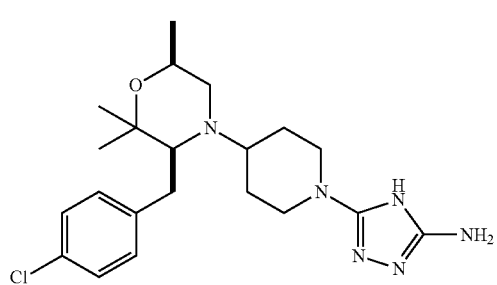 | C | D | 5-(4-((3S,6S)-3-(4-chlorobenzyl)-2,2,6-trimethylmorpholino)piperidin-1-yl)-4H-1,2,4-triazol-3-amine |
| 54 | 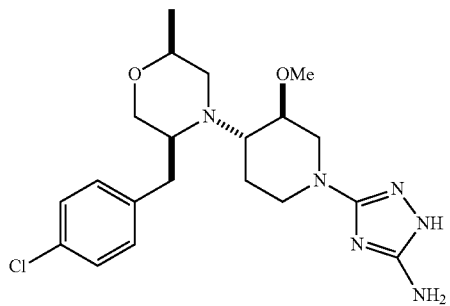 | B | B | 3-((3S,4S)-4-((2S,5S)-5-(4-chlorobenzyl)-2-methylmorpholino)-3-methoxypiperidin-1-yl)-1H-1,2,4-triazol-5-amine |
| 55 | 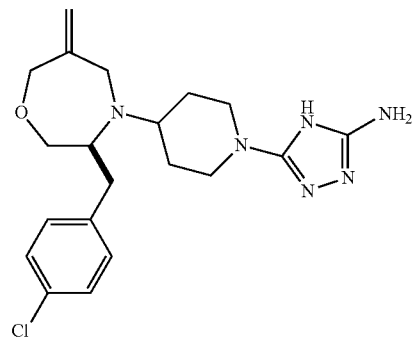 [SMILES: C=C1COC[C@H](Cc2ccc(Cl)cc2)N(C2CCN(c3nnc(N)[nH]3)CC2)C1] | A | B | (S)-5-(4-(3-(4-chlorobenzyl)-6-methylene-1,4-oxazepan-4-yl)piperidin-1-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 56 | 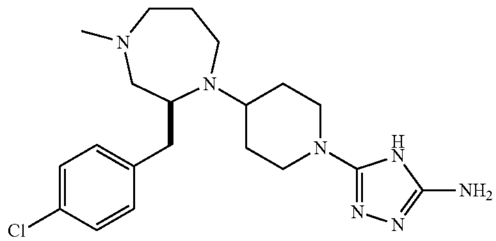 | C | E | (S)-5-(4-(2-(4-chlorobenzyl)-4-methyl-1,4-diazepan-1-yl)piperidin-1-yl)-4H-1,2,4-triazol-3-amine |
| 57 | 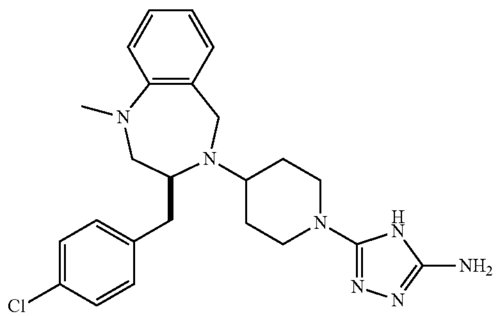 | A | B | (S)-5-(4-(3-(4-chlorobenzyl)-1-methyl-2,3-dihydro-1H-benzo[e][1,4]diazepin-4(5H)-yl)piperidin-1-yl)-4H-1,2,4-triazol-3-amine |
| 58 | 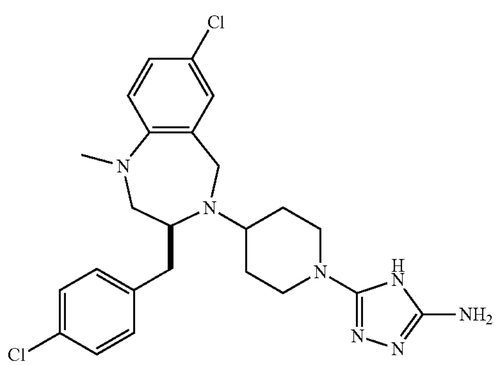 | A | B | (S)-5-(4-(7-chloro-3-(4-chlorobenzyl)-1-methyl-2,3-dihydro-1H-benzo[e][1,4]diazepin-4(5H)-yl)piperidin-1-yl)-4H-1,2,4-triazol-3-amine |
| 59 | 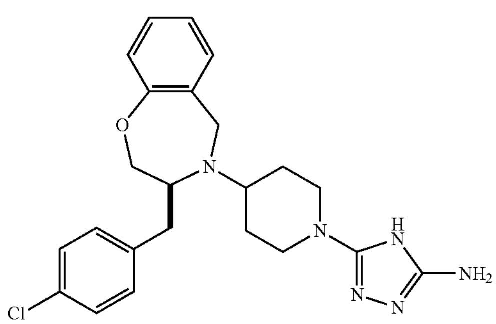 | A | B | (S)-5-(4-(3-(4-chlorobenzyl)-2,3-dihydrobenzo[f][1,4]oxazepin-4(5H)-yl)piperidin-1-yl)-4H-1,2,4-triazol-3-amine |

TABLE 1-continued

| Ex. | Structure | Activity on hAMCase, IC$_{50}$ | Activity on hCHIT1, IC$_{50}$ | IUPAC Name |
|---|---|---|---|---|
| 60 | 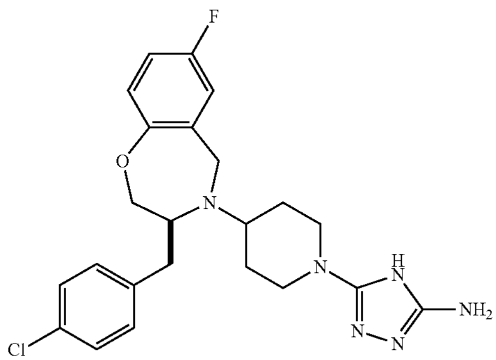 | A | B | (S)-5-(4-(3-(4-chlorobenzyl)-7-fluoro-2,3-dihydrobenzo[f][1,4]oxazepin-4(5H)-yl)piperidin-1-yl)-4H-1,2,4-triazol-3-amine |
| 61 | 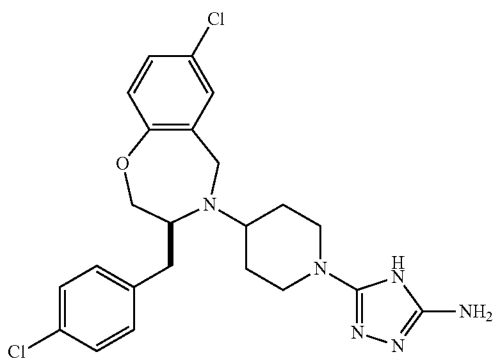 | A | C | (S)-5-(4-(7-chloro-3-(4-chlorobenzyl)-2,3-dihydrobenzo[f][1,4]oxazepin-4(5H)-yl)piperidin-1-yl)-4H-1,2,4-triazol-3-amine |
| 62 | 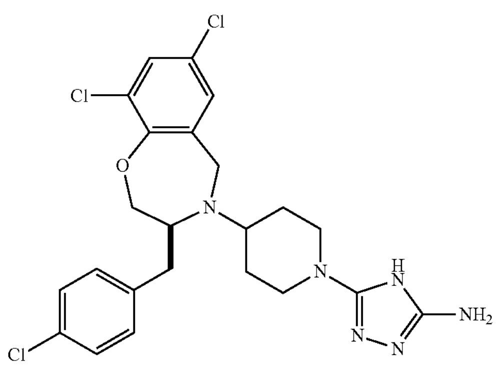 | A | D | (S)-5-(4-(7,9-dichloro-3-(4-chlorobenzyl)-2,3-dihydrobenzo[f][1,4]oxazepin-4(5H)-yl)piperidin-1-yl)-4H-1,2,4-triazol-3-amine |
| 63 | 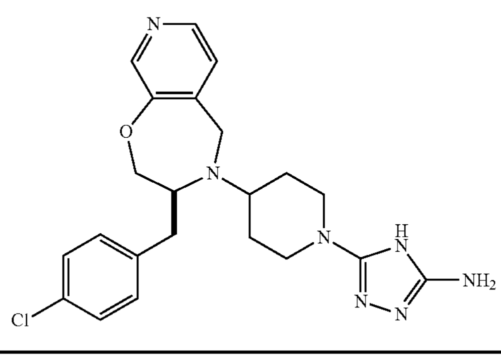 | A | C | (S)-5-(4-(3-(4-chlorobenzyl)-2,3-dihydropyrido[4,3-f][1,4]oxazepin-4(5H)-yl)piperidin-1-yl)-4H-1,2,4-triazol-3-amine |

General Synthetic Procedures
General Procedure I
Reduction of α-amino acid to the Corresponding amino alcohol.

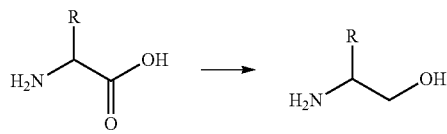

To a suspension of amino acid in anhydrous tetrahydrofuran (THF) (3 mL/mmol) borane-dimethylsulfide complex (BH₃.DMS; 3 equivalents) is added dropwise at 0° C. (Caution: foaming!) The cooling bath is removed and reaction mixture is refluxed overnight, after which time chromatography reveals no starting material presence. The mixture is cooled to room temperature and 6 M HCl (8 equivalents with respect to the starting material) is carefully added (Caution: foaming!) and the mixture is again refluxed for 1.5 hours. The mixture is cooled to room temperature and pH is brought to 10 with 4 M NaOH. Product is extracted several times with ethyl acetate (AcOEt), extracts are combined, dried over MgSO₄, filtered and concentrated in vacuo. The crude product is triturated with ethyl ether (Et₂O) and filtered off.
General Procedure II
Amino-selective acylation of amino Alcohol or N-Boc diamine with chloroacetyl chloride.

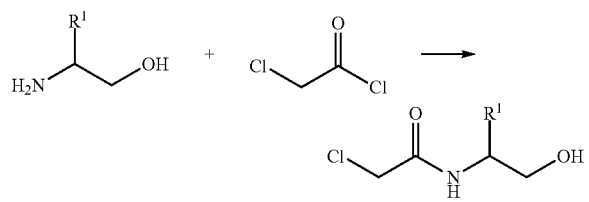

To the solution of amino alcohol or N-Boc diamine in THF (6 mL/mmol) triethylamine (1.2 equivalent with respect to the amino alcohol) is added and the solution is cooled to 0° C. Chloroacetyl chloride (1 equivalent with respect to the amino alcohol) is added slowly in such a manner that the internal temperature of the reaction does not exceed 5° C. The cooling bath is then removed and the mixture is stirred for further 20 minutes. TLC shows complete consumption of the staring material at this point. Diethyl ether is then added (volume twice of that of THF used for the reaction) and the whole reaction mixture is sequentially washed with 1 M HCl, 1 M NaOH, brine, dried over MgSO₄, filtered and evaporated to dryness to give the crude product. Crystallization from hot diethyl ether usually provides the amido alcohol or amido amine of 98%+ purity.
General Procedure III
Amino-selective acylation of amino alcohol with α-bromoacid with the use of an amide-forming reagent.

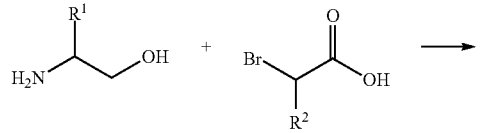

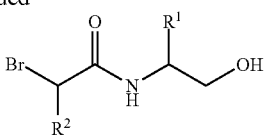

To the solution of α-bromoacid in dichloromethane (7 mL/mmol) diisopropylethylamine (DIPEA, 1 equivalent with respect to the starting α-bromoacid), coupling reagent (1 equivalent; typically TBTU or HATU, but other commonly used coupling reagents may be used as well) and amino alcohol (1 equivalent) are added sequentially and the reaction mixture is stirred for 1.5 hours at room temperature. After this time TLC control shows complete consumption of the starting materials so the reaction mixture is transferred to the separatory funnel and washed sequentially with 1 M HCl, 1 M NaOH, and brine. The organic phase is dried over MgSO₄, filtered and evaporated to dryness to give the crude product which is further purified by crystallization or silica-gel chromatography.
General Procedure IV
Cyclization of α-haloamide to morpholin-3-one

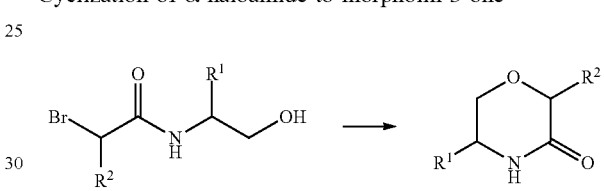

To the solution of the α-haloamide (i.e., α-chloro- or α-bromoamide) in THF (10 mL/mmol) 3 equivalents of sodium hydride (NaH) is added all at once (cooling the solution prior to the addition of NaH may is advisable when working on larger scale) and the reaction mixture is allowed to stir at room temperature for 2 hours. The excess of NaH is then carefully quenched by dropwise addition of brine and then additional volume of brine (equal to the initial volume of THF) is added causing phases separation. The organic layer is separated and the aqueous layer is additionally extracted with diethyl ether. Combined organic extracts are then dried over MgSO₄, filtered and the solvents are evaporated. Crude product is in most cases sufficiently pure to be used in the next step without any additional purification.
General Procedure V
Reduction of morpholin-3-one to morpholine or 2-piperazinone to piperazine or amide to amine.

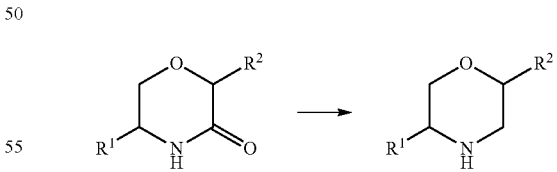

To the solution of either morpholin-3-one or 2-piperazinone or amide in THF (3 mL/mmol) 3 equivalents of BH₃.DMS complex is added and the reaction mixture is refluxed for 3 hours, after which time the TLC control shows complete consumption of the starting material. Reaction mixture is cooled to room temperature and 2 M HCl is cautiously added (6 equivalents with respect to the starting material). The resulting reaction mixture is refluxed for 2 hours and cooled back to room temperature. The pH of the solution is then adjusted to strongly alkaline (~10) by a dropwise addition of 6 M NaOH. The organic layer is separated and the aqueous layer is additionally extracted with diethyl ether. Combined organic extracts are then dried over MgSO$_4$, filtered and the solvents are evaporated. Crude product obtained is, in most cases sufficiently pure to be used in the next step without any additional purification.

General Procedure VI

Reductive amination of the cyclic Ketone (i.e., N-protected piperid-4-one) with Secondary cyclic amine (i.e., morpholine, piperazine, piperazin-3-one, Etc.).

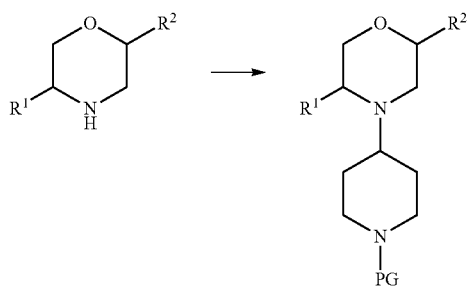

Cyclic secondary amine is dissolved in 1,2-dichloroethane (DCE, 0.65 mL/mmol) and N-Boc-piperid-4-one (1.5 equivalent with respect to the cyclic amine) and glacial acetic acid (AcOH) (2 equivalents with respect to the cyclic amine) are added and the mixture is stirred for 4 hours. Sodium triacetoxyborohydride [NaBH(OAc)$_3$, 2 equivalents] is then added in one portion and the thick mixture is stirred overnight at room temperature. After this time a 5% aqueous solution of sodium bicarbonate (NaHCO$_3$) is added (twice the volume of the DCE used) and the biphasic mixture is stirred for 30 minutes. The layers are separated and the aqueous layer is additionally extracted with dichloromethane. The combined organic extracts are then dried over MgSO$_4$, filtered and the solvents are evaporated providing crude product which typically needs further purification by silica-gel chromatography.

General Procedure VII

Removal of the tert-butoxycarbonyl (Boc-) Group from amine

The N-Boc protected amine is treated with a 4 M solution of HCl (5 mL/mmol of starting material) in an appropriate organic solvent (e.g., AcOEt, 1,4-dioxane, MeOH, DCM) for the time necessary for complete consumption of the starting material (typically 30 minutes-2 hours). The volatiles are then removed in vacuo providing the desired compound in the form of its hydrochloride salt. Crude product is usually sufficiently pure to be used in the following step, but additional trituration with diethyl ether may help to remove any colored impurities.

General Procedure VIII

Installation of the 2,5-diamino-1,2,4-triazole Ring on the hydrochloride salt of the Secondary amine

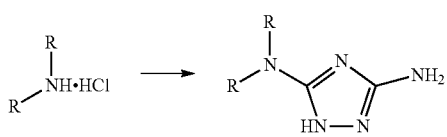

The hydrochloride salt of the secondary amine, anhydrous potassium carbonate (K$_2$CO$_3$) (2 equivalents) and S,S'-dimethyl-N-cyano-dithioiminocarbonate (1.2 molar equivalent) are added to acetonitrile (2 mL/mmol of the starting material) and the resulting solution is refluxed for 1-7 hours (monitoring by TLC). Hydrazine monohydrate (3-5 equivalents) is then added and the reaction is further refluxed for another 2-5 hours after which time it is cooled to room temperature and solids are filtered off. The filtrate is concentrated in vacuo and the crude product is purified either by crystallization from appropriate solvent or chromatography on regular silica-gel or reversed-phase C-18 silica gel.

General Procedure IX

Activation of Carboxylic Group by Mixed Anhydride Followed by Formation of an amide.

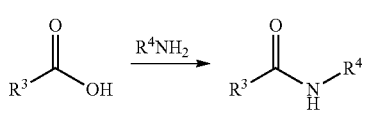

Carboxylic acid is dissolved in dichloromethane (DCM) (3-8 mL/mmol depending on the solubility) and N-methylmorpholine (1.2 equivalent) is added. The solution is cooled to −15° C. and alkyl (typically methyl, ethyl or isobutyl) chloroformate (1.2 equivalent) is added and the mixture is stirred for additional 10 minutes at which time the appropriate amine (neat, 1.2 equivalent) or aqueous ammonia is added. The reaction mixture is allowed to warm to room temperature and is typically stirred overnight, though in the cases of reactive amines the coupling is usually completed within minutes. The crude product is isolated washing of organic phase (DCM) subsequentially with 1 M HCl, 1 M NaOH, and brine. The organic phase is over MgSO$_4$, filtered and evaporated to dryness to give the crude product which is further purified by crystallization or silica-gel chromatography.

General Procedure X

Removal of the tert-butoxycarbonyl (Boc-) from amine Followed by Cyclization to the Six-membered Ring (i.e., morpholin-3-one, piperazin-2-one, Etc.) and Seven-membered Ring (1,4-oxazepine, 1,4-benzoxazepine, 1,4-benzodiazepines, Etc.).

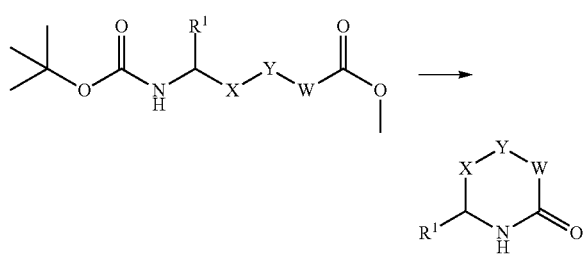

X, Y, W can be CH2, CH(R), C═O, O, NH, NH(alkyl), S, SO, SO2, etc

The crude amine hydrochloride salt of the typical Boc-group removal procedure (see the General Procedure VII) is suspended in methanol (3 mL/mmol), triethylamine (5 equivalents) is added and the mixture is refluxed for the appropriate time (TLC control). Methanol and excess of triethylamine are removed in vacuo, the residue is taken into ethyl acetate and aqueous acid/base wash, dried over MgSO$_4$, filtered off and filtrate is concentrated in vacuo. The crude product is purified by crystallization or silica-gel chromatography.

General Procedure XI
Reduction of Boc-protected amino acid to the Corresponding Boc-protected amino alcohol Via Mixed anhydride

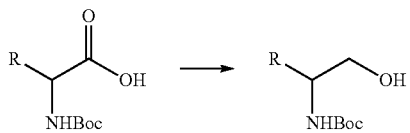

The starting Boc-protected amino acid is dissolved in THF (4 mL/mmol) and the carboxylic group is activated by formation of the mixed anhydride as it is described in the General Procedure IX. The precipitated N-methymorpholine hydrochloride is filtered off quickly and filtrate is transferred into a larger round bottomed flask. The suspension of NaBH$_4$ (2 equivalents) in water (1 mL/mmol) is then cautiously added (Caution: intense foaming!) and the reaction mixture is allowed to stir at room temperature overnight. 1 M NaOH is added in volume equal to that of THF used and the mixture is stirred for additional 30 minutes after which time it is extracted 3 times with ethyl acetate. Drying the solution and removal of the solvent yield product that is usually sufficiently pure to be directly used in the next step, though crystallization or trituration with appropriate solvent may further improve its purity.

General Procedure XII
Oxidation of Boc-protected amino alcohol to the Corresponding N-protected amino aldehyde with Dess-Martin periodinane

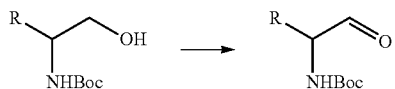

To the solution of Boc-protected amino alcohol in dichloromethane (1.5 mL/mmol), Dess-Martin periodinane is added (1.1 equivalent) and the progress of reaction is followed by TLC. Typically after 2 hours the complete conversion is achieved, and reaction is quenched with 10% aqueous solution of sodium thiosulfate in order to remove any oxidative species. The reaction mixture is diluted 5 times with dichloromethane and product is isolated by basic work-up with 1 M NaOH. The organic phase is dried over MgSO$_4$, filtered and evaporated to dryness to give the crude product which is usually sufficiently pure to be directly used in the next step, though crystallization or trituration with appropriate solvent may further improve its purity.

General Procedure XIII
Reductive Amination of the Boc-protected amino aldehyde with methyl ester of amino acid

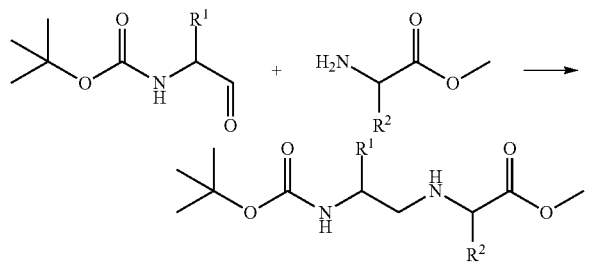

To the suspension of hydrochloride salt of methyl ester of amino acid in DCE (3 ml/mmol) Boc-protected amino aldehyde (1 equivalent) and glacial acoh (1-2 equivalents) are added and the mixture is stirred for 2 hours at room temperature before nabh(oac)$_3$ (3 equivalents) is added in one portion. The resulting mixture is stirred overnight at room temperature and the product is isolated in the same manner as it is described in the General Procedure VI. Provided the starting materials used are reasonably pure, the crude product in most cases does not need further purification.

General Procedure XIV
N-Methylation of Secondary amine (Either Linear or cyclic) with formaldehyde.

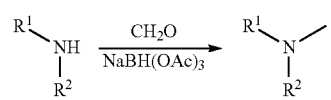

The secondary amine (or its salt) is dissolved in dichloroethane (3 ml/mmol) and 3 equivalents of aqueous formalin followed by nabh(oac)$_3$ (4 equivalents) are added to this solution. The reaction mixture is vigorously stirred for 2-3 hours at room temperature (TLC control), after which time the crude product is isolated in the same manner as it is described in the General Procedure VI.

General Procedure XV
N-sulfonylation of Secondary amine

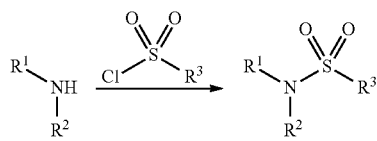

Starting amine, triethylamine (6 equivalents), sulfonyl chloride (3 equivalents) are dissolved in anhydrous pyridine (5 ml/mmol of starting material) and the resulting red-orange solution is stirred at room temperature for 2 hours. Ethylene diamine (3 equivalents with respect to the starting material) is then added and the reaction mixture is stirred for further 12 hrs at room temperature, after which time it is diluted with ethyl acetate (4 times amount of the pyridine used) and washed with saturated sodium bicarbonate and brine. It is further dried with anhydrous mgso$_4$, filtered, and the solvent is removed in vacuo. The crude product usually needs further purification either by crystallization or silica-gel chromatography.

General Procedure XVI
Deprotection of Allyloxycarbonyl (Alloc-) Group

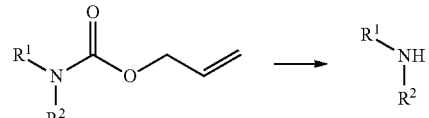

To a solution of Alloc-protected amine in anhydrous, degassed dichloromethane (5 mL/mmol), 5 mol % of Pd(PPh$_3$)$_4$ and phenylsilane (10 equivalents) are added. The reaction mixture is vigorously stirred for 1-3 hours at room temperature (TLC control). After this 2 M HCl is added to the reaction and phases are separated. The aqueous phase is alkalized to pH 12 with 6 M NaOH and extracted 3 times with dichloromethane. Combined organic extracts are dried over anhydrous MgSO$_4$, filtered and the solvent is removed in vacuo providing the crude amine that is usually sufficiently pure to be used in the next step.

General Procedure XVII

Formation of the sulfinimine from aldehyde and chiral sulfonamide

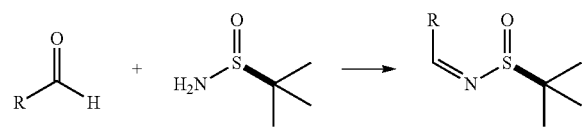

A solution of aldehyde (S or R)-2-methyl-2-propanesulfinamide (1 equivalent), Ti(OEt)$_4$ (2 equivalents) in anhydrous dichloromethane (2 mL/mmol) is refluxed for 2 hours, then slightly heated overnight with stirring. Anhydrous MgSO$_4$ is added (200 mg/l mL of solvent used) and after 15 minutes the reaction is filtered through a pad of Celite. The filtrate is concentrated and the crude product is purified by column chromatography in AcOEt/hexanes solvent system.

General Procedure XVIII

Addition of an allyl-Grignard reagent to the chiral sulfinimine

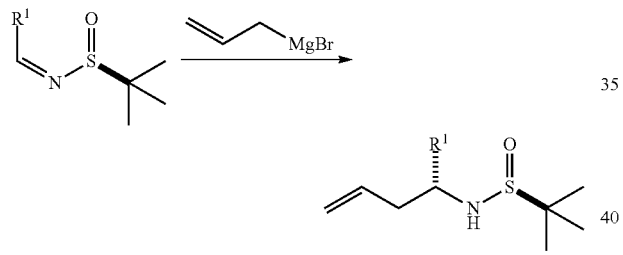

To a cooled (−20° C.) solution of optically pure (S)-tert-butylsulfimine in dichloromethane (2 mL/mmol), a solution of appropriate Grignard reagent (1.5 equivalent, 1 M in diethyl ether or THF) is added dropwise. Upon completion of the addition, the cooling bath is removed and the reaction is allowed to warm to room temperature. After this reaction mixture is poured into a saturated solution of ammonium chloride and extracted 3 times with diethyl ether. Combined organic extracts are washed with brine, dried over anhydrous MgSO$_4$, filtered and concentrated. The crude product is purified by column chromatography in AcOEt/hexanes solvent system.

General Procedure XIX

N-alkylation of the chiral homoallylsulfinamide with (Substituted)allyl bromide

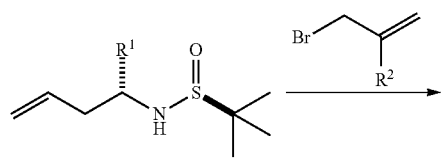

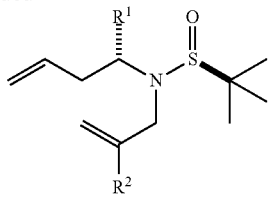

To a solution of sulfinamide in DMF (2 mL/mmol), sodium hydride (2 equivalents) is added. After 20 minutes the (substituted)allyl bromide (1.5 equivalent) is added dropwise and the reaction mixture is allowed to stir for 1 hour. After this time the reaction mixture is poured into a saturated solution of ammonium chloride and extracted several times with diethyl ether. Combined organic extracts are washed with brine, dried over anhydrous MgSO$_4$, filtered and concentrated. The crude product is purified by column chromatography in AcOEt/hexanes solvent system.

General Procedure XX

Ring Closing metathesis of the N-allylated chiral homoallylsulfinamide

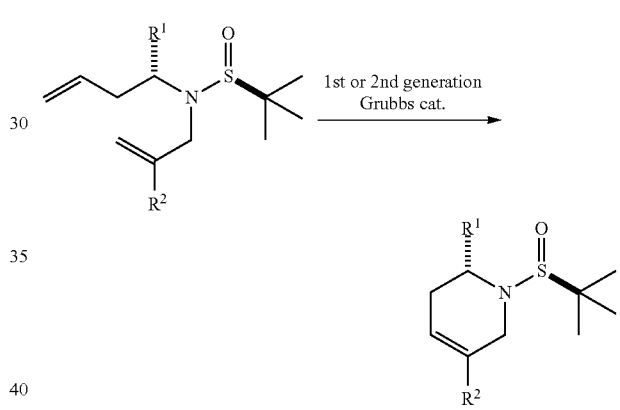

To a solution of starting material in dichloromethane (20 mL/mmol) 1$^{st}$ or 2$^{nd}$ generation Grubbs catalyst (5 mol %) is added and the reaction mixture is refluxed for 1.5 hours. After this time, reaction mixture is cooled down and concentrated. The desired product is isolated by silica-gel column chromatography in AcOEt/hexanes solvent system.

General Procedure XXI

Alkylation of the hydroxyl Group with alkyl halide

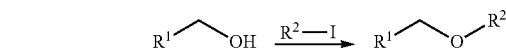

To a solution of alcohol in dry THF (10 mL/mmol), sodium hydride (3 equivalents) is added. After 5 minutes an appropriate alkyl halide (1.5 equivalents) is added and the reaction mixture is stirred at room temperature full consumption of starting material (TLC control). It is then poured into a saturated solution of ammonium chloride and extracted 3 times with diethyl ether. Combined organic extracts are washed with brine, dried over anhydrous MgSO$_4$, filtered and concentrated. The crude product is purified by column chromatography in AcOEt/hexanes solvent system.

General Procedure XXII
Formation of Weinreb amide from carboxylic acid and N,O-dimethylhydroxylamine hydrochloride with the use of the amide Forming Reagent

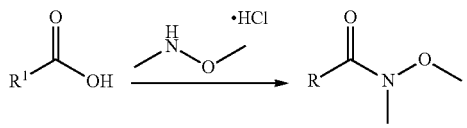

To a solution of carboxylic acid in dichloromethane (2 mL/mmol), DIPEA (2.1 equivalents) is added, followed by N,O-dimethylhydroxylamine hydrochloride (1.1 equivalent). TBTU (1.1 equivalent) is added to the reaction mixture and reaction is stirred at room temperature for the time necessary for the complete consumption of the starting material (usually 16-24 hours) as judged by TLC. Reaction mixture is diluted with dichloromethane, then washed with 2 M HCl and brine. Organic layer is dried over anhydrous MgSO$_4$, filtered and concentrated. Product is purified by silica-gel column chromatography in AcOEt/hexanes system.

General Procedure XXIII
Coupling of Boc-protected aminoalcohol with phenol Via Mitsunobu Reaction

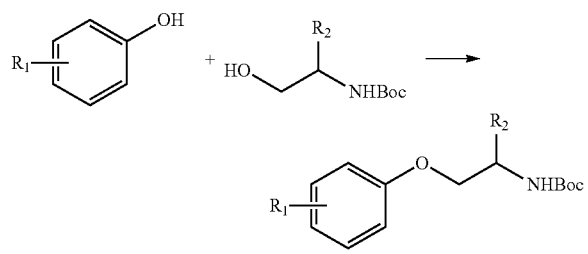

To a solution of phenol (1 mmol) and Boc-protected aminoalcohol (1.25 equivalent) in dry THF (3 mL/mmol) under atmosphere of inert gas (usually argon), triphenylphosphine (1.5 equivalent) is added and the mixture is cooled down to −15° C. DIAD (1.5 equivalent) is added dropwise at this temperature, then cooling bath is removed and the reaction is stirred at room temperature for 24 hours. The reaction mixture is concentrated and the oily residue is purified by silica-gel column chromatography in AcOEt/hexanes system.

General Procedure XXIV
Reduction of Weinreb amide to the Corresponding aldehyde

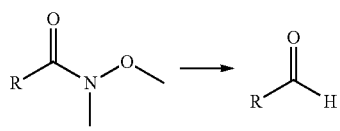

To a solution of Weinreb amide (1 mmol) in dry THF (5 mL/mmol) under atmosphere of inert gas, lithium aluminum hydride is added at 0° C. and the mixture is stirred at this temperature until starting material is consumed (usually 30 minutes-2 hours) as judged by TLC. Reaction is quenched with saturated aqueous solution of potassium hydrogen sulfate and product extracted with diethyl ether (4×10 mL).

Combined organic layers are washed with brine, dried over anhydrous MgSO$_4$, filtered and concentrated. The crude aldehyde is sufficiently pure to be directly used in the next step.

General Procedure XXV
Removal of tert-butoxycarbonyl (Boc-) from amine Followed by Cyclisation of Seven-membered Ring (i.e. benzoxazepine) and Subsequent Reduction of imine to amine

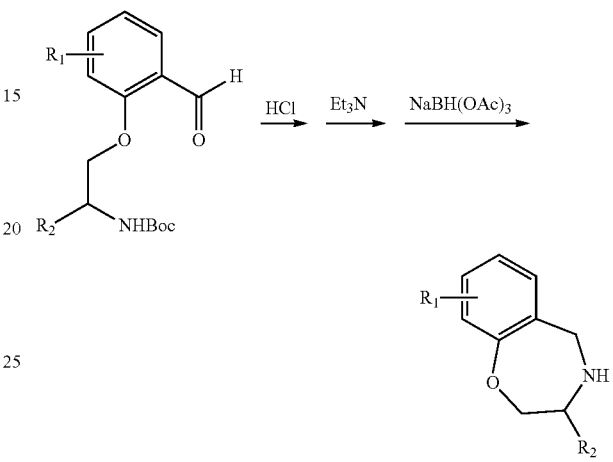

The crude amine hydrochloride salt of the typical Boc-group removal procedure (see the General Procedure VII) is suspended in 1,2-dichloroethane (2 mL/mmol) triethylamine (1.1 equivalent) is added and the mixture is heated to 70° C. for 1-2 hours. After cooling down to room temperature sodium triacetoxyborohydride (2.5 equivalents) is added and the mixture is stirred overnight. The excess of reducing agent is decomposed with 5% aqueous solution of sodium hydrogen carbonate (twice the volume of DCE used) and the product is extracted with dichloromethane. The layers are separated and the aqueous one is additionally extracted with dichloromethane. Combined organic extracts are dried over anhydrous MgSO$_4$, filtered and concentrated. The crude amine is sufficiently pure to be used in the next step without additional purification.

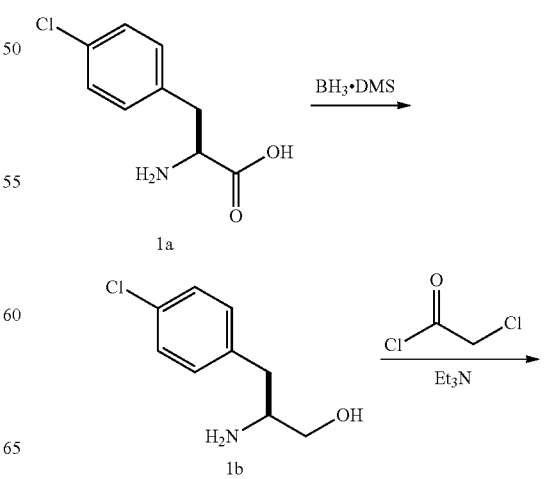

-continued

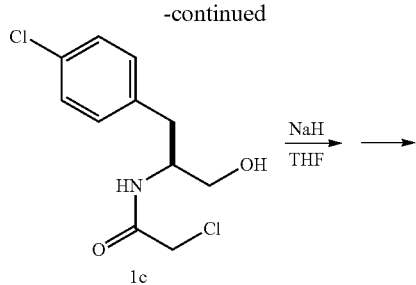
1c

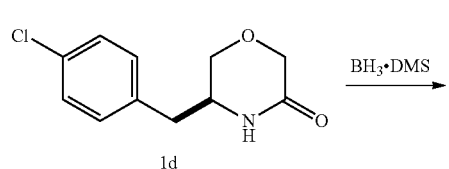
1d

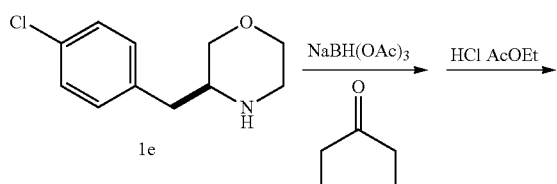
1e

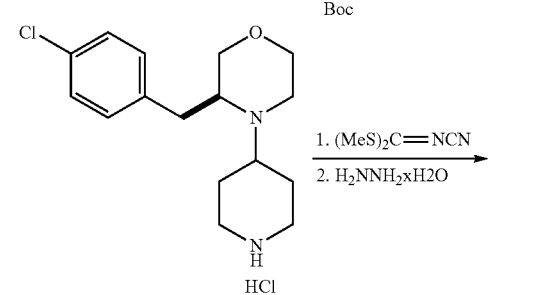
1f

1

Synthesis of Example 1

Example 1

(S)-3-(4-(3-(4-chlorobenzyl)morpholino)piperidin-1-yl)-1H-1,2,4-triazol-5-amine (1)

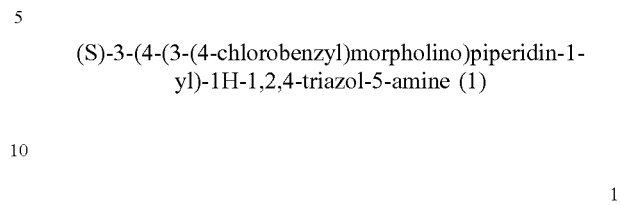

Step 1

Synthesis (2S)-2-amino-3-(4-chlorophenyl)propan-1-ol (1b)

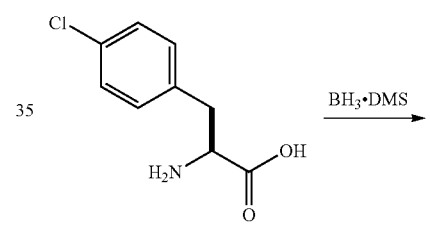
1a

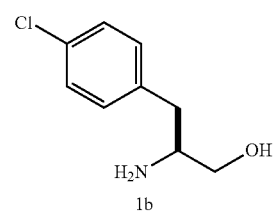
1b

The title compound (1b) was obtained as described in the General Procedure I starting with optically pure L-p-chlorophenalanine ((2S)-2-amino-3-(4-chlorophenyl)propanoic acid)—1a. 8.6 g of compound 1b (87% yield, 46.5 mmol) was synthesized.

ESI-MS m/z for $C_9H_{12}ClNO$ found 185.7/187.7 $(M+1)^+$ $^1$H NMR (CDCl$_3$, 500 MHz) δ 7.28 (d, J=8.3 Hz, 2H), 7.11 (d, J=8.3 Hz, 2H), 3.62 (dd, J=10.6, 3.8 Hz, 1H), 3.37 (dd, J=10.5, 6.9 Hz, 1H), 3.11-3.07 (brs, 1H), 2.76 (dd, J=13.6, 5.4 Hz, 1H), 2.50 (dd, J=13.6, 8.6 Hz, 1H).

Step 2

Synthesis of 2-chloro-N-[(1S)-1-(4-chlorobenzyl)-2-hydroxyethyl]acetamide (1c)

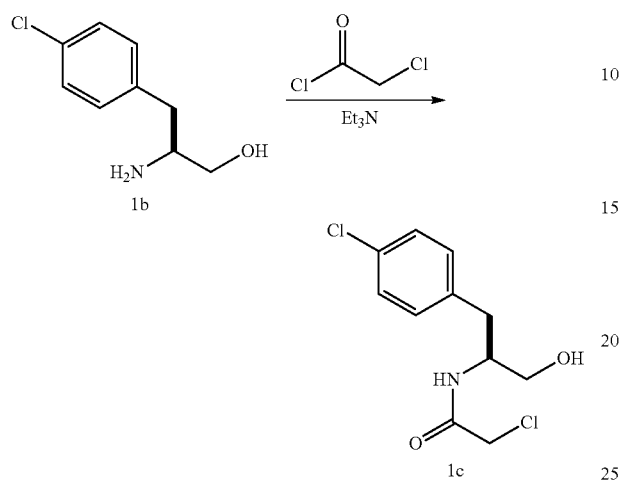

The title compound was obtained from compound 1b as described in the General Procedure II. 85% yield was obtained.

ESI-MS m/z for $C_{11}H_{13}Cl_2NO_2$, found 262.2/264.2 (M+1)$^+$ $^1$H NMR (CDCl$_3$, 500 MHz) δ 8.05 (d, J=8.5 Hz, 1H), 7.27 (d, J=8.3 Hz, 2H), 7.18 (d, J=8.3 Hz, 2H), 4.85 (t, J=5.5 Hz, 1H), 3.95 (s, 2H), 3.88-3.81 (m, 1H), 3.36-3.27 (m, 2H), 2.8 (dd, J=5.5, 13.7 Hz, 1H), 2.6 (dd, J=8.6, 13.7 Hz, 1H)

Step 3

Synthesis of (5S)-5-(4-chlorobenzyl)morpholin-3-one (1d)

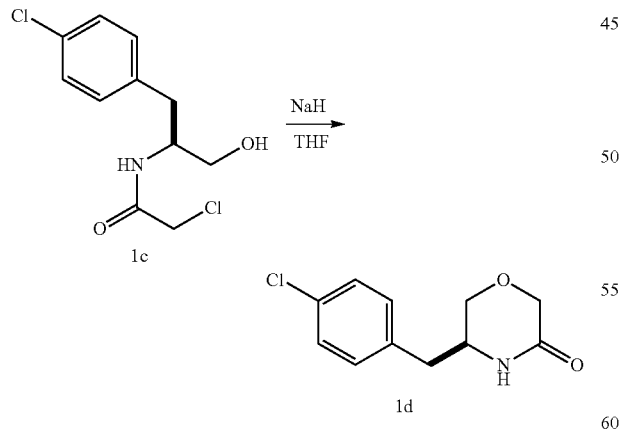

The title compound (1d) was obtained from compound 1c according to the General Procedure IV in 59% yield.

ESI-MS m/z for $C_{11}H_{12}ClNO_2$; found 226.2/228.2 (M+1)$^+$ $^1$H NMR (CDCl$_3$, 500 MHz) δ 7.30 (d, J=8.3 Hz, 2H), 7.11 (d, J=8.3 Hz, 2H), 4.15 (d, J=2.8 Hz, 2H), 3.87 (dd, J=3.5, 11.8 Hz, 1H), 3.73-3.67 (m, 1H), 3.57-3.52 (m, 1H), 2.85 (dd, J=6.0, 13.7 Hz, 1H), 2.71 (dd, J=8.6, 13.7 Hz, 1H)

Step 4

Synthesis of (5S)-5-(4-chlorobenzyl)morpholine (1e)

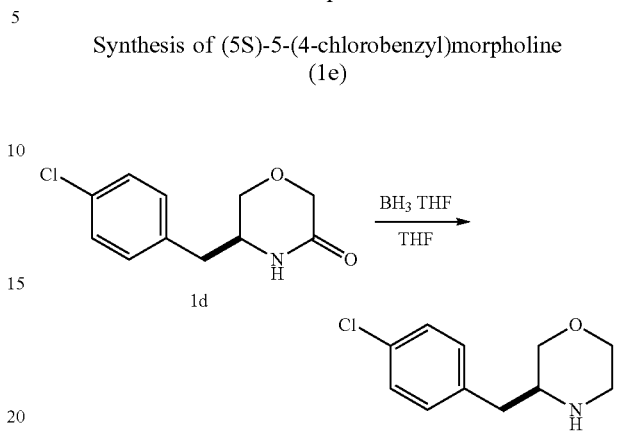

The title compound (1e) was obtained from compound 1d according to the General Procedure V in 64% yield.

ESI-MS m/z for $C_{11}H_{14}ClNO$; found 212.2/214.2 (M+1)$^+$ $^1$H NMR (CDCl$_3$, 500 MHz) δ 7.28 (d, J=8.3 Hz, 2H), 7.11 (d, J=8.3 Hz, 2H), 3.81-3.75 (m, 2H), 3.55-3.49 (m, 1H), 3.24 (t, J=10 Hz, 1H), 3.0-2.98 (m, 1H), 2.89-2.8 (m, 2H), 2.62 (dd, J=4.9, 13.5 Hz, 1H), 2.44 (dd, J=9.2, 13.5 Hz, 1H)

Step 5

Synthesis of (S)-3-(4-chlorobenzyl)-4-(piperidin-4-yl)morpholine (1f)

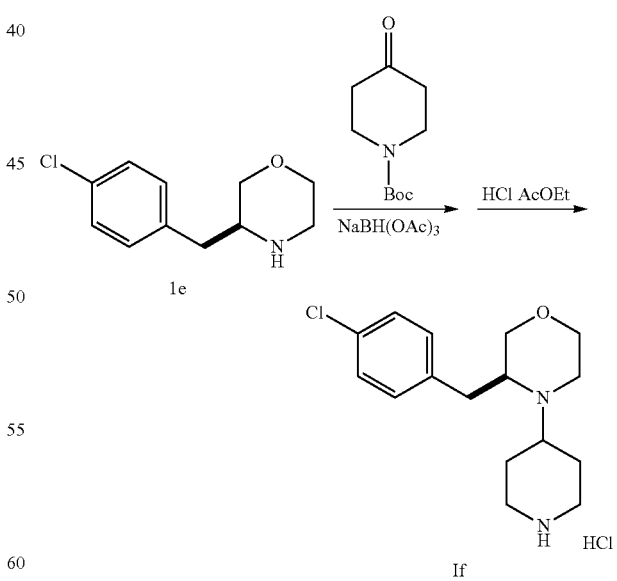

The product of Step 4 (compound 1e) was subjected to the reductive amination reaction with N-Boc-piperid-4-one as described in the General Procedure VI. The crude product of reductive amination was directly subjected to removal of Boc-group according to the General Procedure VII. The such obtained crude hydrochloride salt of the title compound was taken between ethyl acetate and 2 M NaOH and the organic layer was separated and washed with 2 M NaOH, water and brine. It was dried over anhydrous $MgSO_4$ and filtered and the solvent was removed in vacuo yielding product (1f) sufficiently pure to be used in the next step. 78% yield over two steps was obtained.

ESI-MS m/z for $C_{16}H_{23}ClN_2O$; found 295.1/297.1 $(M+1)^+$ $^1$H NMR ($CDCl_3$, 500 MHz) δ 7.26 (d, J=8.1 Hz, 2H), 7.11 (d, J=8.1 Hz, 2H), 3.75-3.71 (m, 2H), 3.49 (dd, J=2.6, 11.2 Hz, 1H), 3.41 (dd, J=5.5, 11.2 Hz, 1H), 3.2-3.14 (m, 2H), 2.97-2.93 (m, 1H), 2.86 (dd, J=4.0, 13.5 Hz, 1H), 2.84-2.8 (m, 1H), 2.76-2.7 (m, 2H), 2.68-2.6 (m, 2H), 2.58-2.53 (m, 1H), 1.88-1.84 (m, 1H), 1.82-1.77 (m, 1H), 1.51 (dq, J=3.8, 11.8 Hz, 1H), 1.41 (dq, J=3.8, 11.8 Hz, 1H).

Step 6

Synthesis of (S)-5-(4-(3-(4-chlorobenzyl)morpholino)piperidin-1-yl)-4H-1,2,4-triazol-3-amine (1)

The title compound was synthesized according to the General Procedure VIII starting from compound 1f. 56% yield was obtained.

ESI-MS m/z for $C_{18}H_{25}ClN_6O$; found 377.1/379.1 $(M+1)^+$ $^1$H NMR (DMSO-$d_6$, 700 MHz) δ 7.31 (d, J=8.3 Hz, 2H), 7.20 (d, J=8.3 Hz, 2H), 5.70 (brs, 2H), 3.80 (brs, 2H), 3.59-3.53 (m, 2H), 3.36-3.33 (m, 1H), 3.24-3.21 (m, 1H), 2.89-2.83 (m, 2H), 2.80 (brs, 1H), 2.69-2.62 (m, 3H), 2.53-2.51 (m, 2H), 1.77-1.73 (m, 1H), 1.69-1.65 (m, 1H), 1.47 (dq, J=4.0, 12.0 Hz, 1H), 1.34 (dq, J=4.2, 12.0 Hz, 1H).

Example 2

Synthesis of 5-(4-(3-(4-chlorobenzyl)morpholino) piperidin-1-yl)-4H-1,2,4-triazol-3-amine (2)

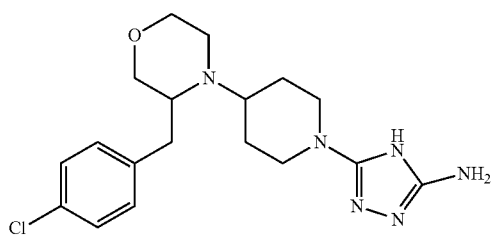

2

The title compound 2 was obtained (51% overall yield) the similar way to Example 1 starting with racemic p-chlorophenylalanine (2-amino-3-(4-chlorophenyl)propanoic acid).

ESI-MS m/z for $C_{18}H_{25}ClN_6O$; 376.9 found 377.1/379.1 $(M+1)^+$ $^1$H NMR (DMSO-$d_6$, 700 MHz) δ 7.31 (d, J=8.3 Hz, 2H), 7.20 (d, J=8.3 Hz, 2H), 5.70 (brs, 2H), 3.80 (brs, 2H), 3.59-3.53 (m, 2H), 3.36-3.33 (m, 1H), 3.24-3.21 (m, 1H), 2.89-2.83 (m, 2H), 2.80 (brs, 1H), 2.69-2.62 (m, 3H), 2.53-2.51 (m, 2H), 1.77-1.73 (m, 1H), 1.69-1.65 (m, 1H), 1.47 (dq, J=4.0, 12.0 Hz, 1H), 1.34 (dq, J=4.2, 12.0 Hz, 1H).

Example 3

Synthesis of (S)-5-(4-(3-(4-bromobenzyl)morpholino)piperidin-1-yl)-4H-1,2,4-triazol-3-amine (3)

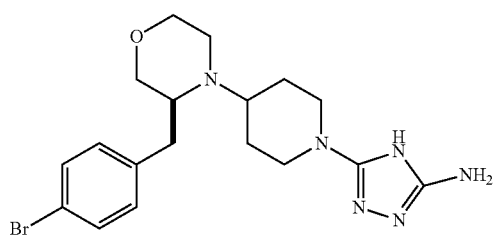

3

The title compound 3 was obtained (62% overall yield) according to a procedure similar to example 1, starting with L-p-bromophenylalanine ((2S)-2-amino-3-(4-bromophenyl) propanoic acid).

ESI-LCMS m/z for $C_{18}H_{25}BrN_6O$ found 421.5/423.5 $(M+1)$ $^1$H NMR (DMSO-$d_6$, 500 MHz) δ 7.50 (d, J=8.3 Hz, 2H), 7.21 (d, J=8.3 Hz, 2H), 3.84 (brs, 2H), 3.73-3.70 (m, 1H), 3.69 (brs, 1H), 3.67 (brs, 1H), 3.58-3.53 (m, 1H), 3.36-3.31 (m, 1H), 3.26 (brs, 1H), 3.17-3.13 (m, 1H), 2.96-2.88 (m, 2H), 2.81-2.76 (m, 1H), 2.02 (brs, 2H), 1.75-1.62 (m, 2H).

Example 4

Synthesis of 5-(4-((2S,5S)-5-(4-chlorobenzyl)-2-methylmorpholino)piperidin-1-yl)-4H-1,2,4-triazol-3-amine (4)

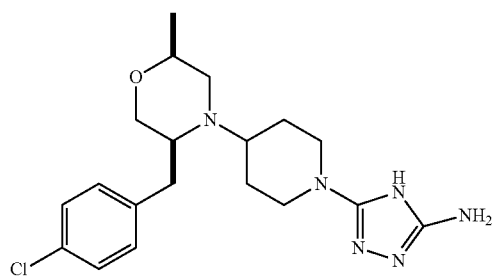

4

Step 1

Synthesis of (R)-2-bromo-N-((S)-1-(4-chlorophenyl)-3-hydroxypropan-2-yl)propanamide (4a)

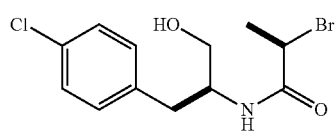

4a (2S)-2-amino-3-(4-chlorophenyl)propan-1-ol (1b) was coupled with (R)-2-bromopropionic acid in a way described in the General Procedure III using TBTU as an amide bond forming reagent. 1.1 g of the title compound 4a was obtained from 1.0 g of the starting material (64% yield, white solid after chromatography on silica-gel using DCM/MeOH 100:1 solvent system.

ESI-MS m/z for $C_{12}H_{15}BrClNO_2$ found 320.7/322.7 $(M+1)^+$ $^1$H NMR (CDCl$_3$, 500 MHz) δ 7.25 (d, J=8.2 Hz, 2H), 7.14 (d, J=8.2 Hz, 2H), 6.58 (d, J=6.7 Hz, 1H), 4.33 (dd, J=14.1, 7.1 Hz, 1H), 4.13-4.06 (m, 1H), 3.69-3.64 (m, 1H), 3.61-3.57 (m, 1H), 2.90-2.81 (m, 2H), 2.17 (brs, 1H), 1.82 (d, J=6.9 Hz, 3H).

Step 2

Synthesis of (2S,5S)-5-(4-chlorobenzyl)-2-methyl-morpholin-3-one (4b)

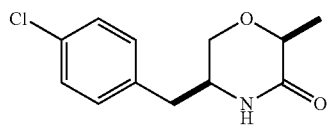

The title compound (4b) was obtained from 1.1 g of compound 4a according to the General Procedure IV in 79% yield (2.71 mmol, 650 mg). Crude product of 92% purity by HPLC was used directly in a subsequent step ESI-LCMS m/z for $C_{12}H_{14}ClNO_2$ found 240.1/242.1 $(M+1)+$ $^1$H NMR (CDCl$_3$, 500 MHz) δ 7.27 (d, J=8.2 Hz, 2H), 7.10 (d. J=8.2 Hz, 2H), 6.13 (brs, 1H), 4.18 (m, 1H), 3.76 (d, J=3.0 Hz, 2H), 3.55-3.50 (m, 1H), 2.91-2.83 (m, 2H), 1.46 (d, J=6.9 Hz, 3H)

Step 3

Synthesis of (2S,5S)-5-(4-chlorobenzyl)-2-methyl-morpholine (4c)

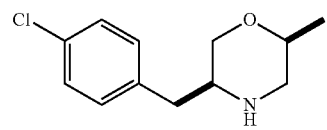

The title compound (4c) was obtained from 1.1 g of the morpholinone 4b according to the General Procedure V in 90% yield (>95% purity).

ESI-MS m/z for $C_{12}H_{16}ClNO$ found 226.4/228.4 $(M+1)^+$ $^1$H NMR (DMSO-d$_6$+D$_2$O; 500 MHz) δ 7.33 (d, J=8.3 Hz, 2H), 7.23 (d, J=8.3 Hz, 2H), 3.50-3.48 (m, 1H), 3.49-3.47 (m, 2H), 2.87-2.81 (m, 1H), 2.80-2.76 (m, 2H), 2.65 (dd, J=12.4 Hz, 8.3 Hz, 1H), 2.58 (dd, J=12.4 Hz, 3.0 Hz, 1H), 1.09 (d, J=6.2 Hz, 3H)

Step 4

Synthesis of tert-butyl 4-((2S,5S)-5-(4-chlorobenzyl)-2-methylmorpholino)piperidine-1-carboxylate (4d)

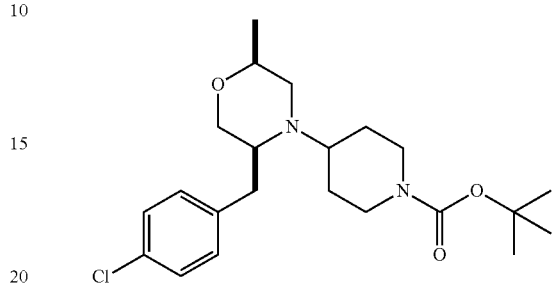

The title compound (4d) was obtained from 4c (6.02 mmol, 1.36 g) according to the General Procedure VI. After chromatography in DCM/MeOH 200:1 solvent system 4d was obtained in 45% yield (2.71 mmol, 1.1 g).

ESI-LCMS m/z for $C_{22}H_{33}ClN_2O_3$ found 409.2/411.2 $(M+1)^+$ $^1$H NMR (DMSO-d$_6$+D$_2$O; 500 MHz) δ 7.33 (d, J=8.3 Hz, 2H), 7.21 (d, J=8.3 Hz, 2H), 3.84 (brs, 2H), 3.51-3.46 (m, 1H), 3.44-3.40 (m, 1H), 3.35-3.33 (m, 1H), 2.90-2.85 (m, 3H), 2.82 (brs, 1H), 2.73-2.69 (m, 2H), 2.64-2.60 (m, 1H), 2.28-2.25 (m, 1H), 1.90-1.85 (m, 2H), 1.40 (s, 9H), 1.26-1.21 (m, 1H), 1.20-1.14 (m, 1H), 1.1 (d, J=6.2 Hz, 3H)

Step 5

Synthesis of (2S,5S)-5-(4-chlorobenzyl)-2-methyl-4-(piperidin-4-yl)morpholine hydrochloride (4e)

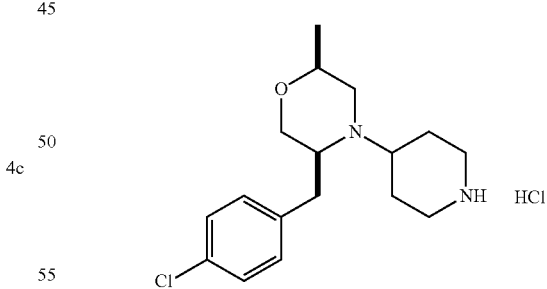

The title compound (4e) was obtained from the compound 4b according to the General Procedure VII in 79% yield, after trituration of the crude product with diethyl ether.

ESI-MS m/z for $C_{17}H_{25}ClN_2O$ found 309.9/311.9 $(M+1)^+$ $^1$H NMR (DMSO-d$_6$, 500 MHz): δ 7.35 (d, J=8.4 Hz, 2H), 7.33 (d, J=8.4 Hz, 2H), 4.04 (brs, 2H), 3.59 (brs, 2H), 3.45 (brs, 1H), 3.40 (m, 1H), 3.39-3.36 (m, 2H), 3.10 (brs, 2H), 2.98 (brs, 1H), 2.87 (brs, 2H), 2.31 (brs, 2H), 2.17 (brs, 2H), 1.21 (d, J=6.2 Hz, 3H)

Step 6

Synthesis of 5-(4-((2S,5S)-5-(4-chlorobenzyl)-2-methylmorpholino)piperidin-1-yl)-4H-1,2,4-triazol-3-amine (4)

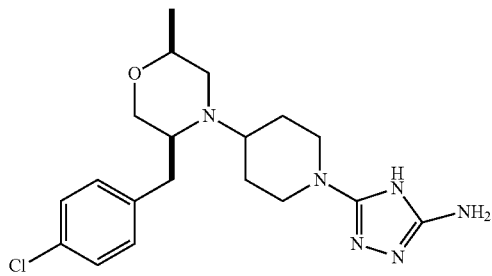

The title compound (4) was obtained from the compound 4e (1.86 mmol, 640 mg) according to the General Procedure VIII in 72% yield (1.34 mmol, 455 mg), after silica-gel chromatography in AcOEt/MeOH (100:1) solvent system followed by crystallization from MeOH/Et$_2$O.

ESI-MS m/z for C$_{19}$H$_{27}$ClN$_6$O found 341.8/343.8 (M+1)$^+$ $^1$H NMR (DMSO-d$_6$, 500 MHz): δ 7.39 (d, J=8.3 Hz, 2H), 7.30 (d, J=8.3 Hz, 2H), 3.87-3.79 (m, 3H), 3.66 (brs, 2H), 3.58 (brs, 1H), 3.52-3.45 (m, 2H), 3.09 (brs, 2H), 3.00-2.93 (m, 2H), 2.92-2.88 (m, 1H), 2.20 (brs, 2H), 1.67 (brs, 2H), 1.20 (d, J=6.2 Hz, 3H)

Example 5

Synthesis of 5-(4-((2S,5S)-5-(4-chlorobenzyl)-2-ethylmorpholino)piperidin-1-yl)-4H-1,2,4-triazol-3-amine (5)

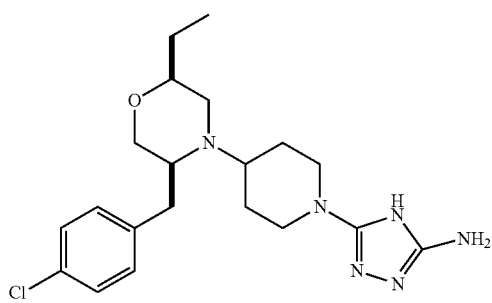

The title compound was prepared in the same manner as Example 4 with the exception that (2R)-2-bromobutanoic acid instead of (2R)-2-bromopropanoic acid was used in the first synthetic step.

ESI-MS m/z for C$_{20}$H$_{29}$ClN$_6$O found 405.1/407.0 (M+1)$^+$, 403.1/405.1 (M−1)$^−$ $^1$H NMR (DMSO-d$_6$+D$_2$O, 500 MHz): δ 7.38 (d, J$_{AA'BB'}$=8.5 Hz, 2H), 7.27 (d, J$_{AA'BB'}$=8.3 Hz, 2H), 3.81 (brd, J=12.8 Hz, 2H), 3.67-3.69 (m, 1H), 3.52-3.56 (m, 4H), 3.38-3.41 (m, 1H), 2.99-3.06 (m, 3H), 2.85-2.93 (m, 2H), 2.15-2.21 (m, 2H), 1.48-1.60 (m, 4H), 0.89 (t, J=7.5 Hz, 3H).

Example 6

Synthesis of 5-(4-((2S,5S)-5-(4-chlorobenzyl)-2-isopropylmorpholino)piperidin-1-yl)-4H-1,2,4-triazol-3-amine (6)

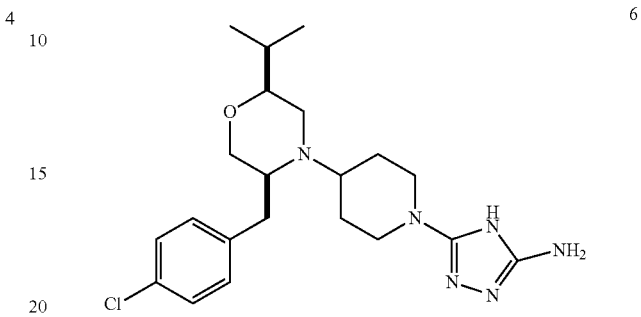

The title compound 6 was prepared in the same manner as Example 4 with the exception that (2R)-2-bromo-3-methylbutanoic acid instead of (2R)-2-bromopropanoic acid was used in the first synthetic step.

ESI-MS m/z for C$_{21}$H$_{31}$ClN$_6$O found 419.0/421.0 (M+1)$^+$ $^1$H NMR (DMSO-d$_6$, 700 MHz): δ 10.15 (s, 1H), 7.45-7.41 (m, 2H), 7.36-7.31 (m, 2H), 7.05 (bs, 2H), 3.88 (t, J=16.8 Hz, 2H), 3.83-3.75 (m, 1H), 3.63-3.53 (m, 3H), 3.49-3.37 (m, 2H), 3.17-3.07 (m, 1H), 3.03 (t, J=12.5 Hz, 1H), 2.94 (t, J=12.8 Hz, 1H), 2.84 (t, J=12.5 Hz, 1H), 2.28 (d, J=12.0 Hz, 1H), 2.22 (d, J=12.2 Hz, 1H), 1.82 (ddd, J=13.7, 9.4, 5.9 Hz, 1H), 1.69-1.59 (m, 2H), 0.97 (d, J=6.9 Hz, 3H), 0.96 (d, J=6.9 Hz, 3H).

Example 7

Synthesis of 5-(4-((2S,5S)-5-(4-chlorobenzyl)-2-isobutylmorpholino)piperidin-1-yl)-4H-1,2,4-triazol-3-amine (7)

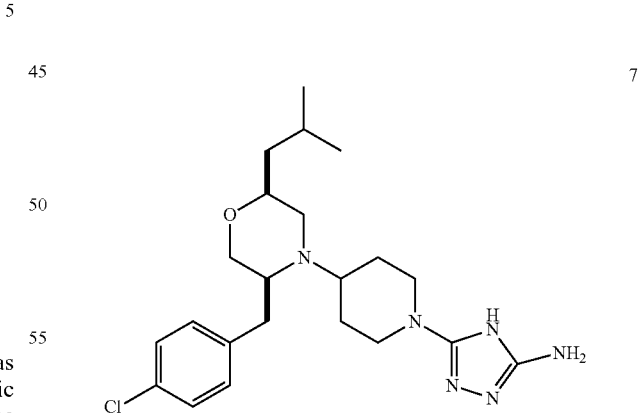

The title compound 7 was prepared in the same manner as Example 4 with the exception that (2R)-2-bromo-4-methylpentanoic acid instead of (2R)-2-bromopropanoic acid was used in the first synthetic step.

ESI-MS m/z for C$_{22}$H$_{33}$ClN$_6$O found 433.1/434.9 (M+1)$^+$ $^1$H NMR (DMSO-d$_6$, 700 MHz): δ 7.43 (d, J=8.4 Hz, 2H), 7.34 (d, J=8.4 Hz, 2H), 6.99 (br s, 1H), 3.89-3.85 (m, 3H), 3.79-3.47 (m, 7H), 3.12 (d, J=7 Hz, 2H), 3.00 (s, 1H), 2.95-2.91 (m, 1H), 2.86-2.83 (m, 1H), 2.23-2.18 (m, 2H), 1.82-1.76 (m, 1H), 1.64-1.59 (m, 2H), 1.53-1.49 (m, 1H), 1.31-1.27 (m, 1H), 0.91-0.87 (m, 6H).

Example 8

Synthesis of (2S,5S)-4-(1-(5-amino-4H-1,2,4-triazol-3-yl)piperidin-4-yl)-5-(4-chlorobenzyl)morpholine-2-carboxamide (8)

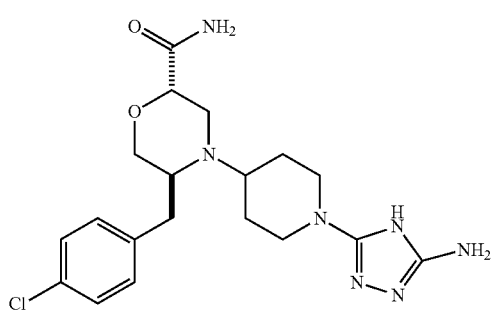

Step 1

Synthesis of (S)-2-(((S)-3-((tert-butyldimethylsilyl)oxy)-2-hydroxypropyl)amino)-3-(4-chlorophenyl)propan-1-ol (8a)

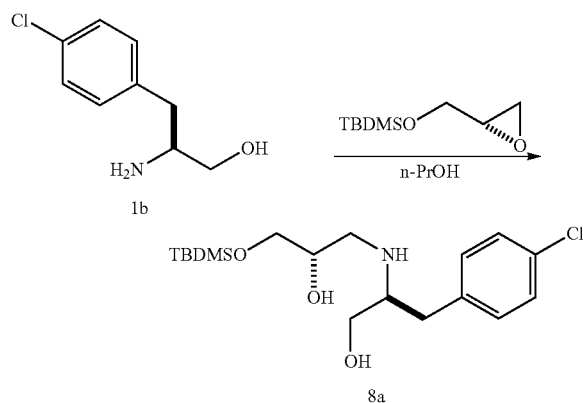

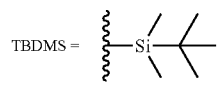

A solution of (S)-tert-butyldimethyl(oxiran-2-ylmethoxy)silane (4.5 mL, 26.54 mmol) and (2S)-2-amino-3-(4-chlorophenyl)propan-1-ol (1b) (4.9 g, 26.39 mmol) in 1-propanol was heated at reflux for 15 hours. The resulting yellow solution was concentrated in vacuo, and the title compound was isolated by flash chromatography on silica-gel (gradient from 0 to 10% of MeOH in AcOEt). 6.06 g (15.6 mmol) of compound 8a was obtained (75% yield).

ESI-MS m/z for $C_{18}H_{32}ClNO_3Si$ found 374.0/376.0 $(M+1)^+$ $^1$H NMR (CDCl$_3$, 500 MHz) δ 7.25 (AA'BB', J=8.3 Hz, 2H), 7.12 (AA'BB', J=8.1 Hz, 2H), 3.72-3.65 (m, 1H), 3.65-3.52 (m, 3H), 3.39-3.31 (m, 1H), 2.9-2.83 (m, 1H), 2.83-2.65 (m, 3H), 2.64-2.58 (m, 2H), 0.88 (s, 9H), 0.05 (s, 6H).

Step 2

Synthesis of (S)-3-((tert-butyldimethylsilyl)oxy)-N-((S)-1-(4-chlorophenyl)-3-((trimethylsilyl)oxy)propan-2-yl)-2-((trimethylsilyl)oxy)propan-1-amine (8b)

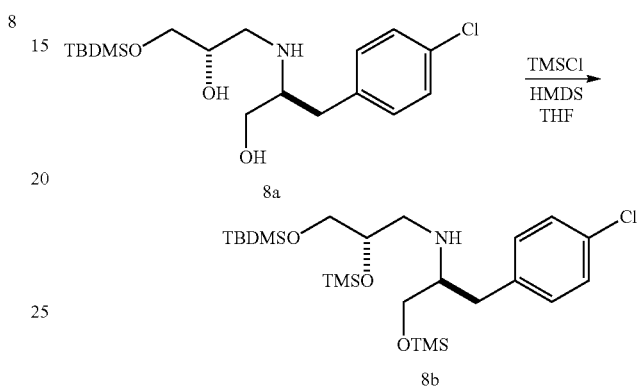

Hexamethyldisilazane (HMDS, 6.9 mL, 33.21 mmol) and trimethylsilyl chloride (TMSCl, 0.4 mL, 3.24 mmol) were added sequentially to a solution of amino diol 8a (6.06 g, 16.2 mmol) in THF (160 mL) at 0° C. After 2 minutes, the cooling bath was removed, and the resulting white suspension was stirred at RT for 70 minutes, then additional portion of TMSCl (0.8 mL, 6.44 mmol) was added and suspension was stirred for further 30 minutes. The reaction mixture was partitioned between ether and a 1/1 mixture of aqueous phosphate buffer solution (0.05 M) and brine (200 mL). The organic layer was separated and the aqueous layer was extracted with ether. The combined organic extracts were dried over MgSO$_4$ and concentrated, providing bis-trimethylsilyl ether 8b as a light yellow liquid (8.3 g, 99% yield).

$^1$H NMR (CDCl$_3$, 500 MHz) δ 7.24 (AA'BB', J=8.1 Hz, 2H), 7.13 (AA'BB', J=7.7 Hz, 2H), 3.78-3.72 (m, 1H), 3.65-3.40 (m, 4H), 2.92-2.51 (m, 4H), 1.87-1.82 (m, 1H), 1.70-1.68 (m, 1H), 0.88 (s, 9H), 0.11 (s, 9H), 0.07 (s, 9H), 0.05 (s, 6H)

Step 3

Synthesis of N-((S)-3-((tert-butyldimethylsilyl)oxy)-2-((trimethylsilyl)oxy)propyl)-N-((S)-1-(4-chlorophenyl)-3-((trimethylsilyl)oxy)propan-2-yl)-4-methylbenzenesulfonamide (8c)

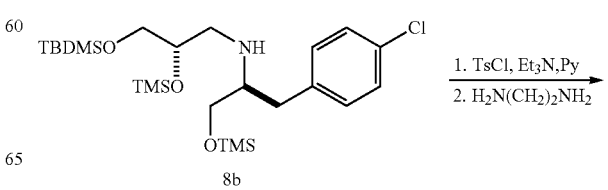

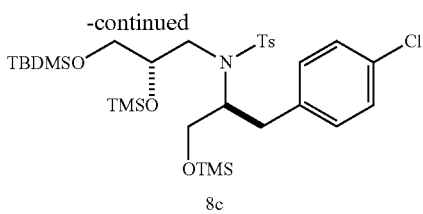

8c

The title compound (8c) was obtained from the compound 8b (8.3 g, 16.01 mmol) according to the General Procedure XV in 71% yield (7.6 g, colorless oil), after silica-gel chromatography in AcOEt/hexane 1:10 solvent system. (8.3 g, 16.01 mmol)

$^1$H NMR (CDCl$_3$, 500 MHz) δ 7.65 (d, 2H, J=8.2 Hz), 7.19 (m, 4H), 7.08 (d, J=8.2 Hz, 2H), 4.14-4.05 (m, 1H), 4.00-3.90 (m, 1H), 3.62-3.52 (m, 2H), 3.51-3.45 (m, 1H), 3.41 (dd, J=5.2, 15.2 Hz, 1H), 3.36 (dd, J=5.1, 11.0 Hz, 1H), 3.14 (dd, J=6.9, 15.4 Hz, 1H), 2.95-2.83 (m, 2H), 2.41 (s, 3H), 0.91 (s, 9H), 0.16 (s, 9H), 0.06 (s, 9H), −0.11 (s, 6H).

Step 4

Synthesis of N-((S)-3-((tert-butyldimethylsilyl)oxy)-2-hydroxypropyl)-N-((S)-1-(4-chlorophenyl)-3-hydroxypropan-2-yl)-4-methylbenzenesulfonamide (8d)

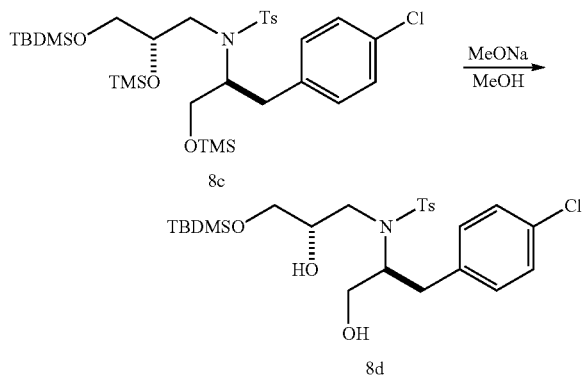

Sodium methoxide (122 mg, 2.26 mmol) was added in one portion to a solution of sulfonamide 8c (7.6 g, 11.3 mmol) in methanol (112 mL) at RT. The resulting solution was stirred for 40 minutes, and then it was concentrated in vacuo. The concentrate was partitioned between ethyl acetate and a 1/1 mixture of saturated aqueous solution of ammonium chloride and brine. The organic layer was separated, and the aqueous layer was extracted with additional portion of ethyl acetate. The combined organics were dried over MgSO$_4$ and dried filtered and concentrated to provide diol 8d as a white solid (5.47 g, 92% yield).

ESI-MS m/z for C$_{25}$H$_{38}$ClNO$_5$SSi found 528.3/530.3 (M+1)$^+$ $^1$H NMR (CDCl$_3$, 500 MHz) δ 7.60 (d, J=8.3 Hz, 2H), 7.23 (d, J=8.1 Hz, 2H), 7.14 (d, J=8.3 Hz, 2H), 6.93 (d, J=8.3 Hz, 2H), 4.09-4.00 (m, 1H), 3.91-3.83 (m, 1H), 3.72-3.57 (m, 4H), 3.51-3.27 (m, 4H), 3.04-2.96 (m, 1H), 2.74 (dd, J=8.2, 13.7 Hz, 1H), 2.58 (dd, J=6.5, 13.7 Hz, 1H), 2.42 (s, 3H), 0.91 (s, 9H), 0.09 (s, 6H).

Step 5

Synthesis of (S)-2-(N-((S)-3-((tert-butyldimethylsilyl)oxy)-2-hydroxypropyl)-4-methylphenylsulfonamido)-3-(4-chlorophenyl)propyl 4-methylbenzenesulfonate (8e)

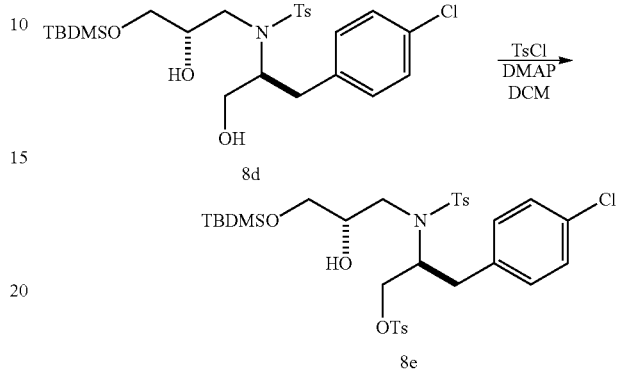

To a solution of diol 8d (5.47 g, 10.35 mmol), triethylamine (Et$_3$N, 5.9 mL, 41.4 mmol) in DCM, 4-dimethylaminopyridine (DMAP, 0.5 g, 4.14 mmol) and tosyl chloride (TsCl, 2.0 g, 10.86 mmol), were added sequentially and the resulting solution was stirred at RT for 1 hour. The reaction was washed with saturated solution of ammonium chloride and brine. The organics were dried over MgSO$_4$ and concentrated. The oily residue was purified by flash chromatography (ethyl acetate/hexanes), affording 8e as a transparent oil (5.6 g, 80% yield).

ESI-MS m/z for C$_{32}$H$_{44}$ClNO$_7$S$_2$Si found 705.4/707.4 (M+Na)$^+$ $^1$H NMR (CDCl$_3$, 500 MHz) δ 7.63 (d, J=8.3 Hz, 2H), 7.53 (d, J=8.3 Hz, 2H), 7.3 (d, J=7.9 Hz, 2H), 7.19 (d, J=8.1 Hz, 2H), 7.09 (d, J=8.3 Hz, 2H), 6.91 (d, J=8.3 Hz, 2H), 4.22 (dd, J=6.7, 10.3 Hz, 1H), 4.13-4.04 (m, 1H), 3.96 (dd, J=5.4, 10.3 Hz, 1H), 3.80-3.72 (m, 1H), 3.58-3.47 (m, 2H), 3.38-3.33 (m, 1H), 3.13 (dd, J=8.1, 15.8 Hz, 1H), 2.95-2.83 (m, 3H), 2.45 (s, 3H), 2.42 (s, 3H), 0.9 (s, 9H), 0.08 (s, 6H)

Step 6

Synthesis of (2S,5S)-2-(((tert-butyldimethyl silyl)oxy)methyl)-5-(4-chlorobenzyl)-4-tosylmorpholine (8f)

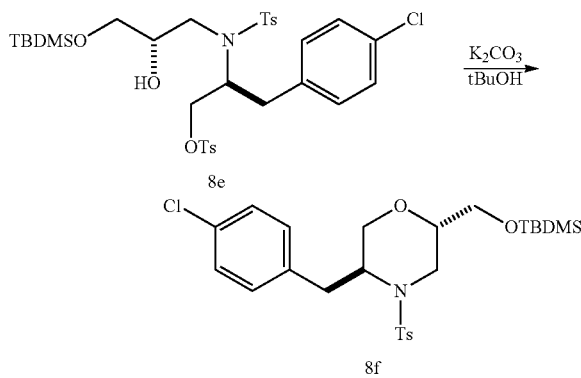

Potassium carbonate (2.3 g, 16.41 mmol) was added to a solution of tosylate 8e (5.6 g, 8.2 mmol) in tert-butyl alcohol (300 mL). The resulting mixture was heated at reflux for 2 hours, and then was partitioned between ethyl acetate and a mixture 1/1 of sat. aqueous solution of ammonium chloride and brine. The organic layer was separated, and the aqueous layer was extracted with additional portion of ethyl acetate. The combined organics were dried over MgSO$_4$ and dried extracts were concentrated. The residue was purified by flash column chromatography (AcOEt/hexanes 1/20) to provide N-tosyl morpholine 8f as a white solid (2.7 g, 66% yield).

ESI-MS m/z for C$_{25}$H$_{36}$ClNO$_4$SSi found 533.4/535.4 (M+Na)$^+$ $^1$H NMR (CDCl$_3$, 500 MHz) δ 7.65 (d, J=8.3 Hz, 2H), 7.29 (d, J=8.1 Hz, 2H), 7.22 (d, J=8.3 Hz, 2H), 7.08 (d, J=8.3 Hz, 2H), 3.84-3.77 (m, 1H), 3.70-3.61 (m, 3H), 3.54 (dd, J=2.6, 12.0 Hz, 1H), 3.49 (dd, J=3.9, 12.8 Hz, 1H), 3.40 (dd, J=3.7, 12.7 Hz, 1H), 3.35 (dd, J=2.4, 12.0 Hz, 1H), 3.03 (dd, J=11.0, 13.3 Hz, 1H), 2.89 (dd, J=4.1, 13.3 Hz, 1H), 2.42 (s, 3H), 0.85 (s, 9H), 0.02 (s, 3H), 0.01 (s, 3H).

Step 7

Synthesis of ((2S,5S)-5-(4-chlorobenzyl)-4-tosyl-morpholin-2-yl)methanol (8g)

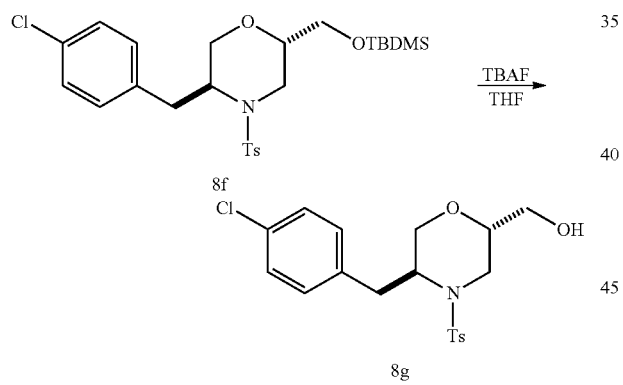

Solution of N-tosyl morpholine 8f (0.63 g, 1.23 mmol) in THF (2 mL) was treated with tetrabutylammonium fluoride (TBAF) (2.5 mL, 2.46 mmol, 1 M in THF) at room temperature for 2 hours. The reaction mixture was absorbed onto silica gel and purified by column chromatography (AcOEt/hexanes, then AcOEt neat) to give alcohol 8g (0.56 g, 99% yield).

ESI-MS m/z for C$_{19}$H$_{22}$ClNO$_4$S found 396.0/398.0 (M+1)$^+$ $^1$H NMR (CDCl$_3$, 500 MHz) δ 7.58 (d, J=8.1 Hz, 2H), 7.27 (d, 8.4 Hz, 2H), 7.18 (d, 8.3 Hz, 2H), 7.03 (d, J=8.3 Hz, 2H), 3.93-3.86 (m, 1H), 3.81-3.66 (m, 4H), 3.53 (dd, J=3.9, 13.1 Hz, 1H), 3.45-3.37 (m, 2H), 3.00-2.87 (m, 2H), 2.43 (s, 3H).

Step 8

Synthesis of (2S,5S)-5-(4-chlorobenzyl)-4-tosylmorpholine-2-carboxylic acid (8h)

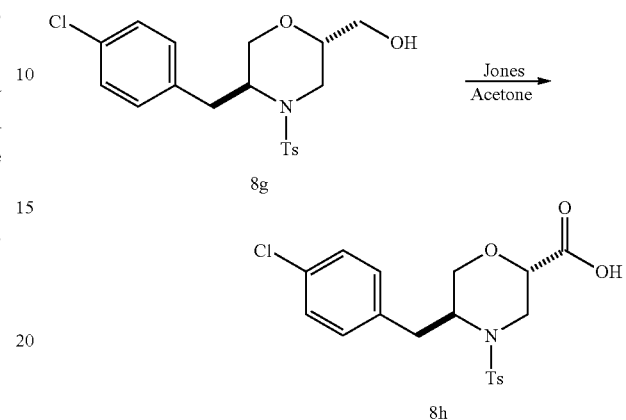

To a cooled to 0° C. solution of alcohol 8g (0.97 g, 2.45 mmol) in acetone, Jones reagent (solution of chromium trioxide in diluted sulfuric acid and acetone) was added dropwise until all substrate was consumed (4.3 mL of 2.6 M Jones reagent). The reaction was then diluted with AcOEt, washed subsequently with water, and a mixture of brine/0.5 M EDTA, dried, and concentrated to yield acid 8h as a white foam (0.92 g, 92% yield).

ESI-MS m/z for C$_{19}$H$_{20}$ClNO$_5$S found 432.0/434.0 (M+Na)$^+$ $^1$H NMR (CDCl$_3$, 500 MHz) δ 7.65 (d, J=7.9 Hz, 2H), 7.30-7.22 (m, 4H), 7.11 (d, J=8.3 Hz, 2H), 4.55-4.49 (m, 1H), 4.08-4.00 (m, 1H), 3.90-3.83 (m, 2H), 3.63-3.50 (m, 2H), 3.14-3.04 (m, 1H), 2.83-2.76 (m, 1H), 2.41 (s, 3H).

Step 9

Synthesis of (2S,5S)-5-(4-chlorobenzyl)-4-tosylmorpholine-2-carboxamide (8i)

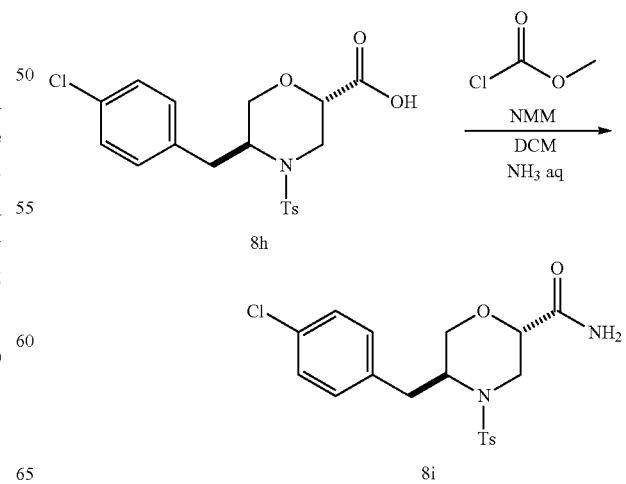

The title compound (8i) was obtained from the compound 8h (0.9 g, 2.19 mmol) according to the General Procedure IX in 92% yield (2.01 mmol, 0.82 g) as a white foam.

ESI-MS m/z for $C_{19}H_{21}ClN_2O_4S$ found 409.0/411.0 $(M+1)^+$, 431.0/433.0 $(M+Na)^+$ $^1$H NMR (CDCl$_3$, 500 MHz) δ 7.72 (d, J=8.1 Hz, 2H), 7.30 (d, J=7.9 Hz, 2H), 7.26 (d, J=7.3 Hz, 2H), 7.13 (d, J=8.3 Hz, 2H), 6.35 (bs, 1H), 5.63 (bs, 1H), 4.30-4.25 (m, 1H), 3.95-3.87 (m, 1H), 3.69-3.58 (m, 2H), 3.57-3.45 (m, 2H), 3.08-3.01 (m, 2H), 2.42 (s, 3H).

Step 10

Synthesis of (2S,5S)-5-(4-chlorobenzyl)morpholine-2-carboxamide (8j)

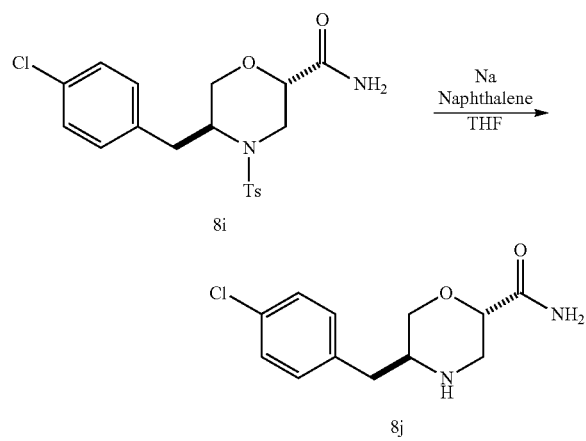

Naphthalene (1.4 g, 10.95 mmol) was added in one portion to a vigorously stirred suspension of sodium (0.31 g, 13.68 mmol) in dry THF (6.8 mL, 0.5 mL/1 mmol Na). The resulting green suspension was stirred for 2 hours at room temperature. Then the green solution was added dropwise into solution of amide 8i (0.82 g, 2.00 mmol) in THF (30 mL) at −70° C. until reaction solution changed to dark-green (5 mL of NaC$_{10}$H$_8$ was added). The reaction was quenched after 10 minutes at −70° C. with sat. solution of ammonium chloride and allowed to warm to RT. Then the mixture was partitioned between ether and mixture of NaHCO$_3$ and brine. The organic phase was separated, dried over MgSO$_4$ and concentrated. The residue was purified by column chromatography AcOEt/hexanes 1/2 then AcOEt neat, then AcOEt/MeOH 2/1 solvent system. Morpholine 8j was obtained as white solid (0.29 g, 56% yield).

ESI-MS m/z for $C_{12}H_{15}ClN_2O_2$ found 255.6/257.6 $(M+1)^+$ $^1$H NMR (CDCl$_3$, 500 MHz) δ 7.28 (d, J=8.3 Hz, 2H), 7.12 (d, 8.1 Hz, 2H), 6.46 (bs, 1H), 5.65 (bs, 1H), 3.98-3.93 (m, 1H), 3.91-3.86 (m, 1H), 3.39-3.29 (m, 2H), 2.99-2.90 (m, 1H), 2.70-2.59 (m, 2H), 2.54-2.45 (m, 1H).

Step 11

Synthesis of tert-butyl 4-((2S,5S)-2-carbamoyl-5-(4-chlorobenzyl)morpholino)piperidine-1-carboxylate (8k)

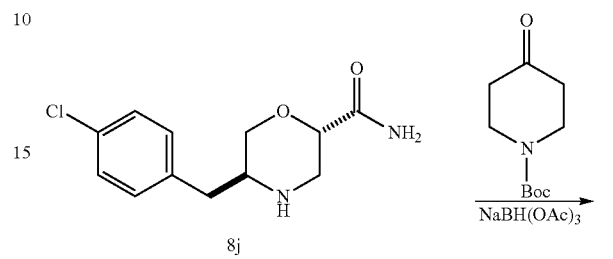

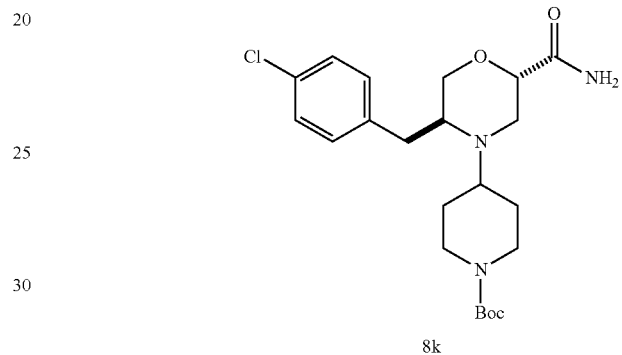

The title compound (8k) was obtained from the compound 8j (0.29 g, 1.13 mmol) according to the General Procedure VI in 32% yield (3.65 mmol, 0.16 g), after silica-gel chromatography (gradient elution AcOEt/hexane 1/1, then AcOEt neat, then AcOEt/MeOH 10/1).

ESI-MS m/z for $C_{22}H_{32}ClN_3O_4$ found 438.2/440.2 $(M+1)^+$

Step 12

Synthesis of (2S,5S)-5-(4-chlorobenzyl)-4-(piperidin-4-yl)morpholine-2-carboxamide hydrochloride (8l)

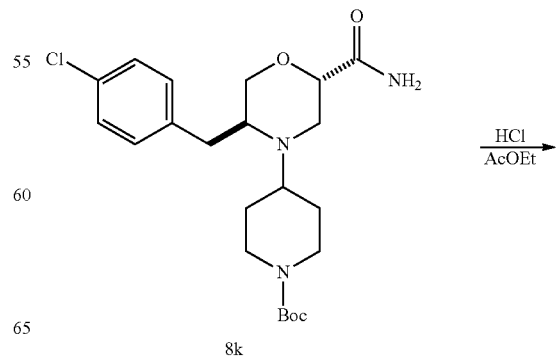

-continued

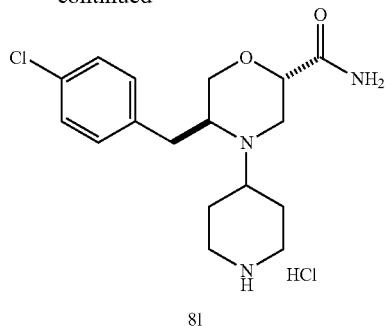

81

The Boc-protecting group was removed from compound 8k (0.37 mmol, 160 mg) according to the General Procedure VII providing the crude title compound 8l in 87% yield (120 mg) that was directly used in the next step.

Step 13

Synthesis of (2S,5S)-4-(1-(5-amino-4H-1,2,4-triazol-3-yl)piperidin-4-yl)-5-(4-chlorobenzyl)morpholine-2-carboxamide (8)

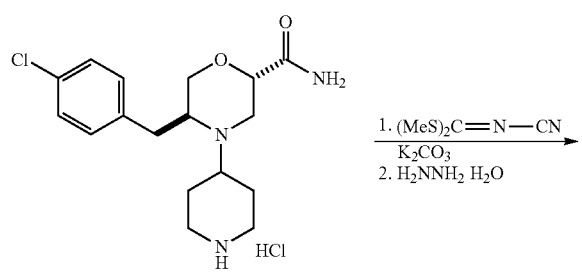

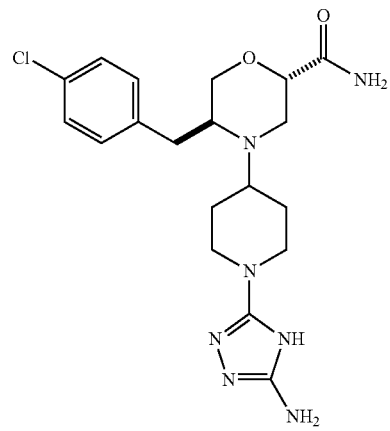

8

Triazole ring was installed on the piperidine 8l according to the General Procedure VIII and the desired product (8) was isolated by preparative HPLC chromatography. Fractions containing the product were combined and freeze-dried providing the title compound 8 as a white powder (28% yield).

ESI-MS m/z for $C_{19}H_{26}ClN_7O_2$ found 420.1/422.1 (M+1)$^+$ $^1$H NMR (DMSO-d$_6$, 500 MHz) δ 7.36 (AA'BB', J=8.3 Hz, 2H), 7.30 (AA'BB', J=8.3 Hz, 2H), 7.21 (bs, 1H), 7.08 (bs, 1H), 3.89-3.84 (m, 1H), 3.81-3.74 (m, 2H), 3.57-3.53 (m, 1H), 3.21-3.18 (m, 1H), 3.11-3.04 (m, 1H), 3.02-2.92 (m, 2H), 2.87-2.80 (m, 1H), 2.73-2.64 (m, 1H), 2.50-2.44 (m, 2H), 2.27-2.19 (m, 1H), 1.67-1.57 (m, 2H), 1.59-1.49 (m, 1H), 1.35-1.27 (m, 1H).

Example 9

(2R,5S)-4-(1-(5-amino-4H-1,2,4-triazol-3-yl)piperidin-4-yl)-5-(4-chlorobenzyl)morpholine-2-carboxamide (9)

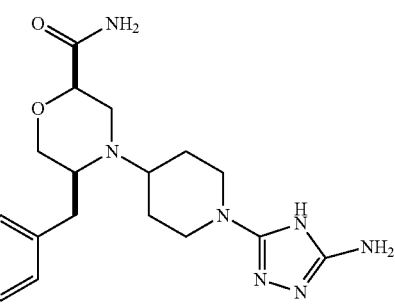

9

With the exception that TBDMS-(R)-glycidyl ether (instead of its (S)-enantiomer) was reacted with (2S)-2-amino-3-(4-chlorophenyl)propan-1-ol (2b) in the first synthetic step, the title compound 9 was prepared in the same manner as Example 8.

ESI-MS m/z for $C_{19}H_{26}ClN_7O_2$ found 420.0/422.0 (M+1)$^+$ $^1$H NMR (DMSO-d$_6$+D$_2$O, 700 MHz) δ 7.38 (d, J=8.5 Hz, 2H), 7.34 (d, J=8.4 Hz, 2H), 4.20 (bs, 2H), 3.83 (d, J=13.8 Hz, 2H), 3.60-3.47 (m,5H), 3.65 (s, 2H), 3.30-3.20 (m, 1H), 3.09-3.02 (m, 2H), 2.91-2.81 (m, 2H), 2.16-2.08(m, 2H), 1.64-1.54(m, 2H).

Example 10

5-(4-((2R,5S)-5-(4-chlorobenzyl)-2-(methoxymethyl)morpholino)piperidin-1-yl)-4H-1,2,4-triazol-3-amine (10)

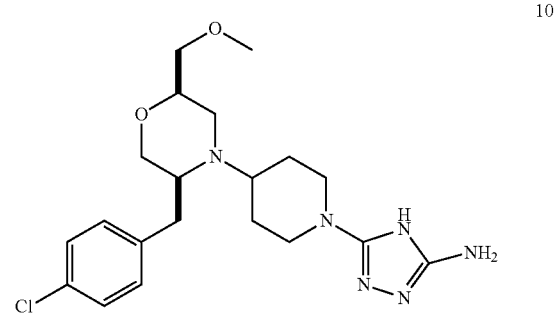

10

Step 1

Synthesis of (2R,5S)-5-(4-chlorobenzyl)-2-(methoxymethyl)-4-tosylmorpholine (10a)

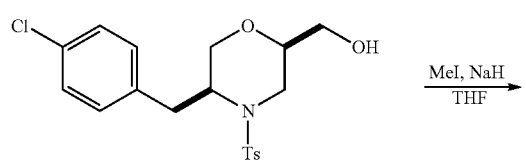

The title compound (10a) was obtained from the compound 8g (0.8 g, 2.02 mmol) according to the General Procedure XXI in 95% yield (1.9 mmol, 0.78 g, white solid), after silica-gel chromatography (gradient elution AcOEt/hexanes 1:10 to 1:1).

ESI-MS m/z for $C_{20}H_{24}ClNO_4S$ found 410.0/412.0 $(M+1)^+$ $^1$H NMR (CDCl$_3$, 500 MHz) δ 7.57 (d, J=8.3 Hz, 2H), 7.24 (d, J=8.1 Hz, 2H), 7.20 (d, J=8.4 Hz, 2H), 7.08 (d, J=8.4 Hz, 2H), 3.97-3.91 (m, 1H), 3.70-3.66 (m, 1H), 3.62 (dd, J=2.8, 13.3 Hz, 1H), 3.59-3.54 (m, 1H), 3.48-3.42 (m, 2H), 3.47-3.41 (m, 1H), 3.37 (s, 3H), 3.06 (dd, J=11.1, 13.1 Hz, 1H), 2.97 (dd, J=9.6, 13.3 Hz, 1H), 2.74 (dd, 5.6, 13.3 Hz, 1H), 2.40 (s, 3H).

Step 2

Synthesis of (2R,5S)-5-(4-chlorobenzyl)-2-(methoxymethyl)morpholine (10b)

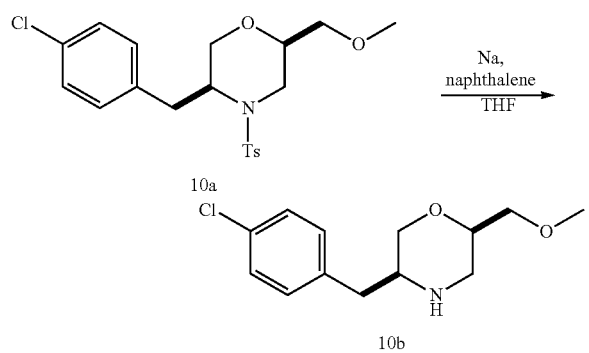

The tosyl protecting group was removed from compound 10a (780 mg, 1.9 mmol) in a manner described earlier for compound 8i. 340 mg of the title compound 10b was obtained in 70% yield.

ESI-MS m/z for $C_{13}H_{18}ClNO_2$ found 255.8/257.8 $(M+1)^+$ $^1$H NMR (CDCl$_3$, 500 MHz) δ 7.27 (AA'BB', J=8.3 Hz, 2H), 7.14 (AA'BB', J=8.3 Hz, 2H), 3.83-3.70 (m, 3H), 3.56 (dd, J=6.4, 10.1 Hz, 1H), 3.45 (dd, J=3.9, 10.1 Hz, 1H), 3.39 (s, 3H), 3.09-3.03 (m, 1H), 3.02-2.95 (m, 2H), 2.90 (dd, J=7.1, 13.3 Hz, 1H), 2.81 (dd, J=3.0, 12.2 Hz, 1H).

Step 3

Synthesis of tert-butyl 4-((2R,5S)-5-(4-chlorobenzyl)-2-(methoxymethyl)morpholino)piperidine-1-carboxylate (10c)

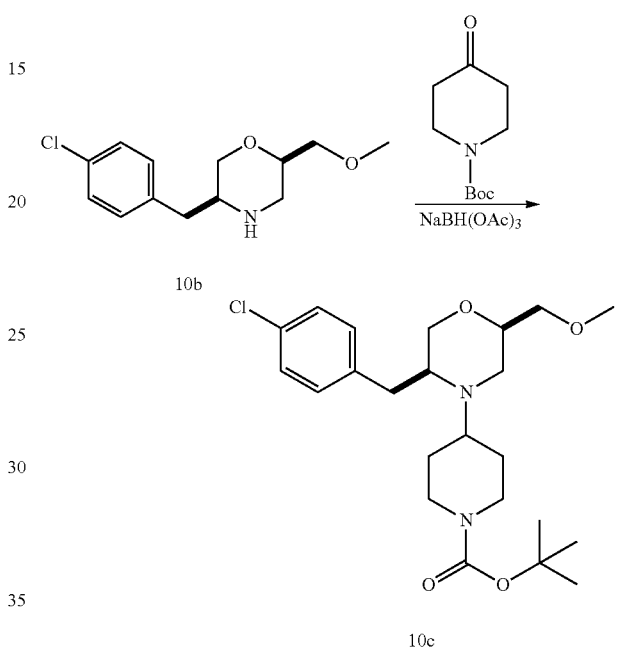

The title compound (10c) was obtained from the compound 10b (1.51 mmol, 340 mg) according to the General Procedure VI in 87% yield.

ESI-MS m/z for $C_{23}H_{35}ClN_2O_4$ found 439.2/441.2 $(M+1)^+$

Step 4

Synthesis of (2R,5S)-5-(4-chlorobenzyl)-2-(methoxymethyl)-4-(piperidin-4-yl)morpholine (10d)

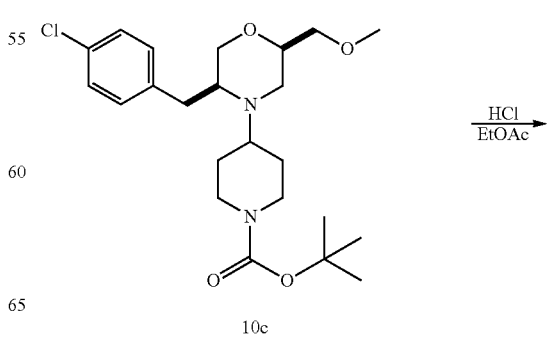

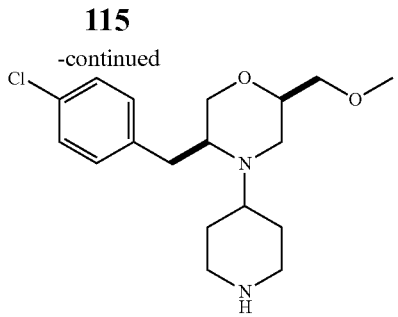

10d

The Boc-protecting group was removed from compound 10c (1.03 mmol, 450 mg) according to the General Procedure VII providing of the title compound 10d (99% yield).

ESI-MS m/z for $C_{18}H_{27}ClN_2O_2$ found 339.0/341.0 $(M+1)^+$

Step 5

Synthesis of 5-(4-((2R,5S)-5-(4-chlorobenzyl)-2-(methoxymethyl)morpholino)piperidin-1-yl)-4H-1,2,4-triazol-3-amine (10)

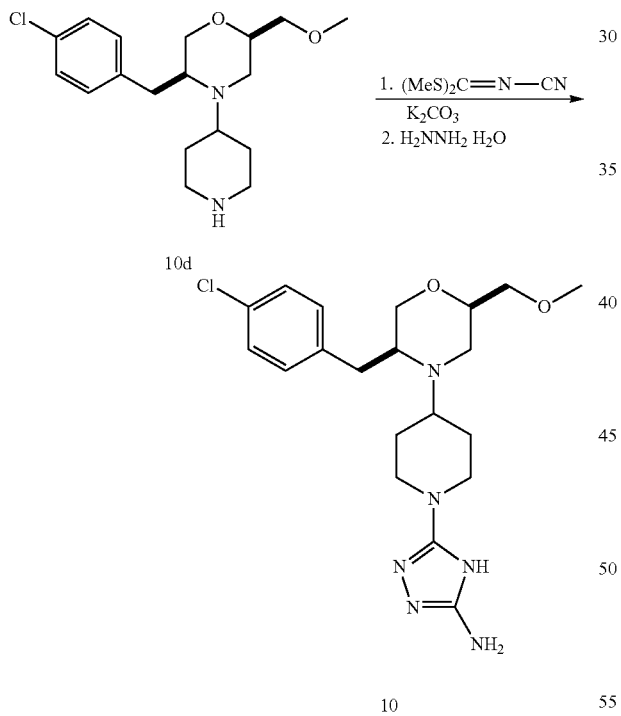

The title compound (10) was synthesized from compound 10d (1.03 mmol, 410 mg) using the General Procedure VIII in 55% yield (0.56 mmol, 237 mg).

ESI-MS m/z for $C_{20}H_{29}ClN_6O_2$ found 421.1/423.1 $(M+1)^+$ $^1$H NMR (DMSO-d$_6$, 500 MHz) δ 7.42 (AA'BB', J=8.3 Hz, 2H), 7.33 (AA'BB', J=8.2 Hz, 2H),3.91-3.80 (m, 4H), 3.64-3.53 (m, 3H), 3.53-3.44 (m, 3H), 3.30 (s, 3H), 3.15-3.02 (m, 3H), 2.94-2.86 (m, 1H), 2.85-2.79 (m, 1H), 2.21-2.12 (m, 2H), 1.66-1.55 (m, 2H).

Example 11

5-(4-((2R,5S)-5-(4-chlorobenzyl)-2-(ethoxymethyl)morpholino)piperidin-1-yl)-4H-1,2,4-triazol-3-amine (11)

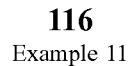

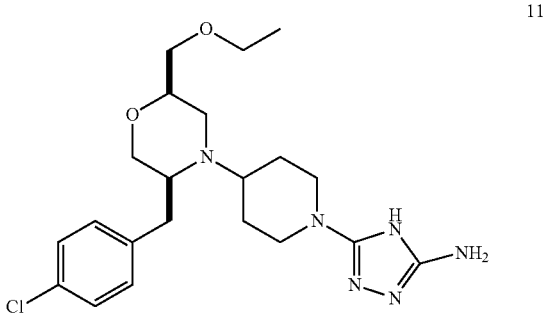

Step 1

Synthesis of (R)-2-bromo-3-(tert-butoxy)-N-((S)-1-(4-chlorophenyl)-3-hydroxypropan-2-yl)propanamide (11a)

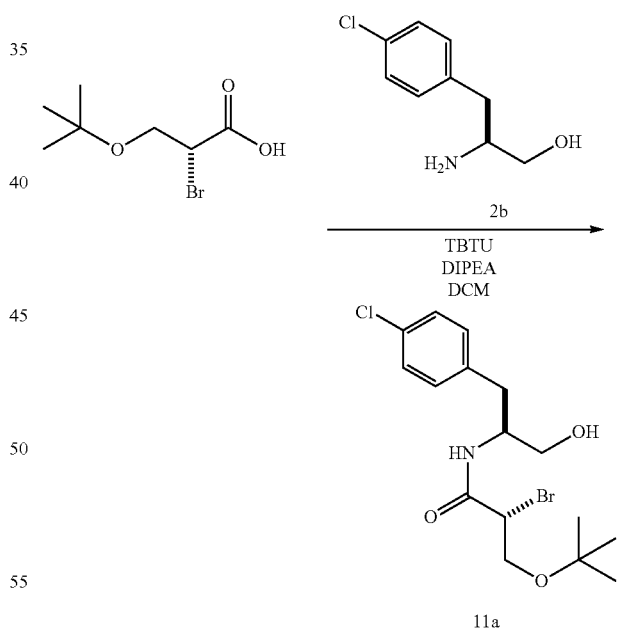

(2S)-2-amino-3-(4-chlorophenyl)propan-1-ol (2b) (10.2 mmol, 1.89 g) was coupled with (2R)-2-bromo-3-tert-butoxypropanoic acid according to the General Procedure III using TBTU as an amide bond forming reagent. Title compound 11a was obtained in 70% yield, 2.96 g).

ESI-MS m/z for $C_{16}H_{23}BrClNO_3$ found 415.3/417.3 $(M+Na)^+$

Step 2

Synthesis of (2S,5S)-2-(tert-butoxymethyl)-5-(4-chlorobenzyl)morpholin-3-one (11b)

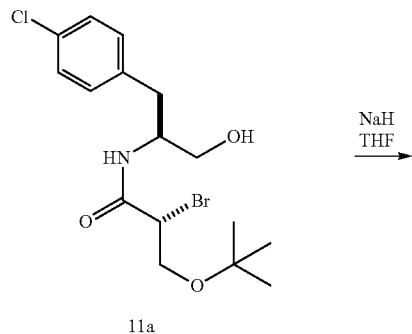

11a

NaH
THF

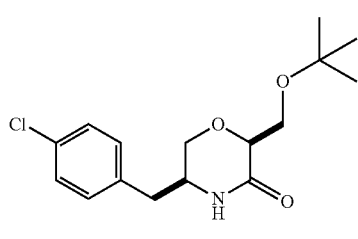

11b

To a solution of compound 11a (1.2 g, 3.05 mmol) in dry THF (30 mL), sodium hydride (NaH) (0.44 g, 9.16 mmol) was added in one portion and then the reaction mixture was stirred at room temperature for 1 hour. The reaction was carefully quenched with 2 M HCl and extracted with ethyl ether. The organics were washed with water, brine, dried over MgSO$_4$ and concentrated gave the title compound 11b as a yellow oil (0.85 g, 89% yield), which was pure enough to be taken to the next step.

ESI-MS m/z for C$_{16}$H$_{22}$ClNO$_3$ found 334.1/336.1 (M+Na)$^+$

Step 3

Synthesis of ((2R,5S)-5-(4-chlorobenzyl)morpholin-2-yl)methanol (11c)

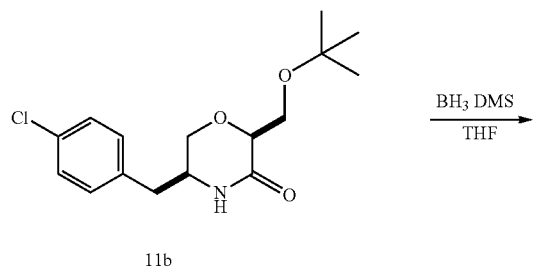

BH$_3$ DMS
THF

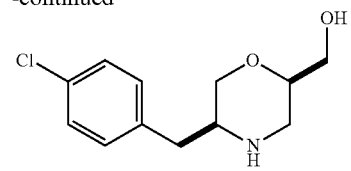

11c

Compound 11b (0.85 g, 2.72 mmol) was dissolved in 27 mL of dry THF and borane-dimethylsulfide complex (0.8 mL, 8.17 mmol) was carefully added and the reaction mixture was heated with stirring for ca. 24 hours. After this time the TLC revealed the complete consumption of the starting material. The reaction mixture was carefully quenched with 2 M HCl and heating was continued for 1 hour. The reaction mixture was cooled down, washed with ether. The water phase was alkalized to pH 12 and extracted with ether. Organic phase was dried over MgSO$_4$ and concentrated. 0.48 g (74% yield) of the title compound 11c was obtained.

ESI-MS m/z for C$_{12}$H$_{16}$ClNO$_2$ found 242.2/244.2 (M+1)$^+$

Step 4

Synthesis of tert-butyl 4-((2R,5S)-5-(4-chlorobenzyl)-2-(hydroxymethyl)morpholino)piperidine-1-carboxylate (11d)

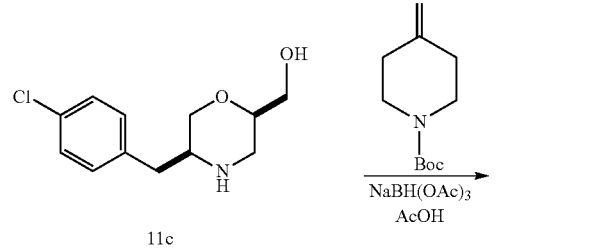

NaBH(OAc)$_3$
AcOH

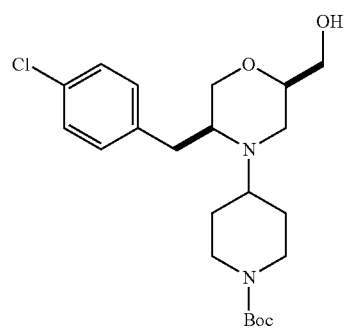

11d

Reductive amination of compound 11c (0.45 g, 1.86 mmol) and Boc-piperid-4-one was accomplished according to the General Procedure VI. The title compound 11d was obtained in 56% yield (0.44 g, 1.04 mmol).

ESI-MS m/z for C$_{22}$H$_{33}$ClN$_2$O$_4$ found 425.1/427.1 (M+H)$^+$ $^1$H NMR (CDCl$_3$, 700 MHz) δ 7.28 (AA'BB', J=8.4 Hz, 2H), 7.21 (AA'BB', J=8.3 Hz, 2H), 4.14-3.98 (m, 2H), 3.72-3.61 (m, 4H), 3.53-3.48 (m, 1H), 3.00-2.91 (m, 2H), 2.91-2.80 (m, 2H), 2.72-2.62 (m, 3H), 2.55-2.49 (m, 1H), 1.97-1.85 (m, 2H), 1.47 (s, 9H).

Step 5

Synthesis of tert-butyl 4-((2R,5S)-5-(4-chlorobenzyl)-2-(ethoxymethyl)morpholino)piperidine-1-carboxylate (11e)

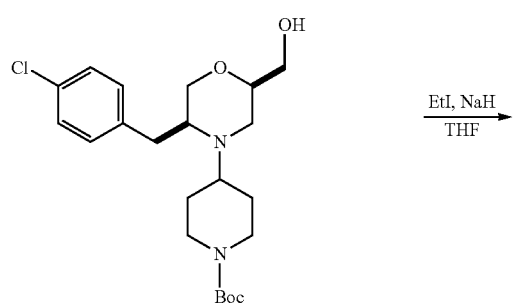

11d

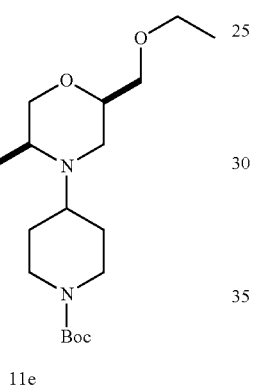

11e

Compound 11d was O-alkylated according to the General Procedure XXI. The title compound 11e was obtained in 74% yield (0.34 g, 0.75 mmol).

ESI-MS m/z for $C_{24}H_{37}ClN_2O_4$ found 453.1/455.1 $(M+1)^+$

Step 6

(2R,5S)-5-(4-chlorobenzyl)-2-(ethoxymethyl)-4-(piperidin-4-yl)morpholine hydrochloride (11f)

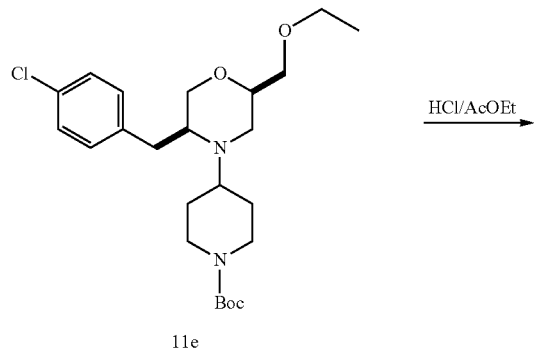

11e

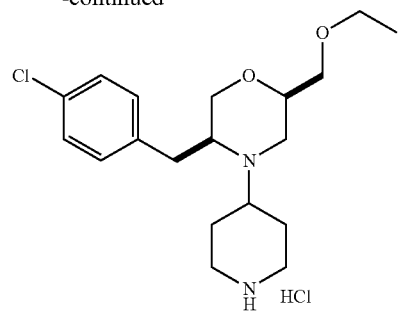

11f

The Boc-protecting group was removed from compound 11e according to the General Procedure VII providing title compound (100, sufficiently pure to be taken to the next step, in 95% yield.

ESI-MS m/z for $C_{19}H_{29}ClN_2O_2$ found 353.2/355.2 $(M+1)^+$

Step 7

Synthesis of 5-(4-((2R,5S)-5-(4-chlorobenzyl)-2-(ethoxymethyl)morpholino)piperidin-1-yl)-4H-1,2,4-triazol-3-amine (11)

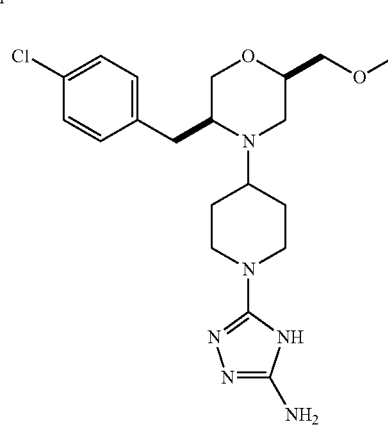

11

The title compound (11) was obtained from compound 11f using the General Procedure VIII in 45% yield (185 mg, 0.43 mmol).

ESI-MS m/z for $C_{21}H_{31}ClN_6O_2$ found 435.1/437.1 $(M+1)^+$

¹H NMR (DMSO-d₆+D₂O, 700 MHz) δ 7.35 (AA'BB', J=8.3 Hz, 2H), 7.25 (AA'BB', J=8.5 Hz, 2H), 3.86-3.74 (m, 3H), 3.71-3.66 (m, 1H), 3.64-3.38 (m, 8H), 3.16-3.00 (m, 3H), 2.98-2.88 (m, 2H), 2.22-2.14 (m, 2H), 2.67-2.49 (m, 2H), 1.07 (t, J=7.1 Hz, 3H).

Example 12

(2R,5S)-4-(1-(5-amino-4H-1,2,4-triazol-3-yl)piperidin-4-yl)-5-(4-chlorobenzyl)-N-methylmorpholine-2-carboxamide (12)

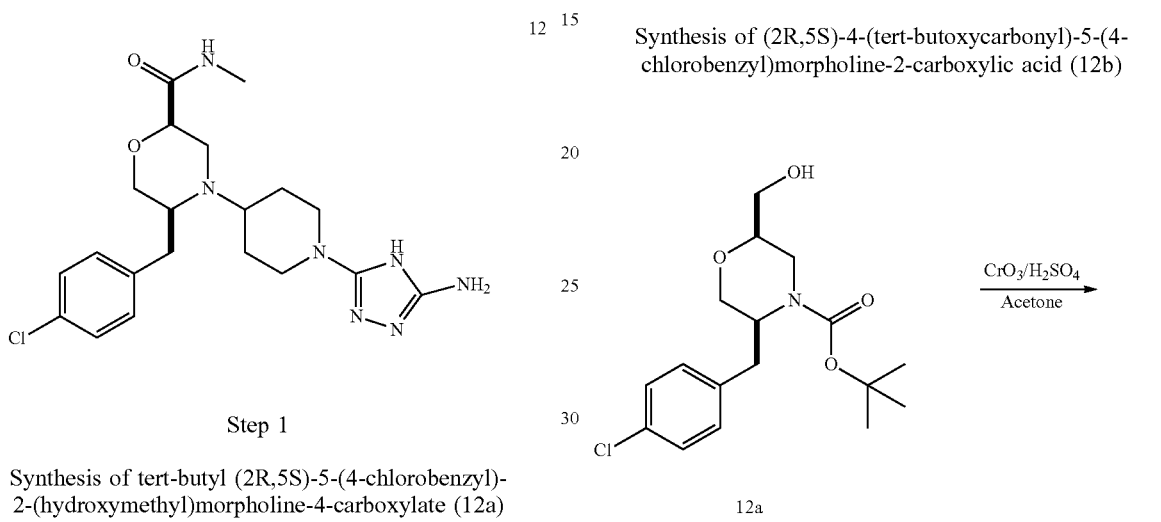

Step 1

Synthesis of tert-butyl (2R,5S)-5-(4-chlorobenzyl)-2-(hydroxymethyl)morpholine-4-carboxylate (12a)

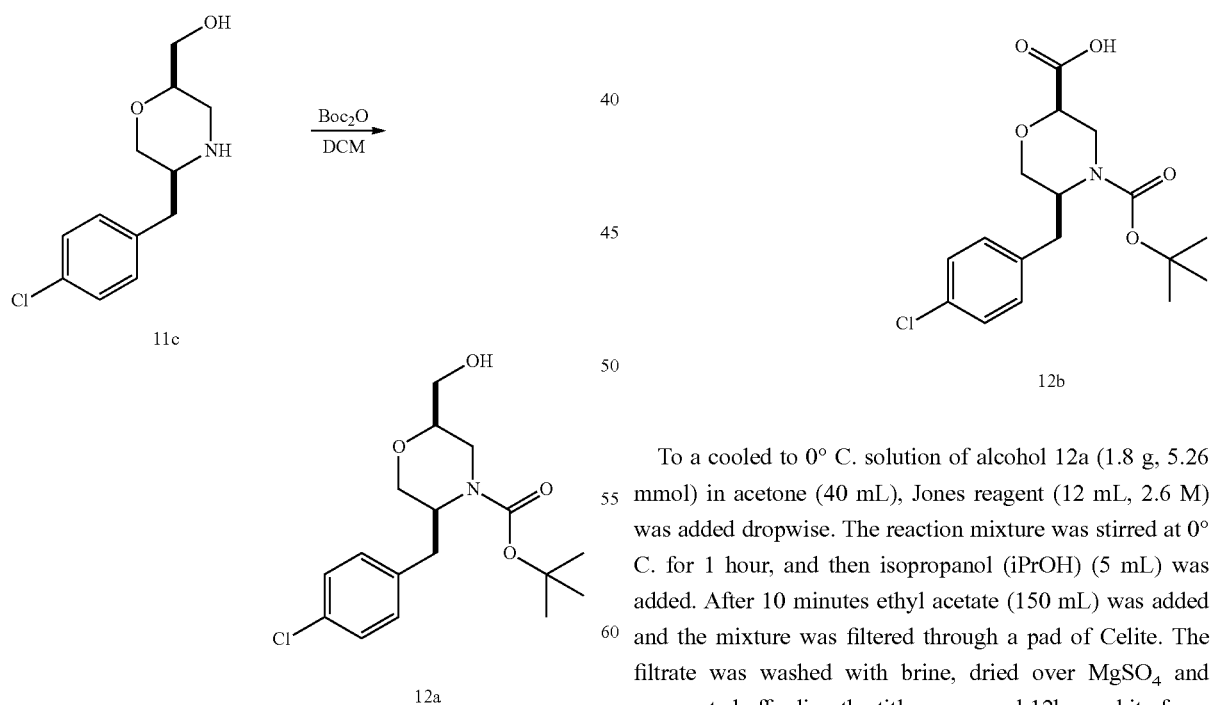

To a solution of amino alcohol 11c (2.87 g, 11.9 mmol) in dichloromethane (110 mL), di-tert-butyl dicarbonate (Boc₂O) (2.46 g, 11.3 mmol) was added and the reaction mixture was stirred at room temperature for 2 hours, after which time TLC showed almost complete consumption of the starting material. Volatiles were removed in vacuo and the residue was purified by column chromatography in AcOEt/hexanes 1:1 providing N-Boc-protected amino alcohol 12a (3.14 g, 77% yield) as colorless oil.

ESI-MS m/z for C₁₇H₂₄ClNO₄ found 242.1/246.1 (M+1-Boc)⁺

Step 2

Synthesis of (2R,5S)-4-(tert-butoxycarbonyl)-5-(4-chlorobenzyl)morpholine-2-carboxylic acid (12b)

To a cooled to 0° C. solution of alcohol 12a (1.8 g, 5.26 mmol) in acetone (40 mL), Jones reagent (12 mL, 2.6 M) was added dropwise. The reaction mixture was stirred at 0° C. for 1 hour, and then isopropanol (iPrOH) (5 mL) was added. After 10 minutes ethyl acetate (150 mL) was added and the mixture was filtered through a pad of Celite. The filtrate was washed with brine, dried over MgSO₄ and evaporated affording the title compound 12b as white foam (1.7 g, 91% yield).

ESI-MS m/z for C₁₇H₂₂ClNO₅ found 378.3/380.3 (M+Na)⁺, 256.1/258.1 (M+1-Boc)⁺

Step 3

Synthesis of tert-butyl (2R,5S)-5-(4-chlorobenzyl)-2-(methylcarbamoyl)morpholine-4-carboxylate (12c)

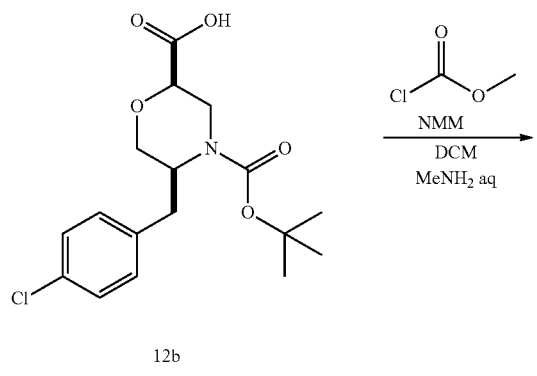

12b

The title compound (12c) was obtained from the compound 12b (0.24 g, 0.8 mmol) according to the General Procedure IX in 79% yield (0.23 g, 0.59 mmol).

ESI-MS m/z for $C_{18}H_{25}ClN_2O_4$ found 391.7/393.7 $(M+Na)^+$

Step 4

Synthesis of (2R,5S)-5-(4-chlorobenzyl)-N-methyl-morpholine-2-carboxamide hydrochloride (12d)

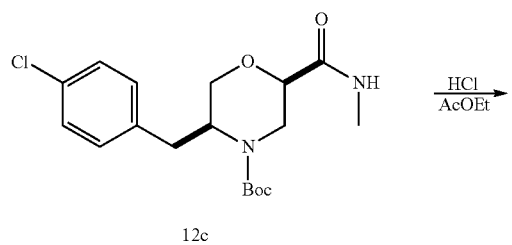

12c

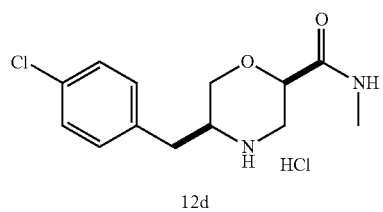

12d

Boc-protected morpholine 12c (0.33 g, 0.89 mmol) was treated with 4 M HCl (gas) in ethyl acetate as described in the General Procedure VII. After 1 hour the reaction was concentrated in vacuo and the crude hydrochloride salt of morpholine 12d was used in the next step.

ESI-MS m/z for $C_{13}H_{17}ClN_2O_2$ found 269.2/271.2 $(M+Na)^+$

Step 5

Synthesis of tert-butyl 4-((2R,5S)-5-(4-chlorobenzyl)-2-(methylcarbamoyl)morpholino)-piperidine-1-carboxylate (12e)

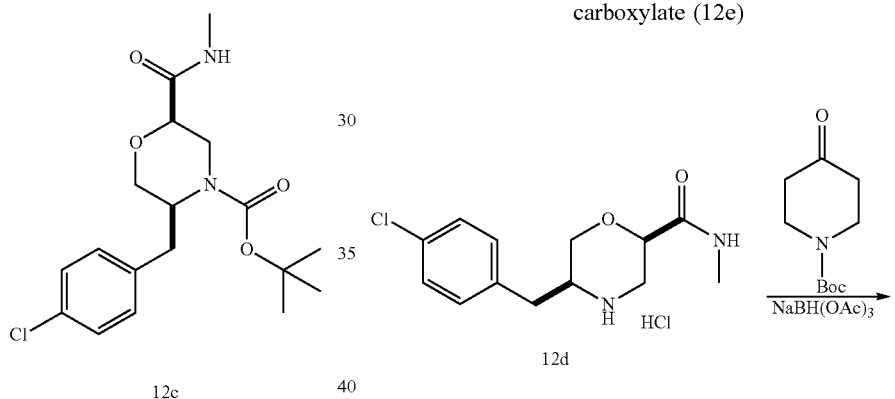

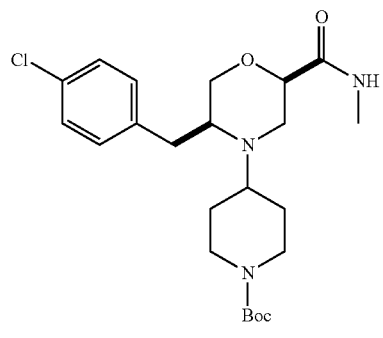

12e

Reductive amination was accomplished according to the General Procedure VI, starting from amine 12d (0.89 mmol, 239 mg) and N-Boc-piperid-4-one. After chromatographic purification the title compound 12e was obtained in 62% yield (0.55 mmol, 249 mg).

ESI-MS m/z for $C_{23}H_{34}ClN_3O_4$ found 452.2/454.2 $(M+1)^+$

Step 6

Synthesis of (2R,5S)-5-(4-chlorobenzyl)-N-methyl-4-(piperidin-4-yl)morpholine-2-carboxamide hydrochloride (12f)

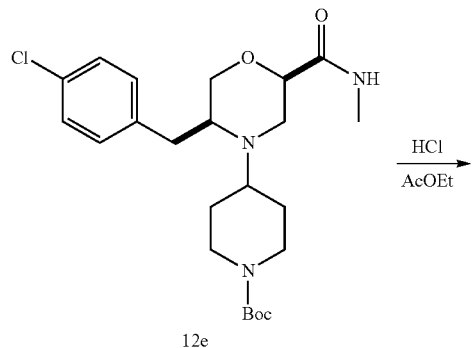

Boc-protected piperidine 12e (0.25 g, 0.55 mmol) was treated with 4 M HCl (gas) in ethyl acetate as described in the General Procedure VII. After 1 hour the reaction mixture was concentrated in vacuo and the crude hydrochloride salt of piperidine 12f was used directly in the next step.

ESI-MS m/z for $C_{18}H_{26}ClN_3O_2$ found 352.4/354.4 $(M+1)^+$

Step 7

Synthesis of (2R,5S)-4-(1-(5-amino-4H-1,2,4-triazol-3-yl)piperidin-4-yl)-5-(4-chlorobenzyl)-N-methylmorpholine-2-carboxamide (12)

Formation of 1,2,4-triazole ring was accomplished according to the General Procedure VIII starting from compound 12f. The final compound 12 was obtained by purification by the reversed-phase chromatography in 67% yield (0.16 g, 0.37 mmol).

ESI-MS m/z for $C_{20}H_{28}ClN_7O_2$ found 434.0/436.0 $(M+1)^+$ $^1$H NMR (DMSO-$d_6$, +75° C., 700 MHz) δ 7.62 (bs, 1H), 7.35 (AA'BB', J=8.5 Hz, 2H), 7.30 (AA'BB', J=8.5 Hz, 2H), 4.05-3.97 (m, 1H), 3.82-3.74 (m, 2H), 3.63-3.54 (m, 2H), 3.30-3.11 (m, 2H), 3.02-2.82 (m, 6H), 2.66 (d, J=4.7 Hz, 3H), 1.98-1.92 (m, 2H), 1.57-1.47 (m, 2H).

Example 13

2-((2R,5S)-4-(1-(5-amino-4H-1,2,4-triazol-3-yl)piperidin-4-yl)-5-(4-chlorobenzyl)morpholin-2-yl)propan-2-ol (13)

Step 1

Synthesis of 4-tert-butyl (2R,5S)-2-methyl 5-(4-chlorobenzyl)morpholine-2,4-dicarboxylate (13a)

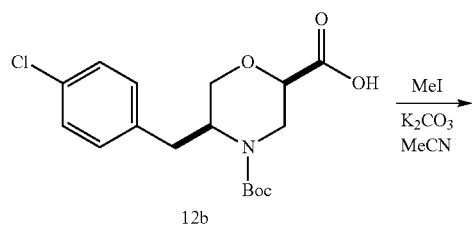

To a solution of Boc-protected amino acid 12b (1 g, 2.81 mmol) in acetonitrile, potassium carbonate (0.77 g, 5.62 mmol) was added followed by methyl iodide (MeI) (0.26 mL, 4.21 mmol) at room temperature. After reaction was completed as judged by TLC, the reaction mixture was filtered and the solvent was evaporated. The residue was dissolved in ethyl acetate, washed with brine and dried over MgSO$_4$. The solvent was evaporated in vacuo to give 0.4 g (40% yield) of the title compound 13a as a yellow oil sufficiently pure to be used in the next step.

ESI-MS m/z for $C_{18}H_{24}ClNO_5$ found 393.1/395.1 (M+Na)$^+$

Step 2

Synthesis of tert-butyl (2R,5S)-5-(4-chlorobenzyl)-2-(2-hydroxypropan-2-yl)morpholine-4-carboxylate (13b)

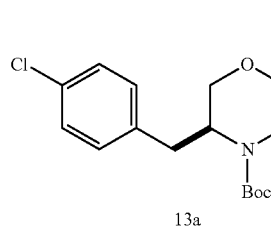

To a solution of ester 13a (0.4 g, 1.08 mmol) in dry THF, solution of methylmagnesium bromide (1.1 mL, 3.24 mmol, 3 M in Et$_2$O) was added dropwise at RT. After 10 minutes the reaction mixture was quenched with saturated solution of ammonium chloride and extracted with ether. Organic phase was washed with brine, dried over MgSO$_4$ and concentrated to afford 0.4 g (1.08 mmol, 100% yield) of crude alcohol 13b which was used in the next step without further purification.

ESI-MS $C_{19}H_{28}ClNO_4$ found 393.2/395.2 (M+Na)$^+$, 270.0/272.0 (M+1-Boc)$^+$

Step 3

Synthesis of 2-((2R,5S)-5-(4-chlorobenzyl)morpholin-2-yl)propan-2-ol 2,2,2-trifluoroacetate (13c)

0.4 g (1.08 mmol) of compound 13b was treated with 3 mL of 50% trifluoroacetic acid (TFA) in dichloromethane for 30 minutes at room temperature, after which time the volatiles were removed in vacuo and the crude title compound 13c (0.37 g; 90% yield) was used in the next step without further purification.

ESI-MS m/z for $C_{14}H_{20}ClNO_2$ found 270.1/272.1 (M+1)$^+$ $^1$H NMR (DMSO-d$_6$+D$_2$O, 500 MHz) δ 7.34 (AA'BB', J=6.2 Hz, 2H), 7.25 (AA'BB', J=6.4 Hz, 2H), 3.65-3.55 (m, 2H), 3.52-3.44 (m, 1H), 2.42-3.36 (m, 1H), 3.15-3.04 (m, 2H), 2.94-2.87 (m, 1H), 2.48 (m, 3H), 1.10 (s, 3H), 1.08 (s, 3H).

Step 4

Synthesis of tert-butyl 4-((2R,5S)-5-(4-chlorobenzyl)-2-(2-hydroxypropan-2-yl)morpholino)piperidine-1-carboxylate (13d)

-continued

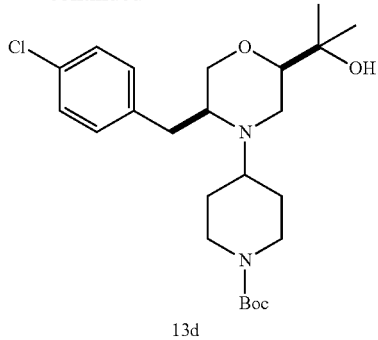

13d

Reductive amination was accomplished according to the General Procedure VI starting from amine 13c (0.97 mmol) and N-Boc-piperid-4-one. The title compound 13d was obtained after chromatographic purification in 79% yield.

ESI-MS m/z for $C_{24}H_{37}ClN_2O_4$ found 454.1/456.1 $(M+1)^+$ $^1$H NMR (DMSO+D$_2$O, 500 MHz) δ 7.29 (AA'BB', J=8.3 Hz, 2H), 7.19 (AA'BB', J=8.1 Hz, 2H), 3.92-3.80 (m, 2H), 3.66-3.55 (m, 3H), 3.45-3.39 (m, 1H), 3.35-3.29 (m, 1H), 3.20-3.13 (m, 1H), 2.84-2.75 (m, 3H), 2.72-2.65 (m, 2H), 1.97-1.84 (m, 2H), 1.69-1.61 (m, 2H), 1.33 (s, 9H), 1.09 (s, 3H), 1.07 (s, 3H).

Step 5

Synthesis of 2-((2R,5S)-5-(4-chlorobenzyl)-4-(piperidin-4-yl)morpholin-2-yl)propan-2-ol 2,2,2-trifluoroacetate (13e)

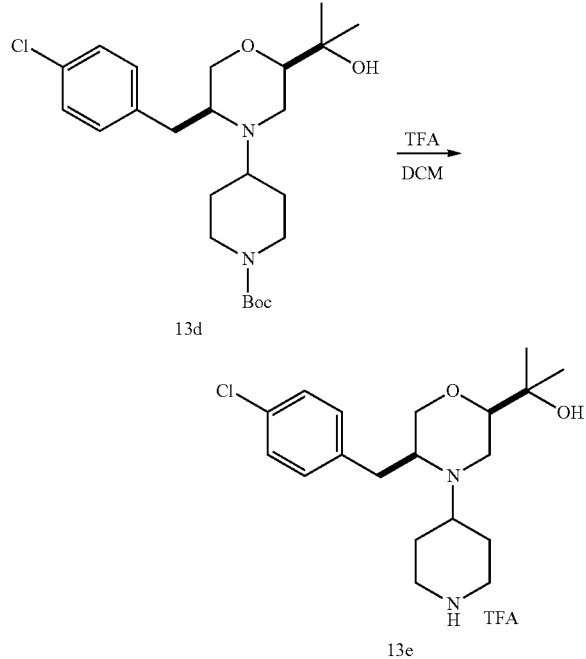

0.38 g (0.77 mmol) of compound 13d was treated with 3 mL of 50% trifluoroacetic acid in dichloromethane for 30 minutes at room temperature, after which time the volatiles were removed in vacuo and the crude title compound 13e (125 mg; 58% yield) was used in the next step without further purification.

ESI-MS m/z for $C_{19}H_{29}ClN_2O_2$ found 353.4/355.1 $(M+1)^+$ $^1$H NMR (DMSO-d$_6$+D$_2$O, 600 MHz) δ 7.39 (AA'BB', J=8.3 Hz, 2H), 7.30 (AA'BB', J=8.1 Hz, 2H), 3.75-3.52 (m, 2H), 3.49-3.33 (m, 4H), 3.20-2.82 (m, 6H), 2.41-2.32 (m, 1H), 1.87-1.68 (m, 2H), 1.57-1.48 (m, 2H), 1.15 (s, 3H), 1.14 (s, 3H).

Step 6

Synthesis of 2-((2R,5S)-4-(1-(5-amino-4H-1,2,4-triazol-3-yl)piperidin-4-yl)-5-(4-chlorobenzyl)morpholin-2-yl)propan-2-ol (13)

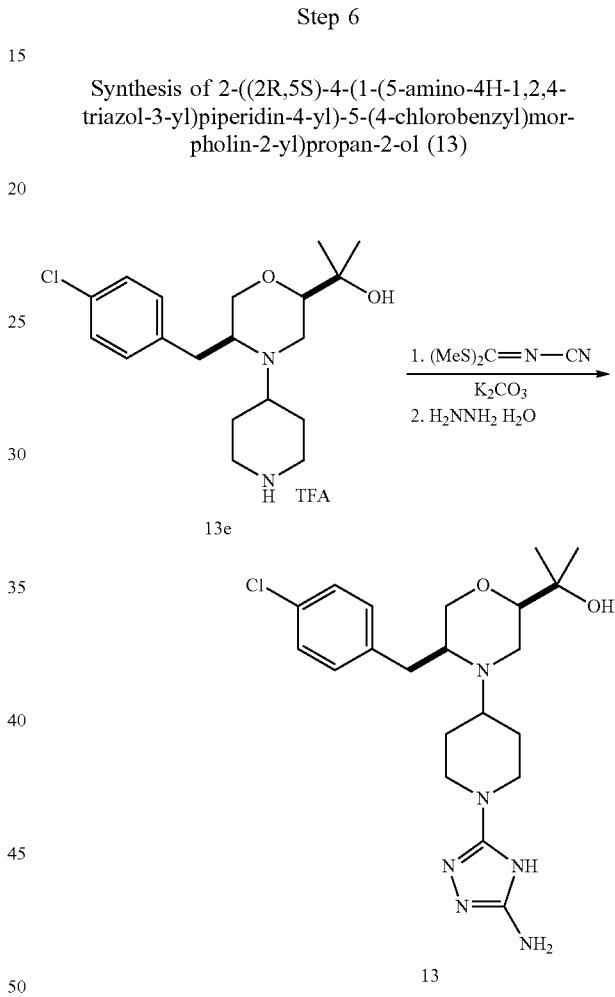

Formation of 1,2,4-triazole ring was accomplished according to the General Procedure VIII starting from compound 13e. The final compound 13 was obtained after purification by the reversed-phase chromatography in yield (120 mg, 0.22 mmol).

ESI-MS m/z for $C_{21}H_{31}ClN_6O_2$ found 435.1/437.1 $(M+1)^+$ $^1$H NMR (DMSO-d$_6$+D$_2$O, 600 MHz) δ 7.39 (AA'BB', J=8.5 Hz, 2H), 7.31 (AA'BB', J=8.5 Hz, 2H), 3.89-3.77 (m, 2H), 3.75-3.69 (m, 1H), 3.67-3.53 (m, 3H), 3.46-3.37 (m, 2H), 3.21-2.97 (m, 3H), 2.97-2.86 (m, 2H), 2.25-2.16 (m, 2H), 1.64-1.55 (m, 2H), 1.15 (s, 3H), 1.14 (s, 3H).

Example 14

5-(4-((2R,5S)-5-(4-chlorobenzyl)-2-(2-methoxypropan-2-yl)morpholino)piperidin-1-yl)-4H-1,2,4-triazol-3-amine (14)

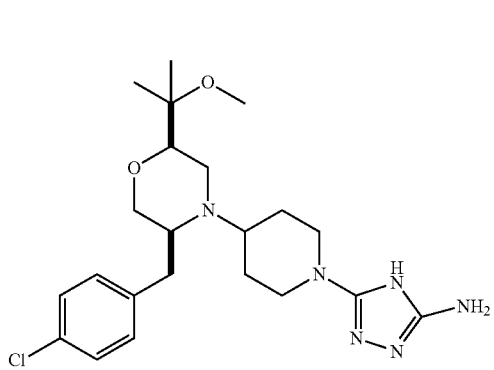

Step 1

Synthesis of tert-butyl 4-((2R,5S)-5-(4-chlorobenzyl)-2-(2-methoxypropan-2-yl)morpholino)piperidine-1-carboxylate (14a)

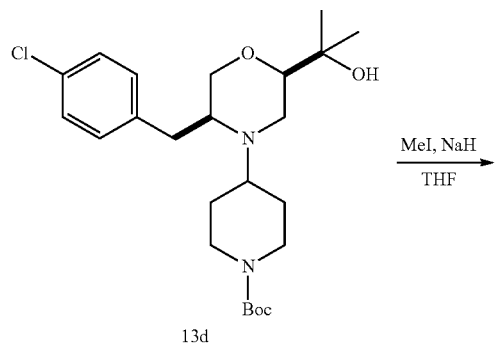

Compound 14a (0.18 g, 0.4 mmol) was obtained according to the General Procedure XXI in 86% yield (0.16 g, 0.34 mmol).

ESI-MS m/z for $C_{25}H_{39}ClN_2O_4$ found 467.2/469.2 $(M+1)^+$

Step 2

Synthesis of (2R,5S)-5-(4-chlorobenzyl)-2-(2-methoxypropan-2-yl)-4-(piperidin-4-yl)morpholine 2,2,2-trifluoroacetate (14b)

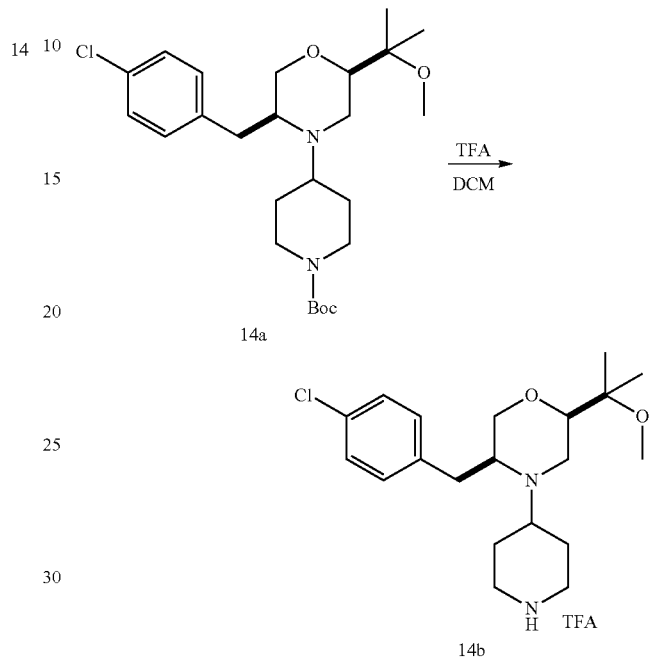

0.16 g (0.34 mmol) of compound 14a was treated with 1.5 mL of 50% trifluoroacetic acid at room temperature, after which time the volatiles were removed in vacuo and the crude title compound 14b was directly used in the next step.

ESI-MS m/z for $C_{20}H_{31}ClN_2O_2$ found 367.2/369.2 $(M+1)^+$ $^1$H NMR (DMSO-$d_6$+$D_2O$, 600 MHz) δ 7.37 (AA'BB', J=8.3 Hz, 2H), 7.25 (AA'BB', J=8.3 Hz, 2H), 3.76-3.51 (m, 4H), 3.48-1.39 (m, 2H), 3.35-3.28 (m, 1H), 3.24-3.16 (m, 1H), 3.12 (s, 3H), 3.09-2.81 (m, 5H), 2.42-2.30 (m, 2H), 1.81-1.68 (m, 2H), 1.14 (s, 6H).

Step 3

Synthesis of 5-(4-((2R,5S)-5-(4-chlorobenzyl)-2-(2-methoxypropan-2-yl)morpholino)piperidin-1-yl)-4H-1,2,4-triazol-3-amine (14)

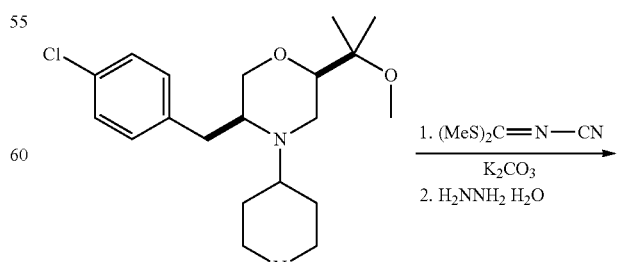

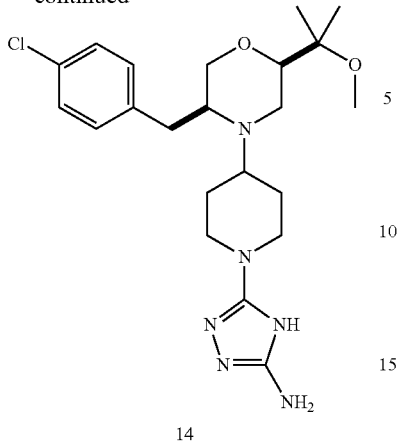

14

Formation of 1,2,4-triazole ring was accomplished according to the General Procedure VIII starting from compound 14b. The final compound 14 was obtained after purification by the reversed-phase chromatography in yield 29%(45 mg, 0.1 mmol).

ESI-MS m/z for $C_{22}H_{33}ClN_6O_2$ found 449.1/451.1 $(M+1)^+$ $^1$H NMR (DMSO-$d_6$+$D_2O$, 600 MHz) δ 7.40 (AA'BB', J=8.4 Hz, 2H), 7.29 (AA'BB', J=8.4 Hz, 2H), 3.88-3.81 (m, 2H), 3.66-3.51 (m, 5H), 3.36-3.30 (m, 1H), 3.23-3.16 (m, 1H), 3.15 (s, 3H), 3.13-3.08 (m, 1H), 3.03-2.96 (m, 1H), 2.94-2.83 (m, 2H), 2.24-2.16 (m, 2H), 1.63-1.54 (m, 2H), 1.17 (s, 6H).

Example 15

(R)-5-(2-(4-chlorobenzyl)-[1,4'-bipiperidin]-1'-yl)-4H-1,2,4-triazol-3-amine (15)

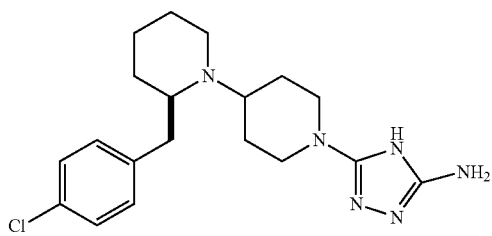

15

Step 1

Synthesis of (S,Z)-N-(2-(4-chlorophenyl)ethyl-idene)-2-methylpropane-2-sulfinamide (15a)

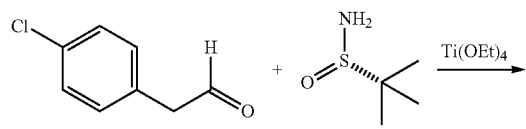

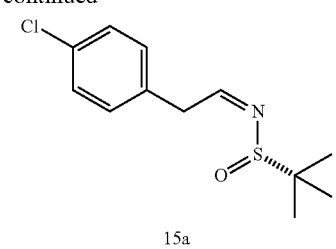

15a

Compound 15a was obtained from p-chlorophenylacetal-dehyde (6.5 g, 42.04 mmol), (S)-2-methyl-2-propanesulfi-namide (5.09 g, 42.04 mmol), according to the General Procedure XVII in 67% yield (7.35 g, 28.5 mmol).

ESI-MS m/z for $C_{12}H_{16}ClNOS$ found 258.1/260.1 $(M+1)^+$

Step 2

Synthesis of (S)-N-((R)-1-(4-chlorophenyl)pent-4-en-2-yl)-2-methylpropane-2-sulfinamide (15b)

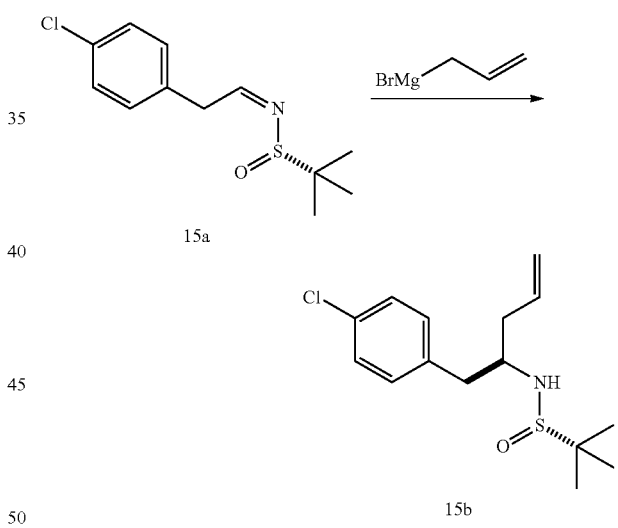

Compound 15b was obtained from 15a (7.35 g, 28.5 mmol) according to the General Procedure XVIII in 58% yield (5.0 g, 16.7 mmol), after column chromatography with AcOEt/hexane 1:4.

ESI-MS m/z for $C_{15}H_{22}ClNOS$ found 300.1/302.1 $(M+1)^+$ $^1$H NMR (CDCl$_3$, 500 MHz) δ 7.21 (AA'BB', J=8.3 Hz, 2H), 7.08 (AA'BB', J=8.5 Hz, 2H), 5.81-5.71 (m, 1H), 5.18-5.10 (m, 2H), 3.54-3.46 (m, 1H), 3.33-3.28 (m, 1H), 2.78 (dd, J=7.1, 13.7 Hz, 1H), 2.69 (dd, J=6.4, 13.7 Hz, 1H), 2.40-2.32 (m, 1H), 2.31-2.23 (m, 1H), 1.08 (s, 9H).

Step 3

Synthesis of (S)-N-allyl-N-((R)-1-(4-chlorophenyl)pent-4-en-2-yl)-2-methylpropane-2-sulfinamide (15c)

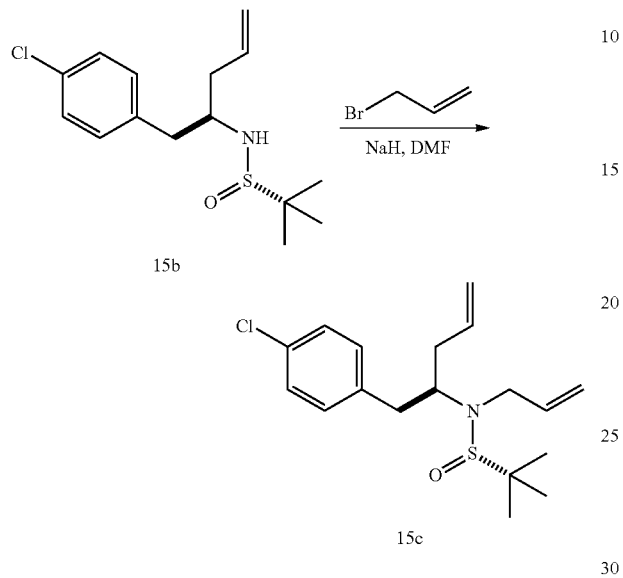

Compound 15c was obtained from 15b (1 g, 3.33 mmol) according to the General Procedure XIX in 71% yield (0.78 g, 2.29 mmol), after column chromatography with AcOEt/hexane 1:3.

ESI MS m/z for $C_{18}H_{26}ClNOS$ found 340.2/342.2 $(M+1)^+$

Step 4

Synthesis of (R)-1-((S)-tert-butylsulfinyl)-2-(4-chlorobenzyl)-1,2,3,6-tetrahydropyridine (15d)

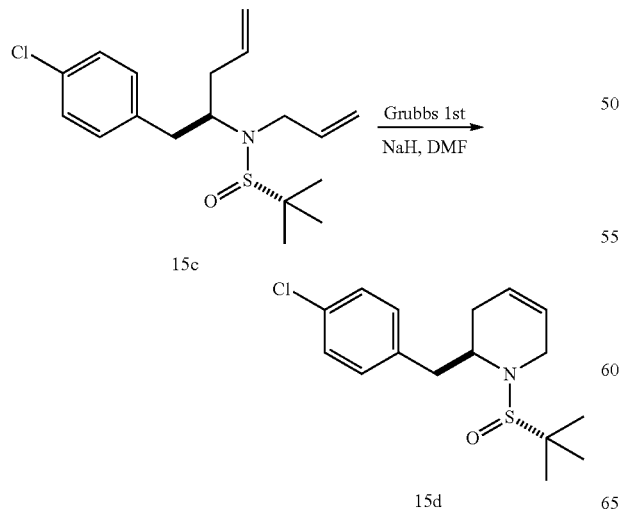

Compound 15d was obtained from 15c (0.78 g, 2.29 mmol) according to the General Procedure XX in 94% yield (0.67 g, 2.15 mmol), after column chromatography with AcOEt/hexane 1:10.

ESI-MS m/z for $C_{16}H_{22}ClNOS$ found 312.2/314.2 $(M+1)^+$

Step 5

Synthesis of (R)-1-((S)-tert-butylsulfinyl)-2-(4-chlorobenzyl)piperidine (15e)

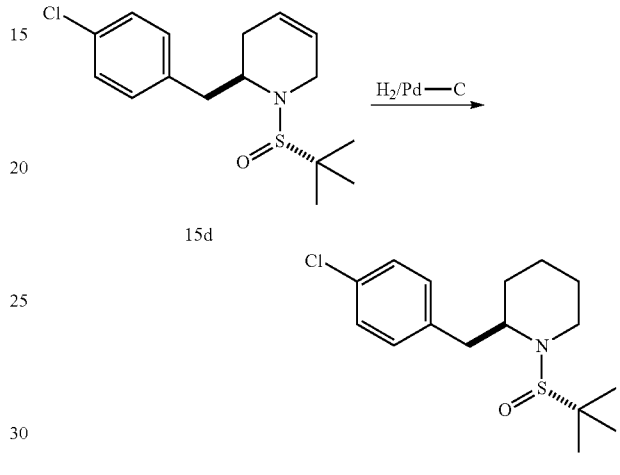

To a solution of substrate 15d (0.62 g, 1.98 mmol) in methanol (5 mL) a catalytic amount of palladium on carbon was added. The reaction mixture was stirred under hydrogen overnight. After this time, the catalyst was filtered off through a Celite pad and the filtrate was concentrated to dryness and purified by column chromatography using AcOEt/hexane (1:4), providing 0.48 g (1.53 mmol, 77% yield) of product 15e.

ESI-MS m/z for $C_{16}H_{24}ClNOS$ found 314.2/316.2 $(M+1)^+$

Step 6

Synthesis of (R)-2-(4-chlorobenzyl)piperidine (15f)

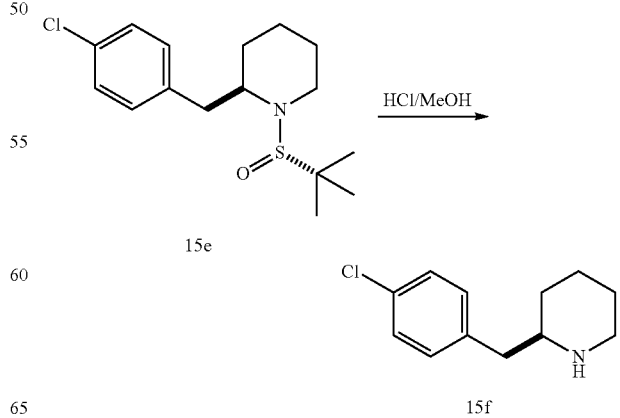

Compound 15e (0.48 g, 1.5 mmol) was treated with HCl/MeOH at RT for 1 hour and then the reaction was concentrated to dryness. The residue was taken between DCM/1 M NaOH and phases were separated. Aqueous phase was extracted with DCM, then organics were combined, dried and concentrated to give 0.23 g of compound 15f (1.1 mmol; 72% yield) as a free amine.

ESI-MS m/z for $C_{12}H_{16}ClN$ found 210.2/212.2 $(M+1)^+$ $^1$H NMR (CDCl$_3$, 500 MHz) δ 7.27-7.21 (m, 2H), 7.14-7.08 (m, 2H), 3.00 (dp, J=11.8, 2.0 Hz, 1H), 2.71-2.60 (m, 2H), 2.54 (m, 2H), 1.80-1.73 (m, 1H), 1.66 (s, 1H), 1.61-1.53 (m, 1H), 1.43 (m, 1H), 1.34-1.23 (m, 1H), 1.22-1.13 (m, 1H).

Step 7

Synthesis of tert-butyl (R)-2-(4-chlorobenzyl)[1,4'-bipiperidine]-1'-carboxylate (15g)

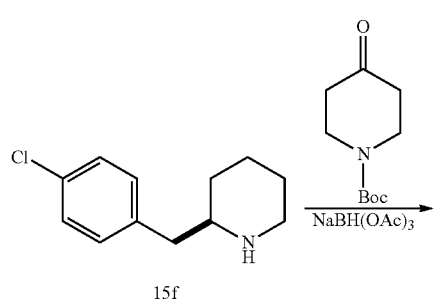

15f

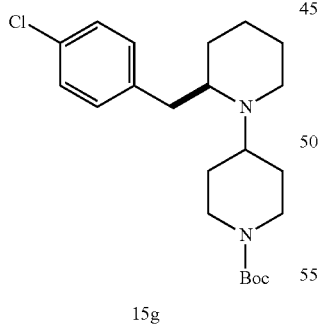

15g

Reductive amination of compound 15f and N-Boc-piperid-4-one was accomplished according to the General Procedure VI. The title compound was obtained in 40% yield (0.17 g, 0.43 mmol).

ESI-MS m/z for $C_{22}H_{33}ClN_2O_2$ found 393.1/395.1 $(M+1)^+$

Step 8

Synthesis of (R)-2-(4-chlorobenzyl)-1,4'-bipiperidine hydrochloride (15h)

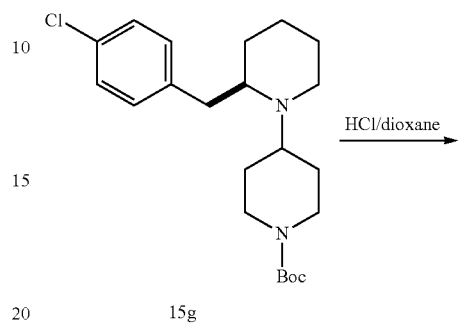

15g

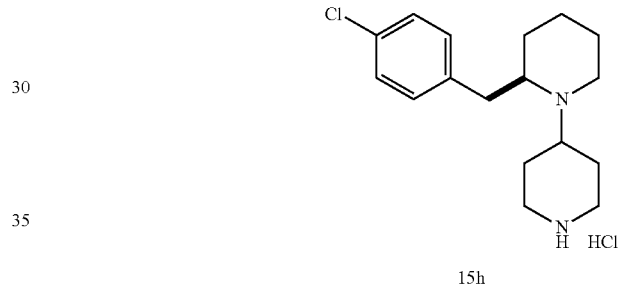

15h

Removal of the Boc-protecting group from compound 15g was accomplished according to the General Procedure VII. The title compound (15h) was obtained in yield 91% as HCl salt (0.13 g, 0.39 mmol).

ESI-MS m/z for $C_{17}H_{25}ClN_2$ found 293.1/295.1 $(M+1)^+$

Step 9

Synthesis of (R)-5-(2-(4-chlorobenzyl)-[1,4'-bipiperidin]-1'-yl)-4H-1,2,4-triazol-3-amine (15)

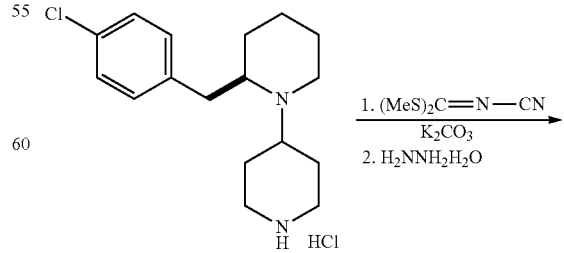

15h

-continued

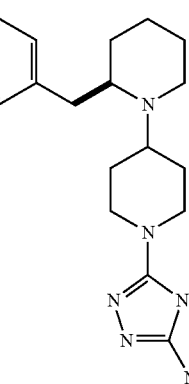

15

Formation of 1,2,4-triazole ring was accomplished according to the General Procedure VIII starting from compound 15h. Title compound (15) was obtained in 28% yield (0.10 mmol; 40 mg).

ESI-MS m/z for $C_{19}H_{27}ClN_6$ found 391.0/393.0 (M+1)$^+$ $^1$H NMR (DMSO-d$_6$, 500 MHz) δ: 7.47-7.37 (m, 2H), 7.34-7.29 (m, 2H), 3.91-3.72 (m, 3H), 3.65-2.34 (m, 5H), 3.02-2.81 (m, 3H), 2.71-2.60 (m, 1H), 2.10-2.00 (m, 1H), 1.92-1.22 (m, 2H), 1.71-1.52 (m, 3H), 1.55-1.32 (m, 2H).

Example 16 ethyl (6R)-1'-(5-amino-4H-1,2,4-triazol-3-yl)-6-(4-chlorobenzyl)-[1,4'-bipiperidine]-3-carboxylate (16)

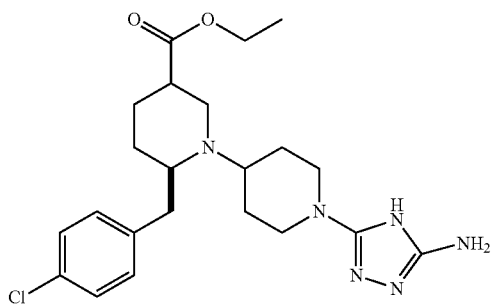

16

Step 1

Synthesis of ethyl 2-(((S)-N-((R)-1-(4-chlorophenyl)pent-4-en-2-yl)-2-methylpropan-2-ylsulfinamido)methyl)acrylate (16a)

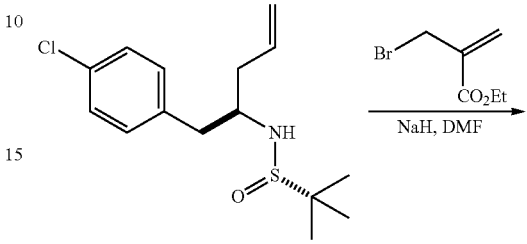

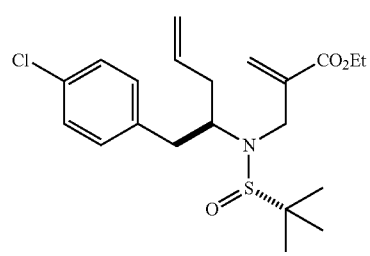

Compound 16a was obtained from 15b (2.0 g, 6.9 mmol) according to the General Procedure XIX in 84% yield (2.4 g, 5.82 mmol), after column chromatography with AcOEt/hexane gradient from 1:20 to 1:8.

ESI-MS m/z for $C_{21}H_{30}ClNO_3S$ found 434.1/436.1 (M+Na)$^+$ $^1$H NMR (CDCl$_3$, 500 MHz) δ: 7.21 (AA'BB', J=8.1 Hz, 2H), 7.12 (AA'BB', J=7.9 Hz, 2H), 6.32 (bs, 1H), 5.81 (bs, 1H), 5.70-5.58 (m, 1H), 5.01-4.92 (m, 2H), 4.24-4.12 (m, 3H), 3.38-3.30 (m, 1H), 3.22-3.09 (m, 2H), 2.85-2.77 (m, 1H), 2.46-2.36 (m, 1H), 2.30-2.21 (m, 1H), 1.26 (t, J=7.1 Hz, 3H), 1.18 (s, 9H).

Step 2

Synthesis of ethyl (R)-1-((S)-tert-butylsulfinyl)-6-(4-chlorobenzyl)-1,2,5,6-tetrahydropyridine-3-carboxylate (16b)

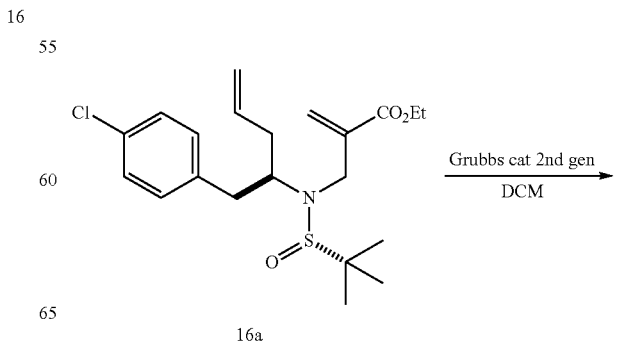

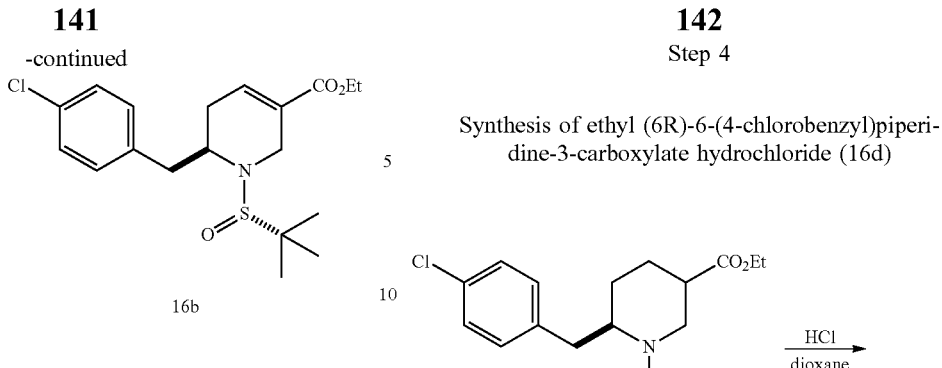

16b

Compound 16b was obtained from 16a (2.4 g, 5.82 mmol) and 2nd generation Grubbs catalyst according to the General Procedure XX in 81% yield (1.8 g, 4.69 mmol), after column chromatography with AcOEt/hexane 1:10.

ESI-MS m/z for $C_{19}H_{26}ClNO_3S$ found 384.1/386.1 $(M+1)^+$ $^1$H NMR (CDCl$_3$, 500 MHz) δ: 7.24 (AA'BB', J=8.3 Hz, 2H), 7.10 (AA'BB', J=8.3 Hz, 2H), 7.03-6.98 (m, 1H), 4.23-4.11 (m, 3H), 3.70-3.58 (m, 2H), 2.88 (dd, J=7.9, 13.5 Hz, 1H), 2.65 (dd, J=7.7, 13.7 Hz, 1H), 2.61-2.53 (m, 1H), 2.15-2.07 (m, 1H), 1.29 (t, J=7.1 Hz, 3H), 0.96 (s, 9H).

Step 3

Synthesis of ethyl (6R)-1-((S)-tert-butylsulfinyl)-6-(4-chlorobenzyl)piperidine-3-carboxylate (16c)

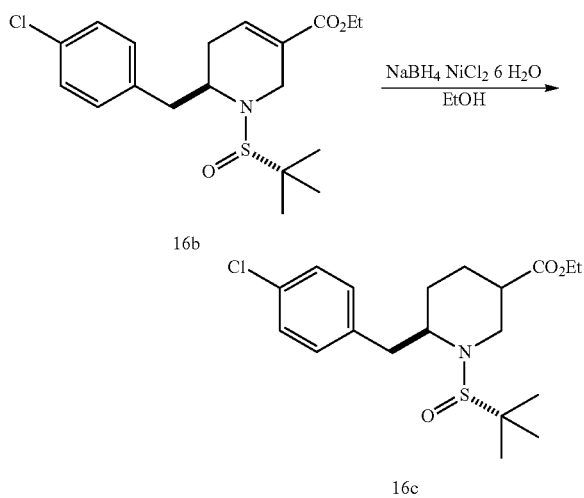

To a solution of compound 16b (1.0 g, 2.6 mmol) and NiCl$_2$×6H$_2$O (61 mg, 0.26 mmol) in 100 mL of absolute ethanol, sodium borohydride (NaBH$_4$) (100 mg, 2.6 mmol) was added portionwise. The reaction was stirred for 1 hour, and then concentrated to ⅓ of its initial volume, DCM (40 mL) was added and the resulting suspension was filtered through a pad of Celite. The filtrate was washed with 1 M HCl, water, brine, dried over MgSO$_4$ and concentrated to provide 1.0 g (2.57 mmol; 99% yield) of the title compound 16c.

ESI-MS m/z for $C_{19}H_{28}ClNO_3S$ found 408.9/410.9 $(M+Na)^+$

Step 4

Synthesis of ethyl (6R)-6-(4-chlorobenzyl)piperidine-3-carboxylate hydrochloride (16d)

Compound 16c (1.0 g, 2.6 mmol) was treated with 1 N HCl(gas)/1,4-dioxane solution at RT for 1 hour. The reaction mixture was then concentrated to dryness affording 0.82 g (2.58 mmol; 99% yield) of piperidine 16d in a form of hydrochloride salt.

ESI-MS m/z for $C_{15}H_{20}ClNO_2$ found 282.2/284.2 $(M+1)^+$

Steps 5-7

Synthesis of ethyl (6R)-1'-(5-amino-4H-1,2,4-triazol-3-yl)-6-(4-chlorobenzyl)-[1,4'-bipiperidine]-3-carboxylate (16)

Piperidine 16d was carried through the remaining synthetic steps as it is described in the General Procedure VI (reductive amination with N-Boc-piperid-4-one), the General Procedure VII (Boc-deprotection) and the General Procedure VIII (triazole ring formation).

180 mg (0.40 mmol, 16% yield) of the title compound 16 was synthesized.

ESI-MS $C_{22}H_{31}ClN_6O_2$ found 447.1/449.1 $(M+1)^+$ $^1$H NMR (DMSO-d$_6$, 500 MHz) δ 7.36 (AA'BB', J=8.3 Hz, 2H), 7.31 (AA'BB', J=8.3 Hz, 2H), 4.17-4.07 (m, 2H), 3.92-3.82 (m, 2H), 3.82-3.12 (m, 4H), 3.20-3.06 (m, 1H), 3.06-2.96 (m, 1H), 2.91-2.79 (m, 3H), 2.16-1.99 (m, 2H), 1.93-1.50 (m, 5H), 1.55-1.43 (m, 1H), 1.21 (t, J=7.1 Hz, 3H).

Example 17

(6R)-1'-(5-amino-4H-1,2,4-triazol-3-yl)-6-(4-chlorobenzyl)-[1,4'-bipiperidine]-3-carboxylic acid (17)

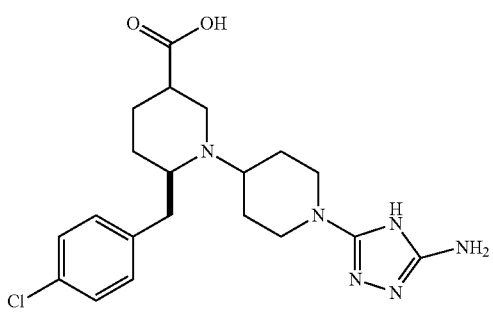

Compound 16 (50 mg, 0.11 mmol) was dissolved in 6 M HCl (2 mL) and refluxed for 1 hour, after which time volatiles were removed in vacuo and the residue was purified by the reversed-phase chromatography. 25 mg (0.059 mmol; 54% yield) of the target compound 17 was obtained.

ESI-MS $C_{20}H_{27}ClN_6O_2$ found 419.1/421.1 (M+1)$^+$ $^1$H NMR (DMSO-d$_6$, 75° C., 500 MHz) δ 7.36 (AA'BB', J=8.3 Hz, 2H), 7.31 (AA'BB', J=8.3 Hz, 2H), 3.94-3.84 (m, 2H), 3.82-3.71 (m, 1H), 3.66-3.56 (m, 1H), 3.52-3.19 (m, 3H), 3.17-3.10 (m, 1H), 3.06-2.97 (m, 1H), 2.87-2.76 (m, 3H), 2.13-1.97 (m, 2H), 1.92-1.60 (m, 5H), 1.56-1.46 (m, 1H).

Example 18

(6R)-1'-(5-amino-4H-1,2,4-triazol-3-yl)-6-(4-chlorobenzyl)-3-methyl-[1,4'-bipiperidine]-3-carboxylic acid (18)

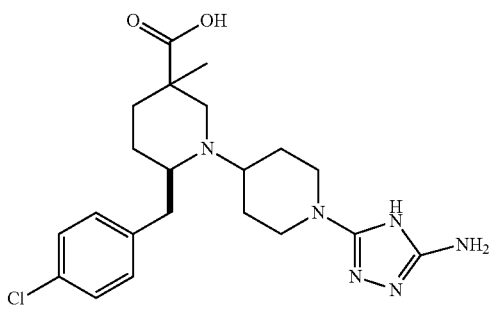

Step 1

Synthesis of ethyl (6R)-1-((S)-tert-butylsulfinyl)-6-(4-chlorobenzyl)-3-methylpiperidine-3-carboxylate (18a)

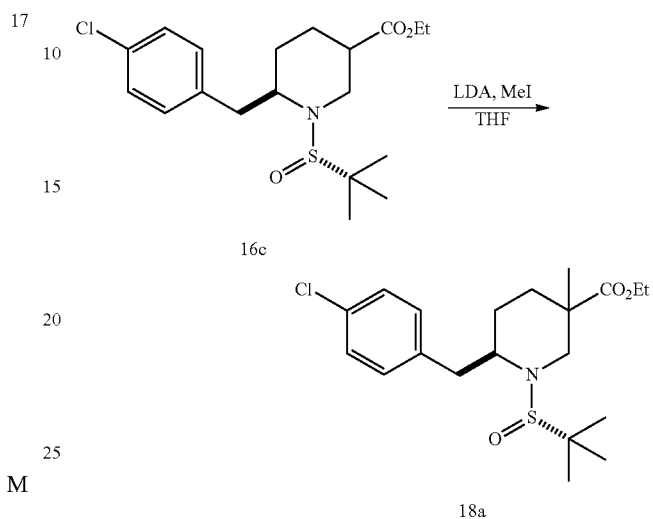

To a freshly prepared solution of LDA (2.32 mmol in 5 mL of THF) a solution of compound 16c (0.62 g, 1.6 mmol) in THF (5 mL) was added dropwise at −78° C. After 1 hour at −78° C. methyl iodide (0.34 g, 2.4 mmol) was added dropwise and the reaction was allowed to warm up to RT and stirred overnight. The reaction mixture was poured into saturated solution of ammonium chloride and extracted with diethyl ether. The organic phase was washed with 1 N HCl, brine, dried over MgSO$_4$ and concentrated. Column chromatography in EtOAc/hexanes 1:6 afforded 0.14 g (0.35 mmol; 22% yield) of the title compound 18a.

ESI-MS m/z for $C_{20}H_{30}ClNO_3S$ found 422.1/424.1 (M+Na)$^+$ $^1$H NMR (CDCl$_3$, 500 MHz) δ 7.24 (AA'BB', J=8.3 Hz, 2H), 7.16 (AA'BB', J=8.3 Hz, 2H), 4.23-4.12 (m, 1H), 4.04-3.95 (m, 1H), 3.65-3.58 (m, 1H), 3.56-3.37 (m, 1H), 3.32-3.23 (m, 2H), 2.88-2.80 (m, 1H), 2.10-2.03 (m, 1H), 1.77-1.55 (m, 1H), 1.55 (s, 3H), 1.24 (t, J=7.1 Hz, 2H), 1.21 (m, 2H), 1.18 (s, 9H).

Step 2

Synthesis of ethyl (6R)-6-(4-chlorobenzyl)-3-methylpiperidine-3-carboxylate (18b)

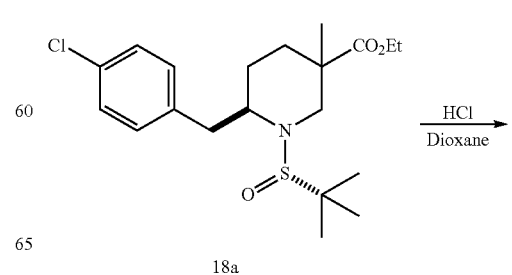

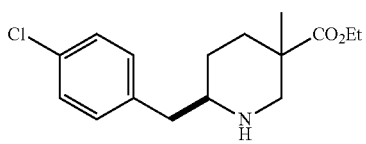
18b

Compound 18a (0.14 g, 0.35 mmol) was treated with 1 N HCl(gas)/1,4-dioxane solution at RT for 1 hour. The reaction mixture was then concentrated to dryness, affording 0.11 g (0.34 mmol; 97% yield) of piperidine 18b in a form of hydrochloride salt.

ESI-MS m/z for $C_{16}H_{22}ClNO_2$ found 296.1/298.1 $(M+1)^+$

Steps 3-5

Synthesis of ethyl (6R)-1'-(5-amino-4H-1,2,4-triazol-3-yl)-6-(4-chlorobenzyl)-3-methyl-[1,4'-bipiperidine]-3-carboxylate (18c)

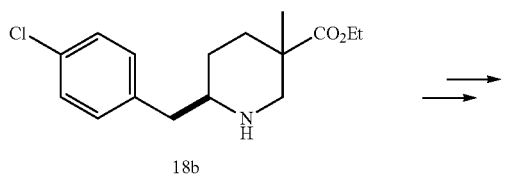
18b

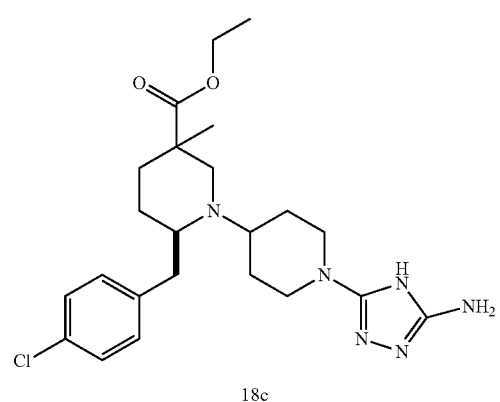
18c

Piperidine 18b was carried through the subsequent three synthetic steps as it is described in the General Procedure VI (reductive amination with N-Boc-piperid-4-one), the General Procedure VII (Boc-deprotection) and the General Procedure VIII (triazole ring formation). 30 mg (0.065 mmol; 19% yield over 3 steps) of compound 18c was synthesized.

ESI-MS m/z for $C_{23}H_{33}ClN_6O_2$ found 461.0/463.0 $(M+1)^+$

Step 6

Synthesis of (6R)-1'-(5-amino-4H-1,2,4-triazol-3-yl)-6-(4-chlorobenzyl)-3-methyl-[1,4'-bipiperidine]-3-carboxylic acid (18)

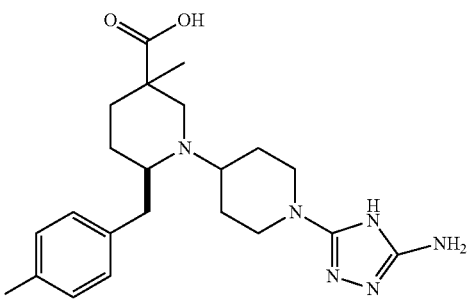
18

Solution of compound 18c (30 mg, 0.065 mmol) in MeOH (1 mL) was treated with 1 M NaOH (2 mL) and heated at 50° C. for 2 hours. Then the reaction was cooled to room temperature, acidified with 2 M HCl to the neutral pH and solvents were removed in vacuo. The residue was purified by the reversed-phase chromatography. 2 mg (0.005 mmol; 7% yield) of the title compound 18 was obtained.

ESI-MS m/z for $C_{21}H_{29}ClN_6O_2$ found 433.1/435.1 $(M+1)^+$ $^1$H NMR (CDCl$_3$, 500 MHz), δ 7.40 (AA'BB', J=8.3 Hz, 2H), 7.34 (AA'BB', J=8.3 Hz, 2H), 3.99-3.89 (m, 2H), 3.71-2.90 (m, 5H), 2.90-2.81 (m, 2H), 2.26-2.13 (m, 1H), 2.04-1.97 (m, 1H), 1.94-1.58 (m, 6H), 1.49-1.38 (m, 1H), 1.26 (s, 3H).

Example 19

5-((2S,4R)-2-(4-chlorobenzyl)-4-methoxy-[1,4'-bipiperidin]-1'-yl)-4H-1,2,4-triazol-3-amine (19)

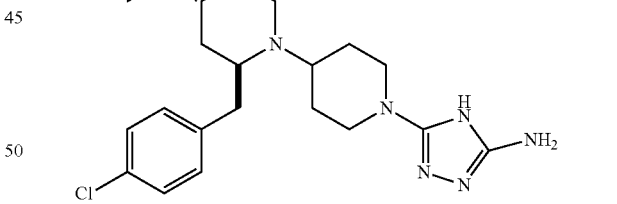
19

Step 1

Synthesis of (S)-2-((tert-butoxycarbonyl)amino)-3-(4-chlorophenyl)propanoic acid (19a)

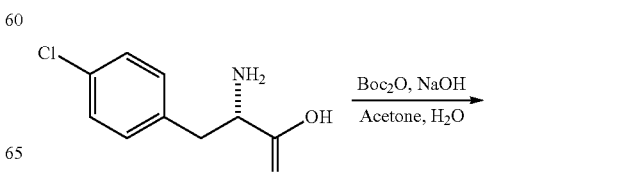

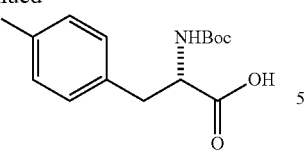

To a solution of p-chloro-L-phenylalanine (18.0 g, 75 mmol) in acetone-water (150 mL: 150 mL) was added sodium hydroxide (6 g, 150 mmol) at 0° C. followed by di-tert-butyl dicarbonate (16.4 g, 75 mmol). The reaction mixture was stirred at room temperature overnight. Acetone was evaporated. Aqueous layer was acidified to pH 2 with 2 M HCl and extracted with ethyl acetate. Organic layer was dried over magnesium sulfate, filtered and concentrated under reduced pressure. The crude product was crystallized from hexane to obtain 18.0 g of product 19a as white solid (80% yield).

ESI-MS m/z for $C_{14}H_{18}ClNO_4$ found 299.8/301.8 (M+1)$^+$ $^1$H NMR (DMSO-d$_6$, 500 MHz) δ: 7.29 (d, J=8.3 Hz, 2H), 7.21 (d, J=8.3 Hz, 2H), 7.02 (d, J=7.3 Hz, 1H), 4.08-3.99 (m, 1H), 2.96 (dd, J=4.3, 13.7 Hz, 1H), 2.76 (dd, J=10.5, 13.6 Hz, 1H).

Step 2

Synthesis of tert-butyl (S)-(1-(4-chlorophenyl)-4-diazo-3-oxobutan-2-yl)carbamate (19b)

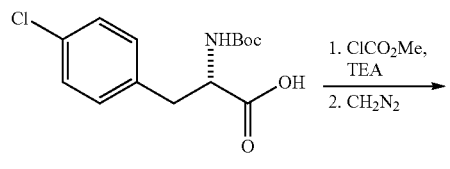

To a solution of acid 19a (17.2 g, 57 mmol) in tetrahydrofuran (200 mL) was added triethylamine (17 mL, 120 mmol) and methyl chloroformate (4.87 mL, 63 mmol) at −10° C. After 15 min a solution of diazomethane (342 mmol) in diethyl ether (400 mL) was added at −30° C. The reaction mixture was stirred overnight at room temperature. The excess of diazomethane was destroyed with acetic acid (15 mL). The mixture was diluted with diethyl ether and washed with 5% NaHCO$_3$, saturated NH$_4$Cl, and brine. The organic layer was dried over magnesium sulfate, filtered and concentrated under reduced pressure to give product 19b as an orange solid (18.0 g, 96% yield).

ESI-MS m/z for $C_{15}H_{18}ClN_3O_3$ found 324.1/326.1 (M+1)$^+$ $^1$H NMR (CDCl$_3$, 700 MHz) δ 7.28 (d, J=8.3 Hz, 2H), 7.13 (d, J=8.2 Hz, 2H), 5.26 (br s, 1H), 5.07 (br s, 1H), 4.40 (br s, 1H), 3.03 (dd, J=7.0, 14.0 Hz, 1H), 2.97 (dd, J=6.1, 13.5 Hz, 1H), 1.42 (s, 9H).

Step 3

Synthesis of (S)-3-((tert-butoxycarbonyl)amino)-4-(4-chlorophenyl)butanoic acid (19c)

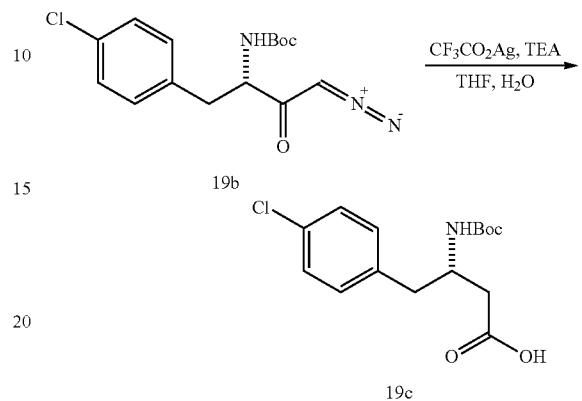

To a solution of compound 19b (18 g, 65 mmol) in tetrahydrofuran:water (135:15 mL) was added a solution of silver trifluoroacetate (1.57 g, 7.1 mmol) in triethylamine (25 mL, 182 mmol) at −5° C. The reaction mixture was stirred for 1 hour. After this time solvent was removed at reduced pressure. The residue was diluted with saturated aq. NaHCO$_3$, and the mixture was extracted with diethyl ether. 1 M HCl was added to the aqueous layer at 0° C. until pH 2-3, and the mixture was extracted three times with ethyl acetate. The organic layers were collected, dried over magnesium sulfate, and evaporated under reduced pressure. The crude product was crystallized from diethyl ether to obtain 7 g of 19c as a white solid in 40% yield.

ESI-MS m/z for $C_{15}H_{20}ClNO_4$ found 312.3/314.3 (M−1)$^-$ $^1$H NMR (DMSO-d$_6$, 500 MHz) δ 12.14 (s, 1H), 7.28 (d, J=8.3 Hz, 2H), 7.14 (d, J=8.3 Hz, 2H), 6.76 (d, J=8.7 Hz, 1H), 3.90-3.86 (m, 1H), 2.68 (dd, J=5.27, 13.4 Hz, 1H), 2.60 (dd, J=8.5, 13.4 Hz, 1H), 2.30 (t, J=7.0 Hz, 2H), 1.25 (s, 9H).

Step 4

Synthesis of tert-butyl (S)-(1-(4-chlorophenyl)-4-(methoxy(methyl)amino)-4-oxobutan-2-yl)carbamate (19d)

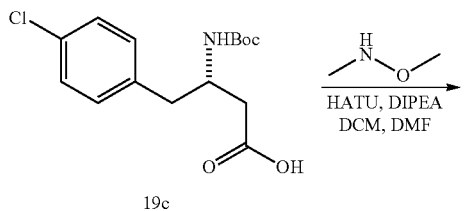

-continued

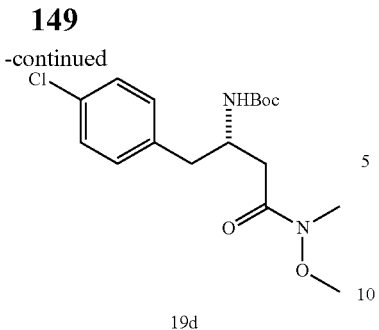

19d

Compound 19d was obtained from 19c (7 g, 22.3 mmol) according to the General Procedure XXII (to improve solubility of 19c, mixture of DCM/DMF 10:1 was used as a reaction solvent) in 93% yield (7.4 g), after flash chromatography using hexane-ethyl acetate (gradient elution from 20:1 to 1:1).

ESI-MS m/z for $C_{17}H_{25}ClN_2O_4$ found 380.1/382.1 $(M+Na)^+$ $^1$H NMR (CDCl$_3$, 500 MHz) δ 7.25 (d, J=8.5 Hz, 2H), 7.13 (d, J=8.3 Hz, 2H), 5.48 (br s, 1H), 4.14-4.10 (m, 1H), 3.57 (s, 3H), 3.17 (s, 3H), 3.00-2.94 (m, 1H), 2.84 (dd, J=7.9, 13.6 Hz, 1H), 2.58 (qd, J=3.8, 16.4 Hz, 2H), 1.39 (s, 9H).

Step 5

Synthesis of tert-butyl (S)-(1-(4-chlorophenyl)-4-oxohex-5-en-2-yl)carbamate (19e)

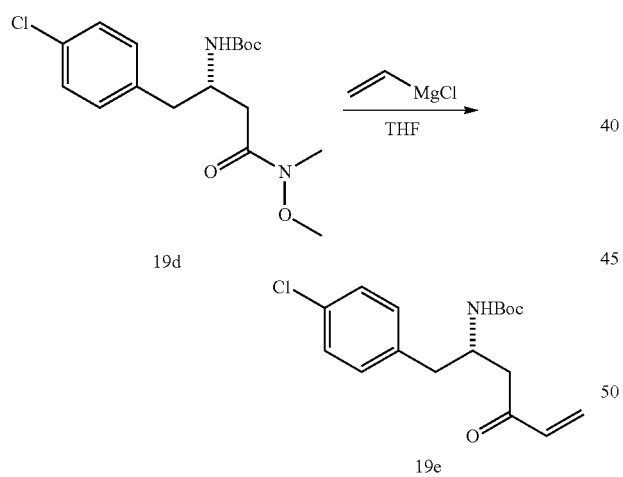

To a solution of 19d (6.9 g, 19.3 mmol) in dry tetrahydrofuran (50 mL) was added vinylmagnesium chloride in THF (48 mL, 77.3 mmol) at 0° C. The mixture was brought to room temperature and stirred for 3 hours. The reaction mixture was poured into saturated aq. NH$_4$Cl and extracted with diethyl ether. The organic layer was washed with 1 M HCl, brine, dried over magnesium sulfate and concentrated under reduced pressure. The product 19e was purified by flash chromatography using hexanes—ethyl acetate (gradient elution from 10:1 to 5:1). 2.0 g was obtained as a white solid (32% yield).

ESI-MS m/z for $C_{17}H_{22}ClNO_3$ found 323.8/325.8 $(M+1)^+$

Step 6

Synthesis of tert-butyl (S)-2-(4-chlorobenzyl)-4-oxopiperidine-1-carboxylate (19f)

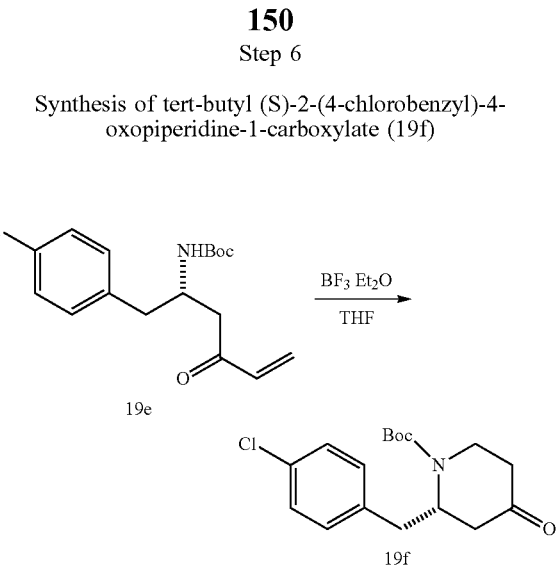

To a solution of 19e (1.1 g, 3.4 mmol) in tetrahydrofuran (10 mL) was added boron trifluoride diethyl ether complex (4.27 mL, 34 mmol). The reaction mixture was stirred at room temperature overnight. Then the mixture was diluted with ethyl acetate and washed with 4 M NaOH. Organic layer was dried over magnesium sulfate, filtered and concentrated under reduced pressure. The product 19f was purified by flash chromatography using hexanes—ethyl acetate (gradient elution from 6:1 to 2:1) to afford 480 mg as a colorless oil (43% yield).

ESI-MS m/z for $C_{17}H_{22}ClNO_3$ found 346.1/348.1 $(M+Na)^+$ $^1$H NMR (CDCl$_3$, 500 MHz) δ 7.26 (d, J=8.3 Hz, 2H), 7.09 (d, J=6.6 Hz, 2H), 4.74 (br s, 1H), 4.37 (br s, 1H), 3.30 (qd, J=3.7, 11.5 Hz, 1H), 2.81 (dd, J=7.3, 13.6 Hz, 1H), 2.68 (dd, J=7.9, 13.7 Hz, 1H), 2.60 (dd, J=6.8, 14.5 Hz, 1H), 2.54-2.49 (m, 1H), 2.39-2.34 (m, 2H), 1.40 (s, 9H).

Step 7

Synthesis of tert-butyl (2S,4R)-2-(4-chlorobenzyl)-4-hydroxypiperidine-1-carboxylate (19g) and tert-butyl (2S,4S)-2-(4-chlorobenzyl)-4-hydroxypiperidine-1-carboxylate (19h)

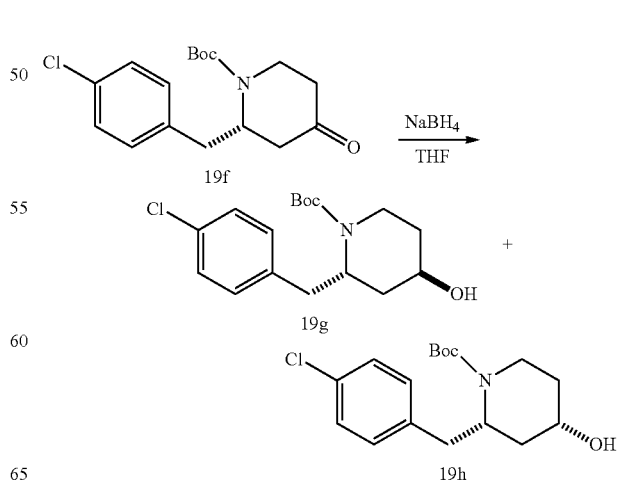

To a solution of 19f (470 mg, 1.45 mmol) in methanol (5 mL) was added sodium borohydride (66 mg, 1.75 mmol) at 0° C. The reaction mixture was stirred at room temperature for 2 hours, then 1 M NaOH was added. Aqueous layer was extracted with ethyl acetate. The combined organic layer was dried over magnesium sulfate filtered and concentrated under reduced pressure. The products were purified by flash chromatograpy using hexanes—ethyl acetate (from 6:1 to 1:1). 187 mg (19g single diastereomer with unknown configuration at hydroxy group) and 200 mg (19h single diastereomer with unknown configuration at hydroxyl group) of products 19g and 19h were obtained as colorless oil in 40% and 42% yield respectively.

19g

ESI-MS m/z for $C_{17}H_{24}ClNO_3$ found 349.0/351.0 (M+Na)$^+$ $^1$H NMR (CDCl$_3$, 500 MHz) δ 7.23 (d, J=8.5 Hz, 2H), 7.15 (d, J=8.3 Hz, 2H), 4.34-4.31 (m, 1H), 4.20 (t, J=3.0 Hz, 1H), 3.96 (d, J=12.4 Hz, 1H), 3.31 (td, J=3.8, 13.4 Hz, 1H), 3.10 (dd, J=7.1, 13.1 Hz, 1H), 3.01 (dd, J=8.1, 13.2 Hz, 1H), 1.71-1.68 (m, 4H), 1.34 (s, 9H).

19h

ESI-MS m/z for $C_{17}H_{24}ClNO_3$ found 349.0/351.0 (M+Na)$^+$ $^1$H NMR (CDCl$_3$, 500 MHz) δ 7.25 (d, J=8.5 Hz, 2H), 7.09 (d, J=6.2 Hz, 2H), 4.50 (br s, 1H), 4.24-4.17 (m, 1H), 4.05-4.00 (m, 1H), 2.94 (td, J=2.6, 13.6 Hz, 1H), 2.82 (dd, J=8.3, 13.4 Hz, 1H), 2.68 (dd, J=7.5, 13.0 Hz, 1H), 2.00 (d, J=11.9 Hz, 1H), 1.87 (d, 12.4 Hz, 1H), 1.45-1.40 (m, 2H), 1.31 (s, 9H).

Step 8

Synthesis of tert-butyl (2S,4R)-2-(4-chlorobenzyl)-4-methoxypiperidine-1-carboxylate (19i)

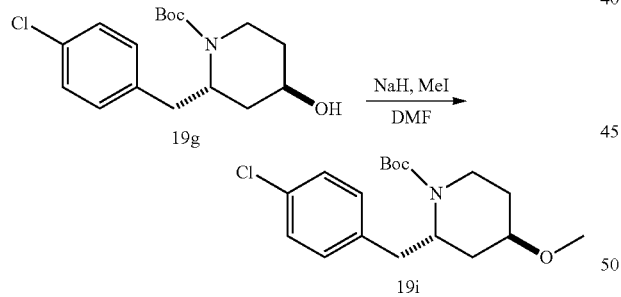

Compound 19i was obtained from 19g (190 mg, 0.58 mmol) according to the General Procedure XXI (to improve solubility DMF was used as a reaction solvent) in 97% yield (190 mg, 0.56 mmol, white solid), after flash chromatograpy using hexanes/EtOAc (gradient elution from 10:1 to 5:1).

ESI-MS m/z for $C_{18}H_{26}ClNO_3$ found 362.1/364.1 (M+Na)$^+$ $^1$H NMR (CDCl$_3$, 700 MHz) δ 7.25 (d, J=8.5 Hz, 2H), 7.16 (d, J=8.1 Hz, 2H), 4.33-4.31 (m, 1H), 3.96-3.94 (m, 1H), 3.59-3.57 (m, 1H), 3.38 (s, 3H), 3.20 (td, J=2.6, 13.3 Hz, 1H), 3.06 (dd, J=8.0, 13.3 Hz, 1H), 2.94 (dd, 7.6, 13.2 Hz, 1H), 1.93-1.91 (m, 1H), 1.86-1.83 (m, 1H), 1.64-1.60 (m, 2H), 1.35 (s, 9H).

Step 9

Synthesis of (2S,4R)-2-(4-chlorobenzyl)-4-methoxypiperidine hydrochloride (19j)

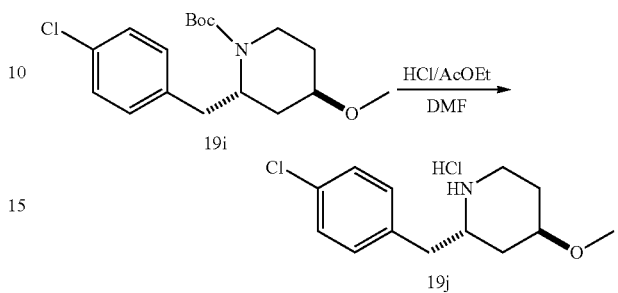

Compound 19j was obtained from 19i (190 mg, 0.56 mmol) according to the General Procedure VII in 93% yield (150 mg, 0.54 mmol) as a white solid.

ESI-MS m/z for $C_{13}H_{18}ClNO$ found 240.1/242.2 (M+1)$^+$

Step 10

Synthesis of (2S,4R)-2-(4-chlorobenzyl)-4-methoxy-1,4'-bipiperidine hydrochloride (19k)

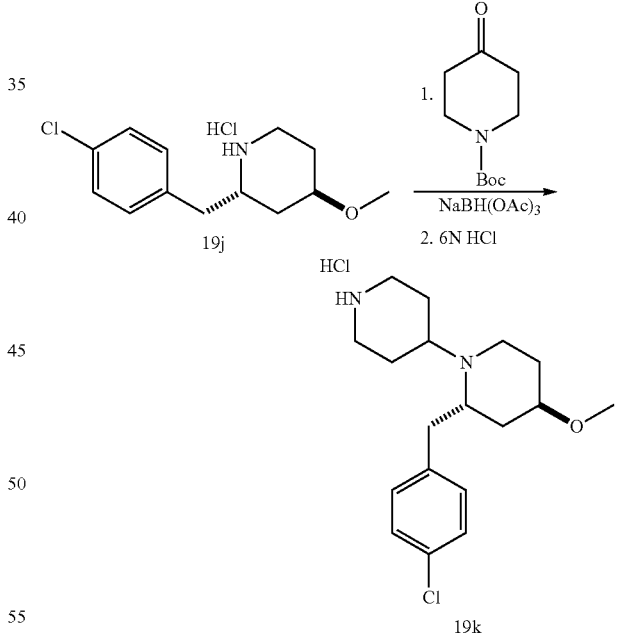

Compound 19k was obtained from 19j (150 mg, 0.54 mmol) according to the General Procedure VI followed by flash chromatography using hexanes/AcOEt (gradient elution from 10:1 to 1:4). In the next step Boc protecting group was removed by dissolving material obtained after flash chromatography in ethyl acetate, and transferring it to 6 M aqueous HCl. To the strongly acidic aqueous layer was basified with 4 M NaOH to bring pH to 10 and then it was extracted three times with ethyl acetate. Combined organics were dried over magnesium sulfate, filtered and concentrated under reduced pressure to afford 90 mg of product 19k as a colorless oil (0.28 mmol; 51% yield).

ESI-MS m/z for $C_{18}H_{27}ClN_2O$ found 323.3/325.2 $(M+1)^+$

Step 11

Synthesis of 5-((2S,4R)-2-(4-chlorobenzyl)-4-methoxy-[1,4'-bipiperidin]-1'-yl)-4H-1,2,4-triazol-3-amine (19)

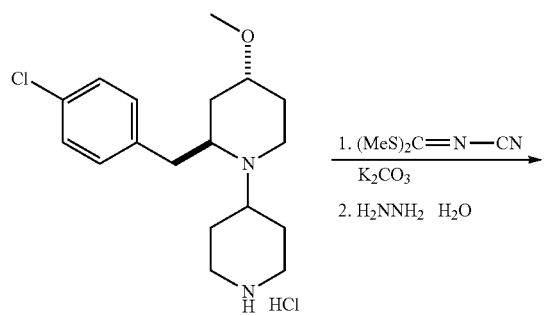

Compound 19 was obtained from 19k (90 mg, 0.28 mmol) according to the General Procedure VIII in 35% yield (50 mg, 0.1 mmol, white solid), after purification by preparative reversed-phase chromatography.

Single Diastereomer with Unknown Configuration at Methoxy Group $^1$H NMR (DMSO-d$_6$+D$_2$O, 700 MHz) δ 7.40 (d, J=8.4 Hz, 2H), 7.31 (d, J=8.2 Hz, 2H), 3.84-3.78(m, 3H), 3.70-3.67 (m, 1H), 3.50-3.48 (m, 1H), 3.42 (dd, J=4.6, 13.6 Hz, 1H), 3.32-3.30 (m, 1H), 3.15 (s, 3H), 3.02-2.99 (m, 1H), 2.93 (td, J=1.8, 13.4 Hz, 1H), 2.87 (td, J=1.3, 13.0 Hz, 1H), 2.71 (dd, J=9.7, 13.1 Hz, 1H), 2.19 (d, 12.1 Hz, 1H), 1.93-1.85 (m, 4H), 1.65 (qd, J=4.6, 12.7 Hz, 1H), 1.48 (qd, J=3.8, 13.5 Hz, 1H), 1.43-1.38 (m, 1H).

Example 20

5-((2S,4S)-2-(4-chlorobenzyl)-4-methoxy-[1,4'-bipiperidin]-1'-yl)-4H-1,2,4-triazol-3-amine (20)

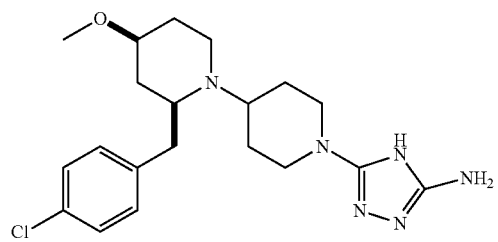

Step 1

Synthesis of tert-butyl (2S,4S)-2-(4-chlorobenzyl)-4-methoxypiperidine-1-carboxylate (20a)

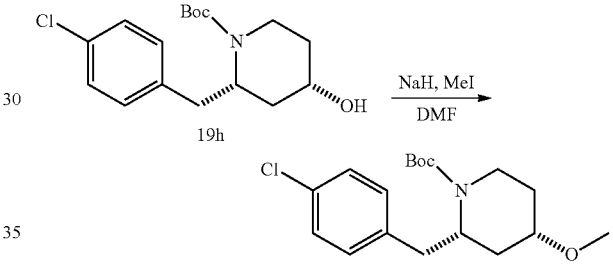

Compound 20a was obtained from 19h (190 mg, 0.58 mmol) according to the General Procedure XXI (to improve solubility DMF was used as a reaction solvent) in 78% yield (0.46 mmol; 150 mg, white solid), after flash chromatography using hexanes/EtOAc (gradient elution from 10:1 to 5:1).

ESI-MS m/z for $C_{18}H_{26}ClNO_3$ found 362.1/364.1 $(M+Na)^+$ $^1$H NMR (CDCl$_3$, 500 MHz) δ 7.25 (d, J=8.5 Hz, 2H), 7.10 (d, J=6.2 Hz, 2H), 4.51 (br s, 1H), 4.21 (br s, 1H), 3.57-3.52 (m, 1H), 3.48 (d, J=5.5 Hz, 2H), 3.35 (s, 3H), 2.92 (td, J=2.6, 13.7 Hz, 1H), 2.83 (dd, J=8.1, 13.4 Hz, 1H), 2.68 (dd, J=7.5, 13.2 Hz, 1H), 2.06 (d, J=10.4 Hz, 1H), 1.94-1.90 (m, 1H), 1.32 (s, 9H).

Step 2

Synthesis of (2S,4S)-2-(4-chlorobenzyl)-4-methoxypiperidine hydrochloride (20b)

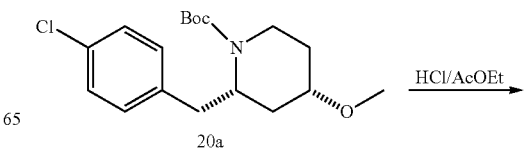

155
-continued

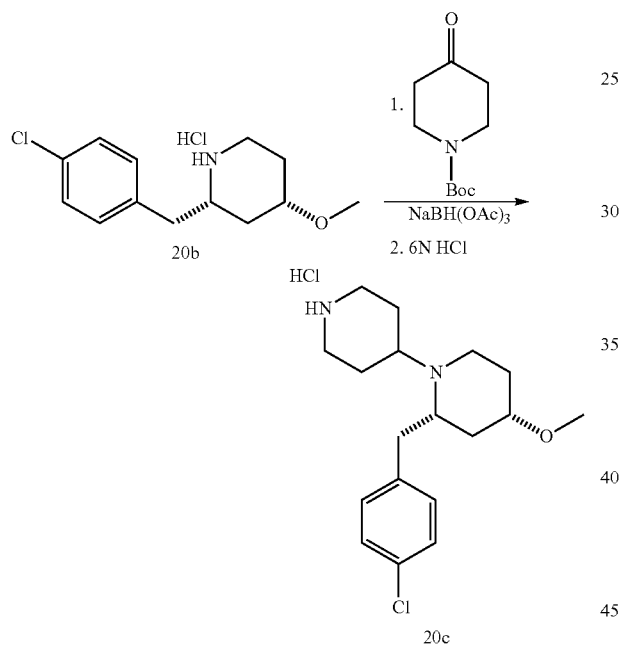

20b

Compound 20b was obtained from 20a (165 mg, 0.48 mmol) according to the General Procedure VII in 90% yield (0.43 mmol; 165 mg).

ESI-MS m/z for $C_{13}H_{18}ClNO$ found 240.2/242.2 $(M+1)^+$.

Step 3

Synthesis of (2S,4S)-2-(4-chlorobenzyl)-4-methoxy-1,4'-bipiperidine hydrochloride (20c)

20c

Compound 20c was obtained from 20b (120 mg, 0.43 mmol) according to the General Procedure VI followed by flash chromatography using hexanes/AcOEt (gradient elution from 10:1 to 1:4). In the next step Boc protecting group was removed by dissolving material obtained after flash chromatography in ethyl acetate, and transferring it to 6 M aqueous HCl. To the strongly acidic aqueous layer was basified with 4 M NaOH to bring pH to 10 and then it was extracted three times with ethyl acetate. Combined organics were dried over magnesium sulfate, filtered and concentrated under reduced pressure to afford 65 mg of product 20c as a colorless oil (0.20 mmol; 46% yield).

ESI-MS m/z for $C_{18}H_{27}ClN_2O$ found 323.2/325.2 $(M+1)^+$

156

Step 4

Synthesis of 5-((2S,4S)-2-(4-chlorobenzyl)-4-methoxy-[1,4'-bipiperidin]-1'-yl)-4H-1,2,4-triazol-3-amine (20)

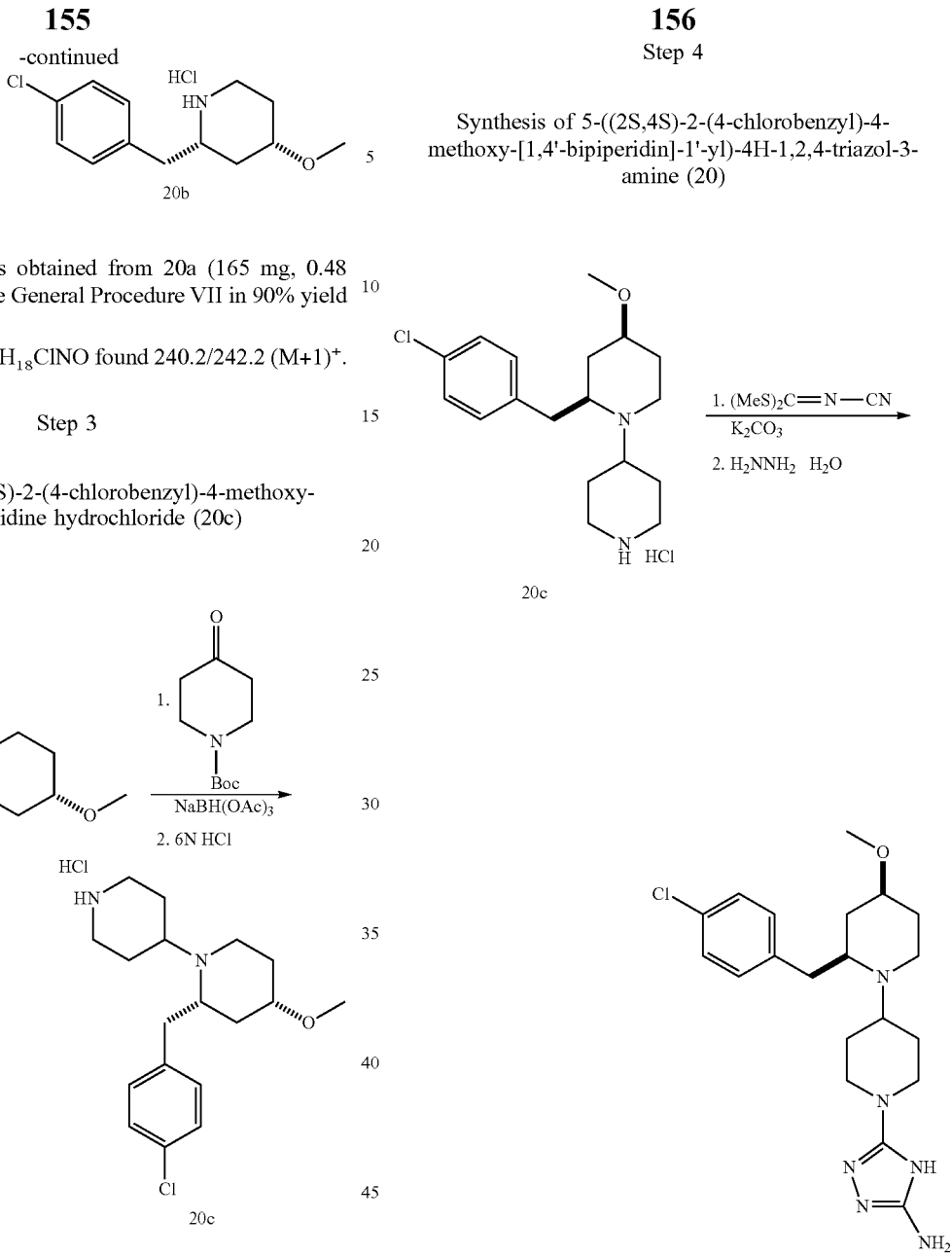

20

Compound 20 was obtained from 20c (65 mg, 0.20 mmol) according to the General Procedure VIII in 56% yield (58 mg, 0.14 mmol, white solid), after purification by preparative reversed-phase chromatography.

Single diastereomer with unknown configuration of the methoxy group.

ESI-MS m/z for $C_{20}H_{29}ClN_6O$ found 405.1/407.1 $(M+1)^+$ $^1$H NMR (DMSO-$d_6$+$D_2O$, 500 MHz) δ 7.36 (d, J=7.9 Hz, 2H), 7.27 (d, J=8.1 Hz, 2H), 3.62-3.57 (m, 1H), 3.49-3.45 (m, 1H), 3.39 (d, J=13.9 Hz, 1H), 3.26 (d, J=12.2 Hz, 1H), 3.11-3.07 (m, 1H), 3.04 (s, 3H), 2.99-2.89 (m, 4H), 2.60 (t, J=13.0 Hz, 1H), 2.23-2.13 (m, 1H), 2.03-1.93 (m, 2H), 1.90-1.93 (m, 2H), 1.77-1.74 (m, 1H), 1.71-1.56 (m, 3H).

Example 21

(1'-(5-amino-4H-1,2,4-triazol-3-yl)-[1,4'-bipiperidin]-2-yl)(4-chlorophenyl)methanol (21)

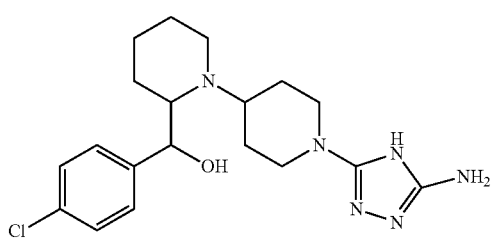

Step 1

Synthesis of tert-butyl 2-(hydroxymethyl)piperidine-1-carboxylate (21a)

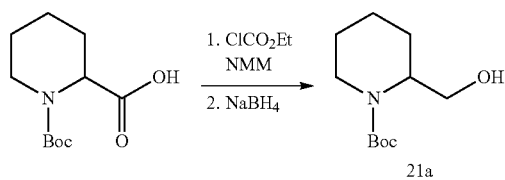 [SMILES: CC(C)(C)OC(=O)N1CCCCC1C(=O)O ; CC(C)(C)OC(=O)N1CCCCC1CO]

Compound 21a was obtained from 1-Boc-pipecolinic acid (25 g, 109 mmol) according to the General Procedure XI in 73% yield (17 g, 79.1 mmol, white solid).

ESI-MS m/z for $C_{11}H_{21}NO_3$ found 216.1 (M+1)$^+$

Step 2

Synthesis of tert-butyl 2-formylpiperidine-1-carboxylate (21b)

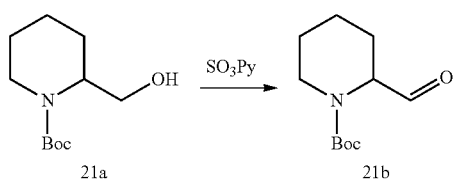 [SMILES: CC(C)(C)OC(=O)N1CCCCC1CO ; CC(C)(C)OC(=O)N1CCCCC1C=O]

Alcohol 21a (2.3 g, 10.68 mmol) was dissolved in DMSO (10 mL), triethylamine (4.44 mL, 32.05 mmol) was added followed by sulfur trioxide pyridine complex (3.4 g, 21.37 mmol). The reaction mixture was stirred at RT for 4 hours and then separated between ethyl acetate and 2 M HCl. Organic layer was washed with 2 M HCl, brine, dried over MgSO$_4$, filtered, and evaporated to dryness. Product was purified by flash chromatography (on silica gel) to give 1.17 g (5.49 mmol; 51% yield) of aldehyde 21b that was immediately taken to the next reaction

Step 3

Synthesis of 1-(4-chlorophenyl)tetrahydro-1H-oxazolo[3,4-a]pyridin-3(5H)-one (21c)

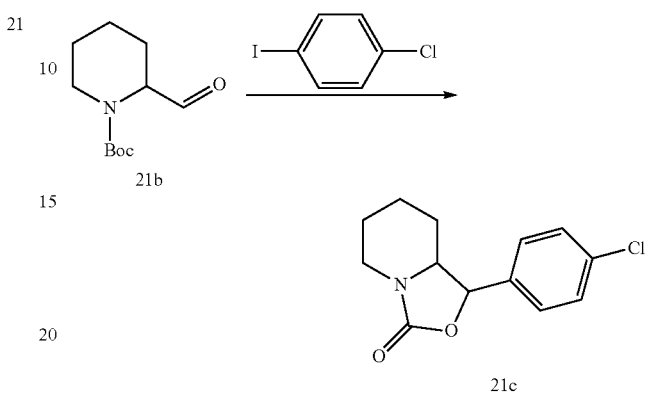

To a solution of 1-chloro-4-iodobenzene (1.57 g, 6.58 mmol) in dry THF (10 mL) under argon at −78° C., isopropylmagnesium chloride lithium chloride complex solution (iPrMgCl.LiCl) (1.3M in THF) (5.1 mL, 6.58 mmol) was added dropwise and then stirred for 1 hour at −78° C. Aldehyde 21b (1.17 g, 5.49 mmol) in 5 mL of dry THF was added dropwise at −78° C. After 20 minutes reaction mixture was quenched with sat. NH$_4$Cl and then left overnight. Product was extracted with ethyl acetate, dried over MgSO$_4$, filtered, and evaporated to dryness to give 1.55 g (6.18 mmol; 94% yield) of bicyclic product 21c.

ESI-MS m/z for $C_{13}H_{14}ClNO_2$ found 252.2/254.2 (M+1)$^+$

Step 4

Synthesis of (4-chlorophenyl)(piperidin-2-yl)methanol (21d)

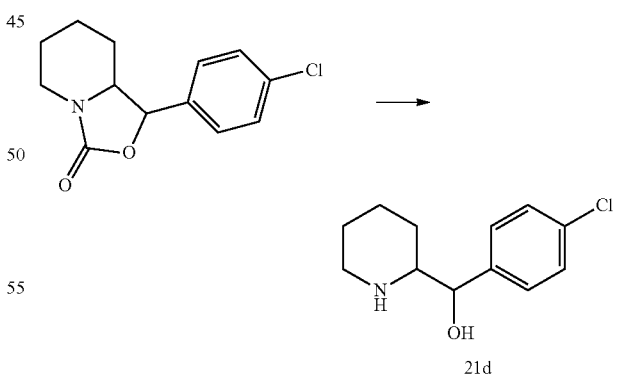

1.55 g (6.18 mmol) of compound 21c was suspended in 6 M HCl, refluxed overnight and then evaporated to dryness. Residue was taken between 1 M K$_2$CO$_3$ and AcOEt. Organic layer was washed with brine, dried over MgSO$_4$, filtered, evaporated to dryness to give 0.80 g of amino alcohol product 21d (3.56 mmol; 58% yield).

ESI-MS m/z for $C_{12}H_{16}ClNO$; 225.1 found 226.2 (M+1)$^+$

Step 5

Synthesis of tert-butyl 2-((4-chlorophenyl)(hydroxy)methyl)-[1,4'-bipiperidine]-1'-carboxylate (21e)

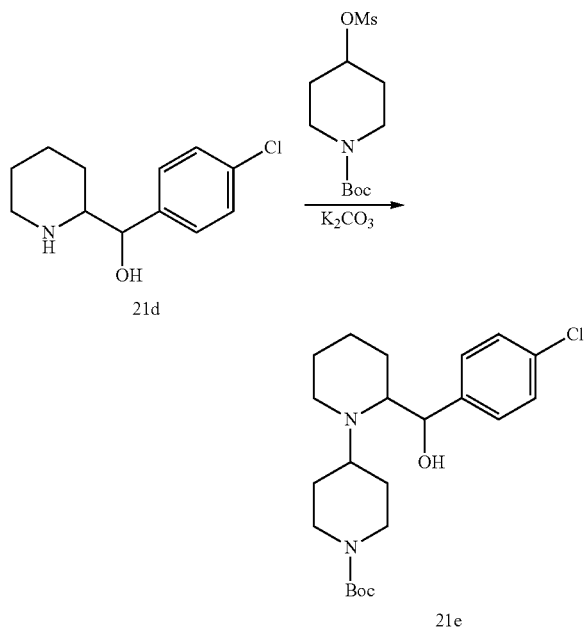

Mixture of amino alcohol 21d (0.4 g, 1.77 mmol), tert-butyl 4-[(methylsulfonyl)oxy]piperidine-1-carboxylate (2.47 g, 8.86 mmol), and K$_2$CO$_3$ (1.22 g, 8.86 mmol) in MeCN were refluxed for 3 days. The reaction mixture was cooled to RT and separated between ethyl acetate and water. Organic layer was washed with water, 1 M HCl, brine, dried over MgSO$_4$, filtered and evaporated to dryness. Crude product was purified on flash chromatography on silica gel to give 0.21 g (0.51 mmol; 29% yield) of compound 21e.

ESI-MS m/z for C$_{22}$H$_{33}$ClN$_2$O$_3$ found 409.6/411.6 (M+1)$^+$

Step 6

Synthesis of [1,4'-bipiperidin]-2-yl(4-chlorophenyl)methanol (21f)

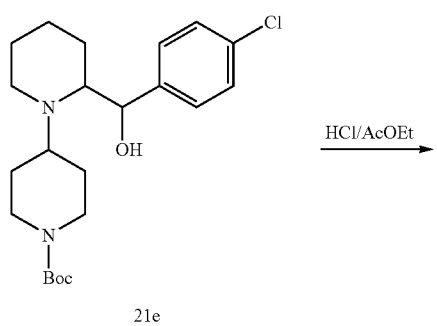

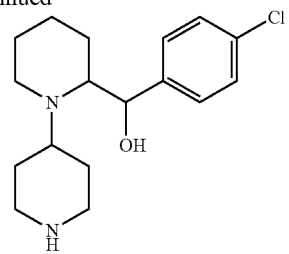

Compound 21e (0.21 g, 0.51 mmol) was dissolved in 3 N HCl/AcOEt (3 mL), reaction mixture was stirred for 30 min., and then evaporated to dryness. Residue was taken between 1 M NaOH and ethyl acetate. Aqueous layer was washed with AcOEt three times. Organic layers were combined, dried over MgSO$_4$, filtered, and evaporated to dryness to give 0.13 g (0.42 mmol; yield 83%) of free amine 21f.

ESI-MS m/z for C$_{17}$H$_{25}$ClN$_2$O found 309.4/310.4 (M+1)$^+$

Step 7

Synthesis of (1'-(5-amino-4H-1,2,4-triazol-3-yl)-[1,4'-bipiperidin]-2-yl)(4-chlorophenyl)methanol (21)

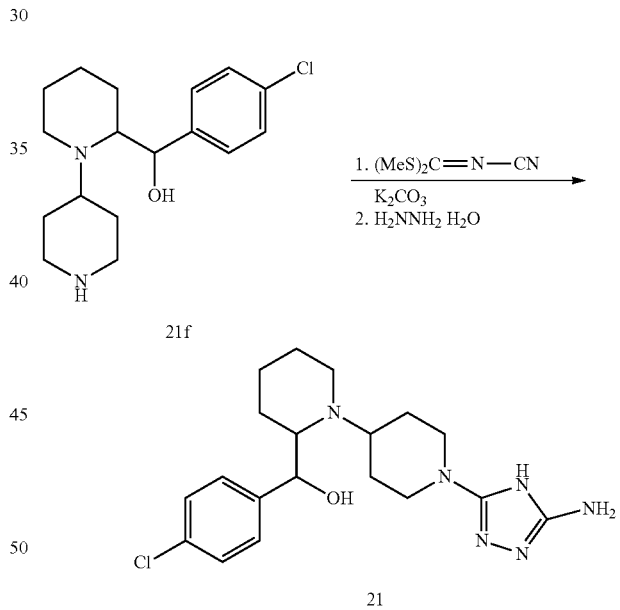

Compound 21 was obtained from 21f (0.13 g, 0.42 mmol) according to the General Procedure VIII. Product was purified by preparative reversed-phase chromatography. Fractions containing pure product were combined and evaporated to dryness. 2 M HCl (3 mL) was added and evaporated to dryness affording product 21 in 6% yield (10 mg, 0.023 mmol) as a hydrochloride salt.

ESI-MS m/z for C$_{19}$H$_{27}$ClN$_6$O found 391.5/393.5 (M+1)$^+$ $^1$H NMR (CD$_3$OD, 500 MHz) δ 7.44 (d, J=8.3 Hz, 2H), 7.39 (d, J=8.3 Hz, 2H), 5.45 (s, 1H), 4.17-4.11 (m, 1H), 4.07-3.98 (m, 2H), 3.67 (d, J=11.3 Hz, 1H), 3.59-3.53 (m, 1H), 3.3-3.25 (m, 1H), 3.24-3.19 (m, 1H), 3.1-3.02 (m, 1H), 2.34-2.27 (m, 1H), 2.18-2.08 (m, 2H), 2.03-1.97 (m, 1H), 1.92-1.86 (m, 1H), 1.84-1.77 (m, 1H), 1.77-1.71 (m, 2H), 1.42-1.33 (m, 2H)

Example 22

5-(4-((2S,3S)-2-(4-chlorobenzyl)-3-methoxyazetidin-1-yl)piperidin-1-yl)-4H-1,2,4-triazol-3-amine (22)

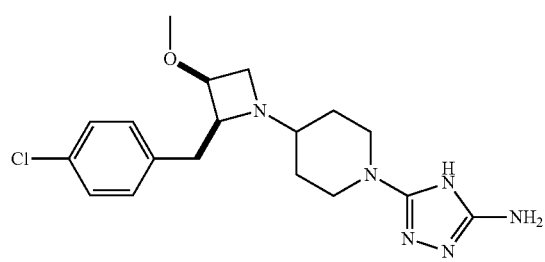

Step 1

Synthesis of tert-butyl (S)-2-(4-chlorobenzyl)-3-oxoazetidine-1-carboxylate (22a)

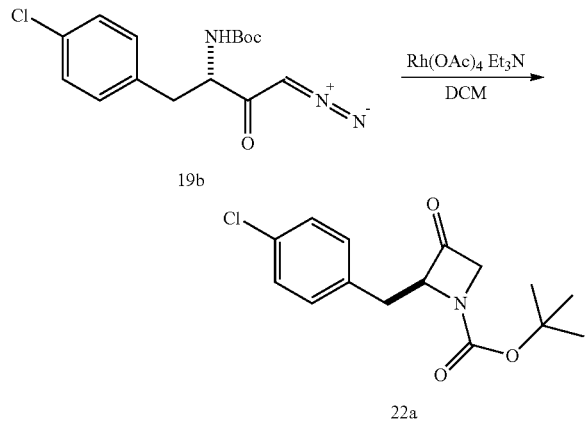

To a solution of compound 19b (3.6 g, 11 mmol) in dichloromethane (55 mL), triethylamine (16 μL, 0.11 mmol) was added. The reaction mixture was cooled to 0° C. and rhodium acetate (25 mg, 0.056 mmol) was added. Cooling bath was removed and the reaction was stirred at room temperature overnight. The mixture was diluted with water (50 mL), phases were separated and the aqueous layer was extracted with dichloromethane (3×25 mL). The combined organics was washed with brine, dried over magnesium sulfate, filtered and concentrated under reduced pressure. The title product (22a) was purified by flash chromatography using in AcOEt/hexanes 1:15 solvent system. 1.5 g (5.1 mmol; 46% yield) of compound 22a was obtained.

ESI-MS m/z for $C_{15}H_{18}ClNO_3$ found 296.1/298.1 (M+1)$^+$
$^1$H NMR (CDCl$_3$, 500 MHz) δ 7.26 (d, J=8.5 Hz, 2H), 7.12 (d, J=8.5 Hz, 2H), 5.11-5.08 (m, 1H), 4.54 (d, J=16.8 Hz, 1H), 4.06 (dd, J=4.3, 16.8 Hz, 1H), 3.16 (dd, J=6.2, 14.3 Hz, 1H), 3.07 (dd, J=4.1, 14.3 Hz, 1H), 1.47 (s, 9H).

Step 2

Synthesis of tert-butyl (2S)-2-(4-chlorobenzyl)-3-hydroxyazetidine-1-carboxylate (22b)

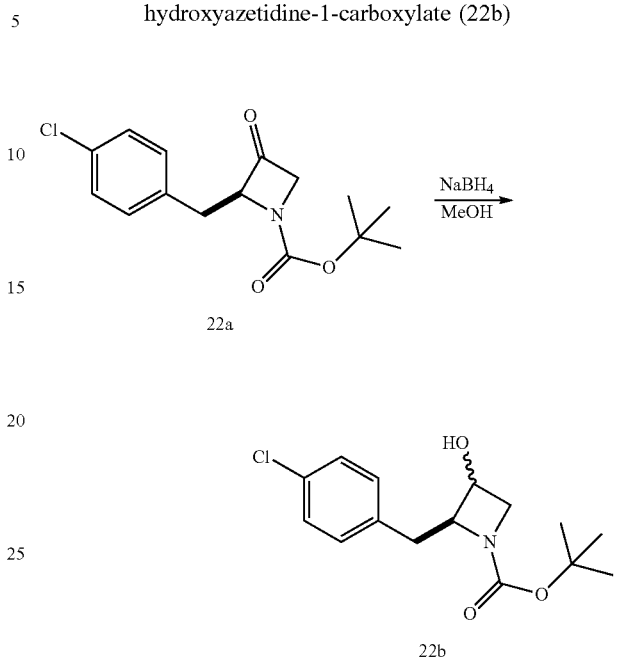

Compound 22a (1.5 g, 5.07 mmol) was dissolved in methanol (20 mL) and sodium borohydride (0.23 g, 6.1 mmol) was added at 0° C. The reaction mixture was stirred at room temperature for 1 hour and then 15 mL of 1 M NaOH was added and methanol was evaporated under reduced pressure. Aqueous layer was extracted with ethyl acetate (3×25 mL). The combined organic layers was dried over magnesium sulfate, filtered and concentrated under reduced pressure. The title product was purified by flash chromatography using AcOEt/hexanes 1:5 solvent system. 1.3 g (4.36 mmol; 86% yield) of compound 22b was obtained (mixture of diastereomers in 10:1 ratio)

ESI-MS m/z for $C_{15}H_{20}ClNO_3$ found 320.2/322.2 (M+Na)$^+$

Diasteroisomer A:
$^1$H NMR (DMSO-d$_6$, 75° C., 700 MHz) δ 7.29 (d, J=8.5 Hz, 2H), 7.24 (d, J=8.6 Hz, 2H), 5.42 (d, J=6.3 Hz, 1H), 4.49-4.45 (m, 1H), 4.00 (dd, J=7.0, 9.0 Hz, 1H), 3.53 (ddd, J=0.9, 4.3, 9.0 Hz, 1H), 3.15 (dd, J=8.6, 14.1 Hz, 1H), 2.92 (dd, J=5.0, 14.0 Hz, 1H), 1.32 (s, 9H).

Diasteroisomer B:
$^1$H NMR (DMSO-d$_6$, 75° C., 700 MHz) δ 7.33 (d, J=8.5 Hz, 2H), 7.24 (d, 2H), 5.33 (d, J=6.7 Hz, 1H), 4.30-4.27 (m, 1H), 4.04-4.02 (m, 1H), 3.76 (ddd, J=0.9, 6.6, 8.8 Hz, 1H), 3.44 (dd, J=4.6, 8.8 Hz, 1H), 2.89 (dd, J=8.3, 14.1 Hz, 1H), 1.39 (s, 9H).

Step 3

Synthesis of tert-butyl (2S)-2-(4-chlorobenzyl)-3-methoxyazetidine-1-carboxylate (22c)

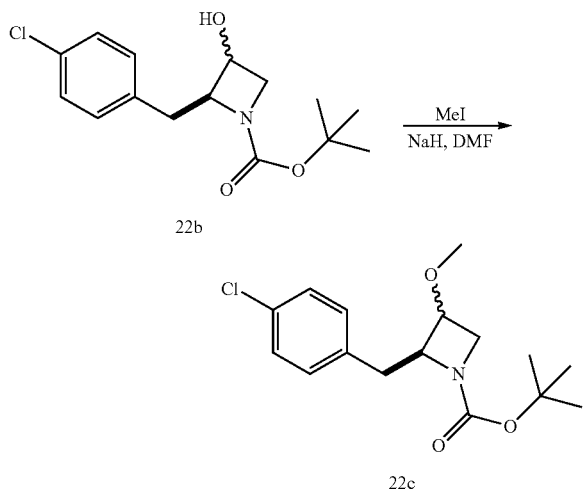

Compound 22c was obtained from 22b (0.40 g, 1.34 mmol) according to the General Procedure XXI (to improve solubility DMF was used as a reaction solvent) in >99% yield (1.34 mmol; 418 mg mixture of diastereomers in 9:1 ratio), after flash chromatography using hexanes/EtOAc (gradient elution from 10:1 to 5:1).

ESI-MS m/z for $C_{16}H_{22}ClNO_3$ found 334.1/336.1 $(M+Na)^+$

Diasteroizomer A:
$^1$H NMR (DMSO-$d_6$, 75° C., 700 MHz) δ 7.29 (d, J=8.4 Hz, 2H), 7.23 (d, J=8.5 Hz, 2H), 4.45-4.42 (m, 1H), 4.18 (td, J=4.3, 6.7 Hz, 1H), 3.96 (dd, J=6.7, 9.2 Hz, 1H), 3.61 (ddd, J=0.9, 4.3, 9.2 Hz, 1H), 3.20 (s, 3H), 3.11-3.06 (m, 1H), 2.97-2.95 (m, 1H), 1.31 (s, 9H).

Diasteroizomer B:
$^1$H NMR (DMSO-$d_6$, 75° C., 700 MHz) δ 7.34 (d, J=8.4 Hz, 2H), 7.26 (d, J=8.3 Hz, 2H), 4.08-4.06 (m, 1H), 3.81-3.77 (m, 2H), 3.50-3.49 (m, 1H), 3.12-3.10 (m, 1H), 2.95 (s, 3H), 2.90 (dd, J=8.7, 13.9 Hz, 1H), 1.40 (s, 9H).

Step 4

Synthesis of (2S)-2-(4-chlorobenzyl)-3-methoxyazetidine hydrochloride (22d)

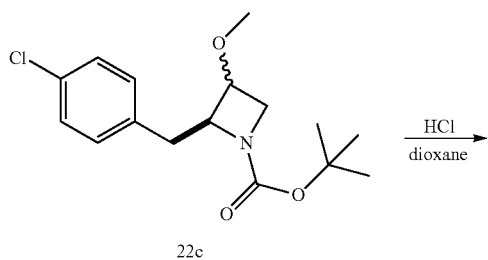

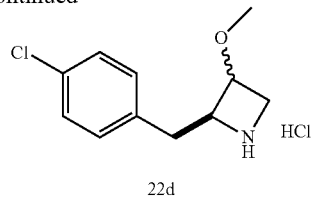

According to the General Procedure VII compound 22c (418 mg, 1.34 mmol) was treated with 4 M HCl (gas) in 1,4-dioxane (2.2 mL, 9.04 mmol). Crude product was triturated with diethyl ether providing 256 mg (1.03 mmol, yield 77%) of azetidine 22d as its hydrochloride salt (a mixture of diastereomers in 9:1 ratio).

ESI-MS m/z for $C_{11}H_{14}ClNO$ found 212.1/214.1 $(M+1)^+$

Diasteroisomer A:
$^1$H NMR (DMSO-$d_6$, 75° C., 600 MHz) δ 7.35-7.33 (m, 4H), 4.73 (dd, J=7.3, 14.1 Hz, 1H), 4.25 (td, J=4.0, 6.2 Hz, 1H), 4.08 (ddd, J=0.8, 6.2, 11.3 Hz, 1H), 3.72 (ddd, J=0.8, 3.9, 11.3 Hz, 1H), 3.18 (d, J=7.7 Hz, 2H), 3.06 (s, 3H).

Diasteroisomer B:
$^1$H NMR (DMSO-$d_6$, 75° C., 600 MHz) δ 7.39-7.37 (m, 4H), 4.33-4.29 (m, 1H), 4.14 (dd, J=6.6, 13.2 Hz, 1H), 4.02 (ddd, J=0.6, 7.2, 10.5 Hz, 1H), 3.96 (dd, J=5.1, 12.2 Hz, 1H), 3.80 (dd, J=4.7, 12.1 Hz, 1H), 3.64 (dd, J=6.4, 10.7 Hz, 1H), 3.45 (s, 3H).

Steps 5-7

Synthesis of 5-(4-((2 S,3S)-2-(4-chlorobenzyl)-3-methoxyazetidin-1-yl)piperidin-1-yl)-4H-1,2,4-triazol-3-amine (22)

Azetidine 22d was carried through the remaining synthetic steps as it is described in the General Procedure VI (reductive amination with N-Boc-piperid-4-one), the General Procedure VII (Boc-deprotection) and the General Procedure VIII (triazole ring formation). 142 mg (0.37 mmol, 37% yield over 3 steps) of the title compound 22 in a form of single diastereomer (unknown configuration; presumably cis) was synthesized (the minor diastereomer was removed in a final purification by reversed-phase chromatography).

ESI-MS m/z for $C_{18}H_{25}ClN_6O$ found 377.0/378.9 $(M+1)^+$, 375.1/377.0 $(M-1)^-$ $^1$H NMR (DMSO-$d_6$+$D_2O$, 500 MHz) δ 7.39 (d, J=8.6 Hz, 2H), 7.33 (d, J=8.5, 2H), 4.88 (br s, 1H), 4.11 (d, J=5.2, 2H), 4.02-4.00 (m, 1H), 3.81 (d, J=13.2 Hz, 1H), 3.77 (d, J=13.2 Hz, 1H), 3.38-3.35 (m, 2H), 3.27 (s, 3H), 2.96 (dd, J=4.8, 13.9 Hz, 1H), 2.78 (q, J=10.5 Hz, 2H), 1.96 (d, J=12.2 Hz, 1H), 1.88 (d, J=11.8 Hz, 1H), 1.43-1.35 (m, 2H).

Example 23

5-(4-((2S,3R)-2-(4-chlorobenzyl)-3-fluoroazetidin-1-yl)piperidin-1-yl)-4H-1,2,4-triazol-3-amine (23)

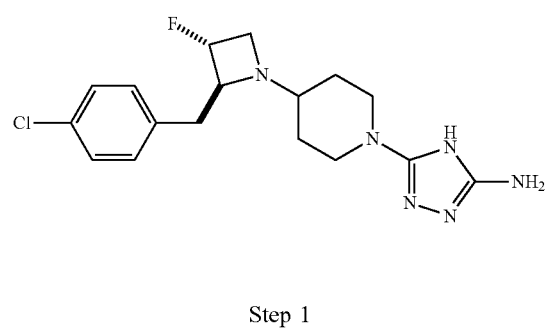

Step 1

Synthesis of tert-butyl (2S,3R)-2-(4-chlorobenzyl)-3-fluoroazetidine-1-carboxylate (23a)

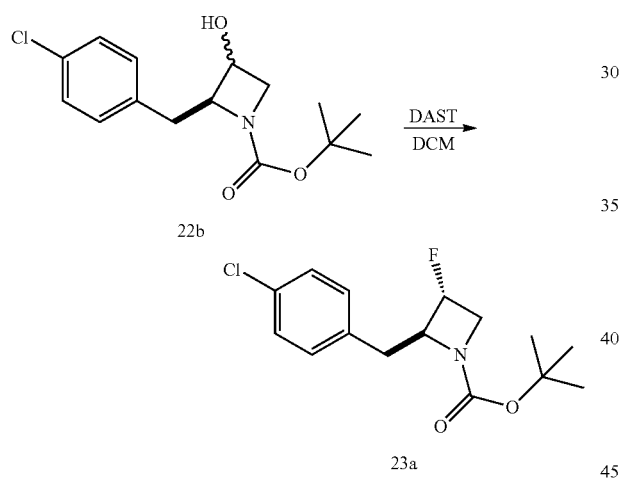

To a cooled (−78° C.) solution of compound 22b (400 mg, 1.34 mmol) in dichloromethane (10 mL) 350 µL of (2.68 mmol) of (diethylamino)sulfur trifluoride (DAST) was added under argon. The reaction mixture was allowed to warm up to the room temperature and was stirred at room temperature overnight. It was quenched with 5% aq. NaHCO$_3$ (20 mL) and extracted with ethyl acetate (3×15 mL). The combined organic extracts were washed with brine, dried over magnesium sulfate, filtered and concentrated under reduced pressure. Flash chromatography purification in AcOEt/hexanes 1:15 afforded 200 mg (0.67 mmol; 50% yield) of the title compound (23a) as single diastereomer (configuration not established; presumably trans).

ESI-MS m/z for $C_{15}H_{19}ClFNO_2$ found 300.2/302.2 (M+1)$^+$ $^1$H NMR (DMSO-d$_6$, 75° C., 600 MHz) δ 7.31 (d, J=8.5 Hz, 2H), 7.22 (d, J=8.3 Hz, 2H), 5.31(dtd, J=3.0, 6.2 Hz, $J_{HF}$=60 Hz, 1H), 4.52-4.47 (m, 1H), 4.13-4.07 (m, 1H), 3.82-3.76 (m, 1H), 3.10-3.04 (m, 2H), 1.34 (s, 9H).

Step 2

Synthesis of (2S,3R)-2-(4-chlorobenzyl)-3-fluoroazetidine hydrochloride (23b)

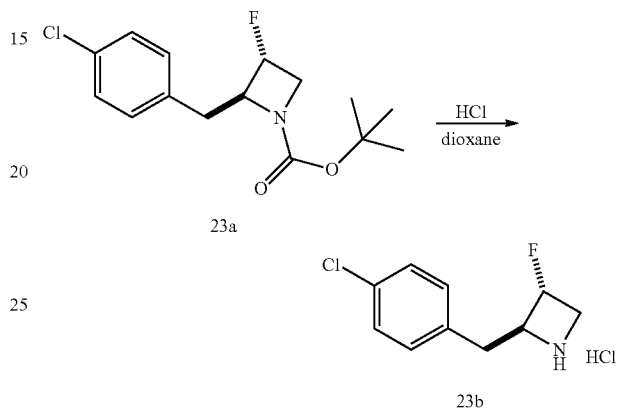

According to the General Procedure VII, compound 23a (190 mg, 0.63 mmol) was treated with 4 M HCl (gas) in 1,4-dioxane (2.2 mL, 9.04 mmol). The crude product was triturated with diethyl ether providing 150 mg (0.63 mmol, 100% yield) of azetidine 23b as hydrochloride salt.

ESI-MS m/z for $C_{10}H_{11}ClFN$ found 200.1/202.1 (M+1)$^+$

Steps 3-5

Synthesis of 5-(4-((2S,3R)-2-(4-chlorobenzyl)-3-fluoroazetidin-1-yl)piperidin-1-yl)-4H-1,2,4-triazol-3-amine (23)

Azetidine 23b (0.63 mmol, 150 mg) was carried through the remaining synthetic steps as it is described in the General Procedure VI (reductive amination with N-Boc-piperid-4-one), General Procedure VII (Boc-deprotection) and the General Procedure VIII (triazole ring formation). 134 mg (0.37 mmol) of the title compound 23 was synthesized in 59% yield over 3 steps.

ESI-MS m/z for $C_{17}H_{22}ClFN_6$ found 365.0/367.0 (M+1)$^+$, 363.0/365.0 (M−1)$^−$ $^1$H NMR (DMSO-d$_6$, 700 MHz) δ 7.41 (d, J=8.5 Hz, 2H), 7.35 (d, J=8.5 Hz, 2H), 5.34 (dt, $J_{HF}$=56 Hz, J=4.95 Hz, 1H), 5.0 (br s, 1H), 4.40-4.36 (m, 1H), 4.26 (dd, J=13.1 Hz, $J_{HF}$=23.3 Hz, 1H), 3.80 (dd, J=12.7 Hz, $J_{HF}$=22.0 Hz, 2H), 3.39-3.37 (m, 1H), 3.33 (dd, J=11.2, 13.9 Hz, 1H), 3.11 (dd, J=3.3, 13.5 Hz, 1H), 2.84-2.80 (m, 2H), 2.02 (d, J=12.7 Hz, 1H), 1.92 (d, J=12.1 Hz, 1H), 1.42 (qd, J=4.4, 12.2 Hz, 2H).

Example 24

(R)-5-(4-(2-(4-chlorobenzyl)pyrrolidin-1-yl)piperidin-1-yl)-4H-1,2,4-triazol-3-amine (24)

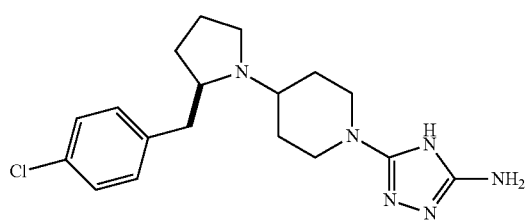

Step 1

Synthesis of (R)-1-(tert-butoxycarbonyl)pyrrolidine-2-carboxylic acid (24a)

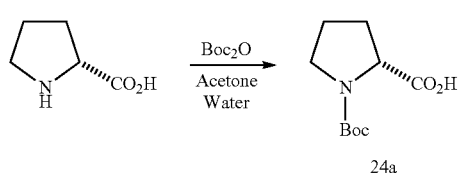 [SMILES: "Boc2O" ; O=C(O)[C@H]1CCCN1 ; CC(C)(C)OC(=O)N1CCC[C@@H]1C(=O)O]

To a solution of D-proline 20 g (173.7 mmol) in acetone/water 1:1, sodium hydroxide 13.9 g (347.44 mmol) was added, followed by Boc$_2$O 39.8 g (182.41 mmol). Reaction was stirred for 2 days at pH~9. LCMS indicated completion of reaction. Acetone was removed by evaporation. The remaining aqueous phase was washed with diethyl ether, acidified to pH~3 and extracted with ethyl acetate. Combined organic layers were washed with brine, dried over anhydrous magnesium sulfate and evaporated to dryness. Solid residue was washed with hexane and dried. 31.1 g (144 mmol; 83% yield) of product 24a was obtained as a white solid.

ESI-MS m/z for $C_{10}H_{17}NO_4$ found 216.1 (M+1)$^+$

Step 2

Synthesis of tert-butyl (R)-2-(methoxy(methyl)carbamoyl)pyrrolidine-1-carboxylate (24b)

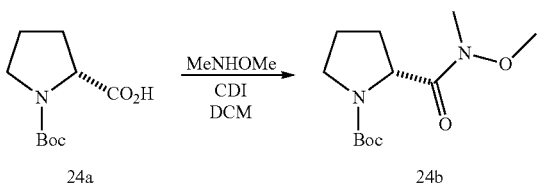 [SMILES: "MeNHOMe" ; CC(C)(C)OC(=O)N1CCC[C@@H]1C(=O)O ; CON(C)C(=O)[C@H]1CCCN1C(=O)OC(C)(C)C]

To a solution of acid 24a 10 g (46.5 mmol) in dichloromethane carbonyldiimidazole 11.3 g (69.7 mmol) was added. After 30 minutes N,O-dimethylhydroxyloamine 6.8 g (69.7 mmol) was added and reaction was stirred overnight. LC/MS indicated completion of reaction. Reaction mixture was washed with hydrochloric acid, 5% aq. solution of sodium bicarbonate and brine. Organic layer was dried over anhydrous magnesium sulfate and concentrated. Product was purified by column chromatography hexane/EtOAc 4/1. 6.19 g (24.2 mmol; yield 52%) of compound 24b was obtained as colorless oil.

ESI-MS m/z for $C_{12}H_{22}NO_4$ found 259.1 (M+1)$^+$, 281.0 (M+Na)$^+$ $^1$H NMR (CDCl$_3$, 600 MHz) δ 4.70, 4.60 (m, m, 1H, 2 conformers), 3.79, 3.72 (s, s, 3H, 2 conformers), 3.58 (m, 1H), 3.48, 3.40 (m, m, 1H, 2 conformers), 3.19 (s, 3H), 2.18 (m, 1H), 1.91 (m, 3H), 1.46, 1.41 (s,s, 9H, 2 conformers).

Step 3

Synthesis of tert-butyl (R)-2-(4-chlorobenzoyl)pyrrolidine-1-carboxylate (24c)

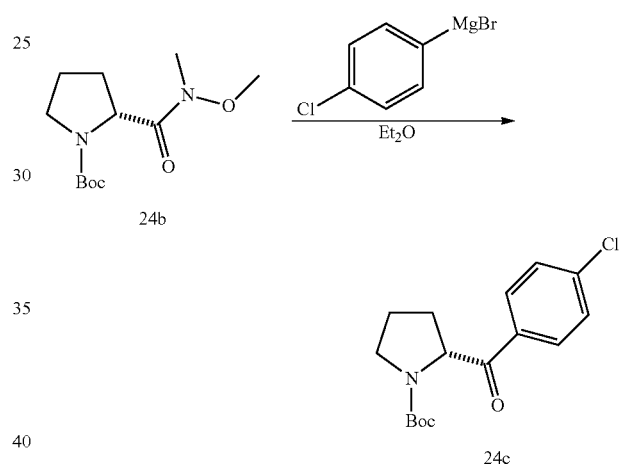

Amide 24b 3.0 g (11.61 mmol) was dissolved in dry diethyl ether under atmosphere of argon and cooled to -70° C. p-Chlorophenylmagnesium bromide, previously generated from magnesium 875 mg (36.0 mmol) and p-bromochlorobenzene 6.67 g (34.8 mmol), was added dropwise to amide 24b solution at -70° C. After addition of Grignard reagent reaction was stirred at room temperature for 2 hours. LCMS indicated completion of reaction. Reaction was quenched with saturated ammonium chloride solution for 15 minutes, and extracted with diethyl ether. Organic layer was washed with 1 M hydrochloric acid and brine. Solvent was evaporated and oily residue was purified by column chromatography hexane/EtOAc 10/1. 2.47 g (8.0 mmol; 69% yield) of product 26c was obtained as a white crystalline solid.

ESI-MS m/z for $C_{16}H_{20}ClNO_3$ found 310.0/312.0 (M+1)$^+$ $^1$H NMR (CDCl$_3$, 600 MHz) δ 7.94, 7.90 (AA'BB', J=8.4 Hz, AA'BB', J=8.4 Hz, 2H, 2 conformers), 7.47, 7.43 (AA'BB', J=8.4 Hz, AA'BB', J=8.4 Hz, 2H, 2 conformers), 5.28, 5.27 (dd, J$_1$=9.0 Hz, J$_2$=3.6 Hz, dd, J$_1$=9.6 Hz, J$_2$=4.8 Hz, 1H, 2 conformers), 3.68, 3.62 (m, m, 1H, 2 conformers), 3.56, 3.48 (m, m, 1H, 2 conformers), 2.30 (m, 1H), 1.92 (m, 3H), 1.46, 1.26 (s, s, 9H, 2 conformers).

Step 4

Synthesis of (R)-2-(4-chlorobenzyl)pyrrolidine (24d)

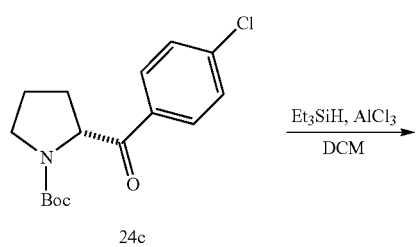
24c

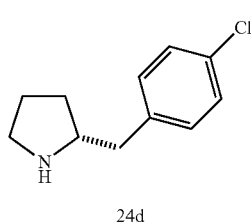
24d

To a solution of ketone 24c 1 g (3.23 mmol) in dichloromethane anhydrous aluminum chloride 1.29 g (9.68 mmol) and triethylsilane 1.55 mL (9.68 mmol) were added. After 1 hour of stirring LCMS indicated completion of reaction. Reaction was quenched with mixture of 4 M NaOH and brine. Aqueous phase was extracted with dichloromethane, dried over anhydrous magnesium sulfate and concentrated. 632 mg (3.22 mmol; 99% yield) of product 24d was obtained as a yellow oil and taken directly to the next step.

ESI-MS m/z for $C_{11}H_{14}ClN$ found 195.9/197.9 $(M+1)^+$

Step 5

Synthesis of tert-butyl (R)-4-(2-(4-chlorobenzyl)pyrrolidin-1-yl)piperidine-1-carboxylate (24e)

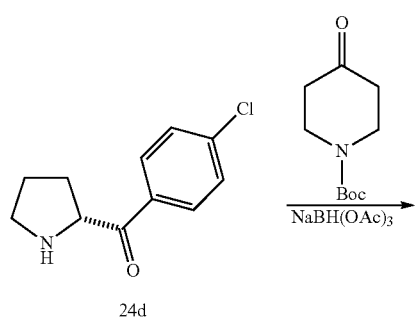
24d

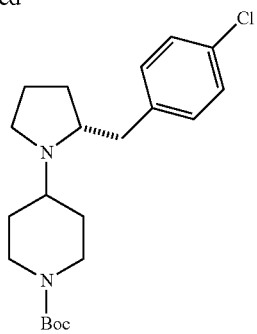
24e

Compound 24e was obtained, from 24d (632 mg, 3.23 mmol) according to the General Procedure VI followed by a flash chromatography using methanol/dichloromethane 1:50, in 44% yield (540 mg, 1.42 mmol, yellow oil).

ESI-MS m/z for $C_{21}H_{31}ClN_2O_2$ found 379.1/381.1 $(M+1)^+$ $^1$H NMR (CDCl$_3$, 600 MHz) δ 7.24 (AA'BB', J=8.4 Hz, 2H), 7.11 (AA'BB', J=8.4 Hz, 2H), 3.03 (brs, 1H), 2.94 (brs, 1H), 2.86 (d, J=12.6 Hz, 1H), 2.70 (brs, 4H), 2.58 (q, J=7.2 Hz, 1H), 2.42 (m, 1H), 1.84 (d, J=7.8 Hz, 1H), 1.78 (d, J=12.6 Hz, 1H), 1.72 (d, J=7.2 Hz, 1H), 1.65 (m, 3H), 1.55 (m, 3H), 1.46 (s, 9H).

Step 6

Synthesis of (R)-4-(2-(4-chlorobenzyl)pyrrolidin-1-yl)piperidine hydrochloride (24f)

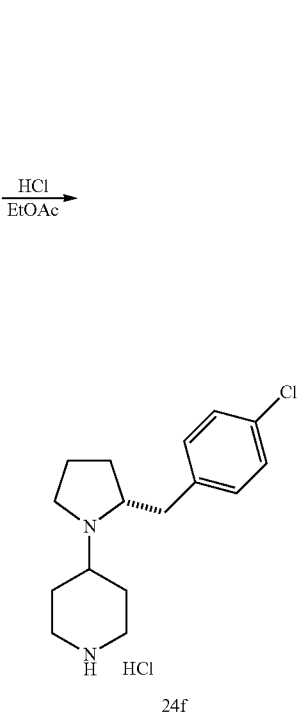

According to the General Procedure VII, compound 24e (540 mg, 1.42 mmol) was treated with 2N HCl (gas) in ethyl acetate (6.5 mL, 12.81 mmol). The crude product was triturated with diethyl ether providing 447 mg (1.42 mmol, >99% yield, yellow crystals) of 24f as hydrochloride salt.

ESI-MS m/z for $C_{16}H_{23}ClN_2$ found 279.2/281.2 (M+1)$^+$

Step 7

Synthesis of (R)-5-(4-(2-(4-chlorobenzyl)pyrrolidin-1-yl)piperidin-1-yl)-4H-1,2,4-triazol-3-amine (24)

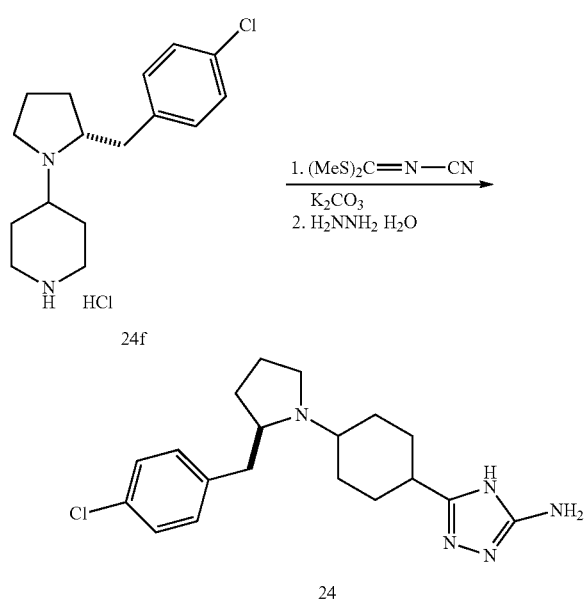

Compound 24 was obtained from 24f (447 mg, 1.42 mmol) according to the General Procedure VIII. Product was purified by preparative reversed-phase chromatography to give 201 mg (0.56 mmol; 39% yield) of the title compound 24.

ESI-MS m/z for $C_{18}H_{25}ClN_6$ found 361.0/363.0 (M+1)$^+$ $^1$H NMR (DMSO-d$_6$+D$_2$O, 600 MHz): δ 7.36 (AA'BB', J=8.4 Hz, 2H), 7.30 (AA'BB', J=8.4 Hz, 2H), 3.83 (m, 1H), 3.78 (d, J=12.6 Hz, 2H), 3.48 (t, J=12.0 Hz, 1H), 3.40 (q, J=5.4 Hz, 1H), 3.16 (m, 2H), 2.90 (q, J=12.0 Hz, 2H), 2.72 (t, J=12.0 Hz, 1H), 2.10 (d, J=11.4 Hz, 1H), 2.02 (d, J=11.4 Hz, 1H), 1.85 (m, 3H), 1.66 (m, 3H).

Example 25

(S)-4-(1-(5-amino-4H-1,2,4-triazol-3-yl)piperidin-4-yl)-5-(4-chlorobenzyl)piperazin-2-one (25)

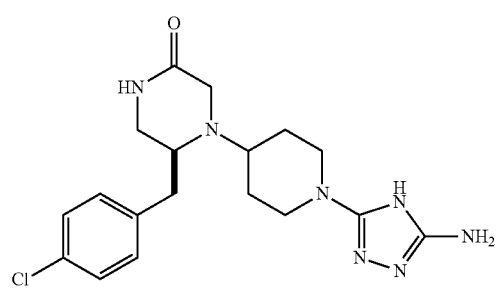

Step 1

Synthesis of tert-butyl (S)-(1-amino-3-(4-chlorophenyl)-1-oxopropan-2-yl)carbamate (25a)

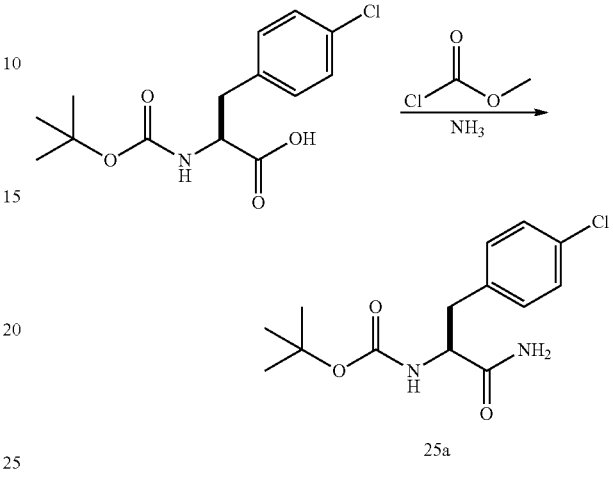

The title compound (25) was obtained from the Boc-L-p-chlorophenylalanine (1.4 g, 4.67 mmol) according to the General Procedure IX in 97% yield (1.36 g, 4.54 mmol) as a white powder.

ESI-MS m/z for $C_{14}H_{19}ClN_2O_3$ found 299.0 (M+1)$^+$, 321.0 (M+Na)$^+$

Step 2

Synthesis of tert-butyl (S)-(1-amino-3-(4-chlorophenyl)propan-2-yl)carbamate (25b)

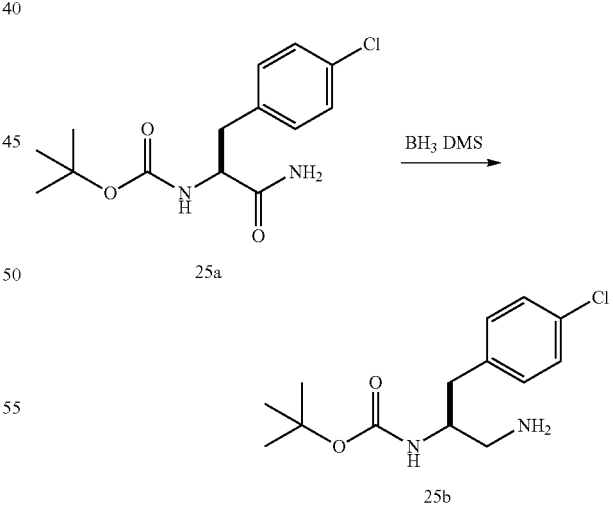

The reduction of the amide 25a to the title compound was accomplished according to the General Procedure V. Flash silica-gel column purification in CH$_2$Cl$_2$/MeOH solvent system (gradient elution from 70:1 to 20:1) provided 360 mg (1.26 mmol, 28% yield) of the pure product 25b.

ESI-MS m/z for $C_{14}H_{21}ClN_2O_2$ found 285.3/287.3 (M+1)$^+$

Step 3

Synthesis of tert-butyl (S)-(1-(2-chloroacetamido)-3-(4-chlorophenyl)propan-2-yl)carbamate (25c)

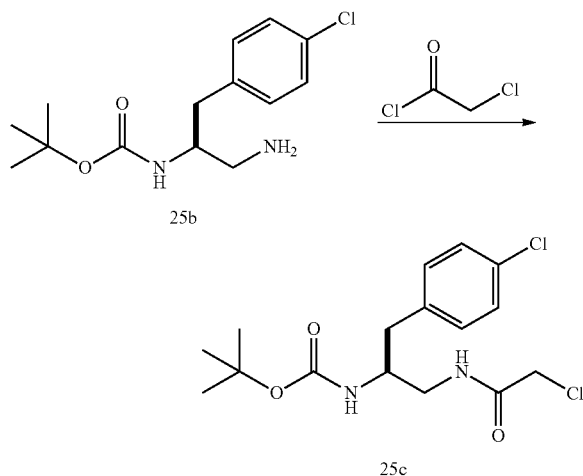

360 mg (1.26 mmol) of amine 25b was reacted with chloroacetyl chloride as described in the General Procedure II. Crude product 25c after aqueous work-up was found to be sufficiently pure to be used in the next step without further purification.

ESI-MS m/z for $C_{16}H_{22}Cl_2N_2O_3$ found 361.3/363.3 $(M+1)^+$, 383.3/385.3 $(M+Na)^+$

Step 4

Synthesis of (S)-N-(2-amino-3-(4-chlorophenyl)propyl)-2-chloroacetamide hydrochloride (25d)

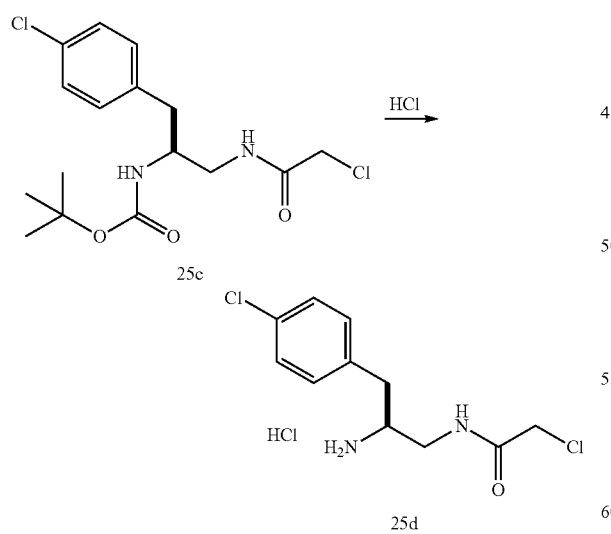

Removal of the Boc-protecting group was accomplished according to the General Procedure VII. 355 mg (1.2 mmol) of the title compound 25d was obtained (90% yield over two steps). The crude product 25d in a form of a hydrochloride salt was taken to the next step.

ESI-MS m/z for $C_{11}H_{14}Cl_2N_2O$ found 261.2/263.2 $(M+1)^+$

Step 5

Synthesis of (S)-5-(4-chlorobenzyl)piperazin-2-one (25e)

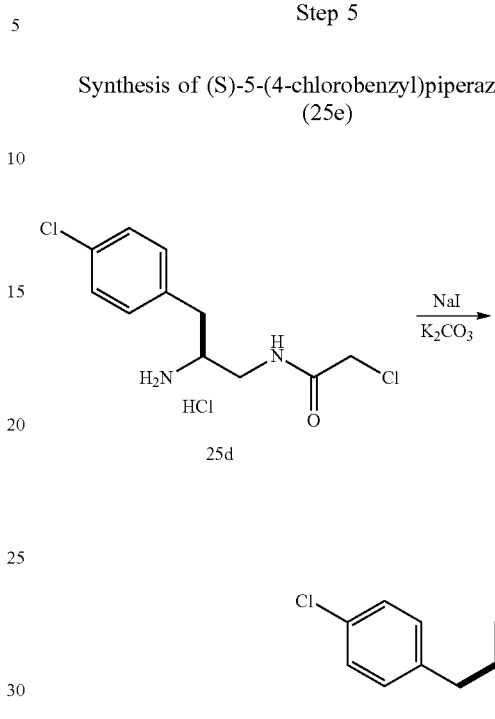

355 mg (1.2 mmol) of compound 25d was dissolved in 50 mL of acetonitrile and anhydrous potassium carbonate (437 mg; 3.16 mmol) and sodium iodide (20 mg) were sequentially added. The reaction was stirred at 50° C. for 5 hours and then at room temperature overnight. The solids were filtered off, the filtrate was concentrated and the product was purified by flash silica-gel column chromatography using gradient eluent $CH_2Cl_2$/MeOH solvent system (gradient elution from 40:1 to 5:1). 160 mg (0.71 mmol, 60% yield) of the title compound (25e) was obtained.

ESI-MS m/z for $C_{11}H_{13}ClN_2O$ found 225.2/227.2 $(M+1)^+$

Step 6

Synthesis of tert-butyl (S)-4-(2-(4-chlorobenzyl)-5-oxopiperazin-1-yl)piperidine-1-carboxylate (25f)

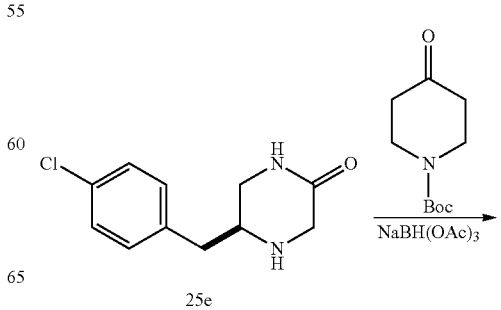

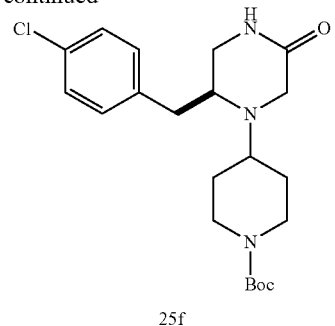

25f

The reductive amination of compound 25e with N-Boc-piperid-4-one was accomplished according to the General Procedure VI. 175 mg (0.43 mmol; 60% yield) of the title compound 25f was obtained after purification by flash silica-gel column chromatography using $CH_2Cl_2$/MeOH 20:1 solvent system.

ESI-MS m/z for $C_{21}H_{30}ClN_3O_3$ found 408.4/410.4 $(M+1)^+$

Step 7

Synthesis of (S)-5-(4-chlorobenzyl)-4-(piperidin-4-yl)piperazin-2-one hydrochloride (25g)

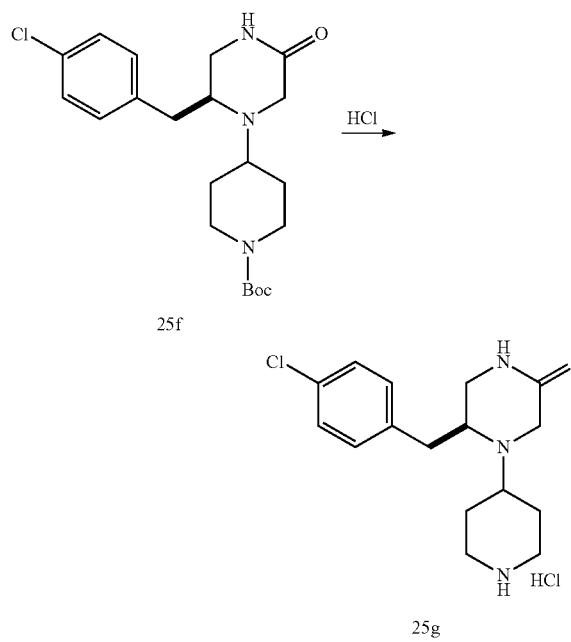

Boc-Deprotection of compound 25f was accomplished according to the General Procedure VII providing 96 mg (0.31 mmol, 72% yield) of the title compound 25g.

ESI-MS m/z for $C_{16}H_{22}ClN_3O$ found 308.4/310.3 $(M+1)^+$ $^1$H NMR (CDCl$_3$, 500 MHz) δ 7.27 (AA'BB', J 8.5 Hz, 2H), 7.08 (AA'BB', J=8.5 Hz, 2H), 6.01 (brs, 1H), 3.19-3.30 (m, 4H), 3.00-3.06 (m, 1H), 2.82-2.88 (m, 1H), 2.64-2.71 (m, 3H), 2.01-2.13 (m, 4H), 1.88-1.95 (m, 2H), 1.47-1.57 (m, 2H).

Step 8

Synthesis of (S)-4-(1-(5-amino-4H-1,2,4-triazol-3-yl)piperidin-4-yl)-5-(4-chlorobenzyl)-piperazin-2-one (25)

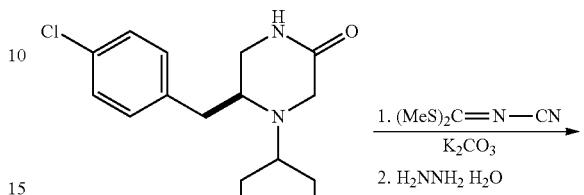

25g

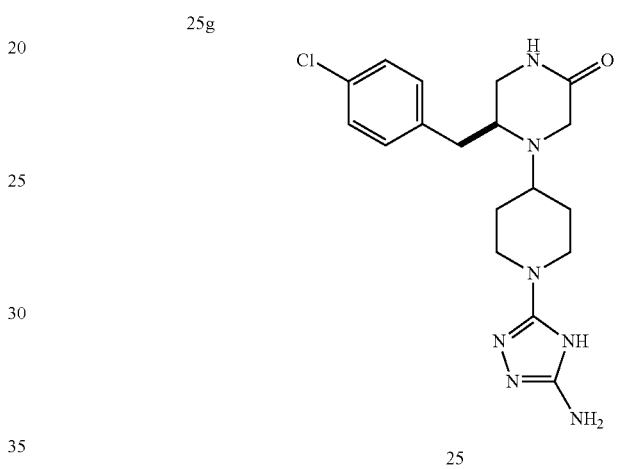

25

The aminotriazole synthesis was accomplished according to the General Procedure VIII. From 90 mg (0.292 mmol) of starting material 25g, 43 mg of the target compound 25 was obtained after purification by the reversed-phase chromatography.

ESI-MS m/z for $C_{16}H_{22}ClN_3O$ found 390.0/392.0 $(M+1)^+$, 388.0/390.1 $(M-1)^-$ $^1$H NMR (D$_2$O, 500 MHz) δ 7.28 (AA'BB', J=7.3 Hz, 2H), 7.14 (AA'BB', J=7.7 Hz, 2H), 4.07-4.12 (m, 1H), 4.01 (d, J=16.7 Hz, 1H), 3.86 (d, J=16.9 Hz, 1H), 3.73-3.77 (m, 2H), 3.32-3.36 (m, 1H), 3.17-3.22 (m, 2H), 2.81-3.04 (m, 4H), 2.09-2.15 (m, 2H), 1.68-1.75 (m, 2H).

Example 26

(S)-5-(4-(2-(4-chlorobenzyl)piperazin-1-yl)piperidin-1-yl)-4H-1,2,4-triazol-3-amine (26)

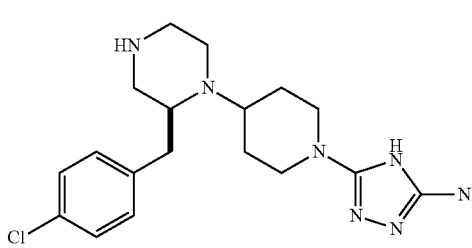

26

The reduction of the 2-piperazinone 25 to the title compound 26 was accomplished according to the General Procedure V. Crupe product was purified by the reversed-phase preparative HPLC column. Fractions containing product were freeze-dried providing 13 mg (34% yield) of the title compound 26.

ESI-MS m/z for $C_{18}H_{26}ClN_7$ found 376.0/378.0 (M+1)$^+$ $^1$H NMR (DMSO-d$_6$+D$_2$O, 700 MHz) δ 7.40 (AA'BB', J=8.5 Hz, 2H), 7.32 (AA'BB', J=8.5 Hz, 2H), 3.74 (t, J=15.1 Hz, 2H), 3.46 (m, 2H), 3.24 (m, 3H), 3.03 (m, 3H), 2.88 (m, 3H), 2.74 (dd, J=9.3, 14.1 Hz, 1H), 1.82 (d, J=12.2 Hz, 1H), 1.78 (d, J=11.9 Hz, 1H), 1.70 (dq, J=4.1, 11.9 Hz, 1H), 1.51 (dq, J=4.2, 12.2 Hz, 1H).

Example 27

5-(4-((2S,5S)-2-(4-chlorobenzyl)-4,5-dimethylpiperazin-1-yl)piperidin-1-yl)-4H-1,2,4-triazol-3-amine (27)

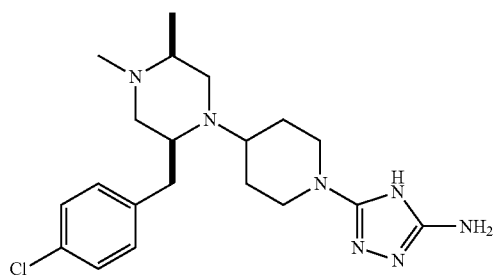

Step 1

Synthesis of methyl (S)-2-(((S)-2-((tert-butoxycarbonyl)amino)-3-(4-chlorophenyl)-N-methylpropanamido)propanoate (27a)

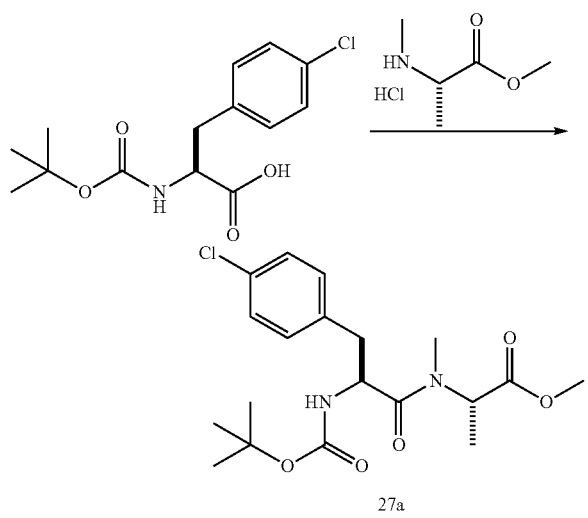

Boc-L-p-chlorophenylalanine was coupled with N-Me-L-alanine methyl ester hydrochloride as described in the General Procedure IX. 1.3 g of the title compound 27a was obtained (99% yield) after crystallization from ethyl acetate.

ESI-MS m/z for $C_{19}H_{27}ClN_2O_5$ found 399.1/401.1 (M+1)$^+$ $^1$H NMR (DMSO-d$_6$, 250 MHz) 7.20 (AA'BB', 2H, J=8.4 Hz), 7.01 (AA'BB', 2H, J=8.4 Hz), 4.87-4.64 (m, 1H), 4.54-4.32 (m, 1H), 3.48 (s, 3H), 2.80 (s, 3H), 2.75-2.54 (m, 2H), 1.19 (s, 9H), 1.14 (d, 3H, J=6 Hz).

Step 2

Synthesis of (3S,6S)-3-(4-chlorobenzyl)-1,6-dimethylpiperazine-2,5-dione (27b)

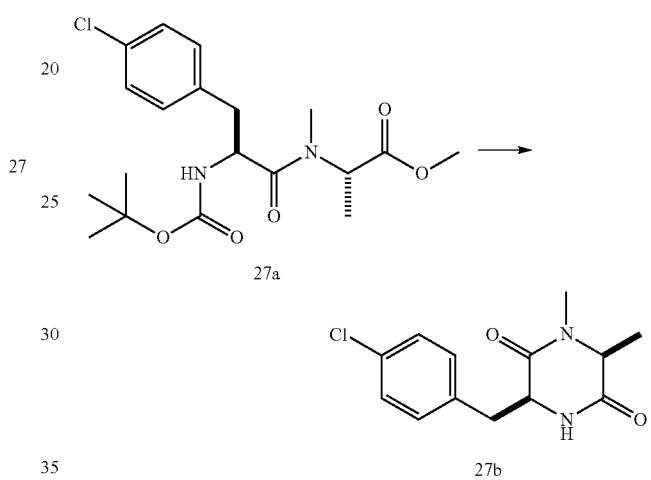

Starting from methyl ester 27a, the title compound was prepared by acidic de-protection of the amino group followed by the immediate ring-closure according to the General Procedure X. 0.64 g of the title compound 27b was obtained (73% yield) after crystallization from ethyl acetate.

ESI-MS m/z for $C_{13}H_{15}ClN_2O_2$ found 266.9/268.9 (M+1)$^+$ $^1$H NMR (DMSO-d$_6$, 250 MHz) δ 8.17 (bs, 1H), 7.25 (AA'BB', J=8.4 Hz, 2H), 6.99 (AA'BB', J=8.4 Hz, 2H), 4.14-4.05 (m, 1H), 3.57 (q, J=7.0 Hz, 1H), 2.99 (dd, J=4.1, 13.2 Hz, 1H), 2.72 (dd, J=4.8, 13.2 Hz, 1H), 2.59 (s, 3H), 1.04 (d, J=7 Hz, 3H).

Step 3

Synthesis of (2S,5S)-5-(4-chlorobenzyl)-1,2-dimethylpiperazine (27c)

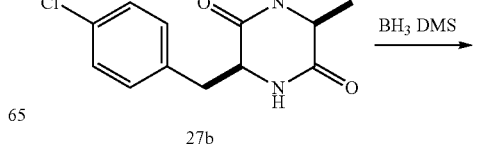

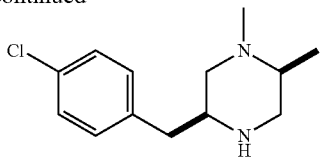

27c

To the solution of 0.62 g (2.32 mmol) of 2,5-diketopiperazine 27b in THF (7 mL/mmol) 2 mL of BH$_3$.DMS complex was added and the reaction mixture was refluxed for 5 hours, after which time the TLC control showed complete consumption of the starting material. It was cooled to room temperature and 8 mL of 2 M HCl was cautiously added (Caution: foaming!) and the reaction mixture was refluxed again for 2 hours and cooled back to the room temperature. The pH of the solution was then brought to 13 by the dropwise addition of 6 M NaOH. The organic layer was separated and the aqueous layer was additionally extracted with ethyl acetate. The combined organic extracts were then dried over MgSO$_4$, filtered and the solvents were evaporated providing 0.53 g of product 27c (2.26 mmol, 94% yield) that was used in the next step without purification.

ESI-MS m/z for C$_{13}$H$_{19}$ClN$_2$ found 238.6/240.6 (M+1)$^+$

Step 4

Synthesis of tert-butyl 4-((2S,5S)-2-(4-chlorobenzyl)-4,5-dimethylpiperazin-1-yl)piperidine-1-carboxylate (27d)

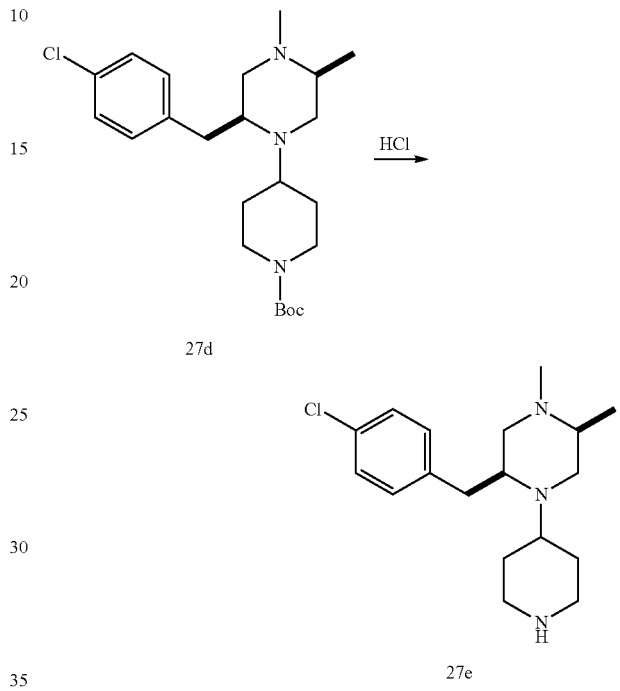

The reductive amination of compound 27c with N-Boc-piperid-4-one was accomplished according to the General Procedure VI. 0.36 g (0.85 mmol; 38% yield) of the title compound 27d was obtained after purification by flash silica-gel column chromatography using CH$_2$Cl$_2$/MeOH 15:1 solvent system.

ESI-MS m/z for C$_{23}$H$_{36}$ClN$_3$O$_2$ found 422.1/424.1 (M+1)$^+$

Step 5

Synthesis of (2S,5S)-2-(4-chlorobenzyl)-4,5-dimethyl-1-(piperidin-4-yl)piperazine (27e)

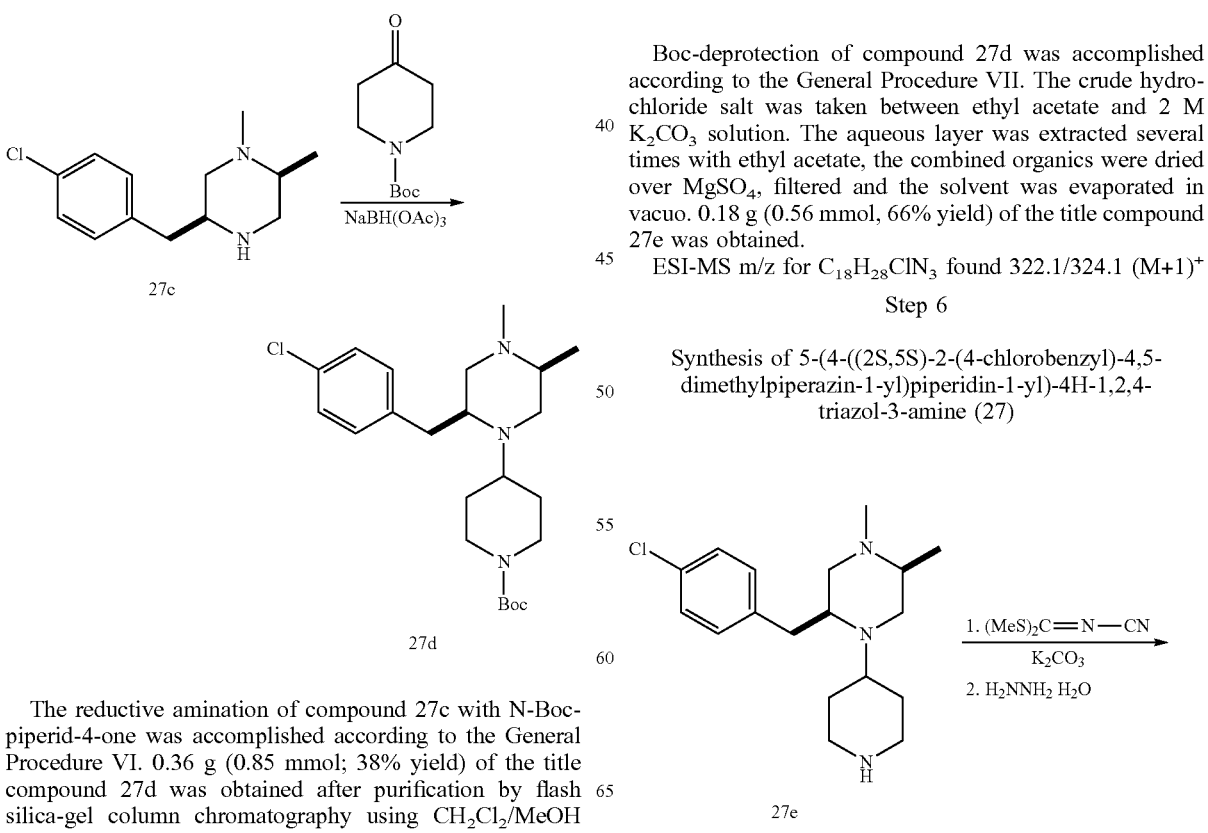

Boc-deprotection of compound 27d was accomplished according to the General Procedure VII. The crude hydrochloride salt was taken between ethyl acetate and 2 M K$_2$CO$_3$ solution. The aqueous layer was extracted several times with ethyl acetate, the combined organics were dried over MgSO$_4$, filtered and the solvent was evaporated in vacuo. 0.18 g (0.56 mmol, 66% yield) of the title compound 27e was obtained.

ESI-MS m/z for C$_{18}$H$_{28}$ClN$_3$ found 322.1/324.1 (M+1)$^+$

Step 6

Synthesis of 5-(4-((2S,5S)-2-(4-chlorobenzyl)-4,5-dimethylpiperazin-1-yl)piperidin-1-yl)-4H-1,2,4-triazol-3-amine (27)

-continued

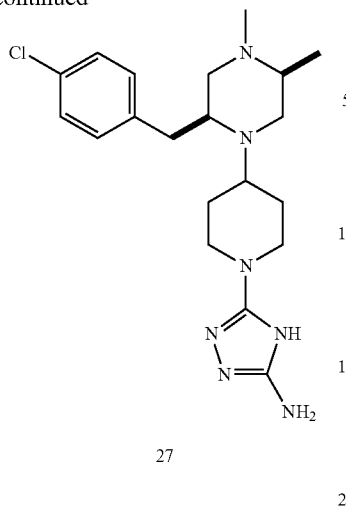

27

The aminotriazole synthesis was accomplished according to the General Procedure VIII.

From 180 mg (0.56 mmol) of starting material 27e, 80 mg (0.20 mmol; yield 35%) of the target compound 27 was obtained after purification by silica-gel chromatography in CHCl$_3$/MeOH 20:1 solvent system.

ESI-MS m/z for C$_{20}$H$_{30}$ClN$_7$ found 404.2/406.2 (M+1)$^+$ $^1$H NMR (DMSO-d$_6$, 250 MHz) δ 7.38 (AA'BB', J=8.4 Hz, 2H), 7.24 (AA'BB', J=8.4 Hz, 2H), 5.58 (bs, 1H), 3.84-3.71 (m, 2H), 3.11-2.99 (m, 2H), 2.86-2.59 (m, 5H), 2.48-2.25 (m, 2H), 2.13 (s, 3H), 2.06-1.88 (m, 4H), 1.49-1.26 (m, 2H), 1.04 (d, J=6.1 Hz, 3H).

Example 28

(S)-5-(4-(2-(4-chlorobenzyl)-4-methylpiperazin-1-yl)piperidin-1-yl)-4H-1,2,4-triazol-3-amine (28)

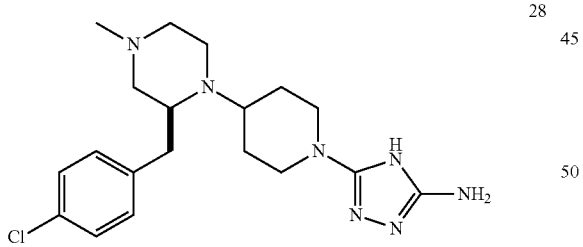

28

With the exception that Boc-L-p-chlorophenylalanine was coupled with methyl (methylamino)acetate hydrochloride (sarcosine methyl ester hydrochloride) instead of N-methyl-L-alanine methyl ester in the first synthetic step, the title compound was prepared in the same manner as Example 27 and its intermediates.

270 mg of the title compound 28 was synthesized.

ESI-MS m/z for C$_{19}$H$_{28}$ClN$_7$ found 390.2/392.3 (M+1)$^+$ $^1$H NMR (DMSO-d$_6$, 500 MHz) δ 10.86 (bs, 1H), 7.32-7.26 (m, 2H), 7.17 (d, J=8.0 Hz, 2H), 5.59 (s, 2H), 3.77-3.67 (m, 2H) 2.91-2.71 (m, 3H), 2.70-2.51 (m, 7H), 2.00 (s, 3H), 1.98-1.90 (m, 2H), 1.75-1.55 (m, 2H), 1.49-1.22 (m, 2H).

Example 29

(S)-5-(4-(2-(4-chlorobenzyl)-4-isobutylpiperazin-1-yl)piperidin-1-yl)-4H-1,2,4-triazol-3-amine (29)

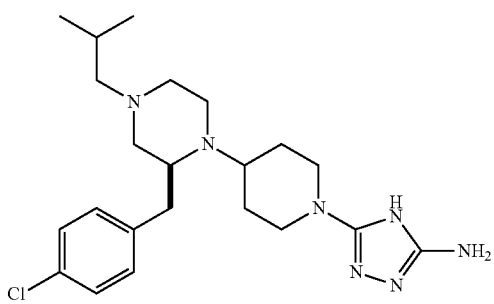

29

With the exception that Boc-L-p-chlorophenylalanine was coupled with methyl (isobutylamino)acetate hydrochloride (N-isobutylglycine methyl ester hydrochloride) instead of N-methyl-L-alanine methyl ester in the first synthetic step, the title compound was prepared in the same manner as Example 27 and its intermediates.

50 mg of the title compound 29 was synthesized.

ESI MS m/z for C$_{22}$H$_{34}$ClN$_7$ found 432.2/434.2 (M+1)$^+$ $^1$H NMR (DMSO-d$_6$, 250 MHz) δ 7.45-7.33 (m, 2H), 7.34-7.21 (m, 2H), 5.57 (bs, 1H), 3.83 (d, 2H, J=12.5 Hz), 3.10-2.63 (m, 7H),2.45-2.03 (m, 4H), 2.01-1.24 (m, 7H), 0.89 (d, J=6.4 Hz, 6H).

Example 30

((2R,5S)-4-(1-(5-amino-4H-1,2,4-triazol-3-yl)piperidin-4-yl)-5-(4-chlorobenzyl)-1-methylpiperazin-2-yl)methanol (30)

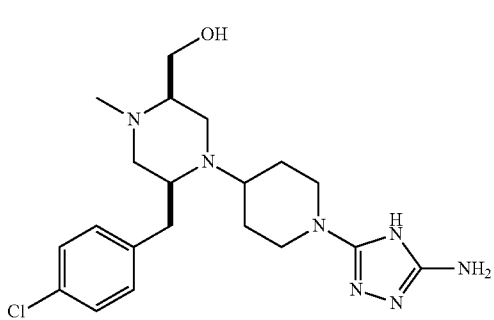

30

Step 1

Synthesis of tert-butyl (S)-(1-(4-chlorophenyl)-3-hydroxypropan-2-yl)carbamate (30)

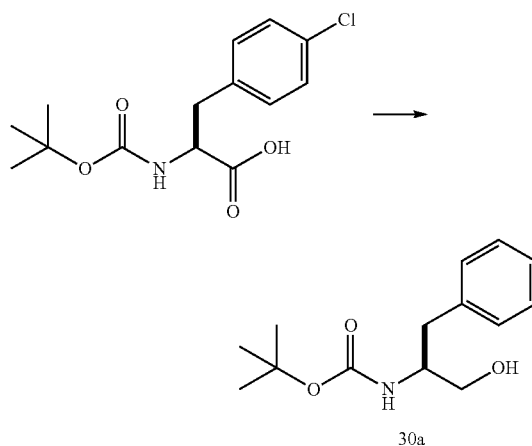

30a

Boc-L-p-chlorophenylalanine was reduced to the title compound as described in the General Procedure XI. From 15 g (50 mmol) of the starting material 11.5 g (40.2 mmol, 81% yield) of compound 30a was obtained.

ESI-MS m/z for $C_{14}H_{20}ClNO_3$ found 285.9/287.9 $(M+1)^+$

Step 2

Synthesis of tert-butyl (S)-(1-(4-chlorophenyl)-3-oxopropan-2-yl)carbamate (30b)

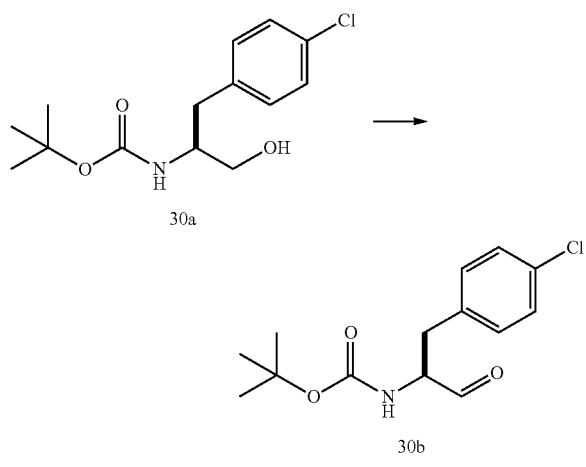

Compound 30a was oxidized to the title compound according to the General Procedure XII. From 10 g (35 mmol) of the starting material, 8.5 g (29.9 mmol, 85% yield) of compound 30b was obtained.

ESI-MS m/z for $C_{14}H_{18}ClNO_3$ found 283.9/285.9 $(M+1)^+$

Step 3

Synthesis of methyl (S)-2-(((S)-2-((tert-butoxycarbonyl)amino)-3-(4-chlorophenyl)propyl)amino)-3-hydroxypropanoate (30c)

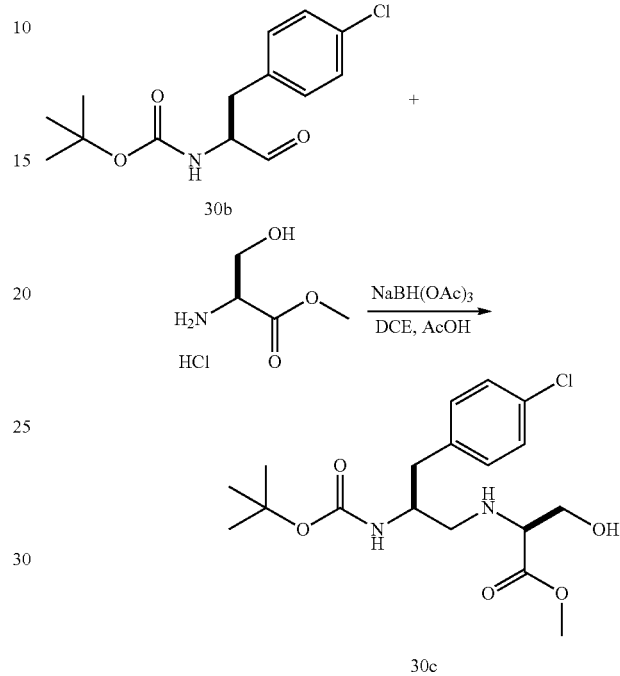

30c

The reductive amination of compound 30b (2.8 g, 9.87 mmol) with L-serine methyl ester hydrochloride (2.3 g, 14.8 mmol) was accomplished according to the General Procedure XIII The crude product 30c (3.0 g, 7.8 mmol; 79% yield) was sufficiently pure to be used in the next step without further purification.

ESI-MS m/z for $C_{18}H_{27}ClN_2O_5$ found 387.1/389.1 $(M+1)^+$

Step 4

Synthesis of methyl (S)-2-(((S)-2-((tert-butoxycarbonyl)amino)-3-(4-chlorophenyl)propyl)-(methyl)amino)-3-hydroxypropanoate (30d)

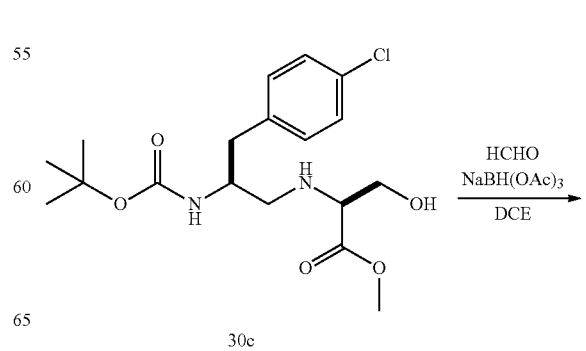

30c

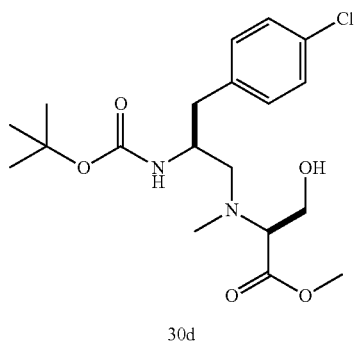

30d

The N-Methylation of amine 30c (3.0 g, 7.75 mmol) with aqueous HCHO (0.72 mL, 9.3 mmol) was accomplished according to the General Procedure XIV. The crude product was purified by flash chromatography on silica gel (chloroform/MeOH 20:1 solvent system) to give 1.2 g (2.99 mmol; 39% yield) of the title compound 30d.

ESI-MS m/z for $C_{19}H_{29}ClN_2O_5$ found 401.1/403.1 $(M+1)^+$

Step 5

Synthesis of (3S,6S)-6-(4-chlorobenzyl)-3-(hydroxymethyl)-4-methylpiperazin-2-one (30e)

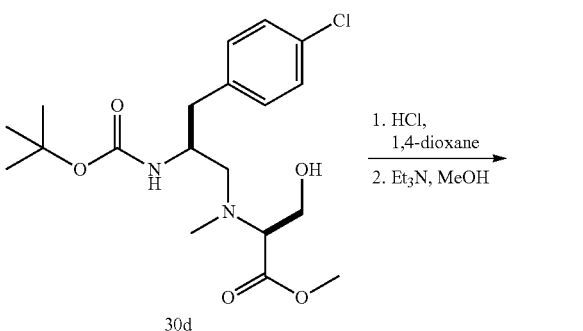

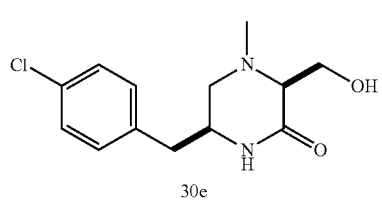

30e

Cyclization of compound 30d (1.2 g, 3 mmol) was accomplished according to the General Procedure X. 0.61 g (2.27 mmol; 76% yield) of product 30e, sufficiently pure to be taken to the next step, was obtained.

ESI-MS m/z for $C_{13}H_{17}ClN_2O_2$ found 269.1/271.1 $(M+1)^+$

Step 6

Synthesis of ((2R,5S)-5-(4-chlorobenzyl)-1-methylpiperazin-2-yl)methanol (30f)

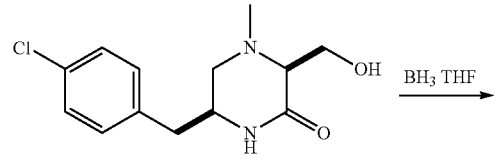

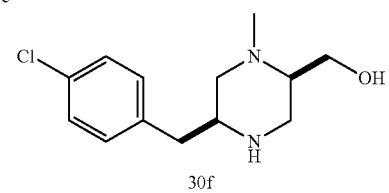

30f

Reduction of 30e (0.61 g, 2.23 mmol) was accomplished according to the General Procedure V. 0.45 g of product 30f (1.76 mmol; 79% yield) was obtained ESI-MS m/z for $C_{13}H_{19}ClN_2O$ found 255.3/257.3 $(M+1)^+$ Step 7

Synthesis of tert-butyl 4-((2S,5R)-2-(4-chlorobenzyl)-5-(hydroxymethyl)-4-methylpiperazin-1-yl)piperidine-1-carboxylate (30g)

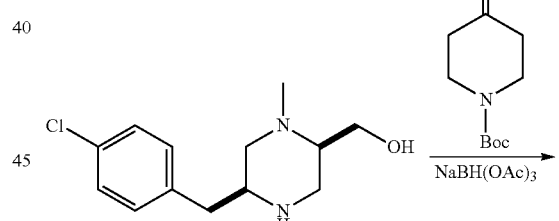

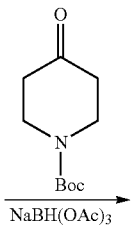

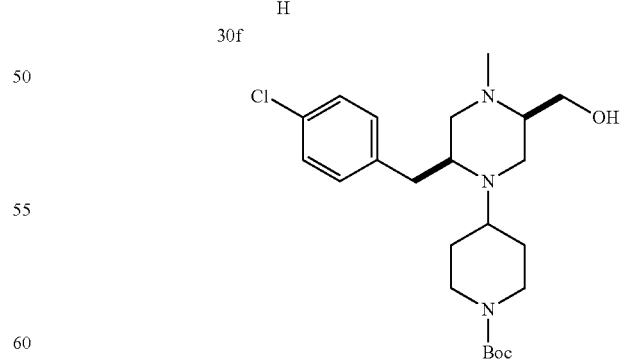

30g

The reductive amination of compound 30f (0.15 g, 0.59 mmol) with N-Boc-piperid-4-one was accomplished according to the General Procedure VI. 71 mg (0.16 mmol, 27% yield) of the title compound 30g was obtained after purification by flash silica-gel column chromatography using CH$_2$Cl$_2$/MeOH 20:1 solvent system.

ESI-MS m/z for C$_{23}$H$_{36}$ClN$_3$O$_3$ found 438.0/440.0 (M+1)$^+$

Step 8

Synthesis of ((2R,5S)-5-(4-chlorobenzyl)-1-methyl-4-(piperidin-4-yl)piperazin-2-yl)methanol hydrochloride (30h)

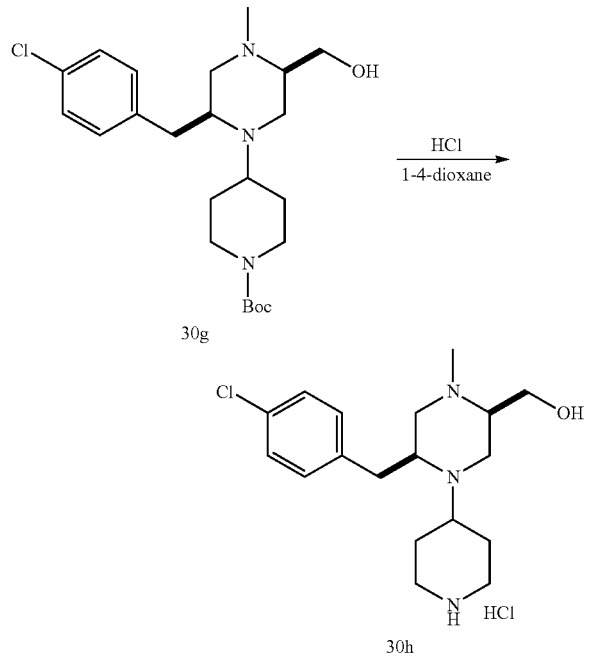

According to the General Procedure VII, 70 mg (0.16 mmol) of compound 30g was stirred for 1 h in 5 mL of 4 M solution of HCl in 1,4-dioxane. Volatiles were removed in vacuo to give 71 mg (100%) of the title compound 30h in a form of hydrochloride salt.

ESI-MS m/z for C$_{18}$H$_{28}$ClN$_3$O found 338.2/340.2 (M+1)$^+$

Step 9

Synthesis of 5-(4-((2S,5S)-2-(4-chlorobenzyl)-4,5-dimethylpiperazin-1-yl)piperidin-1-yl)-4H-1,2,4-triazol-3-amine (30)

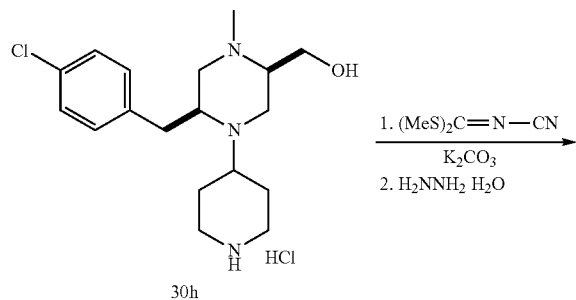

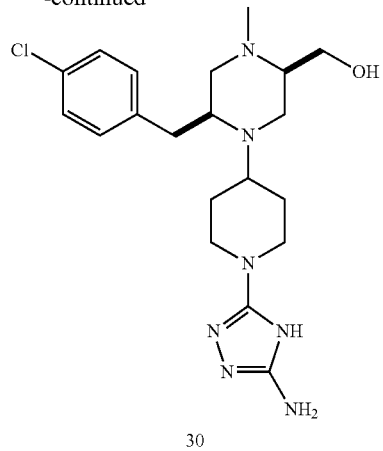

Formation of 1,2,4-triazole ring was accomplished according to the General Procedure VIII starting from compound 30h. 30 mg (0.07 mmol) of the final compound 30 was obtained after purification by the reversed-phase chromatography (44% yield).

ESI-MS m/z for C$_{20}$H$_{30}$ClN$_7$O found 420.1/422.1 (M+1)$^+$ $^1$H NMR (D$_2$O, 700 MHz) δ 7.35-7.33 (m, 2H), 7.27-7.25 (m, 2H), 4.03-3.99 (m, 1H), 3.81 (d, J=13 Hz, 2H), 3.73 (brs, 1H), 3.6-3.56 (m, 1H), 3.45-3.4 (m, 1H), 3.37-3.33 (m, 1H), 3.3 (brs, 3H), 3.28-3.25 (m, 1H), 3.21-3.16 (m, 2H), 2.99-2.94 (m, 1H), 2.92-2.88 (m, 2H), 2.84 (s, 3H), 2.01-1.97 (m, 1H), 1.93-1.89 (m, 1H), 1.62-1.55 (m, 2H).

Example 31

5-(4-((2S,5S)-2,5-bis(4-chlorobenzyl)-4-methylpiperazin-1-yl)piperidin-1-yl)-4H-1,2,4-triazol-3-amine (31)

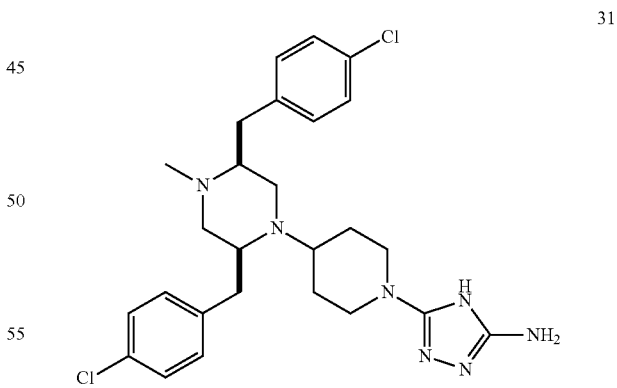

With the exception that compound 30b was reductively aminated with L-p-chlorophenylalanine methyl ester instead of L-serine methyl ester in the third synthetic step, the title compound 31 was prepared in the same manner as Example 30 and its intermediates. 83 mg of the title compound 31 was prepared.

ESI-MS m/z for C$_{26}$H$_{33}$Cl$_2$N$_7$ found 514.2/516.1 (M+1)$^+$ $^1$H NMR (DMSO-d$_6$, 700 MHz) δ 7.34-7.26 (m, 4H), 7.22 (d, J=8.3 Hz, 2H) 7.17 (d, J=8.3 Hz, 2H),5.44 (bs, 2H),3.69-3.60 (m, 2H), 2.95-2.84 (m, 2H), 2.83-2.75 (m, 1H), 2.71-2.52 (m, 5H), 2.38-2.31 (m, 1H), 2.27-2.21 (m, 2H), 2.19 (s, 3H), 2.01-1.98 (m, 1H), 1.75-1.68 (m, 1H), 1.60-1.52 (m, 1H), 1.35-1.07 (m, 2H).

Example 32

5-(4-((2S,5S)-2-(4-chlorobenzyl)-5-(cyclohexylmethyl)-4-methylpiperazin-1-yl)piperidin-1-yl)-4H-1,2,4-triazol-3-amine (32)

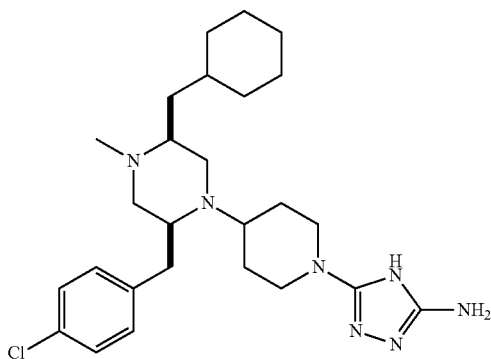

With the exception that compound 30b was reductively aminated with L-cyclohexylalanine methyl ester instead of L-serine methyl ester in the third synthetic step, the title compound was prepared in the same manner as Example 30 and its intermediates. 59 mg of the title compound 32 was prepared.

ESI-MS m/z for $C_{26}H_{40}ClN_7$ found 486.3/488.3 (M+1)$^+$ $^1$H NMR (DMSO-$d_6$, 500 MHz) δ 7.34 (d, J=7.2 Hz, 2H), 7.28 (d, J=8.1 Hz, 2H), 5.55 (bs, 1H), 3.92-3.59 (m, 2H), 3.17-2.49 (m, 12H), 1.79 (m, 7H), 1.45-1.00 (m, 7H), 0.99-0.71 m, 2H).

Example 33

5-(4-((2S,5S)-2-(4-chlorobenzyl)-5-isobutyl-4-methylpiperazin-1-yl)piperidin-1-yl)-4H-1,2,4-triazol-3-amine (33)

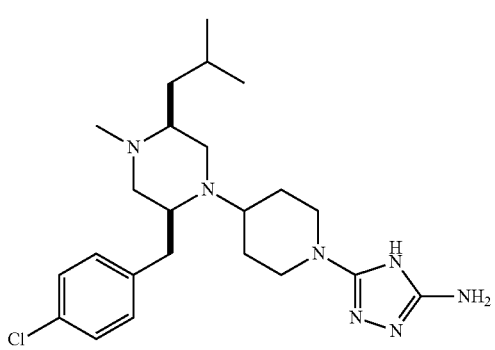

With the exception that compound 30b was reductively aminated with L-leucine methyl ester instead of L-serine methyl ester in the third synthetic step; the title compound was prepared in the same manner as Example 30 and its intermediates. 37 mg of the title compound 33 was prepared.

ESI-MS m/z for $C_{23}H_{36}ClN_7$ found 446.2/448.2 (M+1)$^+$ $^1$H NMR (DMSO-$d_6$, 250 MHz) δ 7.38 (d, J=8.4 Hz, 2H), 7.25 (d, J=8.4 Hz, 2H), 5.58 (s, 1H), 3.79 (dd, J=9.7, 6.6 Hz, 2H), 3.13-2.60 (m, 6H), 2.54-2.30 (m, 2H), 2.18 (s, 3H), 2.17-1.2 (m, 9H), 0.93 (dd, J=11.6, 6.4 Hz, 6H).

Example 34

(S)-5-(4-(2-(4-chlorobenzyl)-4-(methylsulfonyl)piperazin-1-yl)piperidin-1-yl)-4H-1,2,4-triazol-3-amine (34)

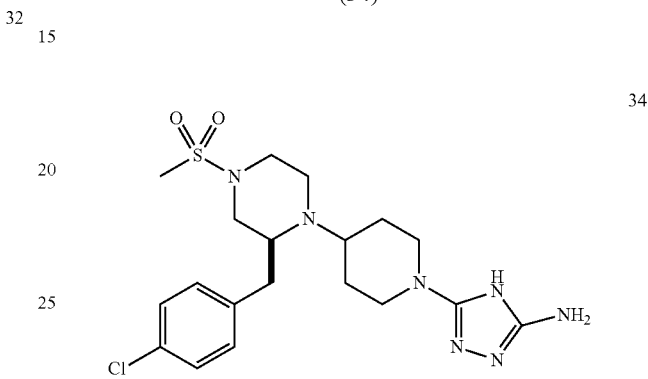

Step 1

Synthesis of methyl (S)-2-((2-((tert-butoxycarbonyl)amino)-3-(4-chlorophenyl)propyl)-amino)acetate (34a)

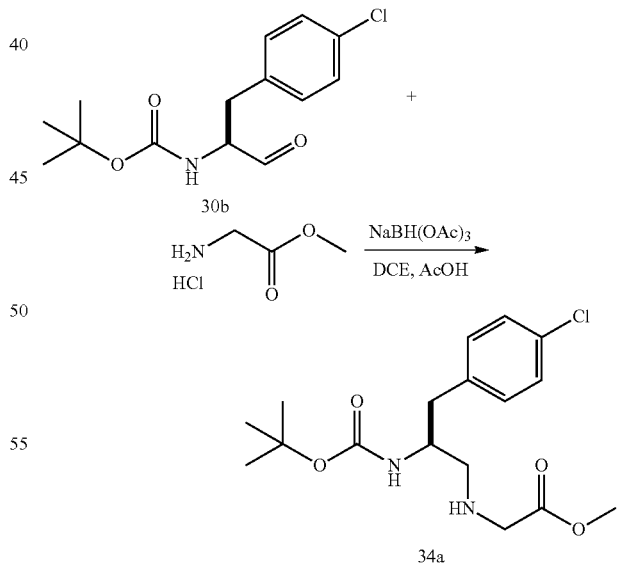

The title compound was synthesized from aldehyde 30b and glycine methyl ester hydrochloride according to the General Procedure XIII 2.49 g (7.0 mmol) of compound 34a was obtained (99% yield).

ESI-MS m/z for $C_{17}H_{25}ClN_2O_4$ found 357.2/359.2 (M+1)$^+$

Step 2

Synthesis of (S)-6-(4-chlorobenzyl)piperazin-2-one (34b)

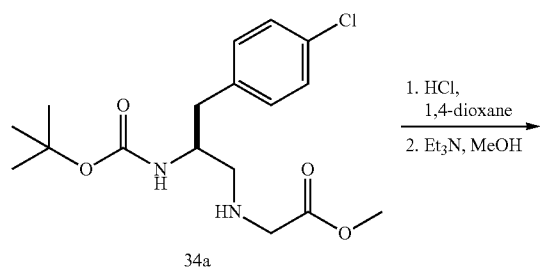

The title compound was synthesized from compound 34a according to the General Procedure X. 0.97 g (4.3 mmol) of compound 34b was obtained (64% yield).

ESI-MS m/z for $C_{11}H_{13}ClN_2O$ found 225.2/227.2 $(M+1)^+$

Step 3

Synthesis of (S)-6-(4-chlorobenzyl)-4-(methyl sulfonyl)piperazin-2-one (34c)

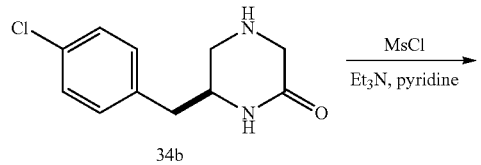

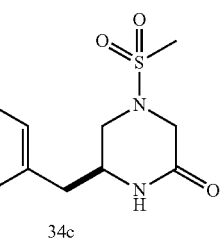

The title compound was synthesized from compound 34b according to the General Procedure XV. 0.45 g (1.5 mmol) of compound 34c was obtained (37% yield).

ESI-MS m/z for $C_{12}H_{15}ClN_2O_3S$ found 303.1/305.1 $(M+1)^+$

Step 4

Synthesis of (S)-3-(4-chlorobenzyl)-1-(methylsulfonyl)piperazine (34d)

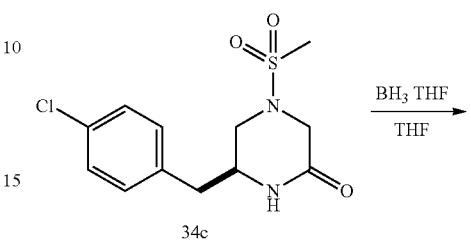

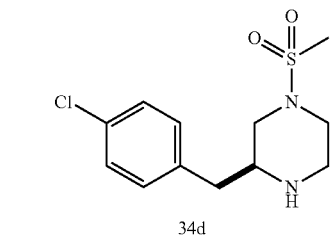

The title compound was synthesized from compound 34c according to the General Procedure VI. 0.29 g (1.0 mmol) of compound 34d was obtained (87% yield).

ESI-MS m/z for $C_{12}H_{17}ClN_2O_2S$ found 289.2/291.2 $(M+1)^+$

Step 5

Synthesis of tert-butyl (S)-4-(2-(4-chlorobenzyl)-4-(methyl sulfonyl)piperazin-1-yl)piperidine-1-carboxylate (34e)

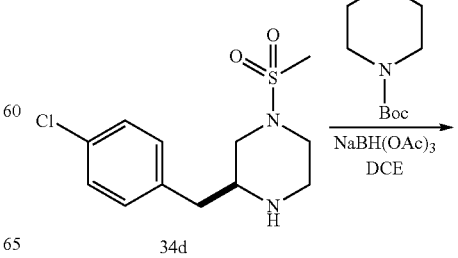

193

-continued

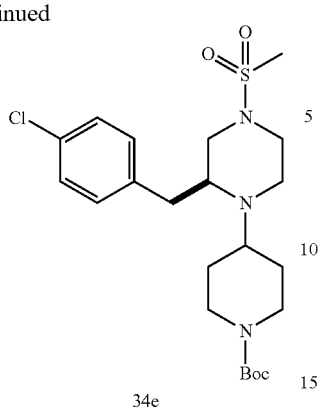

34e

The synthesis of the title compound was accomplished by reductive amination of N-Bocpiperid-4-one with compound 34d according to the General Procedure VII. 0.36 g (0.76 mmol) of compound 34e was obtained (87% yield).

ESI-MS m/z for $C_{22}H_{34}ClN_3O_4S$ found 472.2/474.2 $(M+1)^+$

Step 6

Synthesis of (S)-2-(4-chlorobenzyl)-4-(methylsulfonyl)-1-(piperidin-4-yl)piperazine hydrochloride (34f)

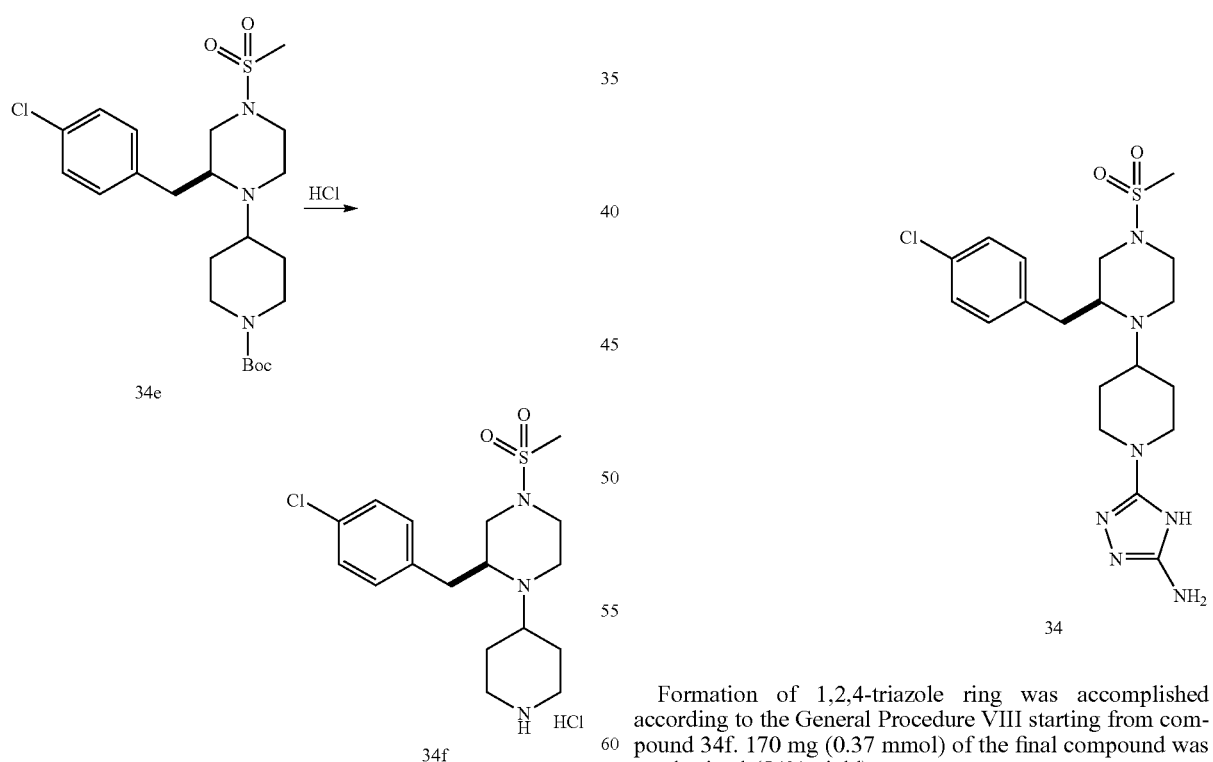

The title compound was synthesized from compound 34e according to the General Procedure VII. 0.26 g (0.7 mmol) of compound 34f was obtained (92% yield).

ESI-MS m/z for $C_{17}H_{26}ClN_3O_2S$ found 372.2/374.2 $(M+1)^+$

194

Step 7

Synthesis of (S)-5-(4-(2-(4-chlorobenzyl)-4-(methylsulfonyl)piperazin-1-yl)piperidin-1-yl)-4H-1,2,4-triazol-3-amine (34)

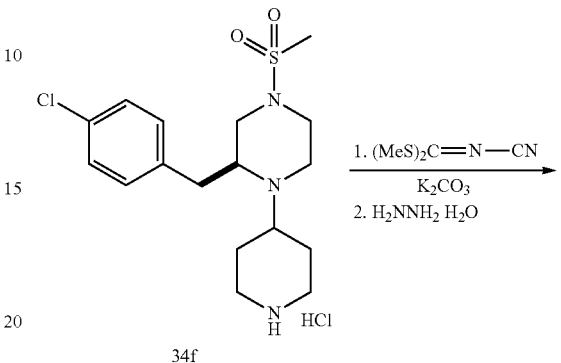

Formation of 1,2,4-triazole ring was accomplished according to the General Procedure VIII starting from compound 34f. 170 mg (0.37 mmol) of the final compound was synthesized (54% yield).

ESI-MS m/z for $C_{19}H_{28}ClN_7O_2S$ found 454.2/456.2 $(M+1)^+$ $^1$H NMR (DMSO-$d_6$, 250 MHz) δ 10.86 (s, 1H), 7.33-7.06 (m, 4H), 5.42 (s, 2H), 3.67 (dd, J=13.1, 3.7 Hz, 2H), 3.13-2.71 (m, 6H), 2.70 (s, 3H), 2.68-2.48 (m, 6H), 1.79-1.56 (m, 2H), 1.46-1.14 (m, 2H).

Example 35

(S)-5-(4-(2-(4-chlorobenzyl)-4-tosylpiperazin-1-yl)piperidin-1-yl)-4H-1,2,4-triazol-3-amine (35)

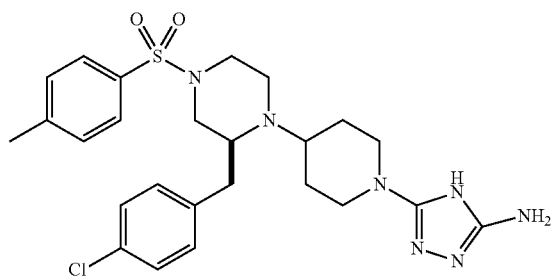

With the exception that compound 34b was sulfonylated with tosyl chloride instead of mesyl chloride in the third synthetic step; the title compound was prepared in the same manner as Example 34 and its intermediates. 37 mg of the title compound 35 was prepared.

ESI-MS m/z for $C_{25}H_{32}ClN_7O_2S$ found 530.1/532.1 $(M+1)^+$ $^1$H NMR (DMSO-$d_6$, 500 MHz) δ 10.91 (s, 1H), 7.52-7.47 (m, 2H), 7.41-7.30 (m, 4H), 7.25-7.19 (m, 2H), 5.48 (bs, 1H), 3.68 (d, J=12.5 Hz, 2H), 3.06-2.93 (m, 2H), 2.83-2.47 (m, 9H), 2.54-2.47 (m, 1H), 2.36 (s, 3H), 1.74-1.57 (m, 2H), 1.33-1.22 (m, 2H).

Example 36

5-(4-((2S,5S)-2,5-bis(4-chlorobenzyl)-4-(methylsulfonyl)piperazin-1-yl)piperidin-1-yl)-4H-1,2,4-triazol-3-amine (36)

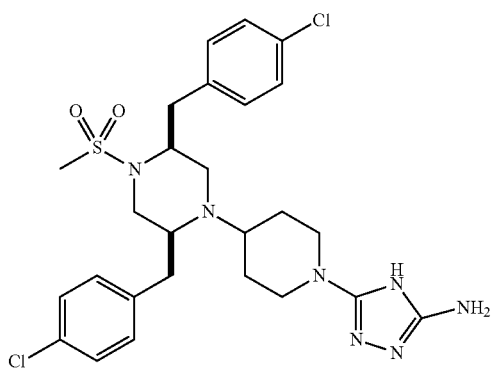

Step 1

Synthesis of (3S,6S)-3,6-bis(4-chlorobenzyl)piperazin-2-one (36a)

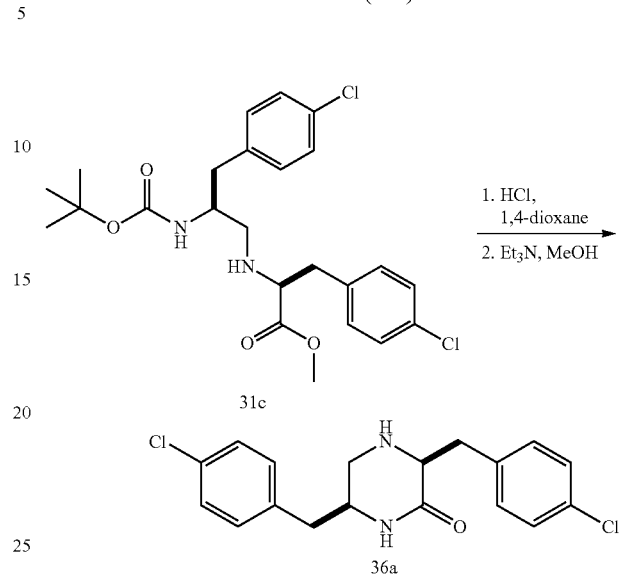

Compound 31c (intermediate in the synthesis of Example 31) that was obtained by reductive amination of L-p-chlorophenalanine methyl ester and N-protected amino aldehyde 30b according to the General Procedure XIII, was deprotected and cyclized according to the General Procedure X providing piperazinone 36a. 1.0 g (2.86 mmol) of compound 36a was synthesized (83% yield)

ESI-MS m/z for $C_{18}H_{18}Cl_2N_2O$ found 349.3/351.3 $(M+1)^+$

Step 2

Synthesis of (3S,6S)-3,6-bis(4-chlorobenzyl)-4-(methylsulfonyl)piperazin-2-one (36b)

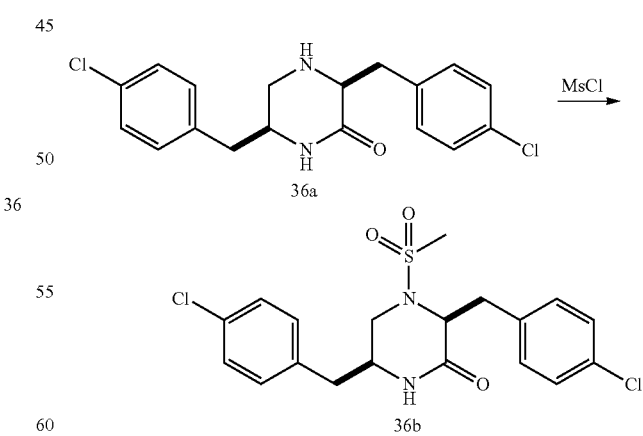

The title compound was synthesized from compound 36a according to the General Procedure XV. 0.21 g (0.49 mmol) of compound 36b was obtained (50% yield)

ESI-MS m/z for $C_{19}H_{20}Cl_2N_2O_3S$ found 427.5/429.5 $(M+1)^+$

197

Step 3

Synthesis of (2S,5S)-2,5-bis(4-chlorobenzyl)-1-(methylsulfonyl)piperazine (36c)

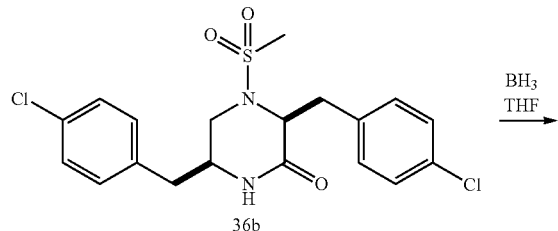

The title compound was synthesized from compound 36b according to the General Procedure VI. 0.20 g (0.48 mmol) of compound 36c was obtained (99% yield).

ESI-MS m/z for $C_{19}H_{22}Cl_2N_2O_2S$ found 413.5/415.5 $(M+1)^+$ $^1$H NMR (CDCl$_3$, 500 MHz) δ 7.33-7.22 (m, 4H), 7.23-7.05 (m, 4H), 4.08-4.00 (m, 1H), 3.71-3.53 (m, 1H), 3.15-2.98 (m, 2H), 2.95-2.70 (m, 4H), 2.56-2.44 (m, 1H), 2.47 (s, 3H), 1.58-1.49 (m, 1H), 1.46-1.32 (m, 1H).

Step 4

Synthesis of tert-butyl 4-((2S,5S)-2,5-bis(4-chlorobenzyl)-4-(methylsulfonyl)piperazin-1-yl)piperidine-1-carboxylate (36d)

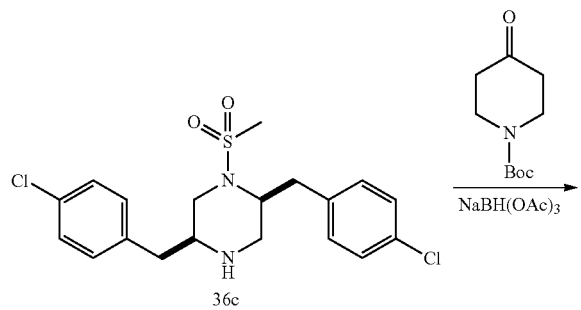

198

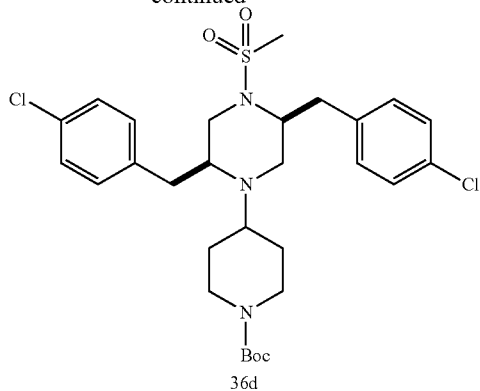

The title compound was synthesized from compound 36c according to the General Procedure VII. 0.30 g (0.50 mmol) of compound 36d was obtained (83% yield).

ESI-MS m/z for $C_{29}H_{39}Cl_2N_3O_4S$ found 597.1/599.1 $(M+1)^+$

Step 5

Synthesis of (2S,5S)-2,5-bis(4-chlorobenzyl)-1-(methylsulfonyl)-4-(piperidin-4-yl)piperazine hydrochloride (36e)

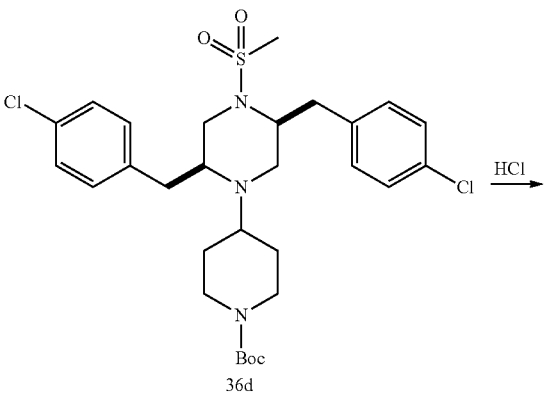

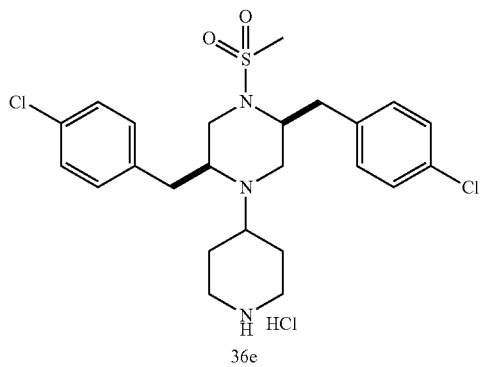

The title compound was synthesized from compound 36d according to the General Procedure VII. 0.16 g (0.32 mmol) of compound 36e was obtained (66% yield).

ESI-MS m/z for $C_{24}H_{31}Cl_2N_3O_2S$ found 497.1/499.1 $(M+1)^+$

Step 6

Synthesis of 5-(4-((2S,5S)-2,5-bis(4-chlorobenzyl)-4-(methyl sulfonyl)piperazin-1-yl)piperidin-1-yl)-4H-1,2,4-triazol-3-amine (36)

Example 37

5-(4-((2S,5S)-2-(4-chlorobenzyl)-5-methyl-4-(methylsulfonyl)piperazin-1-yl)piperidin-1-yl)-4H-1,2,4-triazol-3-amine (37)

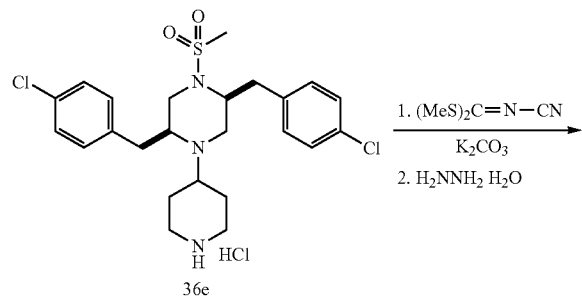

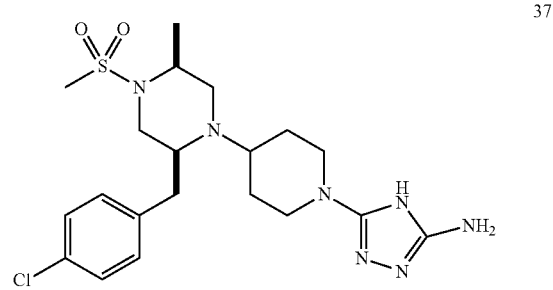

Step 1

Synthesis of methyl (S)-2-(((S)-2-((tert-butoxycarbonyl)amino)-3-(4-chlorophenyl)propyl)amino)propanoate (37)

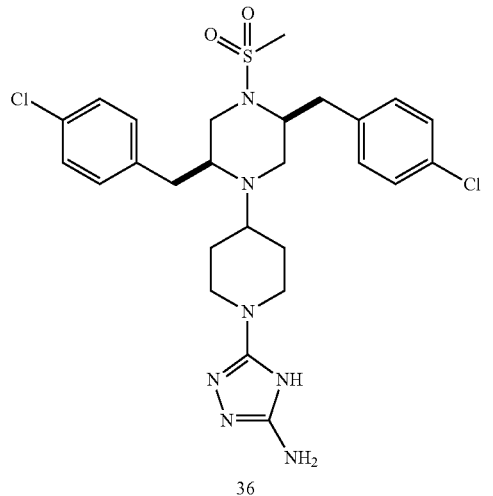

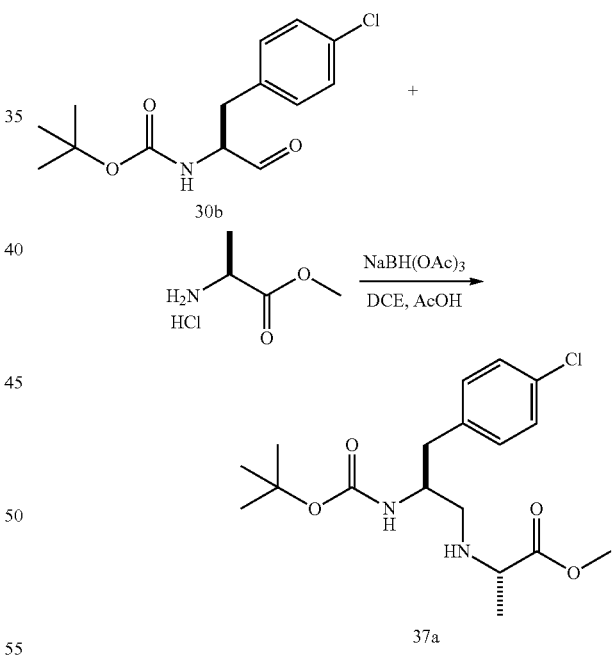

Formation of 1,2,4-triazole ring was accomplished according to the General Procedure VIII starting from compound 36e. 25 mg (0.043 mmol) of the final compound 36 was synthesized (20% yield).

ESI-MS m/z for $C_{26}H_{33}Cl_2N_7O_2S$ found 578.0/580.0 $(M+1)^+$ $^1$H NMR (DMSO-$d_6$, 500 MHz) δ 7.34 (m, 4H), 7.19 (m, 4H), 3.97-3.82 (m, 1H), 3.78 (d, J=12.4 Hz, 1H), 3.68 (d, J=12.4 Hz, 1H), 3.24-2.94 (m, 6H), 2.93-2.72 (m, 3H), 2.65 (s, 3H), 2.61-2.51 (m, 2H), 2.36-2.19 (m, 1H), 1.70-1.39 (m, 3H), 1.31-1.15 (m, 1H).

The title compound was synthesized from intermediate 30b and L-alanine methyl ester hydrochloride according to the General Procedure XIII 10.2 g (27.5 mmol) of compound 37a was obtained after purification by column chromatography in AcOEt/hexanes 1:6 solvent system (72% yield).

ESI-MS m/z for $C_{18}H_{27}ClN_2O_4$ found 371.2/373.2 $(M+1)^+$ $^1$H NMR (DMSO-$d_6$, 500 MHz) δ 7.26 (AA'BB', J=8.3 Hz, 2H), 7.15 (AA'BB', J=8.5 Hz, 2H), 3.57 (s, 3H), 3.55-3.18 (m, 2H), 2.76 (dd, J=5.4, 13.3 Hz, 1H), 2.55-2.46 (m, 2H), 2.38-2.30 (m, 1H), 1.26 (s, 9H), 1.13 (d, J=7 Hz, 3H).

Step 2

Synthesis of (3S,6S)-6-(4-chlorobenzyl)-3-methyl-piperazin-2-one (37b)

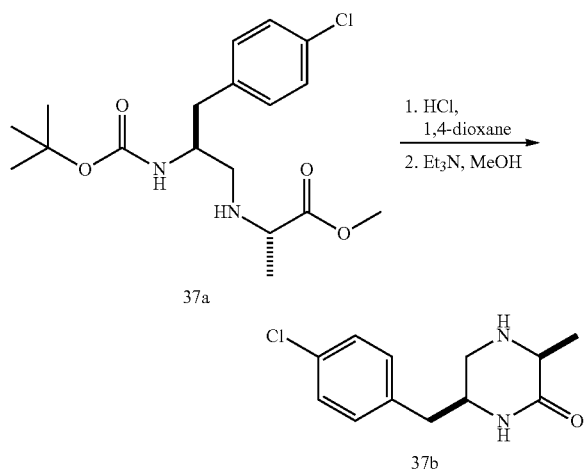

The title compound was synthesized from compound 37a according to the General Procedure X. 5.8 g (24.3 mmol) of the product 37b was obtained (89% yield).

ESI-MS m/z for $C_{12}H_{15}ClN_2O$ found 239.0/241.0 $(M+1)^+$

Step 3

Synthesis of tert-butyl (2S,5S)-5-(4-chlorobenzyl)-2-methyl-3-oxopiperazine-1-carboxylate (37c)

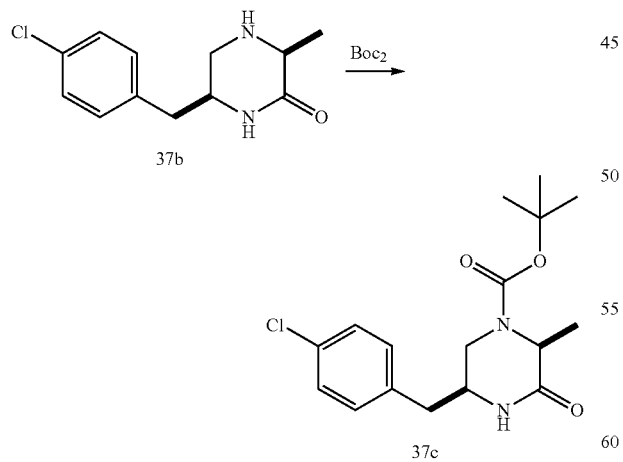

To a solution of compound 37b (3.74 g, 15.6 mmol) in DCM (60 mL), di-tert-butyl dicarbonate (Boc$_2$O) (5.1 g, 23.5 mmol) was added. After 1 hour the reaction mixture was concentrated and directly loaded onto silica gel and purified by column chromatography in AcOEt/hexanes solvent system (gradient elution from 1:8 to 1:1) providing 3.70 g (10.9 mmol; 70% yield) of the title compound 37c.

ESI-MS m/z for $C_{17}H_{23}ClN_2O_3$ found 339.1/341.1 $(M+1)^+$

Step 4

Synthesis of tert-butyl (2S,5S)-5-(4-chlorobenzyl)-2-methylpiperazine-1-carboxylate (37d)

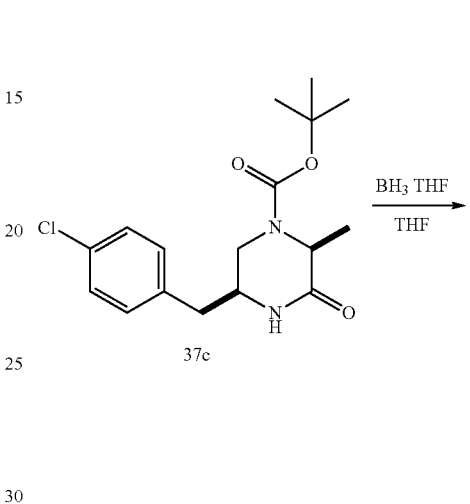

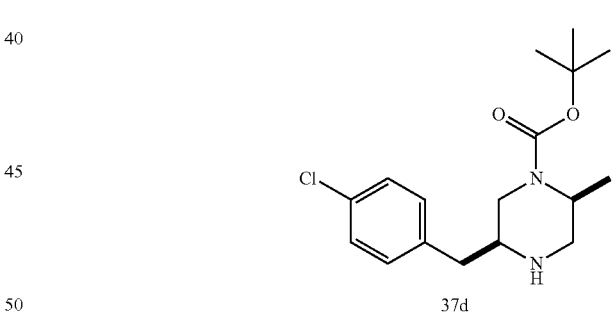

The title compound was synthesized according to the General Procedure V, with the exception that 2 M HCl was not added, instead the reaction mixture was carefully quenched with water (30 mL), then 150 mL of 1 M NaOH was added and the reaction was extracted several times with diethyl ether. Organics were dried over MgSO$_4$, filtered and concentrated providing 5.5 g (16.9 mmol; 99% yield) of compound 37d. It was found to be of sufficient purity to be used in the next step.

ESI-MS m/z for $C_{17}H_{25}ClN_2O_2$ found 269.2/271.2 (M+1-tBu)$^+$, 225.1/227.1 (M+1-Boc)$^+$

Step 5

Synthesis of tert-butyl (2S,5S)-4-(1-((allyloxy)carbonyl)piperidin-4-yl)-5-(4-chlorobenzyl)-2-methyl-piperazine-1-carboxylate (37e)

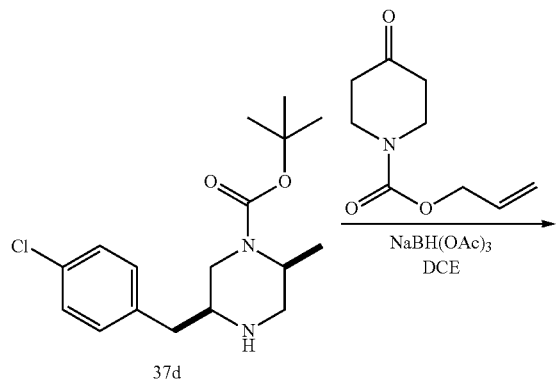

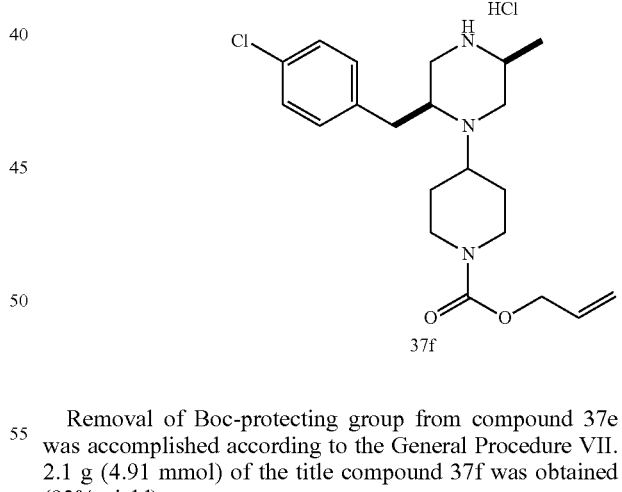

The synthesis of the title compound was accomplished by reacting compound 37d with N-Alloc-piperid-4-one according to the General Procedure VI. From 5.5 g (16.9 mmol) of the starting material 37d, 2.64 g (5.36 mmol, 31% yield) of compound 37e was obtained after chromatographic purification in AcOEt/hexanes 1:2 solvent system.

ESI-MS m/z for $C_{26}H_{38}ClN_3O_4$ found 492.2/494.2 $(M+1)^+$

Step 6

Synthesis of allyl 4-((2S,5S)-2-(4-chlorobenzyl)-5-methylpiperazin-1-yl)piperidine-1-carboxylate hydrochloride (37f)

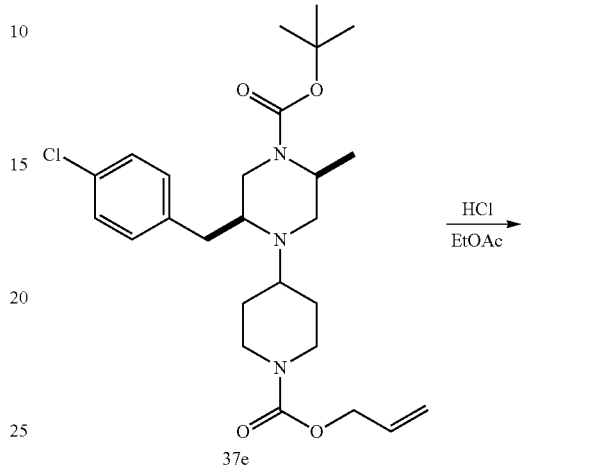

Removal of Boc-protecting group from compound 37e was accomplished according to the General Procedure VII. 2.1 g (4.91 mmol) of the title compound 37f was obtained (92% yield)

ESI-MS m/z for $C_{21}H_{30}ClN_3O_2$ found 392.0/394.0 $(M+1)^+$ $^1$H NMR (DMSO-d$_6$, 500 MHz) δ 7.32 (AA'BB', J=8.5 Hz, 2H), 7.28 (AA'BB', J=8.5 Hz, 2H), 5.92-5.83 (m, 1H), 5.25-5.19 (m, 1H), 5.16-5.12 (m, 1H), 4.48-4.44 (m, 2H), 4.05-3.90 (m, 2H), 3.77-3.70 (m, 1H), 3.12-2.98 (m, 4H), 2.80-2.71 (m, 4H), 2.66-2.60 (m, 1H), 2.53-2.47 (m, 1H), 2.43-2.37 (m, 1H), 1.65-1.57 (m, 1H), 1.49-1.42 (m, 2H), 1.14 (d, J=6.4 Hz, 3H).

Step 7

Synthesis of allyl 4-((2S,5S)-2-(4-chlorobenzyl)-5-methyl-4-(methylsulfonyl)piperazin-1-yl)piperidine-1-carboxylate (37g)

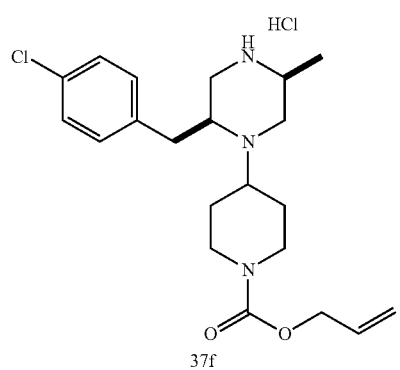

Title compound was synthesized from intermediate 37f according to the General Procedure XV. 0.34 g (0.72 mmol) of compound 37g was obtained (85% yield).

ESI-MS m/z for $C_{22}H_{32}ClN_3O_4S$ found 470.1/472.1 $(M+1)^+$

Step 8

Synthesis of (2S,5S)-2-(4-chlorobenzyl)-5-methyl-4-(methylsulfonyl)-1-(piperidin-4-yl)piperazine (37h)

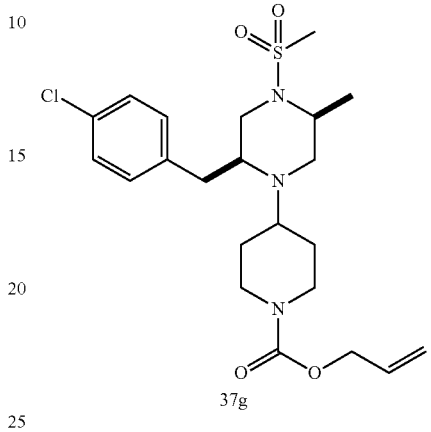

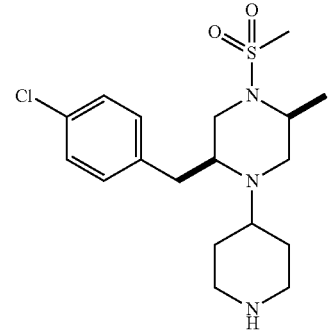

Title compound was synthesized from intermediate 37g according to the General Procedure XVI. 260 mg of the title compound 37h (0.67 mmol; 93% yield), that was sufficiently pure to be used in the next reaction, was obtained.

ESI-MS m/z for $C_{18}H_{28}ClN_3O_2S$ found 386.2/388.2 $(M+1)^+$ $^1$H NMR (DMSO-$d_6$, 500 MHz), δ 7.35-7.22 (m, 4H), 3.81-3.69 (m, 1H), 3.07-2.89 (m, 3H), 2.86-2.72 (m, 5H), 2.78 (s, 3H), 2.68-2.61 (m, 1H), 2.60-2.47 (m, 1H), 1.90-1.81 (m, 1H), 1.72-1.64 (m, 1H), 1.62-1.49 (m, 2H), 1.46-1.37 (m, 1H), 1.30-1.16 (m, 1H), 1.14 (d, J=6.6 Hz, 3H).

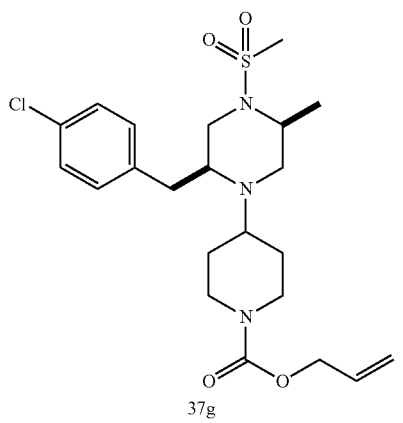

Step 9

Synthesis of 5-(4-((2S,5S)-2-(4-chlorobenzyl)-5-methyl-4-(methylsulfonyl)piperazin-1-yl)piperidin-1-yl)-4H-1,2,4-triazol-3-amine (37)

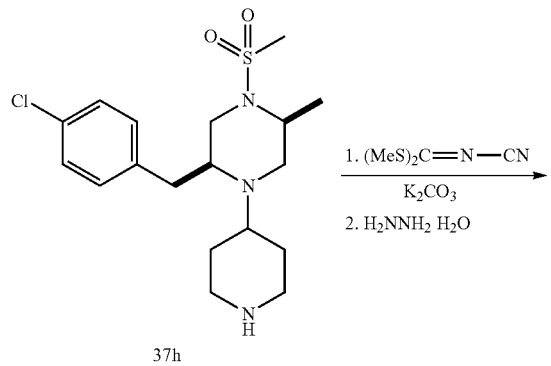

Formation of 1,2,4-triazole ring was accomplished according to the General Procedure VIII starting from compound 37h. 32 mg (0.07 mmol) of the final compound 37 was synthesized.

ESI-MS m/z for $C_{20}H_{30}ClN_7O_2S$ found 468.3/470.3 (M+1)$^+$ $^1$H NMR (DMSO-d$_6$, 500 MHz) δ 7.38 (AA'BB', J=8.3 Hz, 2H), 7.33 (AA'BB', J=8.3 Hz, 2H), 3.85-3.72 (m, 6H), 3.37-3.00 (m, 5H), 2.89 (s, 3H), 2.80-2.64 (m, 2H), 2.03-1.65 (m, 3H), 1.60-1.41 (m, 1H), 1.26 (d, J=4.7 Hz, 3H).

Example 38

1-((2S,5S)-4-(1-(5-amino-4H-1,2,4-triazol-3-yl)piperidin-4-yl)-5-(4-chlorobenzyl)-2-methylpiperazin-1-yl)ethanone (38)

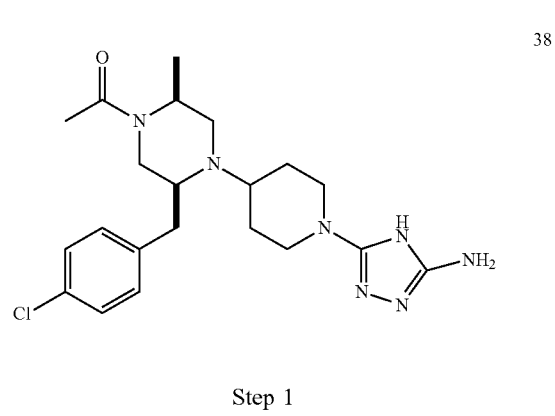

Step 1

Synthesis of allyl 4-((2S,5S)-4-acetyl-2-(4-chlorobenzyl)-5-methylpiperazin-1-yl)piperidine-1-carboxylate (38a)

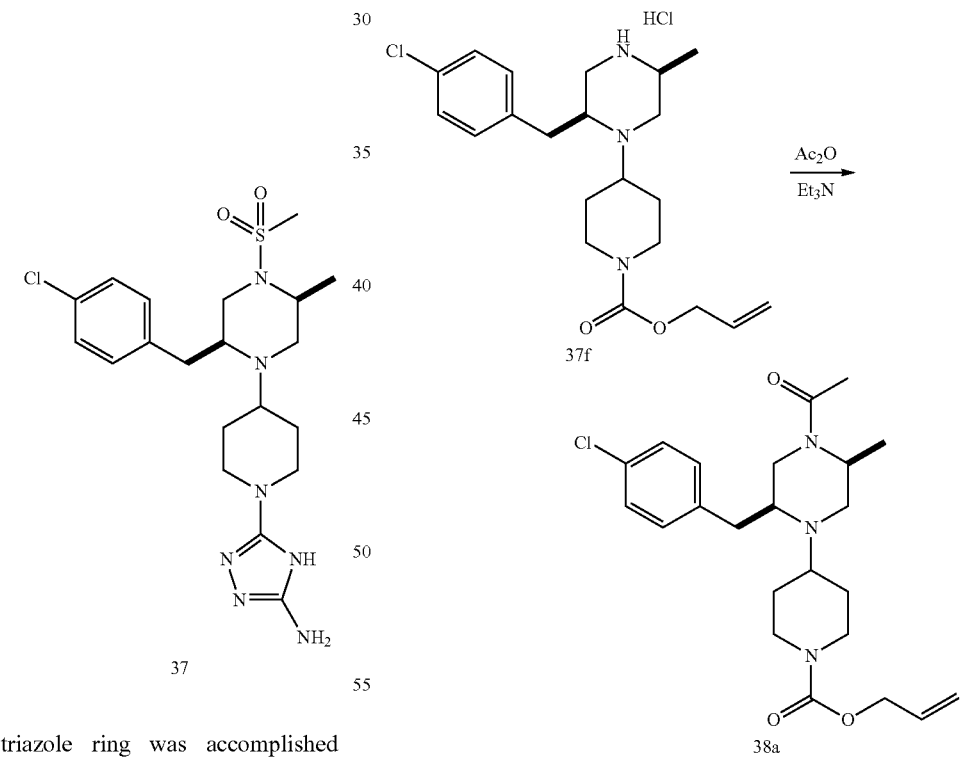

To a solution of intermediate 37f (0.35 g, 0.75 mmol) and triethylamine (Et$_3$N) (0.2 mL, 1.5 mmol) in 5 mL of dichloromethane, acetic anhydride (0.11 g, 1.12 mmol) was added. The reaction mixture was stirred for 2 hours at room temperature and then it was washed with 0.1 M HCl, 5% aq. NaHCO$_3$, brine, dried and concentrated affording 0.23 g (0.53 mmol; 71% yield) of the title compound 38a as a colorless oil.

ESI-MS m/z for $C_{23}H_{32}ClN_3O_3$ found 434.1/436.1 (M+1)+

Step 2 & 3

Synthesis of 1-((2S,5S)-4-(1-(5-amino-4H-1,2,4-triazol-3-yl)piperidin-4-yl)-5-(4-chlorobenzyl)-2-methylpiperazin-1-yl)ethanone (38)

Alloc-group removal and formation of 1,2,4-triazole ring were accomplished according to the General Procedure XVI and the General Procedure VIII respectively starting from compound 38a. 28 mg (0.06 mmol) of the final compound 38 was synthesized.

ESI-MS m/z for $C_{21}H_{30}ClN_7O$ found 432.1/434.1 (M+1)+

$^1$H NMR (DMSO-$d_6$, +75° C., 500 MHz) δ 7.34 (AA'BB', J=8.3 Hz, 2H), 7.31 (AA'BB', J=8.5 Hz, 2H), 3.88-3.71 (m, 4H), 3.48-3.28 (m, 2H), 3.19-3.08 (m, 2H), 3.00-2.64 (m, 5H), 1.86 (s, 3H), 1.82-1.62 (m, 3H), 1.55-1.38 (m, 1H), 1.15 (d, J=5.6 Hz, 3H).

Example 39 methyl (2S,5S)-4-(1-(5-amino-4H-1,2,4-triazol-3-yl)piperidin-4-yl)-5-(4-chlorobenzyl)-2-methylpiperazine-1-carboxylate (39)

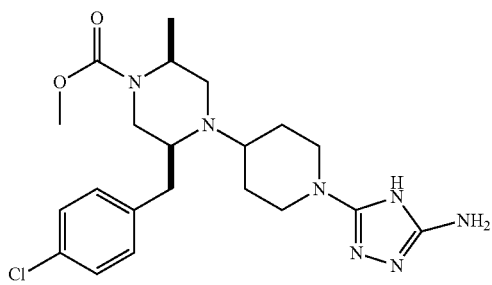

39

Step 1

Synthesis of methyl (2S,5S)-4-(1-((allyloxy)carbonyl)piperidin-4-yl)-5-(4-chlorobenzyl)-2-methylpiperazine-1-carboxylate (39a)

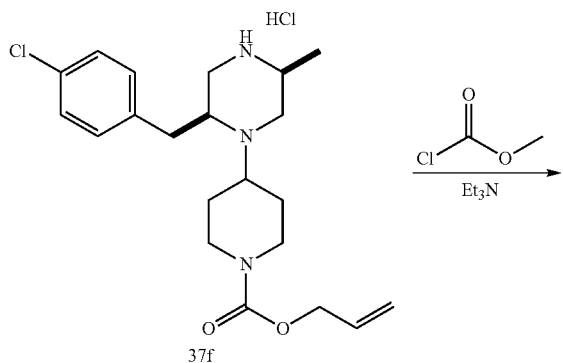

37f

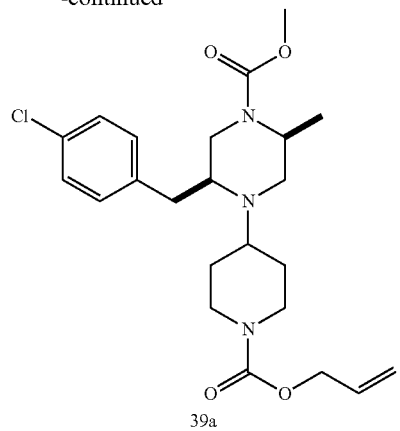

39a

To a solution of intermediate 37f (0.35 g, 0.75 mmol) and triethylamine (Et$_3$N) (0.2 mL, 1.5 mmol) in 5 mL of dichloromethane, methyl chloroformate (0.11 g, 1.2 mmol) was added. The reaction was stirred for 2 hours at room temperature and then it was washed with 0.1 M HCl, 5% NaHCO$_3$, brine, dried and concentrated affording 0.26 g (0.58 mmol, 77% yield) of the title compound 39a as colorless oil.

ESI-MS m/z for $C_{23}H_{32}ClN_3O_4$ found 449.1/451.1 (M+1)+

$^1$H NMR (CDCl$_3$, 500 MHz), δ 7.23 (AA'BB', J=8.3 Hz, 2H), 7.11 (AA'BB', J=8.3 Hz, 2H), 5.96-5.84 (m, 1H), 5.30-5.13 (m, 3H), 4.55-4.51 (m, 2H), 4.30-4.04 (m, 4H), 3.80-3.73 (m, 1H), 3.60 (s, 3H), 3.02-2.86 (m, 3H), 2.85-2.65 (m, 3H), 2.62-2.39 (m, 5H), 1.12 (d, J=6.6 Hz, 3H)

Steps 2 and 3

Synthesis of methyl (2S,5S)-4-(1-(5-amino-4H-1,2,4-triazol-3-yl)piperidin-4-yl)-5-(4-chlorobenzyl)-2-methylpiperazine-1-carboxylate (39)

Alloc-group removal and formation of 1,2,4-triazole ring were accomplished according to the General Procedure XVI and the General Procedure VIII respectively starting from compound 39a. 57 mg (0.06 mmol) of the final compound 39 was synthesized.

ESI-MS m/z for $C_{21}H_{30}ClN_7O_2$ found 448.0/450.0 (M+1)+

$^1$H NMR (DMSO-$d_6$, 500 MHz) δ 7.44 (AA'BB', J=7.9 Hz, 2H), 7.33 (AA'BB', J=8.1 Hz, 2H), 4.30-4.19 (m, 1H), 3.87-3.82 (m, 4H), 3.68-3.54 (m, 3H), 3.50 (s, 3H), 3.40-3.28 (m, 2H), 3.03-2.87 (m, 3H), 2.82-2.70 (m, 1H), 2.02-188 (m, 1H), 1.83-1.72 (m, 1H), 1.67-1.49 (m, 1H), 1.18 (d, J=6.2 Hz, 3H).

Example 40 methyl 2-((2S,5S)-4-(1-(5-amino-4H-1,2,4-triazol-3-yl)piperidin-4-yl)-5-(4-chlorobenzyl)-2-methylpiperazin-1-yl)acetate (40)

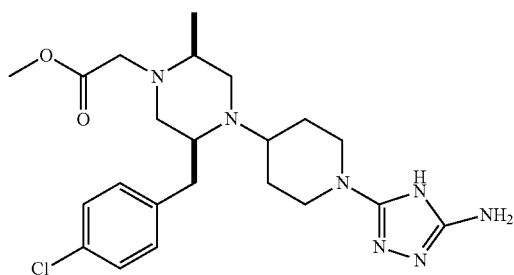

Step 1

Synthesis of allyl 4-((2S,5S)-2-(4-chlorobenzyl)-4-(2-methoxy-2-oxoethyl)-5-methylpiperazin-1-yl)piperidine-1-carboxylate (40a)

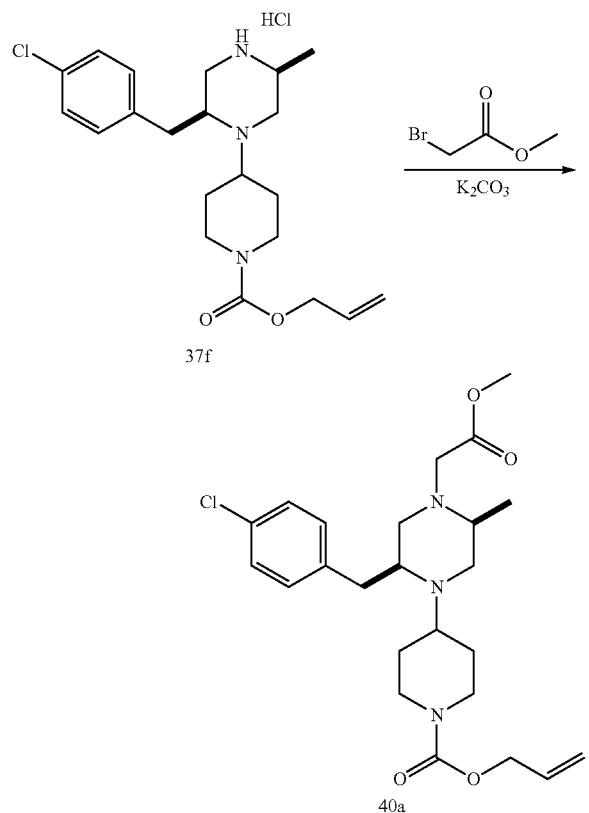

The mixture of compound 37f (0.8 g, 1.72 mmol), methyl bromoacetate (0.47 mL, 5.16 mmol), and potassium carbonate (K$_2$CO$_3$) (0.72 g, 5.16 mmol) in acetonitrile (10 mL) was heated at 60° C. for 2 h. Solid was removed by filtration and filtrate was absorbed onto silica gel and product was purified by column chromatography in AcOEt/hexanes 1:2 providing 0.79 g (1.70 mmol) of the title compound 40a (99% yield).

ESI-MS m/z for C$_{24}$H$_{34}$ClN$_3$O$_4$ found 464.1/466.1 (M+1)$^+$

Steps 2 and 3

Synthesis of methyl 2-((2S,5S)-4-(1-(5-amino-4H-1,2,4-triazol-3-yl)piperidin-4-yl)-5-(4-chlorobenzyl)-2-methylpiperazin-1-yl)acetate (40)

Alloc-group removal and formation of 1,2,4-triazole ring were accomplished according to the General Procedure XVI and the General Procedure VIII respectively starting from compound 40a. 125 mg (0.27 mmol) of the final compound 40 was synthesized.

ESI-MS m/z for C$_{22}$H$_{32}$ClN$_7$O$_2$ found 462.2/464.2 (M+1)$^+$ $^1$H NMR (DMSO-d$_6$, 500 MHz) δ 9.65 (bs, 1H), 7.40 (AA'BB', J=8.5 Hz, 2H), 7.33 (AA'BB', J=8.3 Hz, 2H), 3.92-3.76 (m, 2H), 3.58 (s, 3H), 3.56-3.16 (m, 6H), 3.07-2.96 (m, 2H), 2.95-2.77 (m, 4H), 2.64-2.50 (m, 1H), 2.26-2.10 (m, 2H), 1.69-1.51 (m, 2H), 1.08 (d, J=5.6 Hz, 3H).

Example 41

2-((2S,5S)-4-(1-(5-amino-4H-1,2,4-triazol-3-yl)piperidin-4-yl)-5-(4-chlorobenzyl)-2-methylpiperazin-1-yl)acetic acid (41)

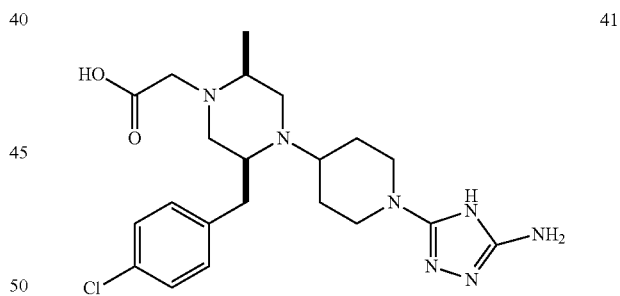

Compound 40 (110 mg; 0.24 mmol) was refluxed in 2 mL of 3 M HCl for 3 hours after which time volatiles were removed in vacuo and the residue was purified by the reversed-phase chromatography. 65 mg (0.14 mmol; 60% yield) of the title compound 41 was obtained.

ESI-MS m/z for C$_{21}$H$_{30}$ClN$_7$O$_2$ found 448.1/450.1 (M+1)$^+$ $^1$H NMR (DMSO-d$_6$, 500 MHz) δ 9.60 (bs, 1H), 7.39 (AA'BB', J=8.3 Hz, 2H), 7.34 (AA'BB', J=8.5 Hz, 2H), 3.94-3.34 (m, 6H), 3.31-3.18 (m, 2H), 3.12-2.96 (m, 2H), 2.96-2.76 (m, 4H), 2.65-2.54 (m, 1H), 2.27-2.08 (m, 2H), 1.70-1.51 (m, 2H), 1.09 (d, J=5 Hz, 3H).

Example 42

(S)-4-(1-(5-amino-4H-1,2,4-triazol-3-yl)piperidin-4-yl)-3-(4-chlorobenzyl)piperazin-2-one (42)

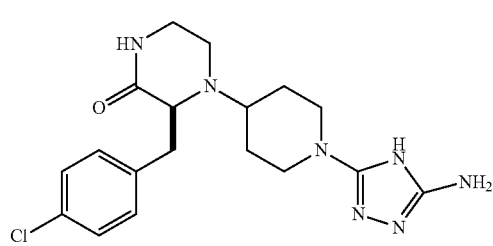

Step 1

Synthesis of tert-butyl (S)-(3-(4-chlorophenyl)-1-((2,2-diethoxyethyl)amino)-1-oxopropan-2-yl)carbamate (42a)

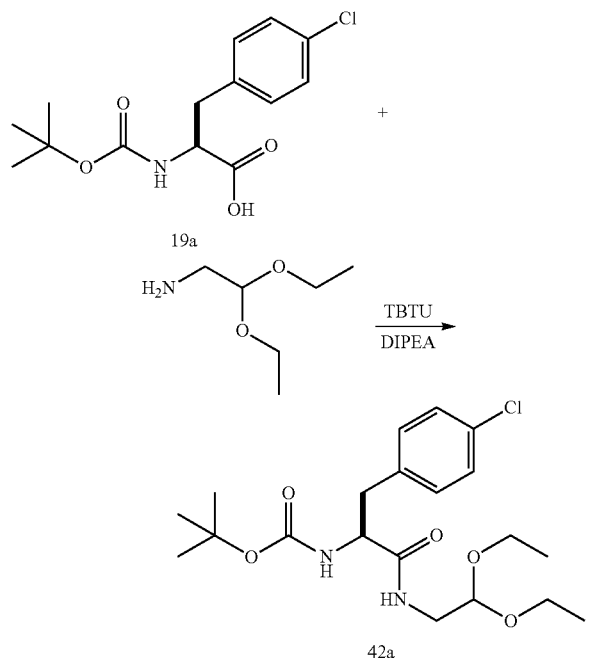

Compound 19a (1.00 g, 3.34 mmol) was dissolved in DCM (13.4 mL) and diisopropylethylamine (0.87 mL, 5.0 mmol) was added at room temperature followed by addition of aminoacetaldehyde diethylacetal (0.54 mL, 3.67 mmol) and O-(benzotriazol-1-yl)-N,N,N',N'-tetramethyluronium tetrafluoroborate (TBTU) (1.13 g, 3.50 mmol). The reaction mixture was stirred for 3 hours at RT, diluted with methylene chloride and washed with 1 M $K_2CO_{3aq}$ and 1 M $HCl_{aq}$, brine, dried over anhydrous $MgSO_4$ filtered and concentrated in vacuo. The residue was purified by flash chromatography using dichloromethane (DCM), then DCM/MeOH 100:1 solvent system. 1.27 g (3.07 mmol; 92% yield) of the title compound 42a was obtained ESI-MS m/z for $C_{20}H_{31}ClN_2O_5$ found 415.4/417.4 $(M+1)^+$ $^1$H NMR (CDCl$_3$, 500 MHz) δ 7.23 (m, 2H), 7.11 (m, 2H), 5.92 (brs, 1H), 5.02 (brs, 1H), 4.28 (brs, 2H), 3.64-3.56 (m, 2H), 3.47-3.43 (m, 1H), 3.40-3.30 (m, 2H), 3.25 (brs, 1H), 2.99 (brs, 2H), 1.38 (s, 9H), 1.14 (q, J=6.9 Hz, 6H)

Step 2

Synthesis of tert-butyl (S)-2-(4-chlorobenzyl)-3-oxo-3,4-dihydropyrazine-1(2H)-carboxylate (42b)

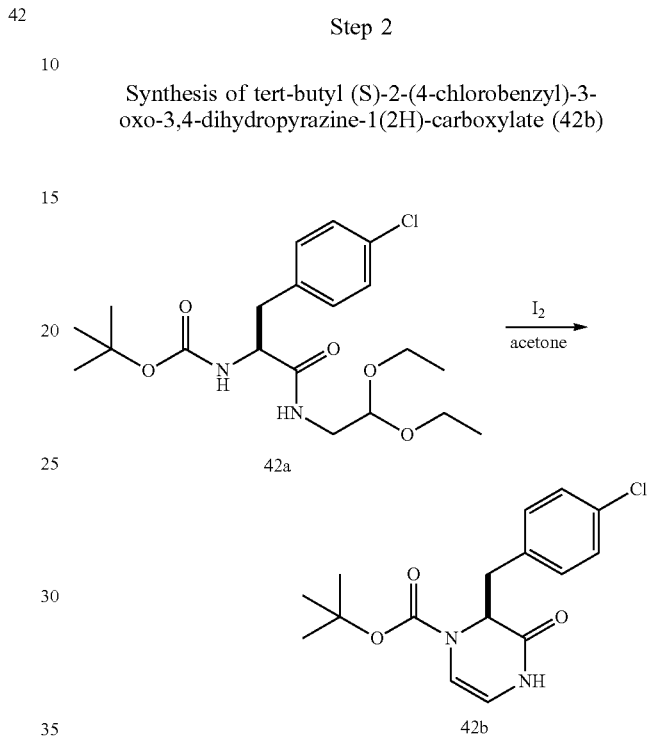

Compound 42a (1.38 g, 3.33 mmol) was dissolved in acetone (33 mL, 10 mL/mmol) then I$_2$ (85 mg, 0.33 mmol) was added and the mixture was stirred overnight at RT. The solvent was removed in vacuo and oily residue was dissolved in Et$_2$O then washed twice with 10% Na$_2$S$_2$O$_4$. The organic layer was dried over MgSO$_4$, filtered and concentrated in vacuo. The residue was purified by flash chromatography using DCM neat, then DCM/MeOH 100:1 solvent system. 0.88 g (2.72 mmol; 82% yield) of the title compound was obtained.

ESI-MS m/z for $C_{16}H_{19}ClN_2O_3$ found 322.7/324.7 $(M+1)^+$ $^1$H NMR (CDCl$_3$, 500 MHz)—two conformers present due to hindered rotation δ {[7.62 (1$^{st}$ isomer, brs), 7.58 (2$^{nd}$ isomer, brs)], 1H}, {[7.25 (2$^{nd}$ isomer, d, J=8.0 Hz), 7.20 (1$^{st}$ isomer, d, J=8.0 Hz)], 2H}, {[7.08 (1$^{st}$ isomer, d, J=8.0 Hz), 7.06 (2$^{nd}$ isomer, d, J=8 Hz)], 2H}, {[6.36 (2$^{nd}$ isomer, d, J=5.8 Hz), 6.10 (1$^{st}$ isomer, d, J=5.8 Hz)], 1H}, {[5.67 (2$^{nd}$ isomer, t, J=5.1 Hz), 5.42 (1$^{st}$ isomer, t, J=5.1 Hz)], 1H}, {[4.99-4.95 (1$^{st}$ isomer, m), 4.80-4.76 (2$^{nd}$ isomer, m)], 1H}, {[3.02-2.96 (1$^{st}$ isomer, m), 2.90-2.86 (2$^{nd}$ isomer, m)], 2H}, {[1.35 (1$^{st}$ isomer, s), 1.17 (2$^{nd}$ isomer, s)], 9H}

Step 3

Synthesis of (S)-3-(4-chlorobenzyl)piperazin-2-one (42c)

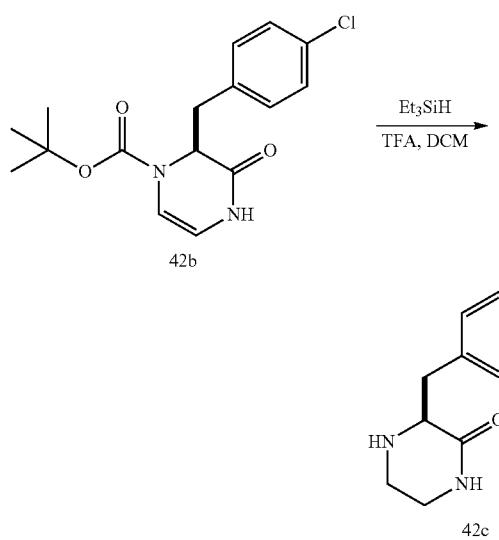

To a solution of compound 42b (0.58 g, 1.80 mmol) in dichloromethane (DCM) (5 mL), triethylsilane Et₃SiH (1.4 mL, 8.9 mmol) was added followed by slow addition of trifluoroacetic acid (TFA) (1.3 mL, 17.8 mmol) and the reaction mixture was stirred overnight at RT. The volatiles were then removed in vacuo and the residue was taken between 1 M NaOH and DCM. The organic phase was washed with brine, dried and concentrated affording 0.32 g (1.42 mmol; 79% yield) of the title compound 42c was obtained.

ESI-MS m/z for $C_{11}H_{13}ClN_2O$ found 225.2/227.2 (M+1)⁺

1H NMR (CDCl₃, 500 MHz) δ 7.29-7.23 (m, 2H), 7.18 (d, J=8.3 Hz, 2H), 6.11 (s, 1H), 3.59 (dd, J=9.6, 3.6 Hz, 1H), 3.41-3.30 (m, 2H), 3.24 (dq, J=11.2, 3.6 Hz, 1H), 3.06 (dt, J=12.6, 3.9 Hz, 1H), 2.93-2.82 (m, 2H).

Steps 4-6

Synthesis of (S)-4-(1-(5-amino-4H-1,2,4-triazol-3-yl)piperidin-4-yl)-3-(4-chlorobenzyl)piperazin-2-one (42)

Piperazinone 42c was carried through the remaining synthetic steps as it is described in the General Procedure VI (reductive amination with N-Boc-piperid-4-one), the General Procedure VII (Boc-deprotection) and the General Procedure VIII (triazole ring formation). 150 mg (0.38 mmol) of the title compound 42 was obtained.

ESI-MS m/z for $C_{18}H_{24}ClN_7O$ found 390.1/392.1 (M+1)⁺

¹H NMR (DMSO-d₆, 500 MHz) δ 7.88 (s, 1H), 7.32-7.22 (m, 4H), 3.85-3.59 (m, 4H), 3.15-2.75 (m, 8H), 1.73 (d, J=12.2 Hz, 1H), 1.66-1.53 (m, 1H), 1.51-1.28 (m, 2H).

Example 43

(S)-4-(1-(5-amino-4H-1,2,4-triazol-3-yl)piperidin-4-yl)-3-(4-chlorobenzyl)thiomorpholine 1,1-dioxide (43)

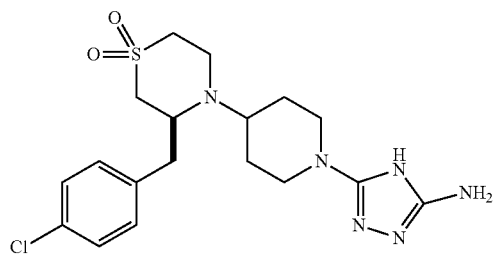

Step 1

Synthesis of (S)-2-((tert-butoxycarbonyl)amino)-3-(4-chlorophenyl)propyl methanesulfonate (45a)

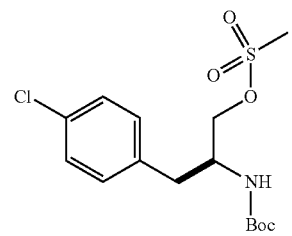

To a solution of substrate 30a (1.8 g, 6.29 mmol) and triethylamine (1.4 mL, 9.44 mmol), in dichloromethane, mesyl chloride (0.73 mL, 9.44 mmol) was added dropwise. After 1 hour of stirring, reaction mixture was diluted with dichloromethane, washed with 2 M HCl, 5% aq. NaHCO₃, brine, dried and concentrated. The residue was washed with ether providing 2.09 g of product 43a as white solid (5.76 mmol; 92% yield).

ESI-MS m/z for $C_{19}H_{28}ClN_3O$ found 386.1/388.1 (M+Na)⁺

Step 2

Synthesis of methyl (S)-2-((2-((tert-butoxycarbonyl)amino)-3-(4-chlorophenyl)propyl)-thio)acetate (43b)

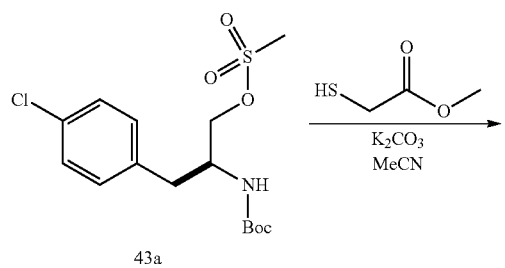

Mesylate 43a (2.09 g, 5.74 mmol), K$_2$CO$_3$ (1.58 g, 11.48 mmol) and methyl thioglycolate (0.65 mL, 11.48 mmol) in acetonitrile were heated under reflux for 30 minutes, then the reaction mixture was diluted with water and product was extracted with diethyl ether. The organics were washed with 2 M HCl, 5% aq. NaHCO$_3$, brine, dried and concentrated providing 2.1 g of product 43b as yellow oil (5.61 mmol; 98% yield).

ESI-MS m/z for C$_{17}$H$_{24}$ClNO$_4$S found 374.1/376.1 (M+1)$^+$

Step 3

Synthesis of methyl (S)-2-((2-((tert-butoxycarbonyl)amino)-3-(4-chlorophenyl)propyl)sulfonyl)acetate (43c)

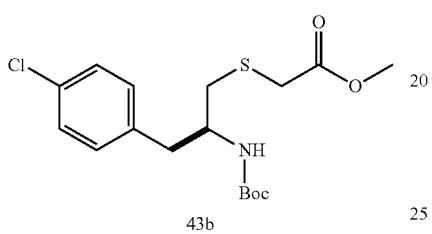

To a solution of 43b (2.1 g, 5.74 mmol) in ethyl acetate, peracetic acid (2.1 mL, 12.83 mmol, 39% in AcOH) was added dropwise, then the reaction was stirred overnight at RT and concentrated to dryness. The residue was triturated with diethyl ether and crude 43c was used in the next step.

ESI-MS m/z for C$_{17}$H$_{24}$ClNO$_6$S found 406.1/408.1 (M+1)$^+$

Step 4

Synthesis of (S)-5-(4-chlorobenzyl)thiomorpholin-3-one 1,1-dioxide (43d)

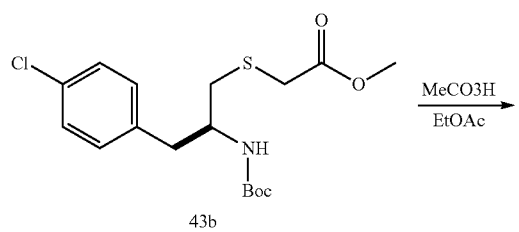

Compound 43c (5.74 mmol) was treated with HCl/dioxane and stirred for 1 hour, then concentrated to dryness. The residue was dissolved in MeOH and treated with Et$_3$N (1.8 mL, 11.48 mmol). After 30 minutes the reaction was concentrated, the residue was taken into dichloromethane, washed with 2 M HCl, 5% aq. NaHCO$_3$, brine, dried with anhydrous MgSO$_4$ and concentrated providing orange solid. Colored impurities were removed by trituration with diethyl ether providing 0.52 g (1.90 mmol; 33% yield over two steps) of compound 43d as a white solid.

ESI-MS m/z for C$_{11}$H$_{12}$ClNO$_3$S found 274.1/276.1 (M+1)$^+$ $^1$H NMR (DMSO-d$_6$, 500 MHz) δ 8.43 (bs, 1H), 7.35 (AA'BB', J=8.3 Hz, 2H), 7.26 (AA'BB', J=8.3 Hz, 2H), 4.17-4.11 (m, 1H), 4.00 (dd, J=2.6, 16.1 Hz, 1H), 3.97-3.90 (m, 1H), 3.23-3.17 (m, 1H), 3.09 (dd, J=11.1, 13.7 Hz, 1H), 2.97 (dd, J=4.7, 13.5 Hz, 1H), 2.82 (dd, J=7.5, 13.5 Hz, 1H).

Step 5

Synthesis of (S)-3-(4-chlorobenzyl)thiomorpholine 1,1-dioxide (43e)

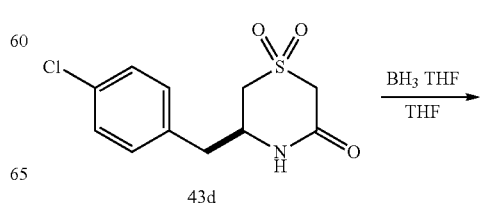

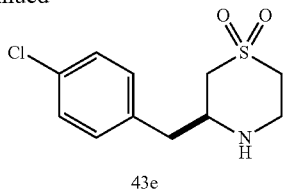

43e

Compound 43d (0.42 g, 1.53 mmol) was dissolved in 15 mL of dry THF and borane-tetrahydrofurane complex (4.6 mL, 4.6 mmol) was carefully added and the reaction was heated with stirring for 1 hours. After this time the TLC revealed the complete consumption of the starting material. The reaction mixture was carefully quenched with water. 1 M NaOH was added and the reaction mixture was extracted with diethyl ether. Organics were dried over MgSO$_4$ and concentrated to yield 0.4 g of product 43e (1.53 mmol; 99% yield).

ESI-MS m/z for C$_{11}$H$_{14}$ClNO$_2$S found 260.1/262.1 (M+1)$^+$ $^1$H NMR (DMSO-d$_6$, 500 MHz) δ 7.31 (AA'BB', J=8.3 Hz, 2H), 7.21 (AA'BB', J=8.3 Hz, 2H), 3.37-3.17 (m, 2H), 3.09-3.00 (m, 1H), 2.97-2.74 (m, 4H), 2.72-2.63 (m, 2H).

Step 6

Synthesis of tert-butyl (S)-4-(3-(4-chlorobenzyl)-1, 1-dioxidothiomorpholino)piperidine-1-carboxylate (43f)

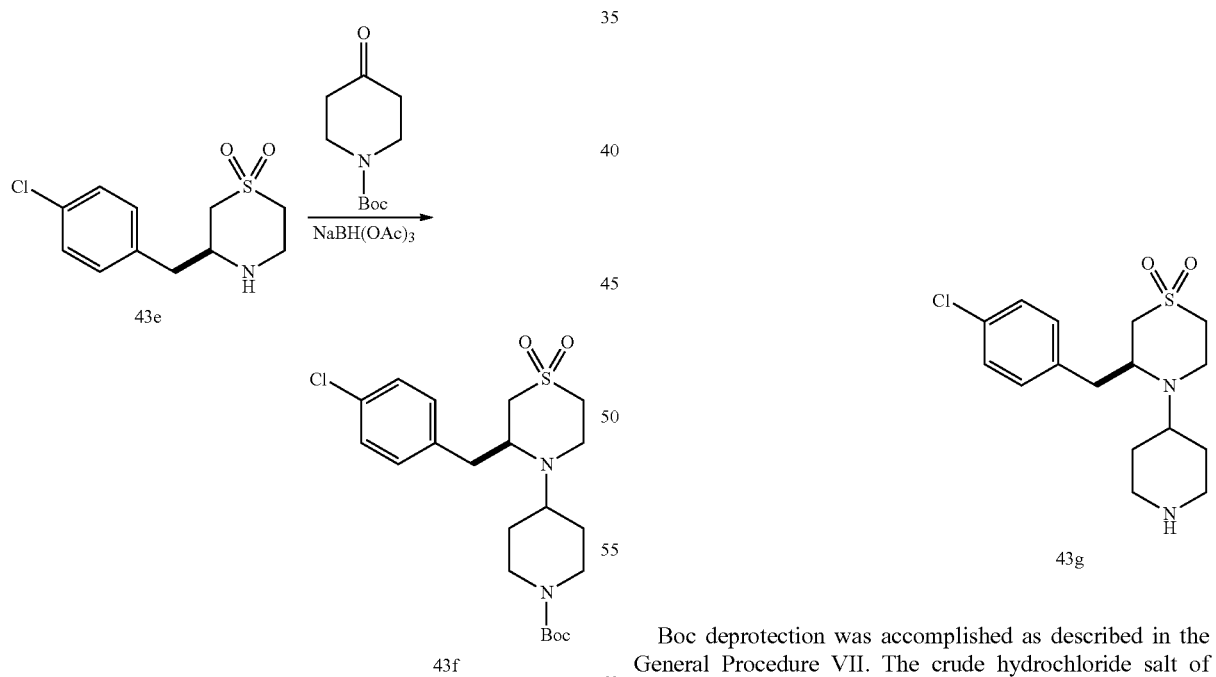

43e

43f

Reductive amination was done according to the General Procedure VI starting from amine 43e (0.4 g, 1.53 mmol) and N-Boc-piperid-4-one to give 0.61 g of product 43f (1.38 mmol; 90% yield).

ESI-MS m/z for C$_{21}$H$_{31}$ClN$_2$O$_4$S found 443.1/445.1 (M+1)$^+$ $^1$H NMR (CDCl$_3$, 500 MHz) δ 7.24 (AA'BB', J=8.3 Hz, 2H), 7.10 (AA'BB', J=8.3 Hz, 2H), 3.85-3.72 (m, 2H), 3.52-3.42 (m, 1H), 3.41-3.32 (m, 1H), 3.14-3.01 (m, 2H), 3.02-2.57 (m, 6H), 2.26-1.98 (m, 2H), 1.84-1.73 (m, 2H), 1.73-1.63 (m, 2H), 1.42 (s, 9H).

Step 7

Synthesis of (S)-3-(4-chlorobenzyl)-4-(piperidin-4-yl)thiomorpholine 1,1-dioxide (43g)

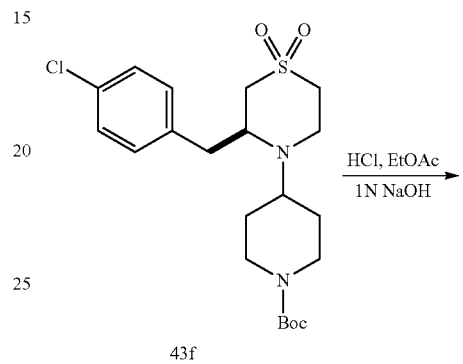

43f

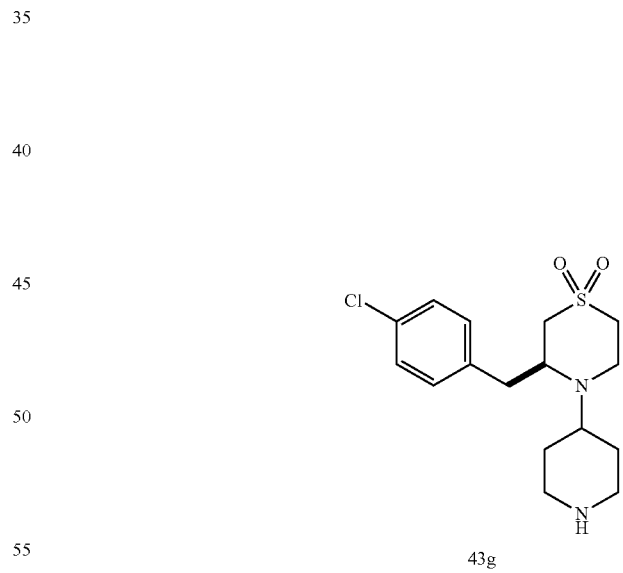

43g

Boc deprotection was accomplished as described in the General Procedure VII. The crude hydrochloride salt of compound 43g was transferred to free base by taking it between 2 M NaOH and ethyl acetate. Phases were separated and the organic phase was dried in usual manner. Evaporation off the solvent provided 0.42 g (1.22 mmol; 89% yield) of the title compound 43g.

ESI-MS m/z for C$_{16}$H$_{23}$ClN$_2$O$_2$S found 343.0/345.0 (M+1)$^+$

Step 8

Synthesis of (S)-4-(1-(5-amino-4H-1,2,4-triazol-3-yl)piperidin-4-yl)-3-(4-chlorobenzyl)thiomorpholine 1,1-dioxide (43)

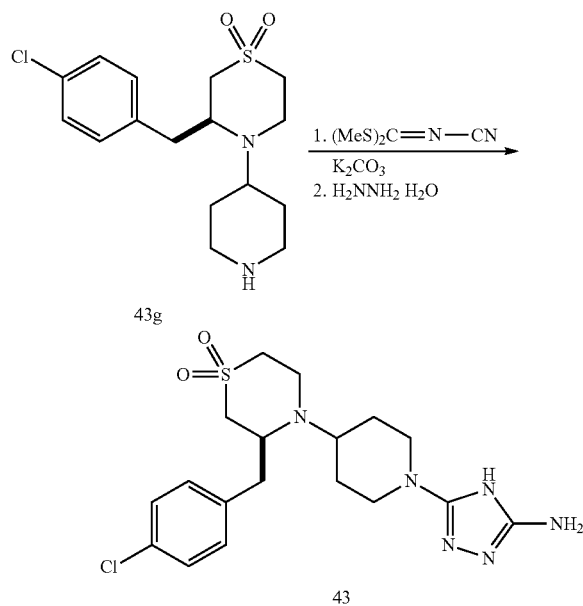

Formation of 1,2,4-triazole ring was accomplished according to the General Procedure VIII starting from compound 43g. 75 mg (0.18 mmol; 15% yield) of the title compound was obtained.

ESI-MS m/z for $C_{18}H_{25}ClN_6O_2S$ found 425.0/427.0 (M+1)$^+$ $^1$H NMR (DMSO-d$_6$, 500 MHz) δ 7.31 (AA'BB', J=8.5 Hz, 2H), 7.24 (AA'BB', J=8.5 Hz, 2H), 5.48 (bs, 2H), 3.71-3.64 (m, 2H), 3.52-3.43 (m, 1H), 3.11-2.96 (m, 3H), 2.94-2.79 (m, 4H), 2.78-2.70 (m, 1H), 2.64-2.52 (m, 2H), 1.65-1.55 (m, 2H), 1.37-1.18 (m, 3H).

Example 44

5-(4-((2R,5S)-5-(4-chlorobenzyl)-2-methylmorpholino)piperidin-1-yl)-4H-1,2,4-triazol-3-amine (44)

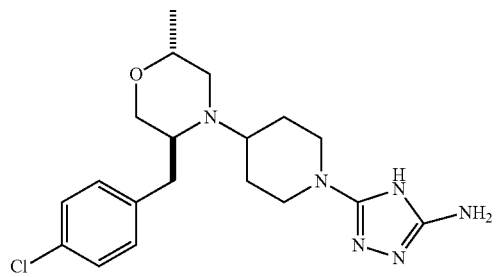

The title compound was prepared in the same manner as Example 4 with the exception that (2S)-2-bromopropionic acid instead of (2R)-2-bromopropionic acid was used in the first synthetic step.

ESI-LCMS m/z for $C_{19}H_{27}ClN_6O$ found 391.1/393.1 (M+1)$^+$ $^1$H NMR (700 MHz, DMSO-d$_6$): δ 7.41 (d, J=8.4 Hz, 2H), 7.35 (d, J=8.4 Hz, 2H), 4.08 (br s, 1H), 3.91-3.84 (m, 2H), 3.83-3.80 (m, 2H), 3.70-3.67 (m, 2H), 3.48 (d, J=12.7 Hz, 2H), 2.87 (t, J=11.6 Hz, 1H), 2.75 (t, J=11.5 Hz, 1H), 2.70 (dd, J=14.5, 7.7 Hz, 1H), 2.65 (t, J=12.0 Hz, 1H), 1.80-1.90 (m, 2H), 1.63 (qd, J=12.3, 4.2 Hz, 1H), 1.11 (d, J=6.2 Hz, 3H).

Example 45

5-(4-((2R,5R)-5-(4-chlorobenzyl)-2-methylmorpholino)piperidin-1-yl)-4H-1,2,4-triazol-3-amine (45)

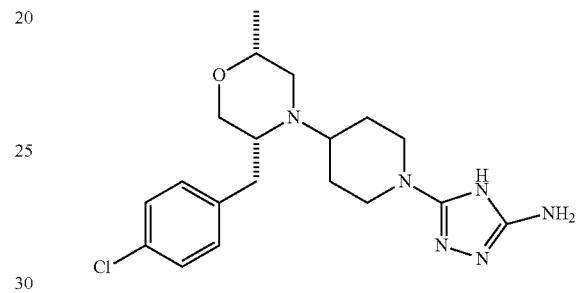

The title compound was prepared in the same manner as Example 4 with the exception that (2R)-2-amino-3-(4-chlorophenyl)propan-1-ol and (2S)-2-bromopropionic acid instead of (2S)-2-amino-3-(4-chlorophenyl)propan-1-ol and (2R)-2-bromopropionic acid were used in the first synthetic step.

ESI-LCMS: m/z for $C_{19}H_{27}ClN_6O$ found: 391.2/392.9 (M+1)$^+$.

$^1$H NMR (DMSO-d$_6$, 700 MHz): δ 7.34 (d, J=8.4 Hz, 2H), 7.21 (d, J=8.4 Hz, 2H), 5.46 (br s, 2H), 4.12 (br s, 1H), 3.74 (br d, J=12.6 Hz, 2H), 3.51-3.47 (m, 1H), 3.43-3.32 (m, 2H), 2.91-2.87 (m, 2H), 2.75-2.68 (m, 4H), 2.60-2.56 (m, 1H), 2.29-2.26 (m, 1H), 1.92-1.88 (m, 2H), 1.38-1.27 (m, 2H), 1.11 (d, J=6.3 Hz, 3H).

Example 46

5-(4-((2S,4S)-2-(4-chlorobenzyl)-4-methoxypyrrolidin-1-yl)piperidin-1-yl)-4H-1,2,4-triazol-3-amine (46)

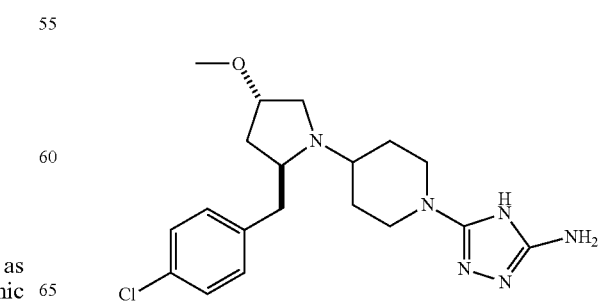

Step 1

Synthesis of (2R,4S)-1-tert-butyl 2-methyl 4-hydroxypyrrolidine-1,2-dicarboxylate (46a)

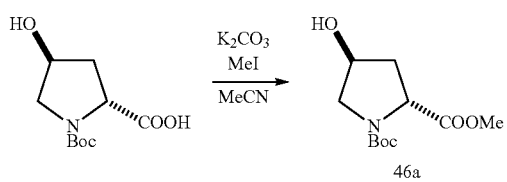 [SMILES: "MeCN" ; CC(C)(C)OC(=O)N1C[C@@H](O)C[C@@H]1C(=O)O ; COC(=O)[C@H]1C[C@H](O)CN1C(=O)OC(C)(C)C]

To a solution of N-Boc-trans-4-hydroxy-D-proline (10.00 g; 43.25 mmol) in MeCN (100 mL), potassium carbonate (11.95 g; 86.50 mmol) was added followed by methyl iodide (5.40 mL, 86.50 mmol) and resulting mixture was stirred overnight. LCMS indicated presence of substrate. Another portion of potassium carbonate (5.98 g; 43.25 mmol) and methyl iodide was added (2.7 mL; 43.25 mmol) and reaction was stirred for 2 days after which time LCMS indicated completion of the reaction. Reaction mixture was filtered and solid residue was washed with EtOAc. After evaporation of organic phase 9.37 g (38.22 mmol; 88% yield) of product was obtained as a yellowish oil.

ESI-MS m/z for $C_{11}H_{19}NO_5$ found 145.9 (M-Boc+1)$^+$, 268.0 (M+Na)$^+$.

Step 2

Synthesis of (2R,4S)-1-tert-butyl 2-methyl 4-((tert-butyldimethylsilyl)oxy)pyrrolidine-1,2-dicarboxylate (46b)

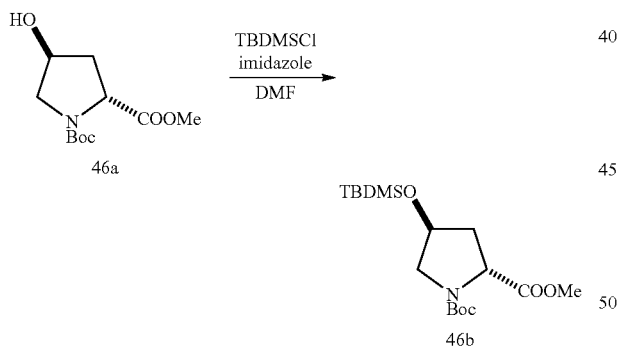

To a solution of 46b (5 g; 20.38 mmol) in DMF (60 mL), imidazole (6.94 g; 101.90 mmol) was added followed by TBDMSCl (4.61 g; 30.57 mmol) and reaction was stirred overnight. After LCMS indicated completion of the reaction, reaction mixture extracted between water and EtOAc. Organic layer was washed with water, brine, dried over anhydrous MgSO$_4$, and concentrated. Crude product was purified by column chromatography (hexane/EtOAc 8:1) to give 6.70 g of 46b as a colorless oil (18.63 mmol; 92% yield).

ESI-MS m/z for $C_{17}H_{33}NO_5Si$ found 260.2 (M-Boc+1)$^+$, 382.1 (M+Na)$^+$.

$^1$H NMR (CDCl$_3$, 700 MHz) δ [4.43-4.40 (m); 4.33 (d, J=7.7 Hz); 2H], [3.74 (s); 3.72 (s); 3H], [3.61 (dd, J=11.2, 4.6 Hz); 3.57 (dd, J=11.0, 4.8 Hz); 1H], [3.40 (dd, J=11.4, 1.3 Hz); 3.37 (dd, J=11.2, 2.4 Hz); 1H], 2.20-2.14 (m, 1H), 2.04-1.98 (m, 1H), [1.46 (s); 1.41 (s); 9H], 087 (s, 9H), 0.06 (s, 6H).

Step 3

Synthesis of (2R,4S)-1-(tert-butoxycarbonyl)-4-((tert-butyldimethylsilyl)oxy)pyrrolidine-2-carboxylic acid (46c)

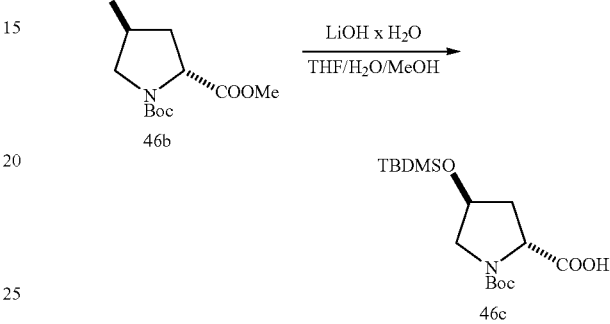

Compound 46b (6.70 g; 18.63 mmol) was dissolved in a mixture of 200 mL THF and 100 mL MeOH. Solution of lithium hydroxide hydrate in 100 mL of water was added to the reaction mixture and resulting mixture was stirred overnight. After LCMS control indicated completion of the reaction, reaction mixture was concentrated. Water residue was acidified to pH 4 with 2 M HCl at 0° C. and product was extracted with EtOAc. Organic layer was washed with brine, dried over anhydrous MgSO$_4$, and evaporated to give 5.13 g of product 46c as a yellowish oil (14.85 mmol; 80% yield).

ESI-MS m/z for $C_{16}H_{31}NO_5Si$ found 246.1 (M-Boc+1)$^+$, 368.1 (M+Na)$^+$, 344.1 (M−1)$^-$.

Step 4

Synthesis of (2R,4S)-tert-butyl 4-((tert-butyldimethylsilyl)oxy)-2-(methoxy(methyl)carbamoyl)pyrrolidine-1-carboxylate (46d)

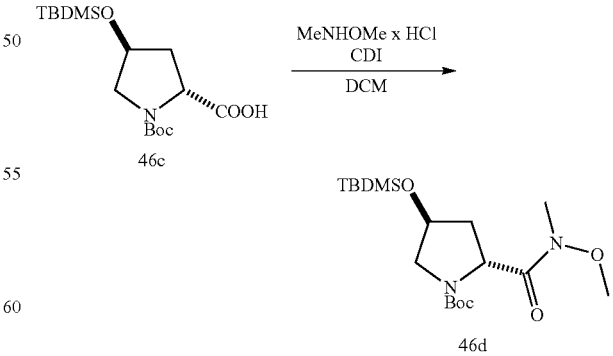

To a solution of compound 46c (10 g; 14.85 mmol) in DCM (40 mL), triethylamine (5.2 mL; 37.12 mmol) was added, followed by carbonyldiimidazole (CDI; 3.61 g; 22.28 mmol), and reaction was stirred for 1 hour. N,O-dimethylhydroxyloamine hydrochloride (2.17 g; 22.28 mmol) was added and reaction was stirred overnight, after which time LCMS control indicated completion of the reaction. Reaction mixture was washed with water and brine. Organic layer was dried over anhydrous MgSO$_4$ and concentrated. Crude product was purified by column chromatography (hexane/EtOAc 5:1) to give 4.15 g of 46d as a colorless oil (10.68 mmol; 72% yield).

ESI-MS m/z for C$_{18}$H$_{36}$N$_2$O$_5$Si found 289.7/290.3 (M-Boc+1)$^+$, 411.1/412.3 (M+Na)$^+$.

$^1$H NMR (CDCl$_3$, 700 MHz) δ [4.82 (brs); 4.73 (t, J=7.0 Hz); 1H], 4.45 (dq, 1H, J=18.0, 4.8 Hz), [3.79 (s); 3.72 (s); 3H], [3.68 (dd, J=11.0, 5.3 Hz); 3.64 (dd, J=11.0, 5.3 Hz); 1H], [3.40 (dd, J=11.0, 3.1 Hz); 3.32 (dd, J=10.8, 3.7 Hz); 1H], 3.20 (s, 3H), 2.18-2.12 (m, 1H), 2.00-1.95 (m, 1H), [1.45 (s); 1.41 (s); 9H], 0.88 (s, 9H), 0.06 (s, 6H).

Step 5

Synthesis of (2R,4S)-tert-butyl 4-((tert-butyldimethylsilyl)oxy)-2-(4-chlorobenzoyl)pyrrolidine-1-carboxylate (46e)

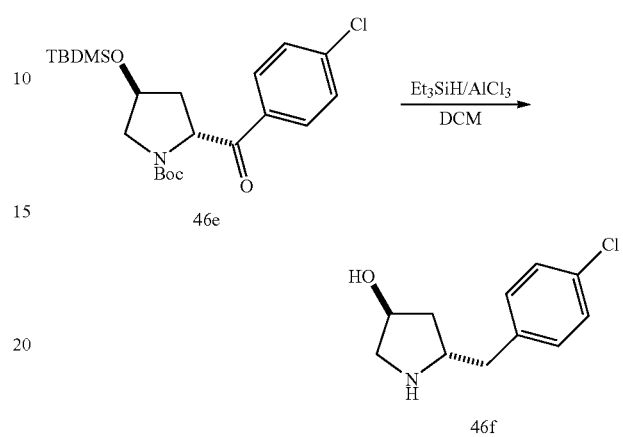

To a solution of compound 46d (1.00 g; 2.57 mmol) in dry Et$_2$O (8 mL), p-chlorophenylmagnesium bromide, previously generated from p-bromochlorobenzene (6.67 g; 34.84 mmol) and magnesium (875 mg; 36.00 mmol) in Et$_2$O (4 mL), was added at −70° C. under argon. Reaction was stirred at −70° C. for 15 minutes and 2 hours at room temperature After which time LCMS control showed completion of the reaction. Reaction was quenched with saturated NH$_4$Cl and product was extracted with EtOAc. Combined organic layers were washed with water, brine and dried over anhydrous MgSO$_4$ and concentrated. Crude product was purified by column chromatography (hexane/EtOAc 10:1) to obtain 970 mg of 46e as a colorless oil (2.20 mmol; 86% yield).

ESI-MS m/z for C$_{22}$H$_{34}$ClNO$_4$Si found 340.0/341.9 (M-Boc+1)$^+$, 462.1 (M+Na)$^+$.

$^1$H NMR (DMSO-d$_6$+D$_2$O, 700 MHz) δ 7.97-7.95 (m, 2H), 7.61-7.59 (m, 2H), 5.27-5.22 (m, 1H), 4.44-4.39 (m, 1H), [3.52 (dd, J=11.4, 4.4 Hz); 3.48 (dd, J=11.4, 4.4 Hz); 1H], [3.34 (m); 3.30 (m); 1H], 2.24-2.19 (m, 1H), [1.92 (ddd, J=12.9, 7.8, 4.8 Hz); 1.85 (ddd, J=13.0, 7.7, 4.8 Hz); 1H], [1.34 (s); 1.11 (s); 9H], 0.83 (s, 9H), [0.04 (s); 0.03 (s); 6H].

Step 6

Synthesis of (3S,5S)-5-(4-chlorobenzyl)pyrrolidin-3-ol (46f)

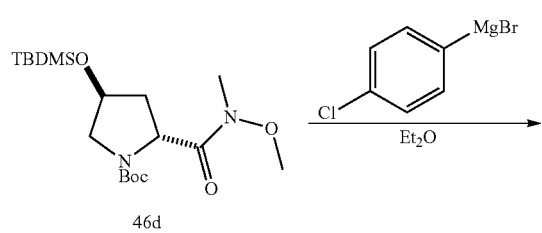

To a solution of compound 46e (970 mg; 2.20 mmol) in DCM (11 mL) AlCl$_3$ (880 mg; 6.60 mmol) was added under argon, followed by triethylsilane (1.05 mL; 6.60 mmol). Reaction was stirred for 45 minutes after which LCMS control indicated completion of the reaction. Reaction was quenched with 4 M NaOH, saturated with sodium chloride, and filtrated through Celite. Product was extracted from water phase with DCM 3 times 20 mL. Combined organic layers were dried over anhydrous MgSO$_4$ and evaporated to give 1.04 g of product 46f (>99% yield) as a yellowish oil.

ESI-MS m/z for C$_{11}$H$_{14}$ClNO found 211.9 (M+1)$^+$.

Step 7

Synthesis of (2S,4S)-tert-butyl 2-(4-chlorobenzyl)-4-hydroxypyrrolidine-1-carboxylate (46g)

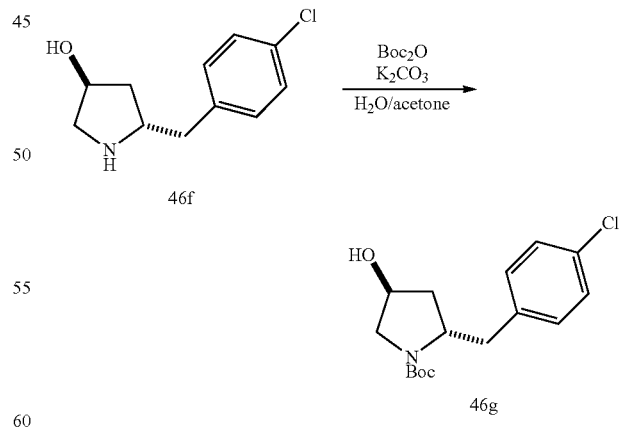

To a solution of compound 46f (840 mg; 3.97 mmol) in acetone (8 mL), water (8 mL) was added and pH was adjusted to 12 with K$_2$CO$_3$ (1.1 g; 7.94 mmol). Boc$_2$O (954 mg; 4.37 mmol) was added in one portion and reaction was stirred overnight after which time LCMS control indicated completion of the reaction. Reaction mixture was concentrated to remove acetone. Water residue was saturated with NaCl and extracted with EtOAc. Organic layer was washed with brine, dried over anhydrous MgSO$_4$ and concentrated. Crude product was purified by column chromatography (hexane/EtOAc 1:1) to give 71 mg of 46g as a colorless oil (0.23 mmol; 6% yield).

ESI-MS m/z for C$_{16}$H$_{22}$ClNO$_3$ found 211.0/213.9 (M-Boc+1)$^+$, 256.0/257.8 (M-$^t$Bu+1)$^+$, 333.9 (M+Na)$^+$.

Step 8

Synthesis of (2S,4S)-tert-butyl 2-(4-chlorobenzyl)-4-methoxypyrrolidine-1-carboxylate (46h)

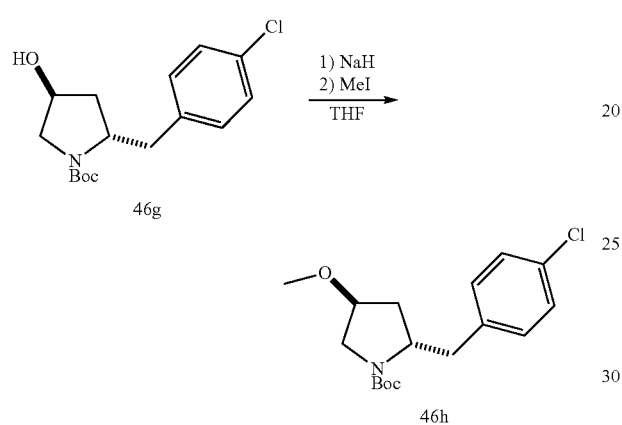

The title compound (46h) was obtained from the compound 46g (71 mg; 0.23 mmol) according to the General Procedure XXI in 99% yield (87 mg, 0.27 mmol, transparent oil).

ESI-MS m/z for C$_{17}$H$_{24}$ClNO$_3$ found 226.0 (M-Boc+1)$^+$, 270.0 (M-$^t$Bu+1)$^+$, 349.9 (M+Na)$^+$.

Step 9

Synthesis of (2S,4S)-2-(4-chlorobenzyl)-4-methoxypyrrolidine hydrochloride (46i)

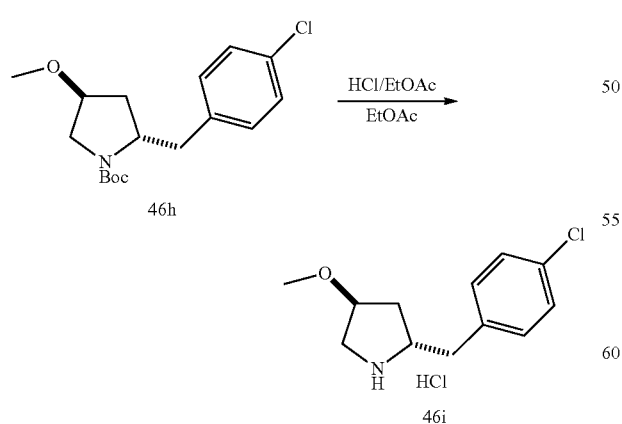

The title compound was prepared from compound 46h (87 mg; 0.27 mmol) according to the General Procedure VII and was obtained as a white solid (70 mg; 99% yield)

ESI-MS m/z for C$_{12}$H$_{16}$ClNO found 226.0/227.9 (M+1)$^+$.

Step 10

Synthesis of tert-butyl 4-((2S,4S)-2-(4-chlorobenzyl)-4-methoxypyrrolidin-1-yl)piperidine-1-carboxylate (46j)

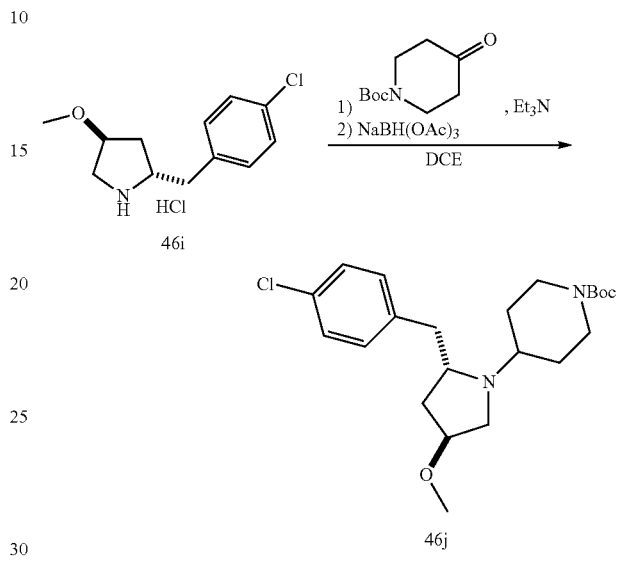

The title compound was prepared from compound 46i (70 mg; 0.27 mmol) according to the General Procedure VI and was obtained as a yellowish oil (129 mg; 99% yield).

ESI-MS m/z for C$_{22}$H$_{33}$ClN$_2$O$_3$ found 409.1 (M+1)$^+$.

Step 11

Synthesis of 4-((2S,4S)-2-(4-chlorobenzyl)-4-methoxypyrrolidin-1-yl)piperidine dihydrochloride (46k)

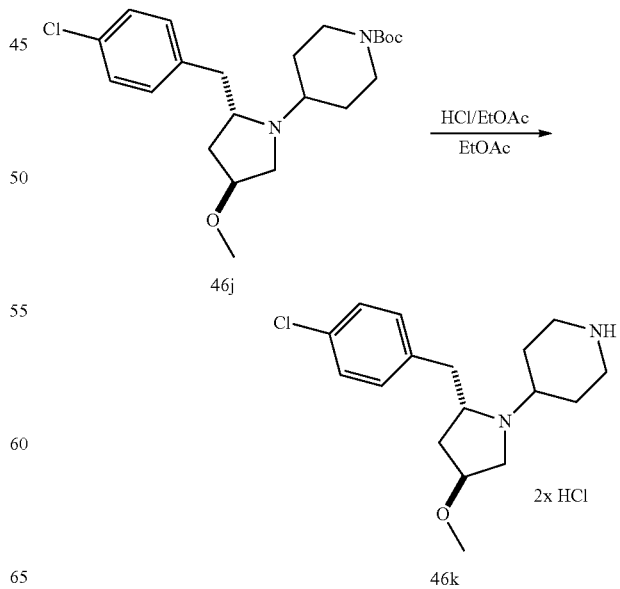

The title compound was prepared from compound 46j (110 mg; 0.27 mmol) according to the General Procedure VII and was obtained as a white solid (103 mg; 99% yield).

ESI-MS m/z for $C_{17}H_{25}ClN_2O$ found 309.2 $(M+1)^+$.

Step 12

Synthesis of 3-(4-((2S,4S)-2-(4-chlorobenzyl)-4-methoxypyrrolidin-1-yl)piperidin-1-yl)-1H-1,2,4-triazol-5-amine (46)

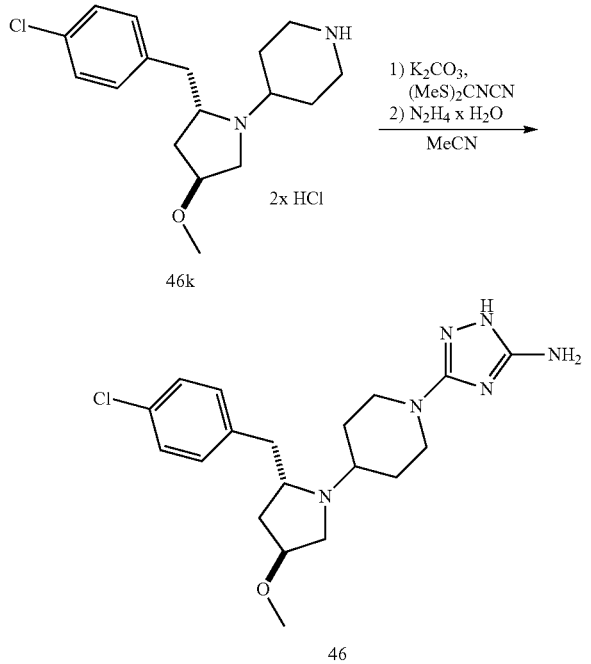

The title compound 46 was prepared from compound 46k (103 mg; 0.27 mmol) according to the General Procedure VIII. Crude product was purified by reversed-phase chromatography to give 46 as a TFA-salt (11 mg; 8% yield).

ESI-MS m/z for $C_{19}H_{27}ClN_6O$ found 391.2 $(M+1)^+$.

$^1$H NMR (DMSO-$d_6$+$D_2O$, 700 MHz) δ 7.40 (d, J=8.5 Hz, 2H), 7.35 (d, J=8.5 Hz, 2H), 4.01 (s, 1H), 3.94-3.80 (m, 3H), 3.56-3.41 (m, 3H), 3.31 (d, J=10.9 Hz, 1H), 3.17 (s, 3H), 2.89-2.77 (m, 3H), 2.02 (brs, 2H), 1.92 (brs, 1H), 1.83-1.76 (m, 1H), 1.65 (dd, J=5.1, 9.7 Hz, 2H).

Example 47

(3S,5S)-1-(1-(5-amino-4H-1,2,4-triazol-3-yl)piperidin-4-yl)-5-(4-chlorobenzyl)pyrrolidin-3-ol (47)

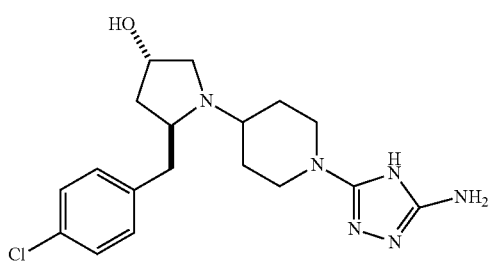

Step 1

Synthesis of (3S,5S)-5-(4-chlorobenzyl)pyrrolidin-3-ol hydrochloride (47a)

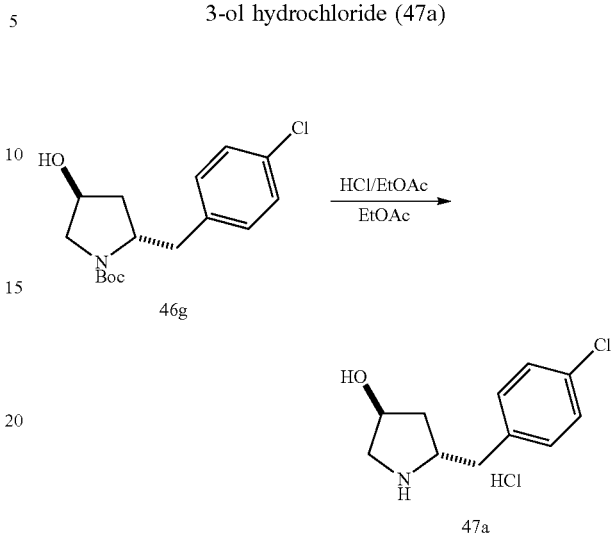

The title compound was synthesized from compound 46g (276 mg; 0.88 mmol) according to the General Procedure VII and was obtained as a white powder (204 mg; 0.82 mmol, 93% yield).

ESI-MS m/z for $C_{16}H_{23}ClN_2$ found 212.0/213.9 $(M+1)^+$.

Step 2

Synthesis of tert-butyl 4-((2S,4S)-2-(4-chlorobenzyl)-4-hydroxypyrrolidin-1-yl)piperidine-1-carboxylate (47b)

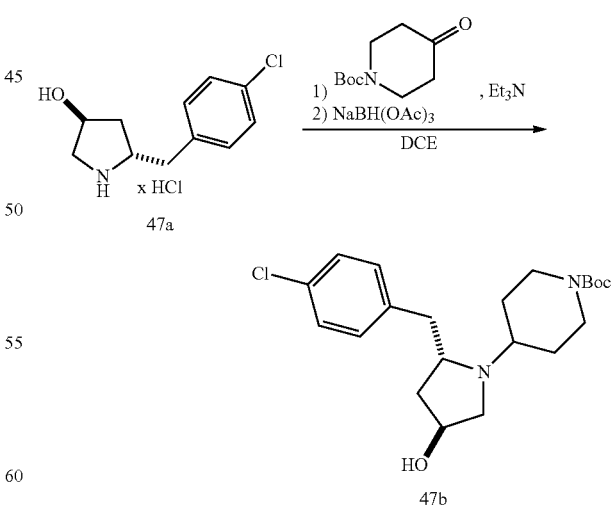

The title compound was prepared from compound 47a (204 mg; 0.82 mmol) according to the General Procedure VI and was obtained as a transparent oil (147 mg; 0.37 mmol; 45% yield).

Step 3

Synthesis of (3S,5S)-5-(4-chlorobenzyl)-1-(piperidin-4-yl)pyrrolidin-3-ol dihydrochloride (47c)

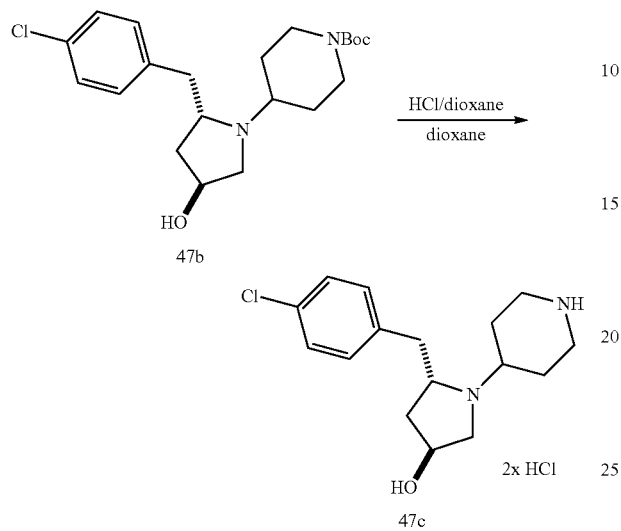

The title compound was prepared from compound 47b (147 mg; 0.37 mmol) according to the General Procedure VII and was obtained as a white powder (135 mg; 99% yield).

ESI-MS m/z for $C_{16}H_{23}ClN_2O$ found 295.1 $(M+1)^+$.

Step 4

Synthesis of (3S,5S)-1-(1-(5-amino-1H-1,2,4-triazol-3-yl)piperidin-4-yl)-5-(4-chlorobenzyl)pyrrolidin-3-ol (47)

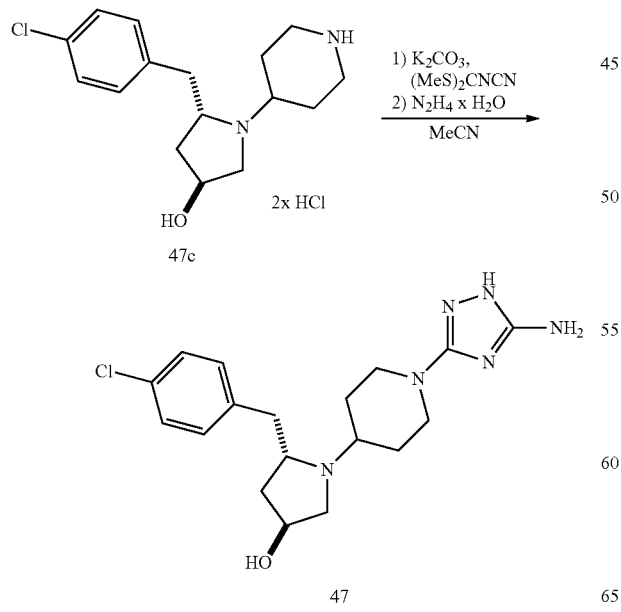

The title compound 47 was synthesized from compound 47c (135 mg; 0.37 mmol) according to the General Procedure VIII. It was purified by reversed-phase chromatography and was obtained as TFA-salt (80 mg, 44% yield).

ESI-MS m/z for $C_{18}H_{25}ClN_6O$ found 377.2 $(M+1)^+$.

Example 48

(5S)-1-(1-(5-amino-4H-1,2,4-triazol-3-yl)piperidin-4-yl)-5-(4-chlorobenzyl)-3-methylpyrrolidin-3-ol (48)

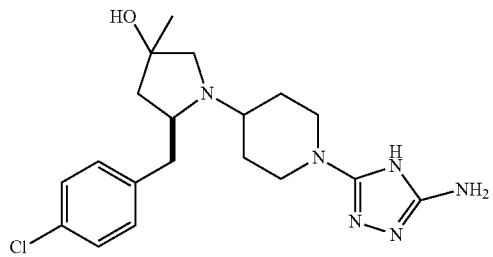

Step 1

Synthesis of (S)-tert-butyl 2-(4-chlorobenzyl)-4-oxopyrrolidine-1-carboxylate (48a)

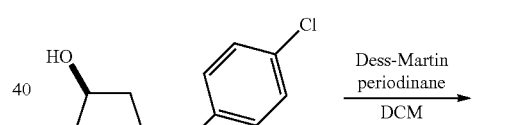

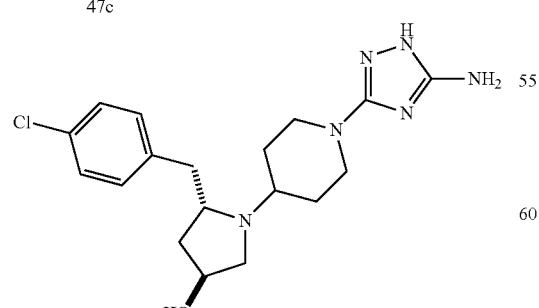

The title compound was prepared from compound 46g (1.00 g; 3.21 mmol) according to the General Procedure XII and was obtained as a white solid (839 mg; 2.71 mmol; 84% yield).

ESI-MS m/z for $C_{16}H_{20}ClNO_3$ found 210.1 $(M-Boc+1)^+$, 254.2 $(M-^tBu+1)^+$.

Step 2

Synthesis of (2S)-tert-butyl 2-(4-chlorobenzyl)-4-hydroxy-4-methylpyrrolidine-1-carboxylate (48b)

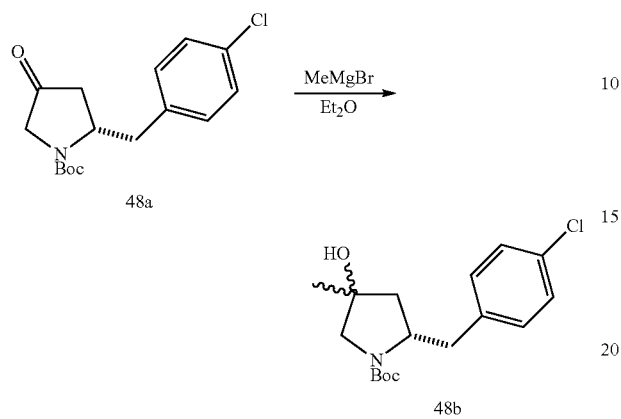

To a solution of compound 48a (400 mg; 1.29 mmol) in dry Et$_2$O (20 mL), methylmagnesium bromide (3.0 M solution in Et$_2$O; 860 μL; 2.58 mmol) was added dropwise at −78° C. under argon. Reaction was stirred for 30 minutes at −78° C. and allowed to warm to room temperature and stirred for 2 days. Reaction was quenched with saturated aqueous solution of NH$_4$Cl, and product was extracted with EtOAc. Organic layer was dried over anhydrous MgSO$_4$ and concentrated. Product was purified by column chromatography (hexane/EtOAc 4:1) and was obtained as a transparent oil (152 mg; 0.47 mmol; 36% yield).

ESI-MS m/z for C$_{17}$H$_{24}$ClNO$_3$ found 270.2 (M-$^t$Bu+1)$^+$.

$^1$H NMR (DMSO-d$_6$+D$_2$O, 700 MHz) δ 7.30 (AA'BB', J=8.4 Hz, 2H), 7.18 (AA'BB', J=8.4 Hz, 2H), 3.87-3.83 (m, 1H), 3.22 (d, J=11.4 Hz, 1H), 3.15 (d, J=11.0 Hz, 1H), 3.07 (dd, J=13.2, 4.0 Hz, 1H), 2.86 (dd, J=12.8, 9.2 Hz, 1H), 1.72 (dd, J=13.2, 8.8 Hz, 1H), 1.67 (dd, J=12.8, 4.0 Hz, 1H), 1.39 (s, 9H), 1.19 (s, 3H).

Step 3

Synthesis of (5S)-5-(4-chlorobenzyl)-3-methylpyrrolidin-3-ol trifluoroacetate (48c)

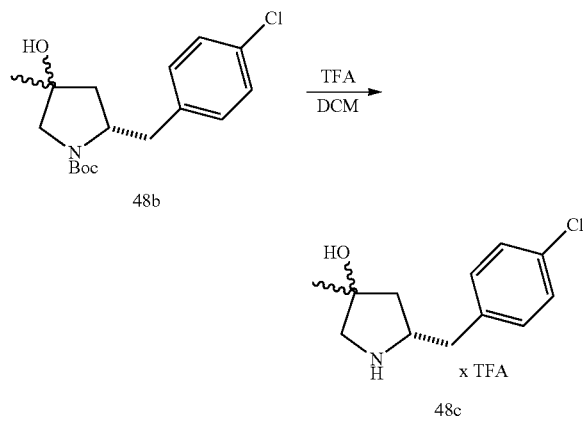

To a solution of compound 48b (150 mg; 0.46 mmol) in DCM (15 mL), TFA (5 mL; 67.09 mmol) was added. Reaction was completed after 1 hour as indicated by LCMS. The mixture was diluted with DCM and evaporated to dryness. Product was obtained as a dark-yellow oil (155 mg; 0.46 mmol; 99% yield).

ESI-MS m/z for C$_{12}$H$_{16}$ClNO found 226.2 (M+1)$^+$.

Step 4

Synthesis of tert-butyl 4-((2S)-2-(4-chlorobenzyl)-4-hydroxy-4-methylpyrrolidin-1-yl)piperidine-1-carboxylate (48d)

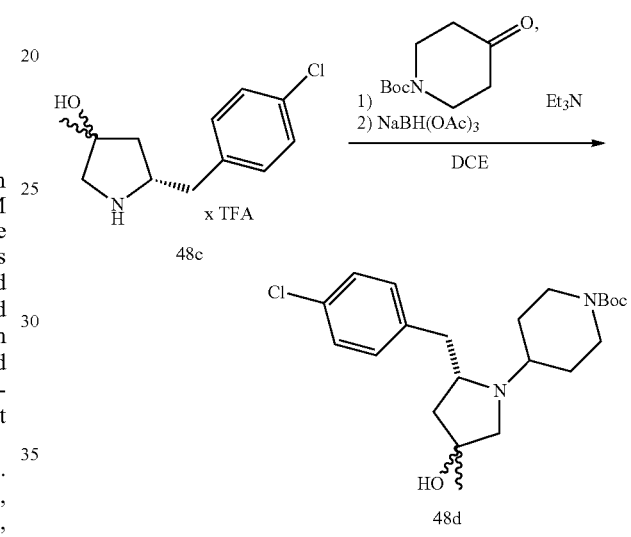

To a solution of compound 48c (156 mg; 0.46 mmol) in DCE (1 mL), Et$_3$N (64 μL; 0.46 mmol) was added followed by 1-Boc-piperid-4-one (102 mg; 0.51 mmol). Reaction mixture was heated to 70° C. and stirred at room temperature for 1 hour. Sodium triacetoxyborohydride (195 mg; 0.92 mmol) was added and reaction was stirred overnight, after which timeLCMS control indicated completion of the reaction. Reaction was quenched with 5% NaHCO$_3$ solution for 30 minutes and layers were separated. Organic layer was washed with 5% NaHCO$_3$ solution, brine, dried over anhydrous MgSO$_4$ and concentrated. Crude product was purified by column chromatography (EtOAc/MeOH 20:1) to obtain 48d as a transparent oil (126 mg; 0.31 mmol; 67% yield).

ESI-MS m/z for C$_{22}$H$_{33}$ClN$_2$O$_3$ found 409.3 (M+1)$^+$.

$^1$H NMR (700 MHz, DMSO-d$_6$+D$_2$O) δ 7.25 (d, J=8.4 Hz, 2H), 7.18 (d, J=8.5 Hz, 2H), 3.93-3.87 (m, 2H), 3.41 (s, 1H), 3.04 (tt, J=9.6, 4.9 Hz, 1H), 2.85 (dd, J=13.2, 4.1 Hz, 1H), 2.74 (d, J=9.1 Hz, 1H), 2.72-2.63 (m, 3H), 2.62-2.57 (m, 1H), 1.72-1.65 (m, 2H), 1.58-1.48 (m, 2H), 1.36 (s, 9H), 1.28 (qd, J=112.3, 4.2 Hz, 1H), 1.20 (qd, J=12.3, 4.3 Hz, 1H), 1.13 (s, 3H).

Step 5

Synthesis of (5 S)-5-(4-chlorobenzyl)-3-methyl-1-(piperidin-4-yl)pyrrolidin-3-ol difluoroacetate (48e)

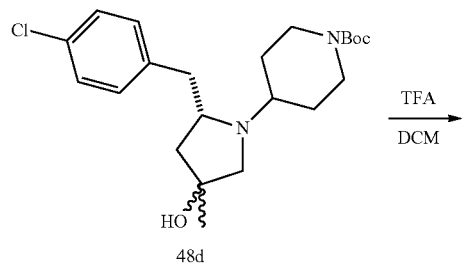

To a solution of compound 48d (150 mg; 0.46 mmol) in DCM (1.2 mL), TFA (231 µL; 3.10 mmol) was added and the mixture was stirred at room temperature. After 1 hour LCMS indicated completion of the reaction. The mixture was diluted with DCM and evaporated to dryness to afford a title product as a yellow oil (166 mg; 99% yield).

ESI-MS m/z for $C_{17}H_{25}ClN_2O$ found 309.3 (M+1)$^+$.

Step 6

Synthesis of (5S)-1-(1-(5-amino-4H-1,2,4-triazol-3-yl)piperidin-4-yl)-5-(4-chlorobenzyl)-3-methylpyrrolidin-3-ol (48)

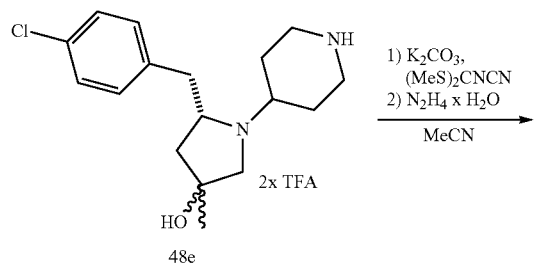

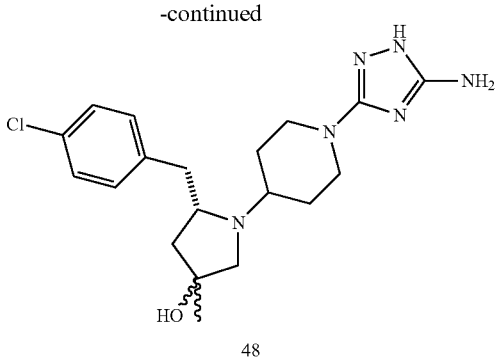

The title compound 48 was synthesized from compound 48e (166 mg; 0.31 mmol) according to the General Procedure VIII. It was purified by reversed-phase chromatography and was obtained as TFA-salt (69 mg, 0.14 mmol, 44% yield).

ESI-MS m/z for $C_{19}H_{27}ClN_6O$ found 391.3 (M+1)$^+$.

$^1$H NMR (DMSO-$d_6$+D$_2$O, 700 MHz) δ 7.39 (AA'BB', J=8.4 Hz, 2H), 7.31 (AA'BB', J=8.4 Hz, 2H), 4.05-4.01 (m, 1H), 3.85-3.80 (m, 2H), 3.48-3.43 (m, 1H), 3.36 (dd, J=11.4, 1.8 Hz, 2H), 3.16 (dd, J=12.8, 3.5 Hz, 1H), 3.11-3.05 (m, 2H), 2.85 (dq, J=11.4, 1.8 Hz, 2H), 2.26-2.24 (m, 1H), 2.02-2.00 (m, 1H), 1.94 (dd, J=13.2, 10.1 Hz, 1H), 1.82-1.66 (m, 3H), 1.29 (s, 3H).

Example 49

5-(4-((3S,8aS)-3-(4-chlorobenzyl)hexahydropyrrolo[1,2-a]pyrazin-2(1H)-yl)piperidin-1-yl)-4H-1,2,4-triazol-3-amine (49)

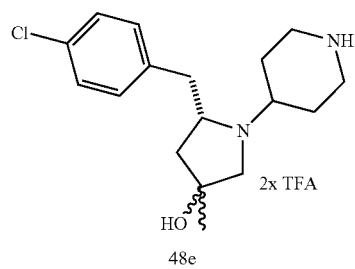

Step 1

Synthesis of (S)-tert-butyl 2-(((S)-3-(4-chlorophenyl)-1-methoxy-1-oxopropan-2-yl)carbamoyl)pyrrolidine-1-carboxylate (49a)

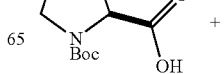

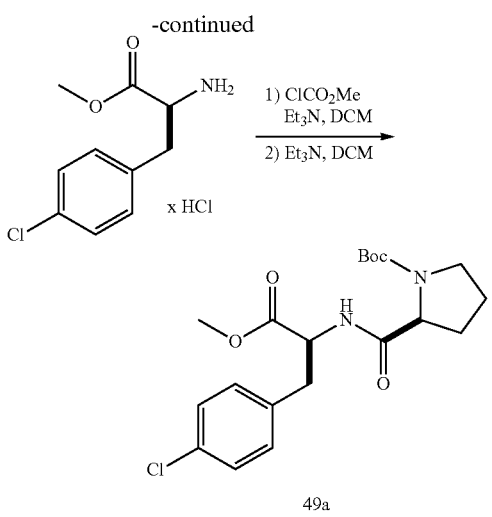

49a

The title compound 49a was synthesized from N-Boc-L-proline (1.5 g; 6.968 mmol) and 4-chloro-L-phenylalanine methyl ester hydrochloride (1.92 g; 7.665 mmol) according to the General Procedure IX with the exception that Et₃N (2.5 equiv.) was used instead of N-methylmorpholine. Product 49a was obtained as a colourless oil (1.42 g; 3.46 mmol; 49% yield) and used in the next step without additional purification.

ESI-LCMS m/z for $C_{20}H_{27}ClN_2O_5$ found 311.0 (M-Boc+1)⁺, 433.0 (M+Na)⁺.

Steps 2-4

Synthesis of tert-butyl 4-((3S,8aS)-3-(4-chlorobenzyl)hexahydropyrrolo[1,2-a]pyrazin-2(1H)-yl)piperidine-1-carboxylate (49b)

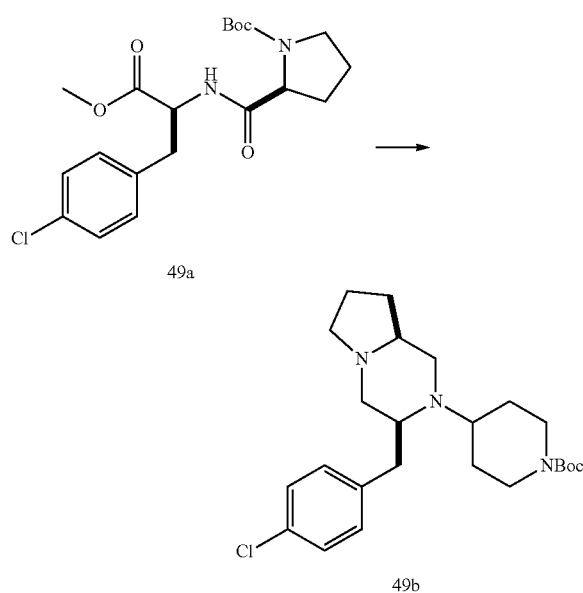

Compound 49b was prepared from compound 49a (1.42 g; 3.46 mmol) in the sequence of the reactions according to the General Procedure X (Boc-deprotection followed by cyclization to diketopiperazine), the General Procedure V (reduction of amide groups) and the General Procedure VI (reductive amination with Boc-piperid-4-one) and was obtained as a colourless oil (720 mg; 1.66 mmol; 48% yield).

ESI-LCMS m/z for $C_{24}H_{36}ClN_3O_2$ found 434.3/436.3 (M+1)⁺.

¹H NMR (CDCl₃, 400 MHz) δ: 7.24 (AA'BB', J=8.4 Hz, 2H), 7.11 (AA'BB', J=8.4 Hz, 2H), 4.07 (bs, 2H), 3.17-3.09 (m, 1H), 3.04 (dd, J=12.5, 10.1 Hz, 1H), 2.99 (dd, J=11.6, 3.0 Hz, 1H), 2.93 (td, J=8.5, 1.7 Hz, 1H), 2.84-2.65 (m, 5H), 2.45 (dd, J=11.5, 9.7 Hz, 1H), 2.22-2.09 (m, 3H), 1.91-1.65 (m, 5H), 1.56-1.33 (m, 3H), 1.45 (s, 9H).

Step 5

Synthesis of (3S,8aS)-3-(4-chlorobenzyl)-2-(piperidin-4-yl)octahydropyrrolo[1,2-a]pyrazine (49c)

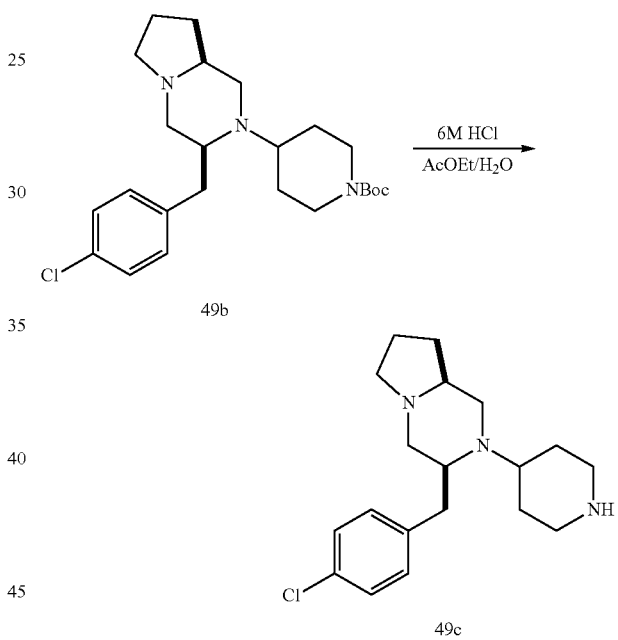

To the solution of compound 49b (698 mg; 1.61 mmol) in AcOEt (6 mL) HCl in AcOEt 2.67 M solution (6 mL; 16.08 mmol) was added and the mixture was stirred at room temperature for 2 hours. Due to poor conversion of the substrate as indicated by TLC (DCM/MeOH 10:1) 6 N aqueous HCl solution (5 mL) was added and the mixture was stirred for 10 minutes. Phases were separated and the organic one was washed with 6 M HCl (5 mL). Combined aqueous phases were alkalized with 4 M NaOH until pH ~14 and the product was extracted with AcOEt (4×20 mL). Combined organic solutions were dried over anhydrous MgSO₄ and concentrated. The crude product (654 mg; 1.607 mmol) was used in the next step without additional purification.

Step 6

Synthesis of 5-(4-((3S,8aS)-3-(4-chlorobenzyl)hexahydropyrrolo[1,2-a]pyrazin-2(1H)-yl)piperidin-1-yl)-4H-1,2,4-triazol-3-amine (49)

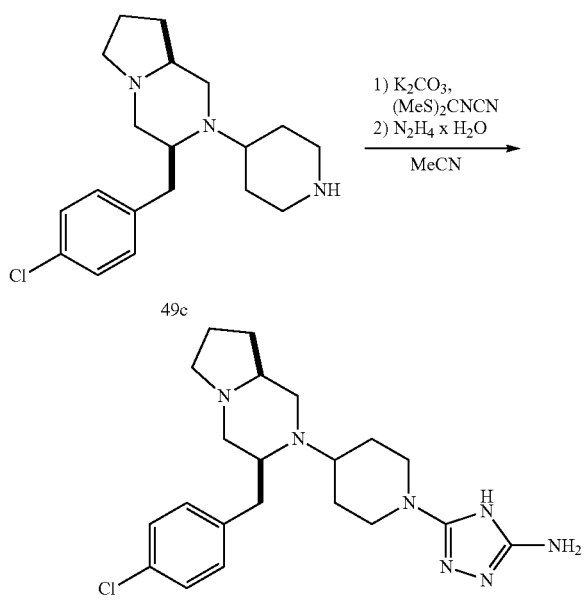

The title compound 49 was prepared from compound 49c (654 mg; 1.607 mmol) according to the General Procedure VIII and was obtained as a white solid (259 mg; 0.622 mmol; 38% yield).

ESI-LCMS m/z for $C_{21}H_{30}ClN_7$ found 208.7 $(M+2)^{2+}$, 416.2 $(M+1)^+$.

$^1$H NMR (MeOH-d$_4$, 400 MHz) δ: 7.27 (AA'BB', J=8.5 Hz, 2H), 7.21 (AA'BB', J=8.4 Hz, 2H), 3.83 (d, J=13.1 Hz, 2H), 3.23-3.14 (m, 1H), 3.08 (dd, J=11.5, 3.0 Hz, 1H), 3.04 (dd, J=12.9, 10.1 Hz, 1H), 2.94 (td, J=8.6, 2.0 Hz, 1H), 2.89-2.73 (m, 3H), 2.82 (dd, J=12.8, 4.0 Hz, 1H), 2.77 (dd, J=11.1, 2.3 Hz, 1H), 2.45 (dd, J=11.4, 10.2 Hz, 1H), 2.10-1.93 (m, 5H), 1.90-1.66 (m, 3H), 1.58-1.40 (m, 3H).

Example 50

(3R,5S)-1-(1-(5-amino-1H-1,2,4-triazol-3-yl)piperidin-4-yl)-5-(4-chlorobenzyl)pyrrolidin-3-ol (50)

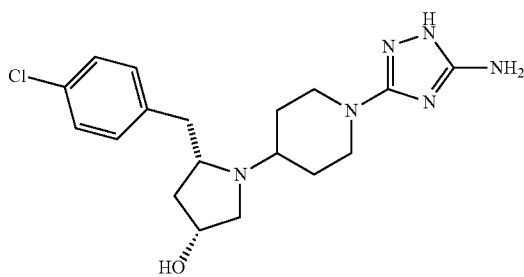

Step 1

Synthesis of (2R,4R)-1-tert-butyl 2-methyl 4-hydroxypyrrolidine-1,2-dicarboxylate (50a)

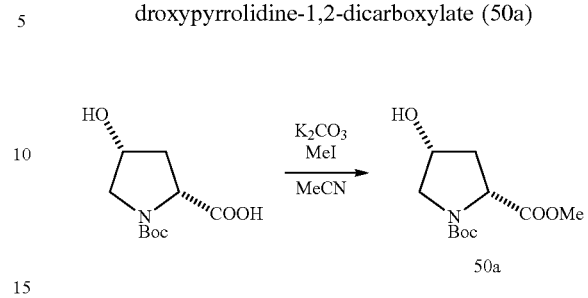

To a solution of N-Boc-cis-4-hydroxy-D-proline (15.00 g, 64.88 mmol) in 325 mL of MeCN, K$_2$CO$_3$ (17.93 g, 129.76 mmol) was added, followed by MeI (8.1 mL, 129.76 mmol) and reaction was stirred overnight after which time LCMS control indicated presence of substrate. Another portion of MeI (4.0 mL, 64.88 mmol) was added and reaction was refluxed overnight. When another LCMS control indicated completion of the reaction the mixture was filtered, and solid residue was washed with EtOAc. After evaporation of solvent 16.06 g (99% yield) of product 50a was obtained as a yellowish oil.

ESI-MS m/z for $C_{11}H_{19}NO_5$ found 146.2 (M-Boc+1)+, 268.2 (M+Na)+.

Step 2

Synthesis of (2R,4R)-1-tert-butyl 2-methyl 4-(tert-butoxy)pyrrolidine-1,2-dicarboxylate (50b)

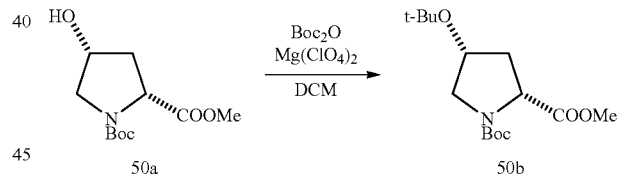

To a solution of compound 50a (16.06 g; 65.48 mmol) in DMF (100 mL), Mg(ClO$_4$)$_2$ (1.46 g; 6.55 mmol) was added, followed by Boc$_2$O (32.87 g; 150.60 mmol) and reaction was stirred overnight. Next day another portion of Mg(ClO$_4$)$_2$ and Boc$_2$O (44.30 g; 203.03 mmol) and reaction was stirred overnight after which time LCMS control indicated completion of the reaction. Reaction mixture was filtrated and evaporated to dryness. Product was purified by column chromatography (hexane/EtOAc 9/1) and was obtained as a white crystalline solid (13.51 g; 68% yield).

ESI-MS m/z for $C_{15}H_{27}NO_5$ found 302, 4.2 (M+1)+, 324.3 (M+Na)+.

$^1$H NMR (DMSO-d$_6$+D$_2$O, 700 MHz) δ: 4.24-4.19 (m, 1H), 4.17-4.13 (m, 1H), [3.61 (s); 3.58 (s); 3H], 3.54-3.51 (m, 1H), 2.99-2.94 (m, 1H), 2.38-2.30 (m, 1H), 1.75-1.71 (m, 1H), [1.36 (s); 1.29 (s); 9H], [1.08 (s); 1.07 (s); 9H].

Step 3

Synthesis of (2R,4R)-4-(tert-butoxy)-1-(tert-butoxycarbonyl)pyrrolidine-2-carboxylic acid (50c)

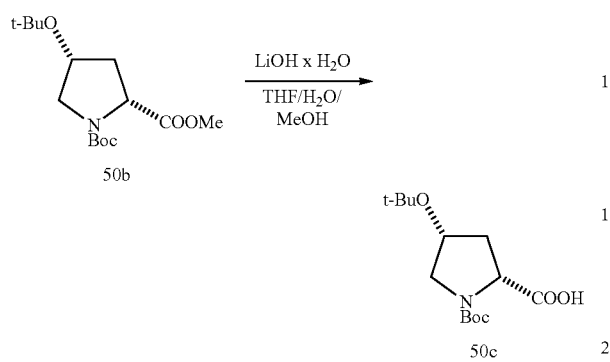

Compound 50b (13.51 g; 44.83 mmol) was dissolved in a mixture THF/MeOH (450 mL/220 mL). Then, the solution of lithium hydroxide hydrate (9.97 g; 237.60 mmol) in water (220 mL) was added and the mixture was stirred overnight- after which time LCMS control indicated completion of the reaction. Reaction mixture was concentrated to remove THF and MeOH, and aqueous residue was acidified to pH 4 with 2 M HCl at 0° C. Product was extracted with EtOAc. and organic layer was washed with brine, dried over anhydrous $MgSO_4$. After evaporation of solvent 12.13 g (94% yield) of product 50c was obtained as a white solid oil.

ESI-MS m/z for $C_{14}H_{25}NO_5$ found 310.3 (M+Na)+, 286.0 (M−1)−.

Step 4

Synthesis of (2R,4R)-tert-butyl 4-(tert-butoxy)-2-(methoxy(methyl)carbamoyl)pyrrolidine-1-carboxylate (50d)

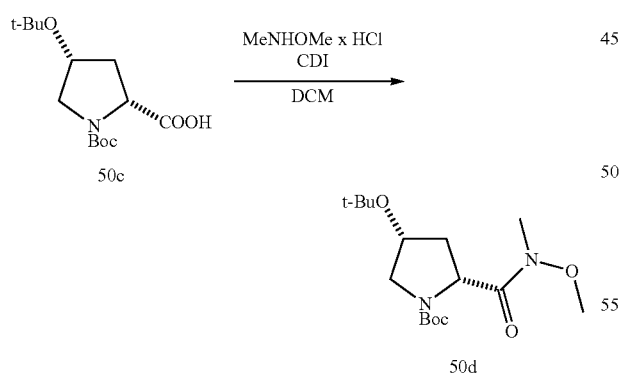

To a solution of compound 50c (12.13 g; 42.21 mmol) in DCM (100 mL), $Et_3N$ (14.7 mL; 105.52 mmol) was added followed by CDI (10.27 g; 63.32 mmol), and reaction was stirred for 30 minutes. N,O-dimethylhydroxyloamine hydrochloride (6.18 g; 63.32 mmol) was added and the reaction was stirred overnight, after which time LCMS control indicated completion of the reaction. Reaction mixture was washed with water and brine, organic layer was dried over anhydrous $MgSO_4$ and concentrated. Crude product was purified by column chromatography (hexane/EtOAc 5/1) to obtain 50d as a white crystalline solid (9.34 g; 67% yield).

ESI-MS m/z for $C_{16}H_{30}N_2O_5$ found 331.4 (M+1)+.

$^1$H NMR (DMSO-$d_6$+$D_2O$, 700 MHz) δ: 4.49 (t, J=8.4 Hz, 1H), 4.20 (q, J=7.7 Hz, 1H), 3.66-3.63 (m, 4H), 3.09 (s, 3H), 2.91 (brs, 1H), 2.47 (dt, J=2.3, 7.9 Hz, 1H), 1.54-1.50 (m, 1H), 1.31 (brs, 9H), 1.11 (s, 9H).

Step 5

Synthesis of (2R,4R)-tert-butyl 4-(tert-butoxy)-2-(4-chlorobenzoyl)pyrrolidine-1-carboxylate (50e)

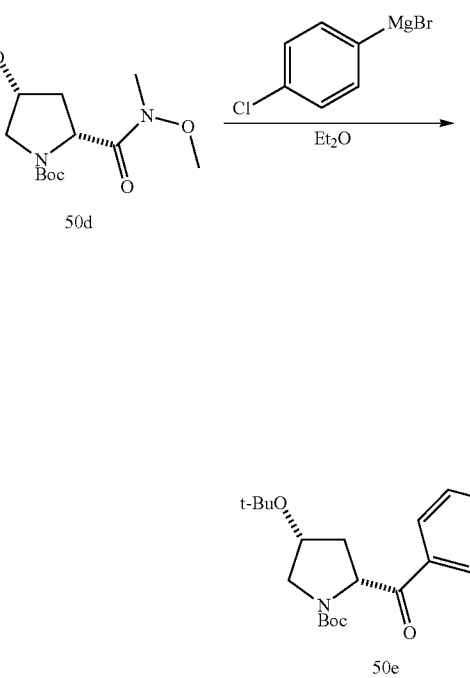

To a solution of 50d (4.50 g; 13.62 mmol) in dry $Et_2O$ (30 mL), p-chlorophenylmagnesium bromide, previously generated from p-bromochlorobenzene (5.22 g; 27.24 mmol) and magnesium (695 mg; 28.60 mmol) in $Et_2O$ (25 mL), was added at −70° C. under argon. Reaction was stirred at −70° C. for 30 minutes. and 2 hours at room temperature After which time LCMS control showed completion of the reaction. The reaction was quenched with saturated $NH_4Cl$ and product was extracted with EtOAc. Combined organic layers were washed with water, brine, dried over anhydrous $MgSO_4$ and concentrated. Crude product was purified by column chromatography (hexane/EtOAc 9/1) to obtain 50e as white crystals (2.11 g; 40% yield).

ESI-MS m/z for $C_{20}H_{28}ClNO_4$ found 326.3 (M-$^t$Bu+1)+.

$^1$H NMR (DMSO-$d_6$+$D_2O$, 700 MHz) δ: 7.94 (AA'BB', J=8.8 Hz, 2H), 7.58 (AA'BB', J=8.4 Hz, 2H), 5.14-5.11 (m, 1H), 4.30-4.26 (m, 1H), 3.65 (dt, J=7.0, 10.6 Hz, 1H), 3.03-2.99 (m, 1H), 2.60-2.54 (m, 1H), 1.58-1.51 (m, 1H), [1.35 (s); 1.12 (s); 9H], [1.05 (s); 1.02 (s); 9H].

Step 6

Synthesis of (2S,4R)-tert-butyl 2-(4-chlorobenzyl)-4-hydroxypyrrolidine-1-carboxylate (50f)

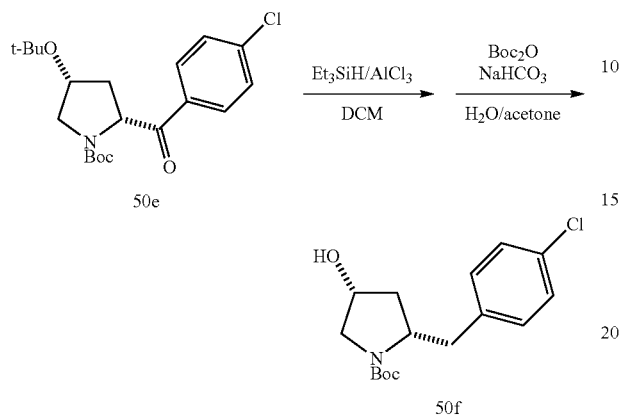

To a solution of compound 50e (2.11 g; 5.52 mmol) in DCM (30 mL), AlCl₃ (2.95 g; 22.08 mmol) was added under argon, followed by triethylsilane (3.5 mL; 22.08 mmol). Reaction was stirred for 30 minutes. LCMS indicated completion of the reaction. Reaction was quenched with ice and layers were separated. Organic layer was extracted with 2 M HCl. Combined aqueous layers were washed with hexane. pH of water residue was adjusted to 8 with KHCO₃ and Boc₂O (1.44 g; 6.62 mmol) in acetone (100 mL) was added. Reaction was stirred overnight after which time LCMS indicated completion of the reaction. Reaction mixture was concentrated and saturated with NaCl. Product was extracted with EtOAc. Combined organic layers were washed with brine and dried over anhydrous MgSO₄. Product was purified by column chromatography (hexane/EtOAc 4:1) and was obtained as a white crystalline solid (928 mg; 54% yield).

ESI-MS m/z for $C_{16}H_{22}ClNO_3$ found 256.2 (M-$^t$Bu+1)+.

¹H NMR (DMSO-d₆+D₂O, 700 MHz) δ: 7.30 (AA'BB', J=8.6 Hz, 2H), 7.18 (AA'BB', J=8.2 Hz, 2H), 4.21-4.18 (m, 1H), 3.87-3.83 (m, 1H), 3.50 (dd, J=5.6, 11.6 Hz, 1H), 3.10-3.05 (m, 2H), 2.81 (dd, J=9.5, 12.9 Hz, 1H), 1.88 (ddd, J=5.6, 8.1, 13.4 Hz, 1H), 1.59 (d, J=12.9 Hz, 1H), 1.39 (s, 9H).

Step 7

Synthesis of (3R,5S)-5-(4-chlorobenzyl)pyrrolidin-3-ol hydrochloride (50g)

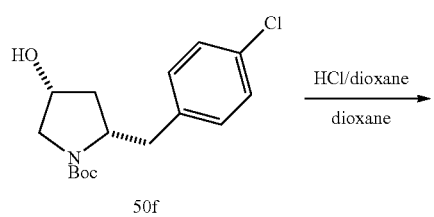

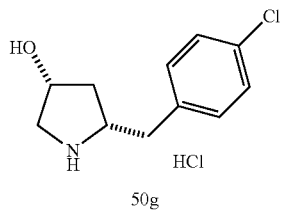

The title compound 50g was synthesized from compound 50f (250 mg; 0.80 mmol) according to the General Procedure VII and was obtained as a white solid (195 mg; 98% yield).

ESI-MS m/z for $C_{11}H_{14}ClNO$ found 212.2 (M+1)+.

Step 8

Synthesis of tert-butyl 4-((2S,4R)-2-(4-chlorobenzyl)-4-hydroxypyrrolidin-1-yl)piperidine-1-carboxylate (50h)

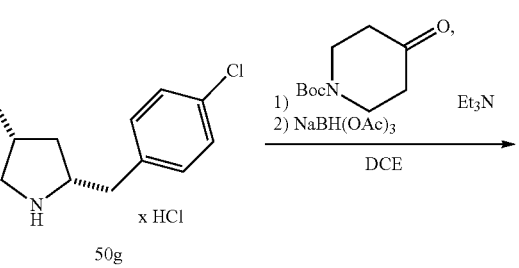

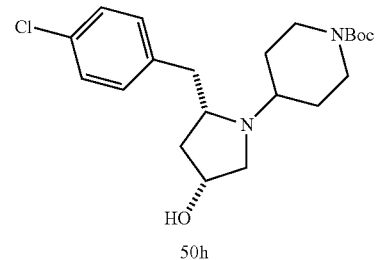

The title compound 50h was prepared from compound 50g (195 mg; 0.78 mmol) according to the General Procedure VI and was obtained as transparent oil (212 mg; 68% yield).

ESI-MS m/z for $C_{21}H_{31}ClN_2O_3$ found 295.4 (M-Boc+1)+, 395.4 (M+1)+.

¹H NMR (DMSO-d₆+D₂O, 700 MHz) δ: 7.27 (AA'BB', J=2.6, 8.6 Hz, 2H), 7.19 (AA'BB', J=2.6, 8.2 Hz, 2H), 4.08-4.05 (m, 1H), 3.92-3.90 (m, 2H), 3.03-2.99 (m, 1H), 2.85 (dd, J=4.7, 13.3 Hz, 1H), 2.76 (dd, J=6.2, 10.1 Hz, 1H), 2.71-2.62 (m, 4H), 2.57 (dd, J=9.0, 12.9 Hz, 1H), 1.81 (dt, J=7.1, 12.9 Hz, 1H), 1.70-1.65 (m, 2H), 1.37 (s, 9H), 1.36-1.34 (m, 1H), 1.29-1.18 (m, 3H).

245

Step 9

Synthesis of (3R,5S)-5-(4-chlorobenzyl)-1-(piperidin-4-yl)pyrrolidin-3-ol dihydrochloride (50i)

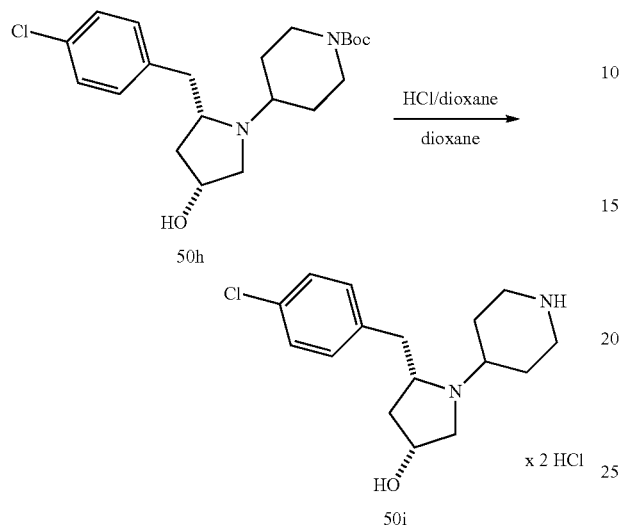

The title compound 50i was prepared from compound 50h (212 mg; 0.54 mmol) according to the General Procedure VII and was obtained as a white solid (193 mg; 98% yield).
ESI-MS m/z for $C_{16}H_{23}ClN_2O$ found 295.4 (M+1)+.

Step 10

Synthesis of (3R,5S)-1-(1-(5-amino-1H-1,2,4-triazol-3-yl)piperidin-4-yl)-5-(4-chlorobenzyl)pyrrolidin-3-ol (50)

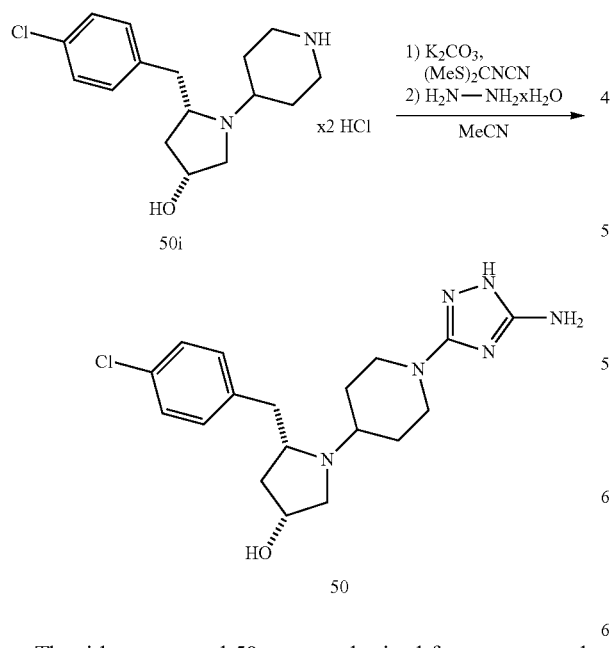

The title compound 50 was synthesized from compound 50i (193 mg; 0.52 mmol) according to the General Proce-

246 dure VIII. It was purified by reversed-phase chromatography and was obtained as a TFA-salt (105 mg; 33% yield).
ESI-MS m/z for $C_{18}H_{25}ClN_6O$ found 377.4 (M+1)+.
$^1$H NMR (DMSO-$d_6$+$D_2O$, 700 MHz) δ: 7.38 (AA'BB', J=2.6, 8.2 Hz, 2H), 7.31 (AA'BB', J=8.6 Hz, 2H), 4.37 (brs, 1H), 3.99-3.96 (m, 1H), 3.84-3.80 (m, 3H), 3.47 (t, J=11.6 Hz, 2H), 3.38 (d, J=11.6 Hz, 1H), 3.21 (m, 1H), 2.99 (t, J=12.5 Hz, 1H), 2.92-2.85 (m, 2H), 2.22 (d, J=11.6 Hz, 1H), 2.07-2.01 (m, 2H), 1.78 (dq, J=4.3, 12.0 Hz, 1H), 1.72-1.66 (m, 2H).

Example 51

3-(4-((2S,4R)-2-(4-chlorobenzyl)-4-methoxypyrrolidin-1-yl)piperidin-1-yl)-1H-1,2,4-triazol-5-amine (51)

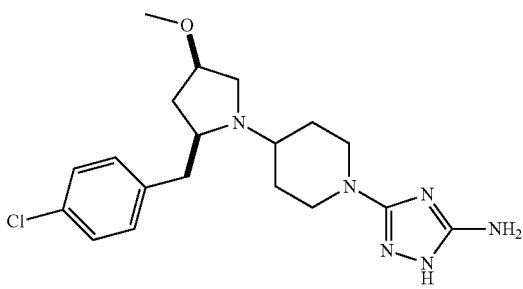

The title compound 51 was synthesized in the same manner as Example 46 with the exception that compound 50f instead of 46g was used in the first synthetic step.
ESI-MS m/z for $C_{19}H_{27}ClN_6O$ found 391.4 (M+1)+
$^1$H NMR (DMSO-$d_6$+$D_2O$, 700 MHz) δ: 7.37 (AA'BB', J=2.6, 8.2 Hz, 2H), 7.29 (AA'BB', J=2.6, 8.6 Hz, 2H), 4.07-4.06 (m, 1H), 4.03-3.98 (m, 1H), 3.89-3.85 (m, 2H), 3.57 (d, J=12.5 Hz, 1H), 3.50 (tt, J=3.0, 12.0 Hz, 2H), 3.28 (s, 3H), 3.22 (dd, J=4.5, 13.6 Hz, 1H), 2.92-2.82 (m, 3H), 2.17-2.11 (m, 2H), 2.30-2.00 (m, 1H), 1.83-1.67 (m, 3H).

Example 52

(S)-5-(4-(3-(4-chlorobenzyl)-2,2-dimethylmorpholino)piperidin-1-yl)-4H-1,2,4-triazol-3-amine (52)

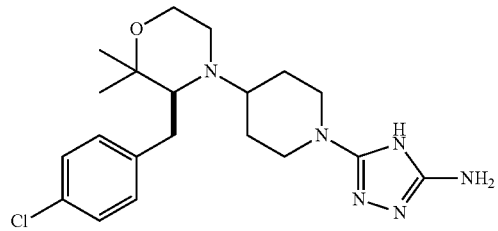

Step 1

Synthesis of (S)-3-amino-4-(4-chlorophenyl)-2-methylbutan-2-ol (52a)

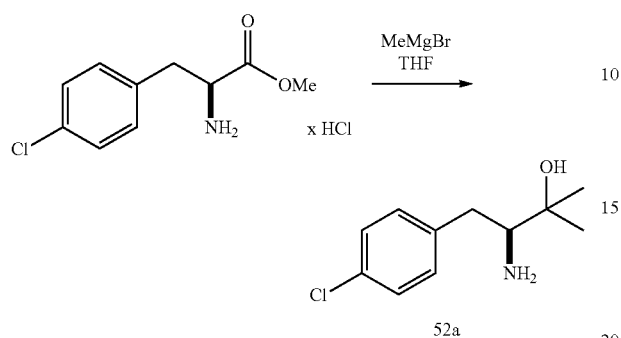

Reaction was carried out under argon atmosphere. To the solution of 4-chloro-L-phenylalanine methyl ester hydrochloride (1 g; 4.69 mmol) in dry THF (13 mL), methylmagnesium bromide 3.0 M solution in Et$_2$O (11.6 mL; 32.9 mmol) was added dropwise at room temperature and stirred overnight. Reaction was quenched with saturated NH$_4$Cl solution, and product was extracted with AcOEt. Organic layer was dried over anhydrous Na$_2$SO$_4$ and concentrated to obtain the product 52a (0.82 g; 82% yield) that was used in the next step without further purification.

ESI-MS m/z for C$_{11}$H$_{16}$ClNO found 214.2 [M+H]$^+$; 196.2 [M+H−H$_2$O]$^+$.

Step 2-5

Synthesis of (S)-tert-butyl 4-(3-(4-chlorobenzyl)-2,2-dimethylmorpholino)piperidine-1-carboxylate (52b)

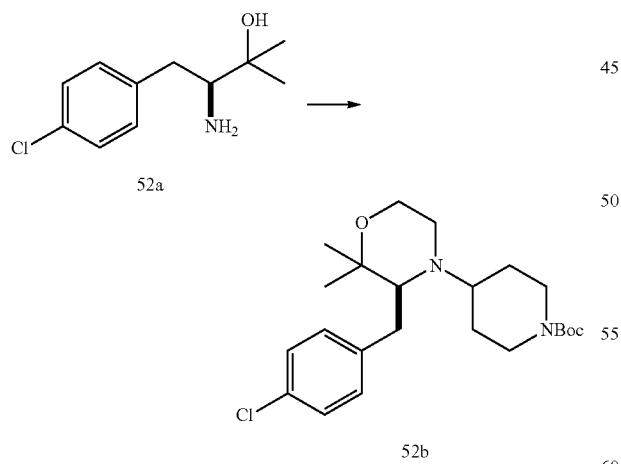

Compound 52b was prepared from compound 52a (0.82 g; 3.85 mmol) in the sequence of the reactions according to the General Procedure II (selective acylation of aminoalcohol with chloroacetyl chloride), the General Procedure IV (cyclization of α-haloamide to morpholin-3-one), the General Procedure V (reduction of morpholin-3-one to morpholine) and the General Procedure VI (Reductive amination with 1-Boc-piperid-4-one) and was obtained as a waxy solid (0.471 g; 29% yield over four steps).

ESI-MS m/z for C$_{23}$H$_{35}$ClN$_2$O$_3$ found 423.3 [M+1]$^+$.

Step 6-7

Synthesis of (S)-5-(4-(3-(4-chlorobenzyl)-2,2-dimethylmorpholino)piperidin-1-yl)-4H-1,2,4-triazol-3-amine (52)

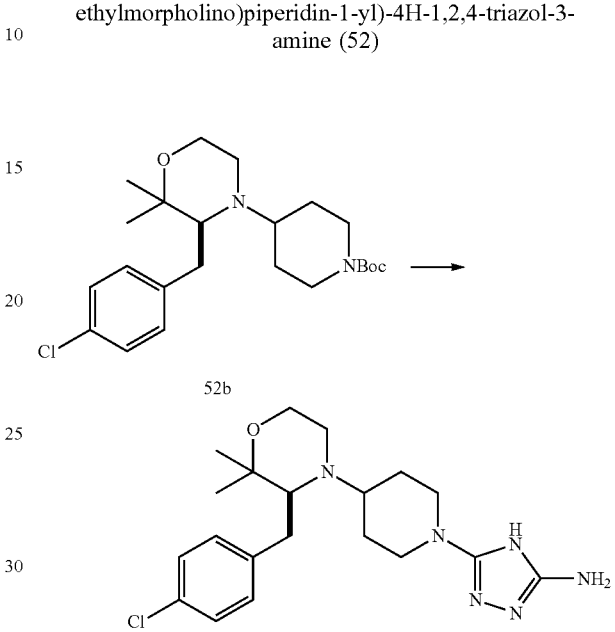

Compound 52 was prepared from compound 52b (0.471 g; 1.115 mmol) in the sequence of the reactions according to the General Procedure VII and the General Procedure VIII and was obtained as a white solid (0.181 g; 40% yield over two steps).

ESI-MS m/z for C$_{20}$H$_{29}$ClN$_6$O found 405.3 [M+1]$^+$.

$^1$H NMR (400 MHz, CD$_3$OD) δ: 7.35-7.27 (m, 4H), 3.82-3.70 (m, 2H), 3.70-3.59 (m, 1H), 3.54-3.44 (m, 1H), 2.96-2.90 (m, 2H), 2.87 (d, J=3.0 Hz, 1H), 2.85-2.78 (m, 1H), 2.74-2.65 (m, 3H), 2.52-2.44 (m, 2H), 1.71-1.59 (m, 2H), 1.37 (s, 3H), 1.29 (dd, J=11.6, 4.2 Hz, 1H), 1.21 (s, 3H).

Example 53

5-(4-((3S,6S)-3-(4-chlorobenzyl)-2,2,6-trimethylmorpholino)piperidin-1-yl)-4H-1,2,4-triazol-3-amine (53)

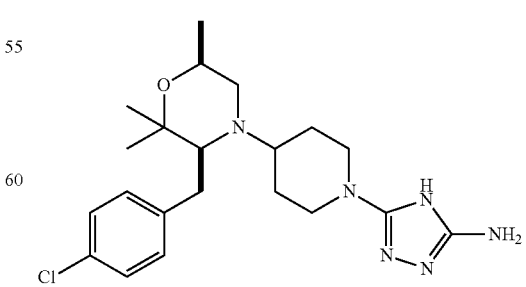

The title compound was prepared in the same manner as Example 52 with the exception that racemic chloropropionyl chloride instead of chloroacetyl chloride was used in the first synthetic step.

ESI-MS m/z for $C_{21}H_{31}ClN_6O$ found 419.4 $[M+1]^+$.

$^1$H NMR (400 MHz, CD$_3$OD) δ: 7.28-7.21 (m, 4H), 3.99-3.89 (m, 1H), 3.73-3.62 (m, 2H), 3.03-2.89 (m, 3H), 2.81-2.76 (m, 1H), 2.72 (dd, J=12.0, 3.3 Hz, 1H), 2.56-2.49 (m, 1H), 2.40-2.31 (m, 1H), 1.89-1.72 (m, 2H), 1.52-1.44 (m, 3H), 1.43 (s, 3H), 1.10 (d, J=6.2 Hz, 3H), 0.99 (s, 3H).

Example 54

3-((3 S,4S)-4-((2S,5S)-5-(4-chlorobenzyl)-2-methyl-morpholino)-3-methoxypiperidin-1-yl)-1H-1,2,4-triazol-5-amine (54)

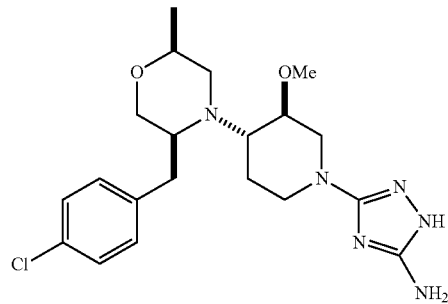

Step 1

Synthesis of diastereomeric mixture of (3R,4R)-1-benzyl-4-((2S,5S)-5-(4-chlorobenzyl)-2-methylmorpholino)piperidin-3-ol (54a-I) and (3S,4S)-1-benzyl-4-((2S,5S)-5-(4-chlorobenzyl)-2-methylmorpholino)piperidin-3-ol (54a-II)

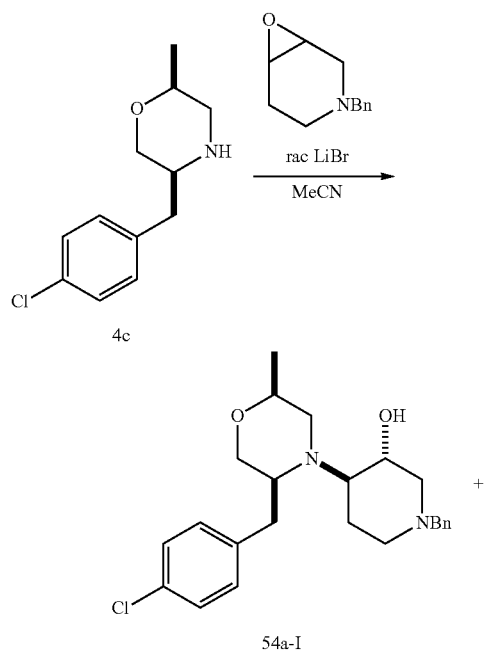

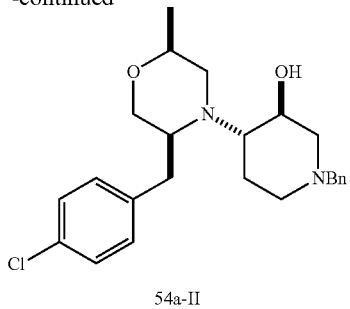

To the solution of rac-1-benzyl-3,4-epoxypiperidine (1.5 g, 8.0 mmol) (prepared according to procedure described in literature: Ian S. Young et al. *Org. Process. Res. Dev.* 2012, 16, 1558-1565) and litium bromide (1.044 g, 5.0 mmol) in dry acetonitrile (30 mL), (2S,5S)-5-(4-chlorobenzyl)-2-methylmorpholine (4c) (1.8 g, 8.0 mmol, 1.0 equiv.) was added and the reaction mixture was stirred for 24 hours at room temperature, then heated to 50° C. for 4 hours. Reaction progress was monitored by LCMS analysis of small samples of reaction mixture. After 28 hours reaction mixture was cooled down to room temperature and 20 mL of water was added. Acetonitrile was evaporated under reduced pressure, and residue was extracted with ethyl acetate (3×100 mL). Organic layers were combined, evaporated under reduced pressure and crude product was purified by flash chromatography using hexane-ethyl acetate (gradient elution from 10:1 to 1:10) to afford 2.3 g of (54a-I) and (54a-II) as a white solid (75% yield, 1:1 mixture of diastereomers). Small fractions of pure diastereomers were obtained by separation of product on preparative TLC using dichloromethane-methanol 25:1 as mobile phase.

ESI-MS m/z for $C_{24}H_{31}ClN_2O_2$ found 415.2/417.2 $(M+1)^+$

Less polar diastereomer: 1H NMR (400 MHz, CD$_3$OD) δ 7.34-7.29 (m, 5H), 7.27-7.22 (m, 2H), 7.21-7.15 (m, J=8.4 Hz, 2H), 3.64-3.42 (m, 6H), 3.14-3.05 (m, 1H), 2.95-2.80 (m, 3H), 2.80-2.74 (m, 1H), 2.67 (dd, J=11.9, 10.2 Hz, 1H), 2.55 (dd, J=12.0, 2.8 Hz, 1H), 2.40 (ddd, J=13.4, 9.4, 4.0 Hz, 1H), 2.09 (td, J=11.7, 2.4 Hz, 1H), 1.92 (t, J=10.4 Hz, 1H), 1.87-1.80 (m, 1H), 1.70 (ddd, J=25.1, 12.2, 4.0 Hz, 1H), 1.15 (d, J=6.0 Hz, 3H).

More polar diastereomer: 1H NMR (400 MHz, CD$_3$OD) δ 7.32-7.29 (m, 5H), 7.27-7.23 (m, 2H), 7.21-7.13 (m, J=7.3 Hz, 2H), 3.66-3.44 (m, 6H), 2.99 (ddd, J=10.7, 4.2, 1.9 Hz, 1H), 2.95-2.73 (m, 5H), 2.69 (dd, J=13.0, 3.1 Hz, 1H), 2.46-2.36 (m, 1H), 1.99 (td, J=11.4, 2.3 Hz, 1H), 1.92-1.79 (m, 2H), 1.59 (ddd, J=24.6, 11.6, 3.9 Hz, 1H), 1.14 (d, J=6.1 Hz, 3H).

Step 2

Synthesis of diastereomeric mixture of (2S,5S)-4-((3R,4R)-1-benzyl-3-methoxypiperidin-4-yl)-5-(4-chlorobenzyl)-2-methylmorpholine (54b-I) and (2S,5S)-4-((3S,4S)-1-benzyl-3-methoxypiperidin-4-yl)-5-(4-chlorobenzyl)-2-methylmorpholine (54b-II)

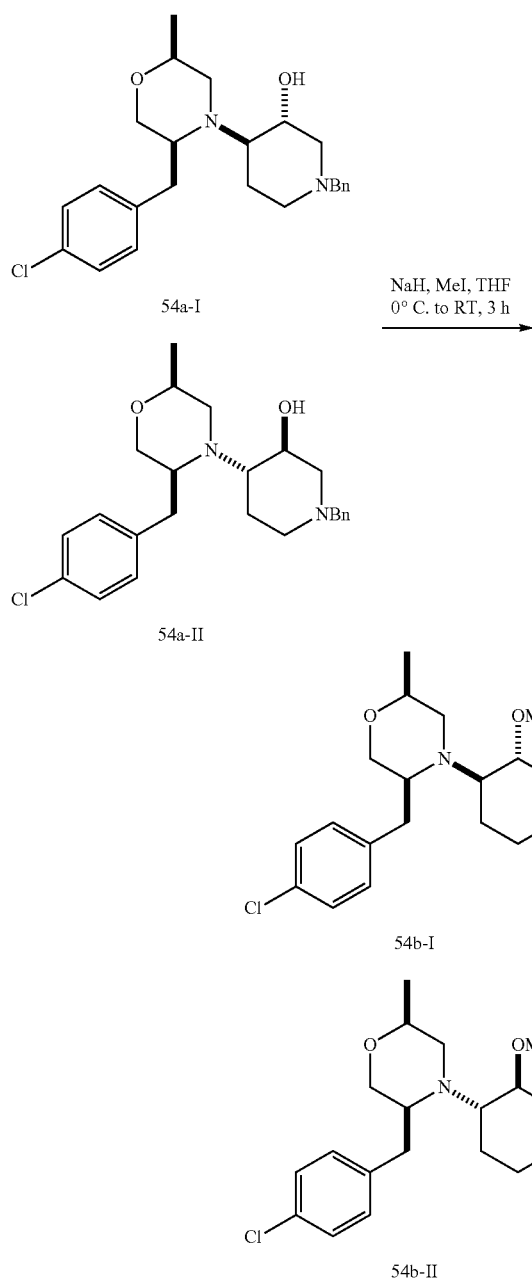

The title compound was synthesized from diastereomeric mixture of compounds (54a-I) and (54a-II) on 3.0 mmol scale according to the General Procedure XXI, using sodium hydride (NaH) and methyl iodide in THF. Crude product was purified by flash chromatography using dichloromethane-methanol (gradient elution from 50:1 to 10:1) to afford 600 mg of (54b-I) and (54b-II) as a yellowish oil (47% yield, 1:1 mixture of diastereomers).

ESI-MS m/z for $C_{25}H_{33}ClN_2O_2$ found 429.2/431.2 $(M+1)^+$.

Step 3

Synthesis of diastereomeric mixture of (3R,4R)-allyl 4-((2S,5S)-5-(4-chlorobenzyl)-2-methylmorpholino)-3-methoxypiperidine-1-carboxylate (54c-I) and (3S,4S)-allyl 4-((2S,5S)-5-(4-chlorobenzyl)-2-methylmorpholino)-3-methoxypiperidine-1-carboxylate (54c-II)

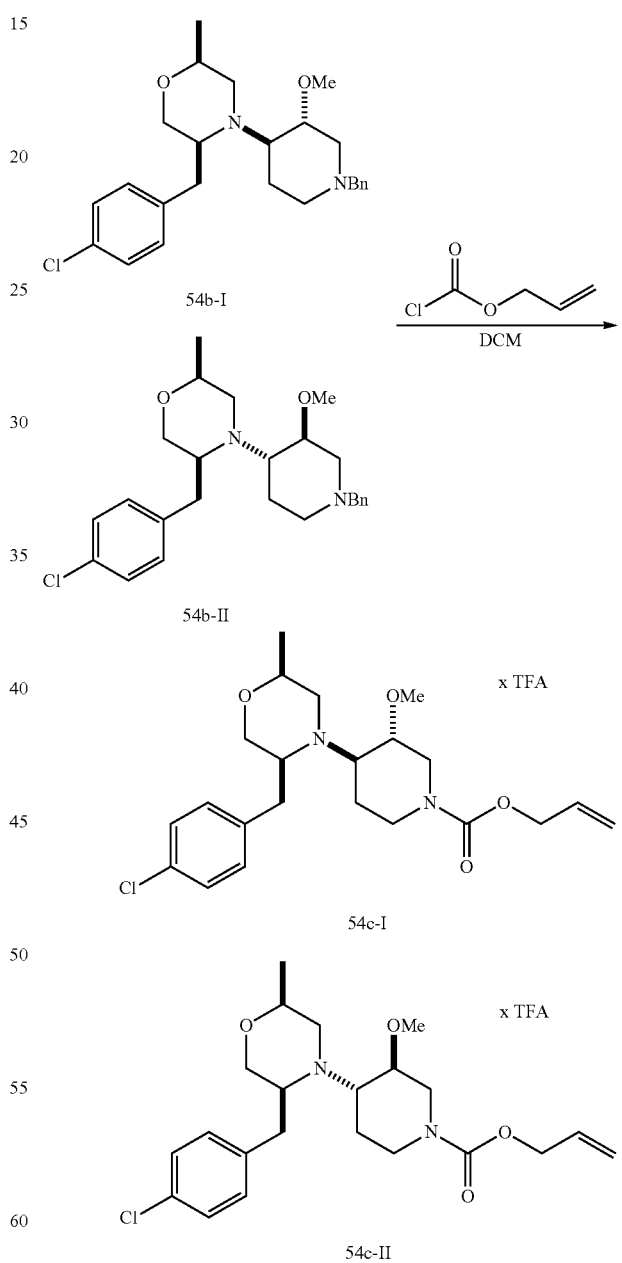

To solution of diastereomeric mixture of (54c-I) and (54c-II) (600 mg, 1.4 mmol, 1.0 equiv.) in dichloromethane (10 mL) at 0° C., was added dropwise allyl chloroformate (224 µL, 2.1 mmol). Upon addition was finished, reaction mixture was warmed up to room temperature and stirred for 16 hours. After this, LCMS analysis of crude reaction mixture showed full conversion and reaction was quenched with 10% aqueous solution of NaHCO₃ (5 mL). Organic phase was separated, and water phase was extracted with dichloromethane (2×20 mL). Combined organic phases were evaporated, and crude product was purified by reverse phase chromatography using water-acetonitrile-0.1% TFA (gradient elution from 10:1 to 1:5) to afford 400 mg of (54c-I•TFA) and (54c-II•TFA) as a yellowish oil (53% yield, 1:1 mixture of diastereomers, TFA salt).

ESI-MS m/z for $C_{22}H_{31}ClN_2O_4$ found 423.2/425.2 $(M+1)^+$

Step 4-5

Synthesis of 3-((3R,4R)-4-((2S,5S)-5-(4-chlorobenzyl)-2-methylmorpholino)-3-methoxypiperidin-1-yl)-1H-1,2,4-triazol-5-amine (54-I) and 3-((3S,4S)-4-((2S,5S)-5-(4-chlorobenzyl)-2-methylmorpholino)-3-methoxypiperidin-1-yl)-1H-1,2,4-triazol-5-amine (54)

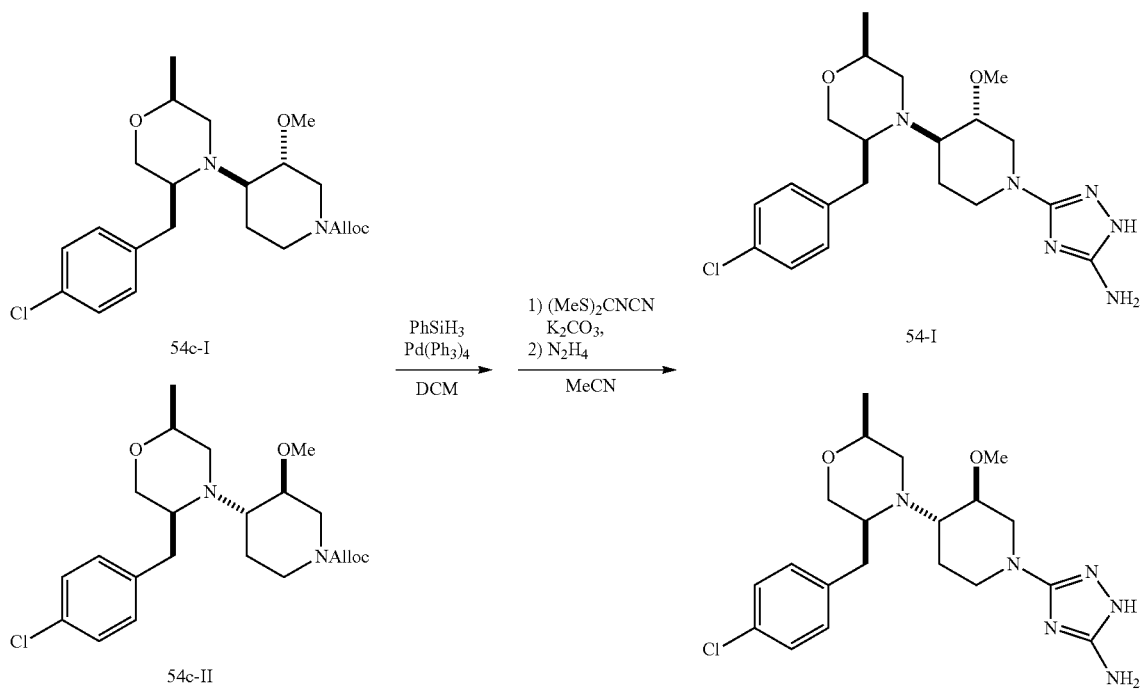

Alloc-group removal and formation of 1,2,4-triazole ring were accomplished according to the General Procedure XVI and the General Procedure VIII respectively starting from 400 mg, 0.75 mmol of compound (54c-I•TFA) and (54c-II•TFA). Diastereomers were separated by reverse phase chromatography using water-acetonitrile-0.1% TFA (gradient elution from 5:1 to 2:1) 30 mg of 54 (dr>95:5, more polar diastereomer). Purification of less polar diastereomer 54-I was not successful.

More Polar Diastereomer 54:
ESI-MS m/z for $C_{20}H_{29}ClN_6O_2$ found 423.2/425.2 $(M+1)^+$ $^1$H NMR (400 MHz, CD₃OD) δ 7.41-7.34 (m, 2H), 7.34-7.26 (m, 2H), 4.29 (dd, J=12.9, 2.6 Hz, 1H), 3.98 (ddd, J=10.5, 6.3, 2.4 Hz, 1H), 3.95-3.88 (m, 1H), 3.83 (td, J=9.5, 4.7 Hz, 2H), 3.77-3.62 (m, 2H), 3.61-3.55 (m, 2H), 3.52 (d, J=10.6 Hz, 3H), 3.33 (dd, J=11.9, 3.7 Hz, 1H), 3.29-3.26 (m, 1H), 3.24-3.15 (m, 1H), 3.11 (ddd, J=14.8, 9.0, 2.6 Hz, 1H), 2.96-2.82 (m, 1H), 2.32 (t, J=19.5 Hz, 1H), 2.07-1.86 (m, 1H), 1.32 (t, J=6.5 Hz, 3H).

Example 55

(S)-5-(4-(3-(4-chlorobenzyl)-6-methylene-1,4-oxazepan-4-yl)piperidin-1-yl)-4H-1,2,4-triazol-3-amine (55)

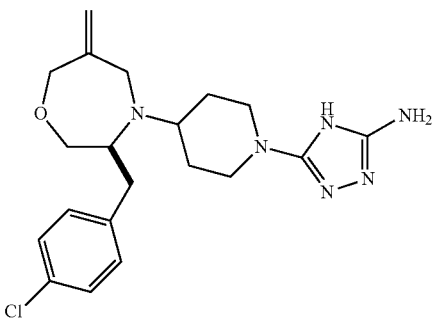 [SMILES: C=C1COC[C@H](Cc2ccc(Cl)cc2)N(C2CCN(c3nnc(N)[nH]3)CC2)C1]

Step 1

Synthesis of (5)-tert-butyl 3-(4-chlorobenzyl)-6-methylene-1,4-oxazepane-4-carboxylate (55a)

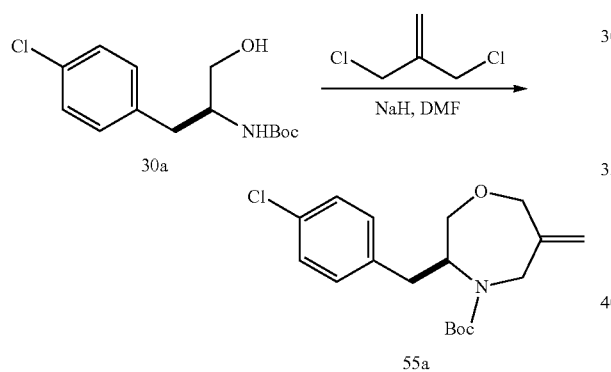

The title compound 55a was synthesized from compounds 30a (520 mg; 1.819 mmol) and 3-chloro-2-chloromethyl-1-propene (0.20 mL; 1.910 mmol) according to the General Procedure XXI and was obtained after as a transparent oil (317 mg; 0.938 mmol; 51% yield).

ESI-LCMS m/z for $C_{18}H_{24}ClNO_3$ found (M-Boc+1)$^+$ 238.1.

Step 2-3

Synthesis of (S)-tert-butyl 4-(3-(4-chlorobenzyl)-6-methylene-1,4-oxazepan-4-yl)piperidine-1-carboxylate (55b)

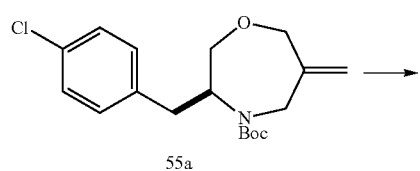

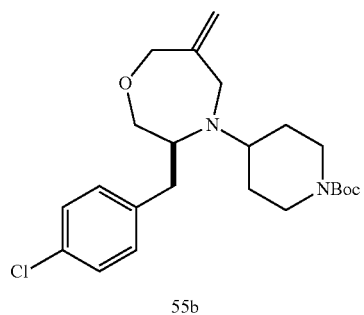

The title compound 55b was prepared from compound 55a (210 mg; 0.621 mmol) in a two-step procedure including removal of Boc-group (the General Procedure VII) and reductive amination with 1-Boc-pipierid-4-one (the General Procedure VI) and was obtained as a yellow oil (236 mg; 0.560 mmol; 90% yield).

ESI-LCMS m/z for $C_{23}H_{33}ClN_2O_3$ found (M-Boc+1)$^+$ 421.3.

Step 4-5

Synthesis of (S)-5-(4-(3-(4-chlorobenzyl)-6-methylene-1,4-oxazepan-4-yl)piperidin-1-yl)-4H-1,2,4-triazol-3-amine (55)

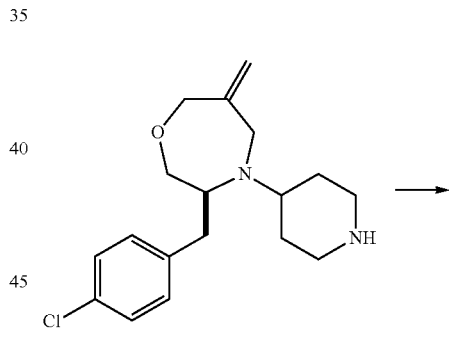

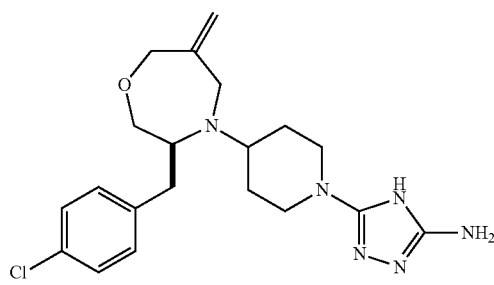

The title compound 55 was synthesized from compound 55b (236 mg; 0.560 mmol) according to the General Procedure VIII. It was purified by column chromatography (AcOEt/MeOH 100:1→100:5) and was obtained a white foam (106 mg; 0.263 mmol; 47% yield).

Example 56

(S)-5-(4-(2-(4-chlorobenzyl)-4-methyl-1,4-diazepan-1-yl)piperidin-1-yl)-4H-1,2,4-triazol-3-amine (56)

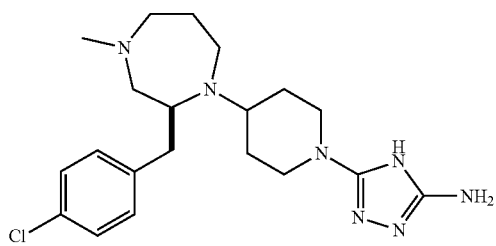

Step 1-2

Synthesis of (S)-methyl 3-((2-((tert-butoxycarbonyl)amino)-3-(4-chlorophenyl)propyl)(methyl)amino)propanoate (56a)

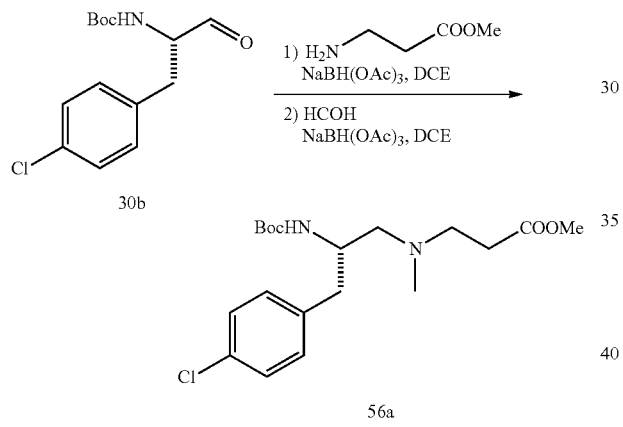

The title compound was synthesized from compound 30b (960 mg; 3.38 mmol) according to the General Procedures XIII and XIV and was obtained as a transparent oil (1.12 g; 2.91 mmol; 86% yield).

ESI-MS m/z for $C_{19}H_{29}ClN_2O_4$ found 285.1 (M-Boc+1)$^+$, 385.2/386.9 (M+1)$^+$.

Step 3-4

Synthesis of (S)-3-(4-chlorobenzyl)-1-methyl-1,4-diazepan-5-one (56b)

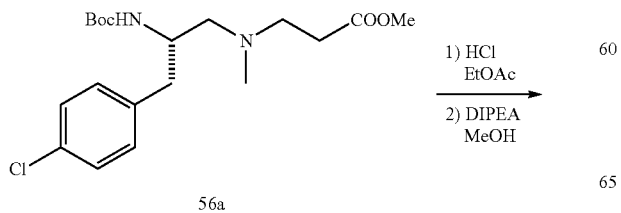

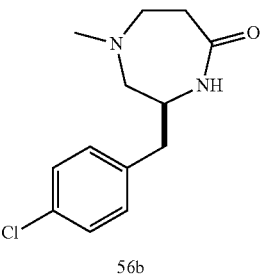

The title compound 56b was prepared from compound 56a (1.04 g; 2.70 mmol) in a two-step procedure including removal of Boc-group (the General Procedure VII) and cyclization of 7-membered ring ((the General Procedure X) with exception that N,N-Diisopropylethylamine was used instead of Et$_3$N. Product 56b was obtained as a brown crystalline solid (698 mg, 99% yield).

ESI-MS m/z for $C_{13}H_{17}ClN_2O$ found 253.1/254.9 (M+1)$^+$.

Step 5

Synthesis of (S)-3-(4-chlorobenzyl)-1-methyl-1,4-diazepane (56c)

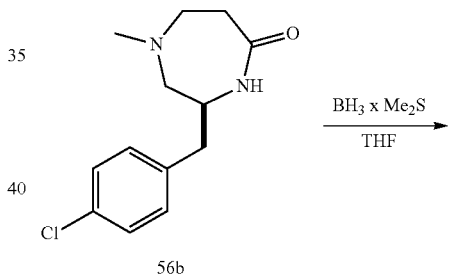

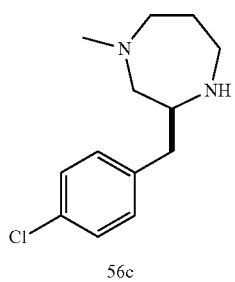

The title compound 56c was synthesized from compound 56b (695 mg; 2.75 mmol) according to the General Procedure V and was obtained as a yellow oil (562 mg; 2.36 mmol; 86% yield).

ESI-MS m/z for $C_{13}H_{19}ClN_2$ found 239.1/241.0 (M+1)$^+$.

Step 6

Synthesis of (S)-tert-butyl 4-(2-(4-chlorobenzyl)-4-methyl-1,4-diazepan-1-yl)piperidine-1-carboxylate (56d)

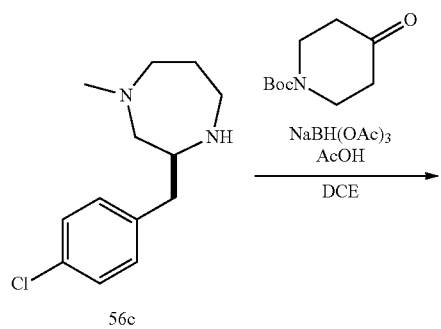

The title compound 56d was synthesized from compound 56c (558 mg; 2.34 mmol) according to the General Procedure VI and was obtained as a yellow oil (885 mg; 2.10 mmol; 90% yield).

ESI-MS m/z for $C_{23}H_{36}ClN_3O_2$ found 322.2 (M-Boc+1)$^+$, 422.2/423.6 (M+1)$^+$.

Step 7

Synthesis of (S)-2-(4-chlorobenzyl)-4-methyl-1-(piperidin-4-yl)-1,4-diazepane dihydrochloride (50e)

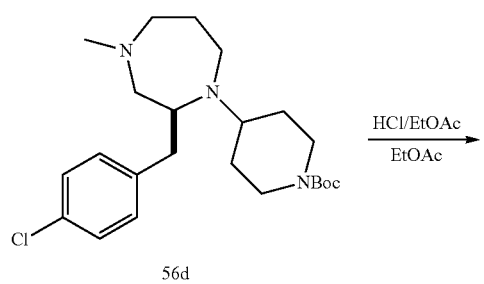

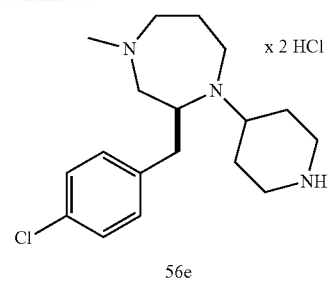

The title compound 56e was synthesized from compound 56d (880 mg; 2.08 mmol) according to the General Procedure VII and was obtained as a white powder (788 mg; 2.00 mmol; 88% yield).

ESI-MS m/z for $C_{18}H_{28}ClN_3$ found 322.2 (M+1)$^+$.

Step 8

Synthesis of (S)-3-(4-(2-(4-chlorobenzyl)-4-methyl-1,4-diazepan-1-yl)piperidin-1-yl)-1H-1,2,4-triazol-5-amine trifluoroacetate (56)

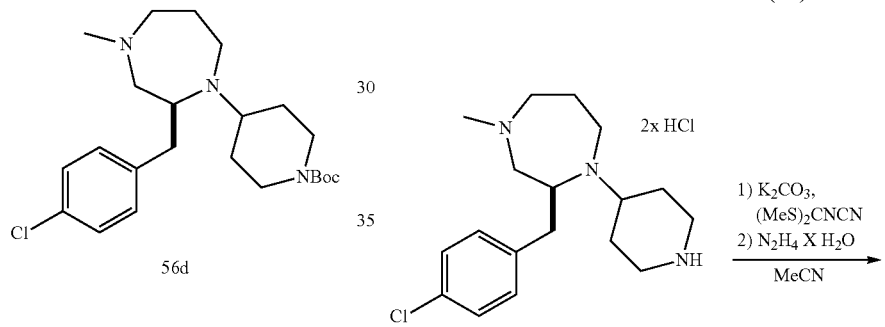

The title compound 56 was synthesized from compound 56e (555 mg; 1.29 mmol) according to the General Procedure VIII. It was purified by reversed-phase chromatography and was obtained as TFA-salt (26 mg; 0.05 mmol; 5% yield).

ESI-MS m/z for $C_{20}H_{30}ClN_7$ found 404.2 (M+1)$^+$.

$^1$H NMR (DMSO-d$_6$+D$_2$O, 700 MHz) δ 7.24 (AA'BB', J=8.4 Hz, 2H), 7.19 (AA'BB', J=8.4 Hz, 2H), 3.64 (m, 2H), 3.47 (ddd, J=13.8, 8.7, 5.4 Hz, 1H), 3.16 (bs, 1H), 3.08 (dd, J=14.5, 8.2 Hz, 1H), 3.01 (dd, J=14.2, 5.4 Hz, 2H), 2.91-2.87 (m, 1H), 2.85-2.77 (m, 6H), 2.65 (s, 3H), 1.75-1.73 (m, 3H), 1.70-1.66 (m, 1H), 1.44 (dq, J=12.3, 4.4 Hz, 1H), 1.36 (dq, J=12.1, 4.2 Hz, 1H).

Example 57

(S)-5-(4-(3-(4-chlorobenzyl)-1-methyl-2,3-dihydro-1H-benzo[e][1,4]diazepin-4(5H)-yl)piperidin-1-yl)-4H-1,2,4-triazol-3-amine (57)

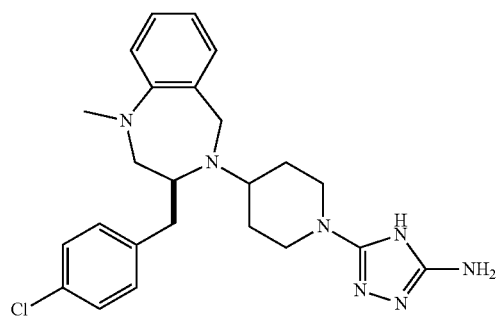

Step 1

Synthesis of (S)-methyl 2-((2-((tert-butoxycarbonyl)amino)-3-(4-chlorophenyl)propyl)amino)benzoate (57a)

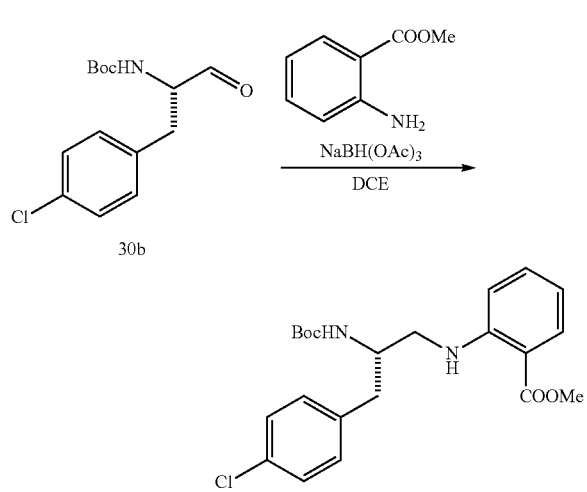

To a solution of 30b 1.50 g (5.29 mmol) in 5 mL 1,2-dichloroethane, methyl 2-aminobenzoate 800 mg (5.29 mmol) was added. Reaction mixture was heated to 70° C. and cooled room temperature over 1 hour. Sodium triacetoxyborohydride 2.80 g (13.22 mmol) was added and reaction was stirred for 2 days after which time LCMS control indicated completion of the reaction. Reaction was quenched with 5% NaHCO$_3$ solution for 30 minutes and layers were separated. Organic layer was washed with 5% NaHCO$_3$ solution, brine and dried over anhydrous MgSO$_4$ and concentrated. Crude product was purified by column chromatography hexane/EtOAc 8/1 to obtain 755 mg of 57a as a white solid (1.80 mmol; 34% yield).

ESI-MS m/z for $C_{22}H_{27}ClN_2O_4$ found 319.1 (M-Boc+1)$^+$, 363.1/364.9 (M-$^t$Bu+1)$^+$.

$^1$H NMR (CDCl$_3$, 700 MHz) δ 7.93 (m, 1H), 7.37 (m, 1H), 7.30, (s, 1H), 7.18 (d, J=8.0 Hz, 2H), 6.75 (d, J=7.7 Hz, 2H), 6.65 (t, J=7.5 Hz, 1H), 4.59 (bs, 1H), 4.13 (bs, 1H), 3.89 (s, 3H), 3.33 (dd, J=13.5, 5.1 Hz, 1H), 3.26 (dd, J=13.0, 5.4 Hz, 1H), 2.92 (d, J=6.3 Hz, 1H), 1.44 (s, 9H).

Step 2

Synthesis of (S)-methyl 2-((2-((tert-butoxycarbonyl)amino)-3-(4-chlorophenyl)propyl(methyl)amino)benzoate (57b)

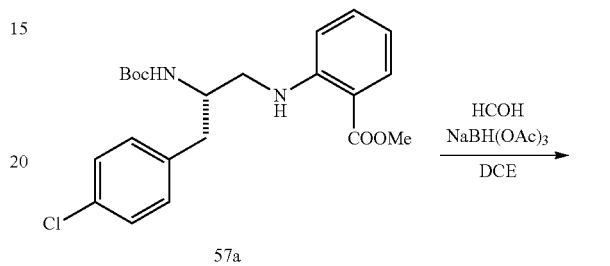

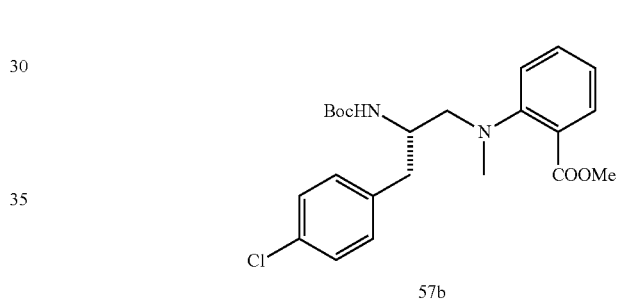

The title compound was synthesized from compound 57a (500 mg; 1.19 mmol according to the General Procedure XIV and was obtained as a transparent oil a transparent oil (461 mg; 1.07 mmol; 89% yield). ESI-MS m/z for $C_{23}H_{29}ClN_2O_4$ found 333.2 (M-Boc+1)$^+$, 433.2/435.0 (M+1)$^+$.

Step 3-4

Synthesis of (S)-3-(4-chlorobenzyl)-1-methyl-3,4-dihydro-1H-benzo[e][1,4]diazepin-5(2H)-one (57c)

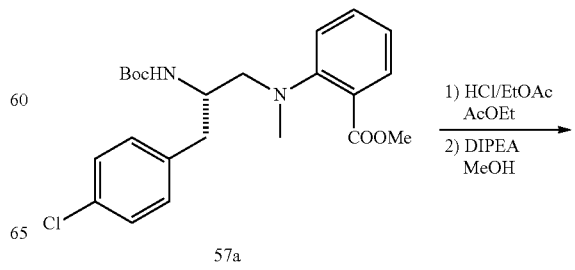

-continued

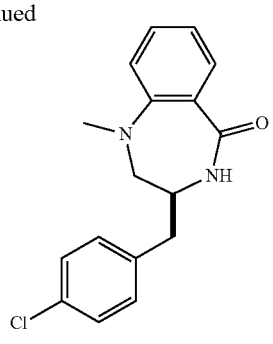

57c

The title compound 57c was prepared from compound 57b (461 mg; 1.06 mmol) in a two-step procedure including removal of Boc-group (the General Procedure VII) and cyclization of 7-membered ring ((the General Procedure X) with exception that N,N-Diisopropylethylamine was used instead of Et₃N. Crude product was purified by column chromatography (hexane/EtOAc 1:2) to obtain 57c as a transparent oil (137 mg; 0.46 mmol; 44% yield).

ESI-MS m/z for $C_{17}H_{17}ClN_2O$ found 301.2/303.0 (M+1)$^+$.

$^1$H NMR (DMSO-d$_6$, 700 MHz) δ 8.15 (d, J=5.7 Hz, 1H), 7.38 (dd, J=7.6, 1.7 Hz, 1H), 7.36 (m, 1H), 7.32 (AA'BB', J=8.7 Hz, 2H), 7.30 (AA'BB', J=8.7 Hz, 2H), 6.93-6.90 (m, 2H), 3.49 (m, 1H), 3.25 (t, J=11.0 Hz, 1H), 2.90 (dd, J=10.8, 3.6 Hz, 1H), 2.80 (dd, J=13.8, 8.3 Hz, 1H), 2.75 (s, 3H).

Step 5

Synthesis of (S)-3-(4-chlorobenzyl)-1-methyl-2,3,4,5-tetrahydro-1H-benzo[e][1,4]diazepine (57d)

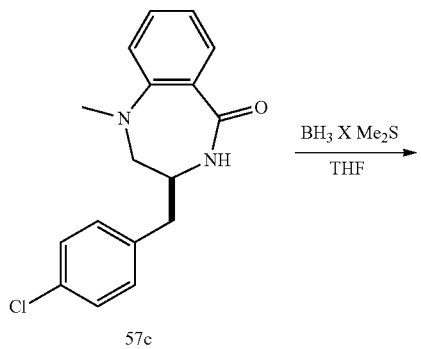

The title compound 57d was synthesized from compound 57c (130 mg; 0.43 mmol) according to the General Procedure V and was obtained as a yellowish oil (122 mg; 0.42 mmol; 98% yield).

ESI-MS m/z for $C_{17}H_{19}ClN_2$ found 287.1 (M+1)$^+$.

$^1$H NMR (DMSO-d$_6$+D$_2$O, 700 MHz) δ 7.33 (AA'BB', J=8.4 Hz, 2H), 7.26 (AA'BB', J=8.4 Hz, 2H), 7.13 (td, J=7.7, 1.5 Hz, 1H), 7.06 (dd, J=7.3, 1.2 Hz, 1H), 6.86 (d, J=7.7 Hz, 1H), 6.80 (m, 1H), 3.83 (d, J=14.2 Hz, 1H), 3.62 (d, J=14.2 Hz, 1H), 3.07 (dd, J=13.5, 2.3 Hz, 2H), 2.78 (s, 3H), 2.63-2.57 (m, 3H).

Step 6

Synthesis of (5)-tert-butyl 4-(3-(4-chlorobenzyl)-1-methyl-2,3-dihydro-1H-benzo[e][1,4]diazepin-4(5H)-yl)piperidine-1-carboxylate (57e)

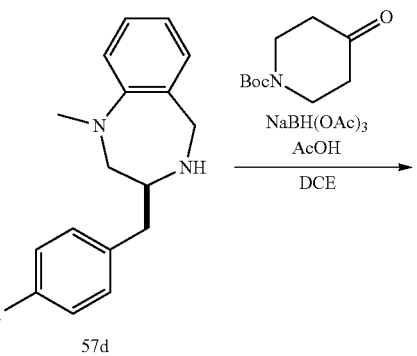

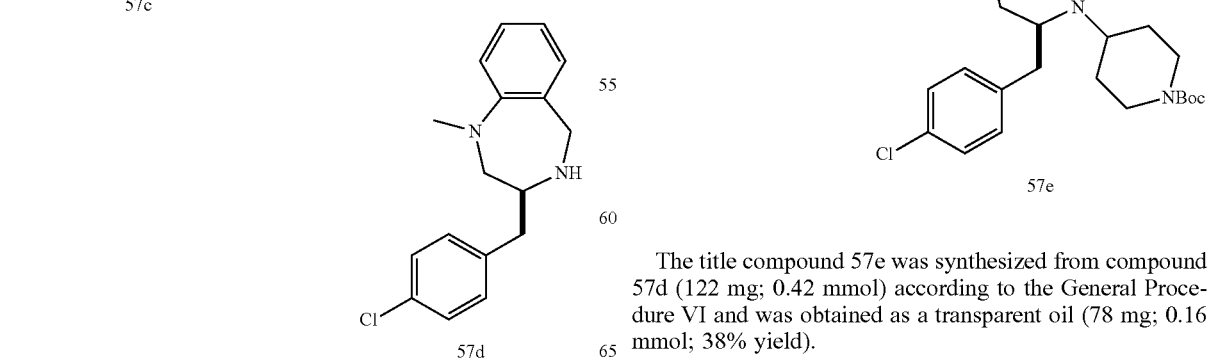

The title compound 57e was synthesized from compound 57d (122 mg; 0.42 mmol) according to the General Procedure VI and was obtained as a transparent oil (78 mg; 0.16 mmol; 38% yield).

ESI-MS m/z for $C_{27}H_{36}ClN_3O_2$ found 470.6/471.6/472.4 (M+1)$^+$.

Step 7

Synthesis of (S)-3-(4-chlorobenzyl)-1-methyl-4-(piperidin-4-yl)-2,3,4,5-tetrahydro-1H-benzo[e][1,4]diazepinedihydrochloride (570

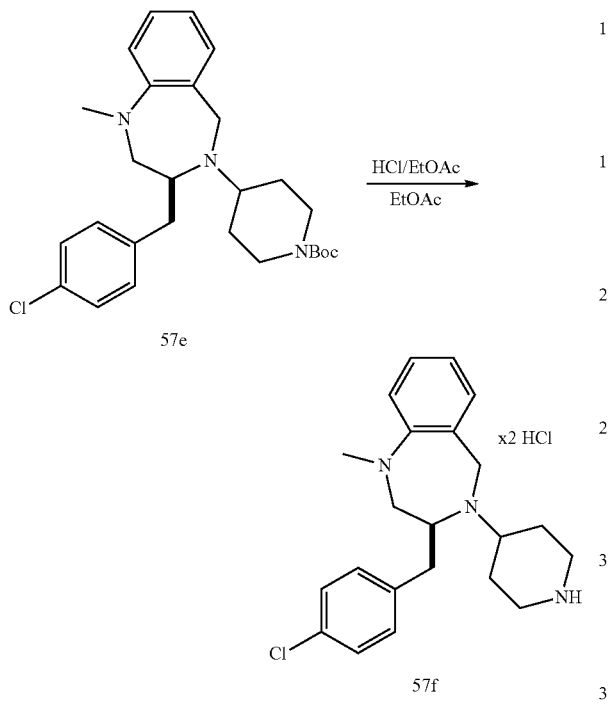

The title compound 57f was synthesized from compound 57e (78 mg; 0.16 mmol) according to the General Procedure VII and was obtained as a white powder (76 mg; 0.16 mmol; 99% yield).

ESI-MS m/z for $C_{22}H_{28}ClN_3$ found 370.1 (M+1)$^+$.

Step 8

Synthesis of (S)-3-(4-(3-(4-chlorobenzyl)-1-methyl-2,3-dihydro-1H-benzo[e][1,4]diazepin-4(5H)-yl)piperidin-1-yl)-1H-1,2,4-triazol-5-amine trifluoroacetate (57)

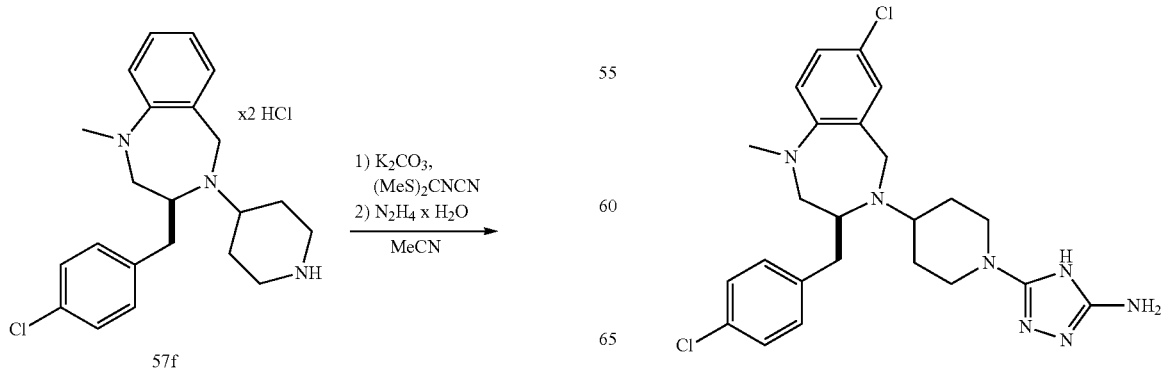

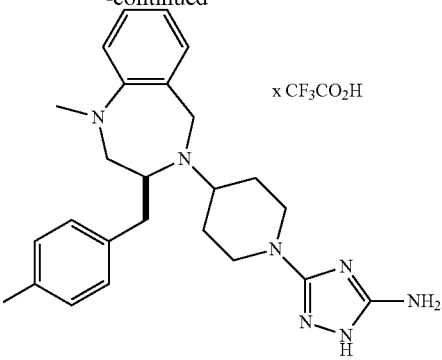

The title compound 57 was synthesized from compound 57f (76 mg; 0.19 mmol) according to the General Procedure VIII. It was purified by reversed-phase chromatography and was obtained as TFA-salt (22 mg; 0.04 mmol; 23% yield).

ESI-MS m/z for $C_{24}H_{30}ClN_7$ found 452.1 (M+1)$^+$.

$^1$H NMR (DMSO-d$_6$+D$_2$O, 700 MHz) δ 7.35 (d, J=8.3 Hz, 2H), 7.28-7.24 (m, 4H), 6.84-6.81 (m, 2H), 4.47-4.37 (m, 2H), 3.86 (bs, 1H), 3.74 (d, J=12.6 Hz, 2H), 3.40 (bs, 2H), 3.08-3.06 (m, 2H), 2.82-2.76 (m, 2H), 2.70 (s, 3H), 2.65-2.63 (m, 1H), 2.12 (bs, 1H), 2.02 (bs, 1H), 1.68 (m, 2H).

Example 58

(S)-5-(4-(7-chloro-3-(4-chlorobenzyl)-1-methyl-2,3-dihydro-1H-benzo[e][1,4]diazepin-4(5H)-yl)piperidin-1-yl)-4H-1,2,4-triazol-3-amine (58)

Step 1

Synthesis of 6-chloro-1H-benzo[d][1,3]oxazine-2,4-dione (58a)

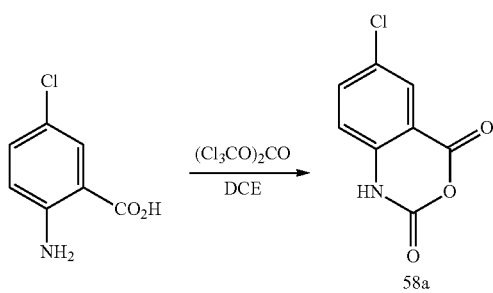 [SMILES: Nc1ccc(Cl)cc1C(=O)O ; "(Cl3CO)2CO" ; O=c1[nH]c2ccc(Cl)cc2c(=O)o1]

To suspension of 5-chloroanthranilic acid (1000 mg; 5.828 mmol) in 1,2-dichloroethane (5 mL) triphosgene (692 mg; 2.331 mmol) in 1,2-dichloroethane solution (10 mL) was added and the mixture was heated to reflux for 4 hours. After cooling down to room temperature the precipitate was filtered, washed with cold DCM and dried to afford a white solid (1.128 g; 5.709 mmol; 98% yield).

Step 2

Synthesis of 6-chloro-1-methyl-1H-benzo[d][1,3]oxazine-2,4-dione (58b)

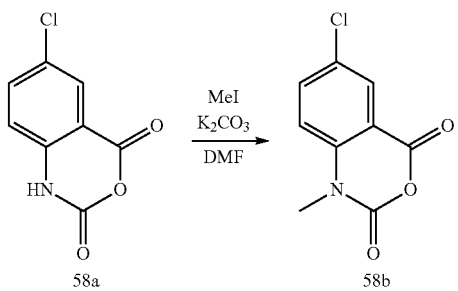

To solution of 58a (1125 mg; 5.694 mmol) in DMF (6 mL) powdered sodium carbonate (724 mg; 6.833 mmol) was added followed by methyl iodide (0.53 mL; 8.541 mmol) and the mixture was stirred at room temperature for 18 hours. After this time the mixture was cooled down 0° C. and crushed ice (5 g) and 1 M HCl (5 mL) were carefully added. The precipitated solid was filtered off, washed with cold water (2×10 mL) and dried under vacuum. The product was obtained as a yellow solid (960 mg; 4.536 mmol; 80% yield) and was used in the next step without additional purification.

$^1$H NMR (DMSO-$d_6$, 400 MHz): δ 7.95 (d, J=2.3 Hz, 1H), 7.89 (dd, J=9.0, 2.6 Hz, 1H), 7.47 (d, J=8.9 Hz, 1H), 3.44 (s, 3H).

Step 3

Synthesis of (S)-7-chloro-3-(4-chlorobenzyl)-1-methyl-3,4-dihydro-1H-benzo[e][1,4]diazepine-2,5-dione (58c)

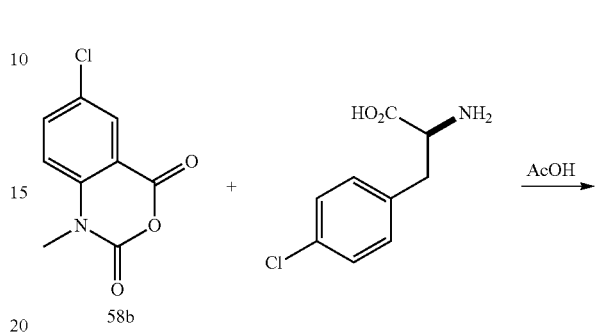

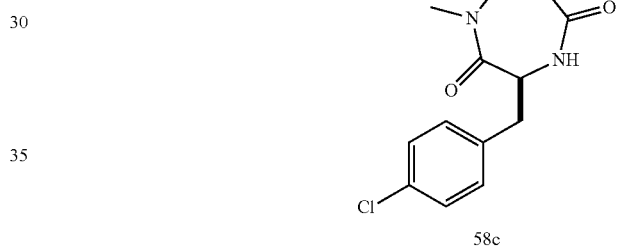

A mixture of 58b (1140 mg; 5.387 mmol) and L-4-chlorophenylalanine (1129 mg; 5.656 mmol) in glacial acetic acid (11 mL) was heated to reflux for 18 hours. After this time TLC (Hexanes/AcOEt 1:1) showed completion of the reaction. The mixture was concentrated and the residue was vigorously stirred with saturated $Na_2CO_3$ (10 mL). The product was then extracted with AcOEt (3×50 mL). Combined organic solutions were washed with saturated $Na_2CO_3$ (10 mL), brine (10 mL) and concentrated. The product was purified by column chromatography (petroleum ether/AcOEt 10:1→1:1) and was obtained as a white solid (1262 mg; 3.613 mmol; 67% yield).

ESI-LCMS: m/z for $C_{17}H_{14}Cl_2N_2O_2$ found 349.1 (M+1)$^+$.

$^1$H NMR (CDCl$_3$, 400 MHz): δ 7.81 (d, J=2.5 Hz), 7.52 (dd, J=8.7, 2.6 Hz, 1H), 7.26 (AA'BB', J=8.5 Hz, 2H), 7.21 (AA'BB', J=8.6 Hz, 2H), 7.17 (d, J=8.9 Hz, 1H), 6.93 (d, J=5.3 Hz, 1H), 3.95 (dd, J=13.4, 6.6 Hz, 1H), 3.39 (s, 3H), 3.39 (dd, J=14.4, 6.7 Hz, 1H), 3.02 (dd, J=14.5, 7.7 Hz, 1H).

Step 4

Synthesis of (S)-7-chloro-3-(4-chlorobenzyl)-1-methyl-2,3,4,5-tetrahydro-1H-benzo[e][1,4]diazepine (58d)

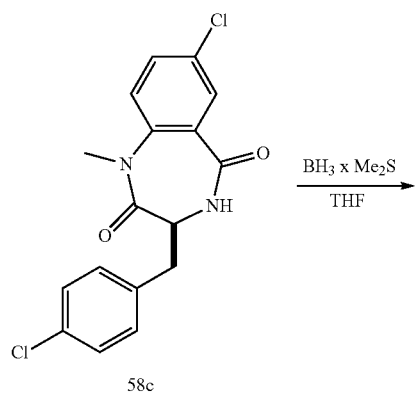

The title compound 58d was synthesized from compound 58c (1245 mg; 3.565 mmol) according to the General Procedure V and was obtained as a yellow oil (1.140 g; 3.548 mmol; 99% yield).

ESI-LCMS: m/z for $C_{17}H_{18}Cl_2N_2$ found 321.2 $(M+1)^+$.

Step 5

Synthesis of (S)-tert-butyl 4-(7-chloro-3-(4-chlorobenzyl)-1-methyl-2,3-dihydro-1H-benzo[e][1,4]diazepin-4(5H)-yl)piperidine-1-carboxylate (58e)

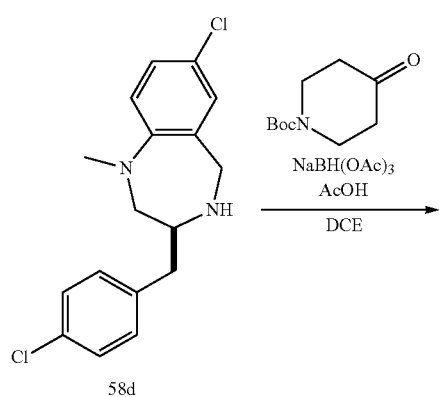

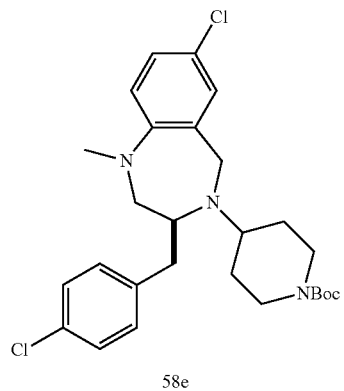

The title compound 58e was synthesized from compound 58d (1140 mg; 3.548 mmol) according to the General Procedure VI and was obtained as yellow oil (1237 mg; 2.451 mmol; 63% yield after two steps).

ESI-LCMS: m/z for $C_{27}H_{35}Cl_2N_3O_2$ found 504.3 $(M+1)^+$.

$^1$H NMR (MeOH-d$_4$, 400 MHz): δ 7.27 (AA'BB', J=8.5 Hz, 2H), 7.21 (AA'BB', J=8.5 Hz, 2H), 7.06 (dd, J=8.5, 2.5 Hz, 1H), 7.03 (d, J=2.5 Hz, 1H), 6.69 (d, J=8.6 Hz, 1H), 4.41 (d, J=16.3 Hz, 1H), 3.84-3.67 (m, 2H), 3.74 (d, J=16.5 Hz, 1H), 3.39-3.32 (m, 1H), 3.25 (dd, J=14.3, 7.3 Hz, 1H), 3.06 (dd, J=14.3, 3.7, 1H), 2.85 (s, 3H), 2.81 (d, J=6.9 Hz, 2H), 2.73-2.56 (m, 3H), 1.73-1.64 (m, 1H), 1.62-1.52 (m, 1H), 1.41 (s, 9H), 1.31-1.01 (m, 2H).

Step 6

Synthesis of (S)-7-chloro-3-(4-chlorobenzyl)-1-methyl-4-(piperidin-4-yl)-2,3,4,5-tetrahydro-1H-benzo[e][1,4]diazepine hydrochloride (58f)

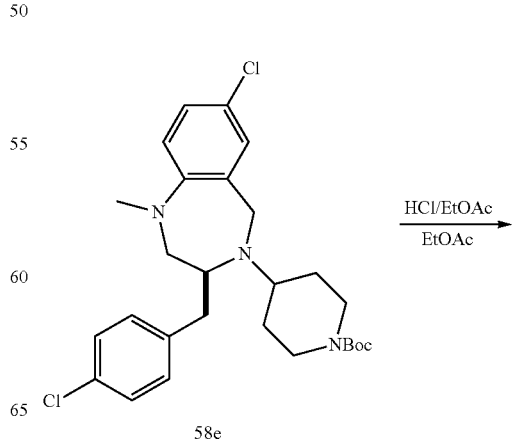

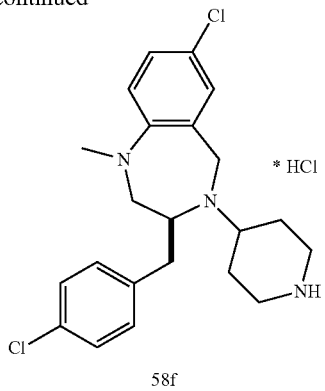

58f

The title compound 58f was synthesized from compound 58e (1.22 g; 2.418 mmol) according to the General Procedure VII and was used in the next step without additional purification.

Step 7

Synthesis of (S)-5-(4-(7-chloro-3-(4-chlorobenzyl)-1-methyl-2,3-dihydro-1H-benzo[e][1,4]diazepin-4(5H)-yl)piperidin-1-yl)-4H-1,2,4-triazol-3-amine (58)

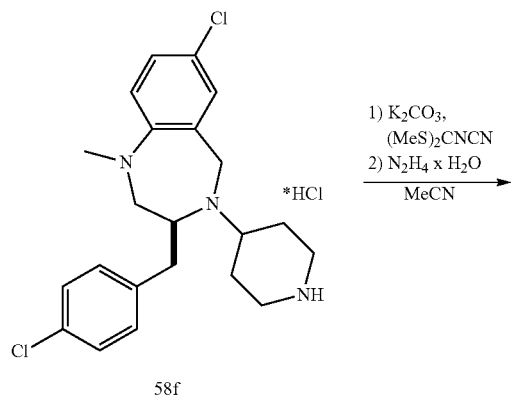

The title compound 58 was synthesized from compound 58f (1.066 g; 2.418 mmol) according to the General Procedure VIII. It was purified by silica-gel chromatography (AcOEt/MeOH system) and was obtained as light-yellow solid (930 mg; 1.916 mmol; 79% yield).

ESI-LCMS: m/z for $C_{24}H_{29}Cl_2N_7$ found 243.8 $(M+2)^{2+}$, 486.3 $(M+1)^+$.

$^1$H NMR (MeOH-$d_4$, 400 MHz): δ 7.26 (AA'BB', J=8.5 Hz, 2H), 7.21 (AA'BB', J=8.5 Hz, 2H), 7.06 (dd, J=8.5, 2.5 Hz, 1H), 7.04 (d, J=2.4 Hz, 1H), 6.70 (d, J=8.5 Hz, 1H), 4.39 (d, J=16.2 Hz, 1H), 3.76 (d, J=16.3 Hz, 1H), 3.69-3.46 (m, 2H), 3.39-3.33 (m, 1H), 3.22 (dd, J=14.4, 6.9 Hz, 1H), 3.06 (dd, J=14.4, 3.6 Hz, 1H), 2.84 (s, 3H), 2.82 (d, J=7.0 Hz, 2H), 2.74-2.50 (m, 3H), 1.78-1.68 (m, 1H), 1.68-1.58 (m, 1H), 1.44-1.20 (m, 2H).

Example 59

(S)-5-(4-(3-(4-chlorobenzyl)-2,3-dihydrobenzo[f][1,4]oxazepin-4(5H)-yl)piperidin-1-yl)-4H-1,2,4-triazol-3-amine (59)

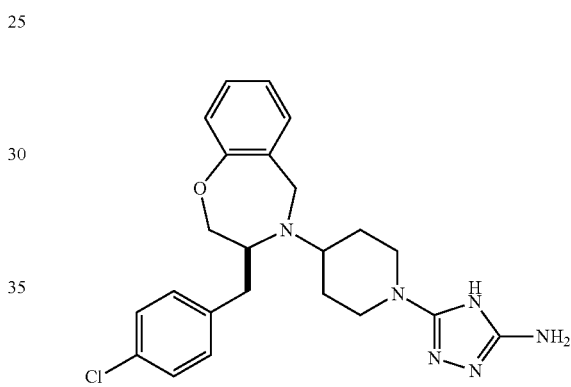

Step 1

Synthesis of 2-hydroxy-N-methoxy-N-methylbenzamide (59a)

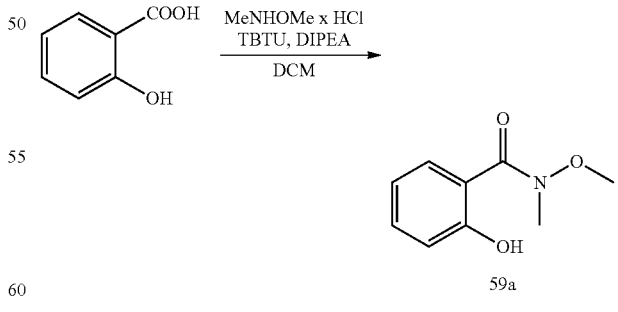

The title compound was prepared from salicylic acid (10.00 g; 72.35 mmol) according to the General Procedure XXII and was obtained as a colorless oil (6.98 g; 38.54 mmol; 53% yield).

ESI-MS m/z for $C_9H_{11}NO_3$ found 182.0 $(M+1)^+$.

Step 2

Synthesis of (S)-tert-butyl (1-(4-chlorophenyl)-3-(2-(methoxy(methyl)carbamoyl)phenoxy)propan-2-yl)carbamate (59b)

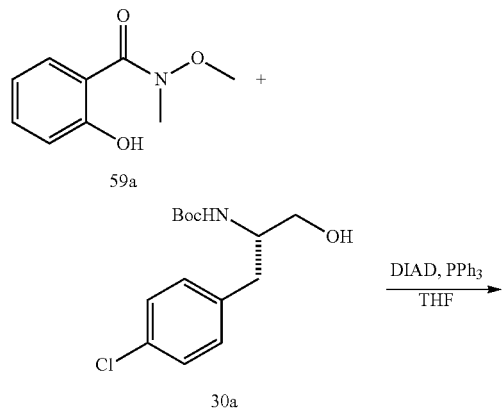

The title compound was synthesized from compounds 59a (1.27 g; 7.00 mmol) and 30a (2.50 g; 8.75 mmol) according to the General Procedure XXIII and was obtained as a white solid (260 mg; 0.58 mmol; 8% yield).

ESI-MS m/z for $C_{23}H_{29}ClN_2O_5$ found 471.1 (M+Na)$^+$.

Step 3

Synthesis of (S)-tert-butyl (1-(4-chlorophenyl)-3-(2-formylphenoxy)propan-2-yl)carbamate (59c)

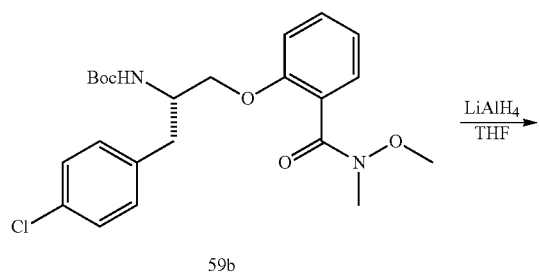

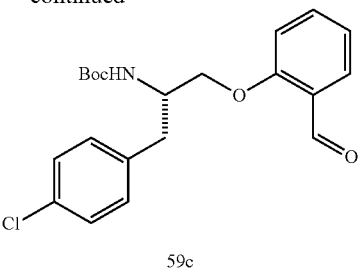

The title compound was prepared from 59b (260 mg; 0.58 mmol) according to the General Procedure XXIV and was obtained as a transparent oil (217 mg; 0.56 mmol; 96% yield).

ESI-MS m/z for $C_{21}H_{24}ClNO_4$ found 290.0/292.0 (M+1)$^+$.

$^1$H NMR (DMSO-d$_6$, 700 MHz) δ 10.38 (s, 1H), 7.66 (dd, 1H), 7.62-7.60 (m, 1H), 7.29 (AA'BB', J=8.3 Hz, 2H), 7.24 (AA'BB', J=8.4 Hz, 2H), 7.14 (d, J=7.1 Hz, 1H), 7.06 (t, J=7.6 Hz, 1H), 4.10 (dd, J=9.5, 4.0 Hz, 1H), 4.07-4.03 (m, 1H), 3.99-3.97 (m, 1H), 3.57 (ddd, J=6.2, 4.2, 2.5 Hz, 1H), 2.89 (dd, J=13.9, 5.3 Hz, 1H), 1.74-1.72 (m, 1H), 1.26 (s, 9H).

Step 4

Synthesis of (S)-3-(4-chlorobenzyl)-2,3,4,5-tetrahydrobenzo[f][1,4]oxazepine (59d)

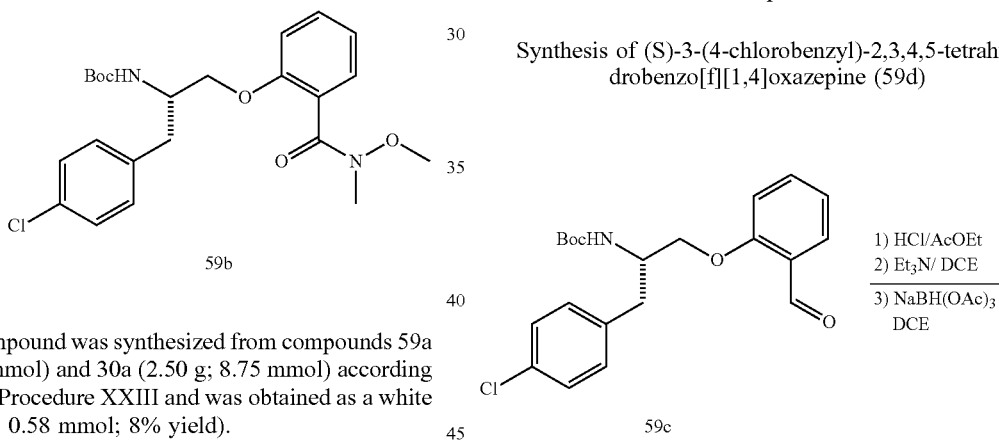

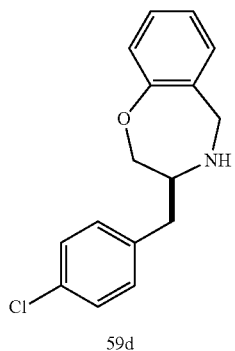

The title compound was synthesized from 59c (217 mg; 0.56 mmol) according to the General Procedure XXV and was obtained as a yellowish oil (150 mg; 0.55 mmol; 98% yield).

ESI-MS m/z for $C_{16}H_{16}ClNO$ found 274.1/276.0 (M+1)$^+$.

$^1$H NMR (DMSO-d$_6$, 700 MHz) δ 7.35 (AA'BB', J=8.3 Hz, 2H), 7.28 (AA'BB', J=8.3 Hz, 2H), 7.16-7.14 (m, 2H), 6.97 (t, J=7.4 Hz, 1H), 6.94 (d, J=7.9 Hz, 1H), 4.20 (dd, J=12.3, 2.5 Hz, 1H), 3.89-3.81 (m, 2H), 3.49 (bs, 1H), 3.07 (bs, 3H), 2.68-2.63 (m, 1H).

Step 5

Synthesis of (S)-tert-butyl 4-(3-(4-chlorobenzyl)-2,3-dihydrobenzo[f][1,4]oxazepin-4(5H)-yl)piperidine-1-carboxylate (59e)

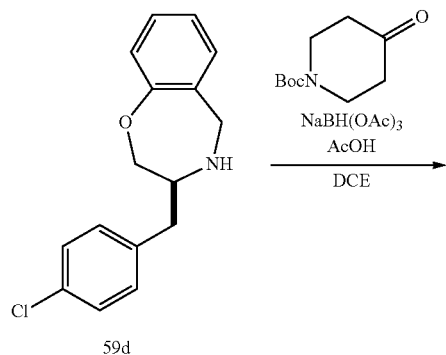

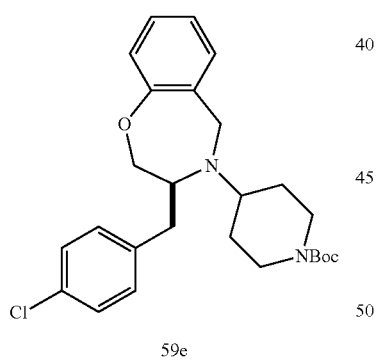

The title compound was prepared from compound 59d (150 mg; 0.55 mmol) according to the General Procedure VI and was obtained as a transparent solid (46 mg; 0.10 mmol; 18% yield).

ESI-MS m/z for $C_{26}H_{33}ClN_2O_3$ found 457.1 $(M+1)^+$.

$^1$H NMR (DMSO-d$_6$+D$_2$O, 700 MHz) δ 7.30 (AA'BB', J=8.4 Hz, 2H), 7.25 (AA'BB', J=7.2 Hz, 2H), 7.13-7.10 (m, 2H), 6.92 (td, J=7.4, 1.1 Hz, 1H), 6.82 (d, J=7.9 Hz, 1H), 4.40 (d, J=16.8 Hz, 1H), 4.13-4.08 (m, 2H), 3.78 (s, 1H), 3.72 (d, J=17.0 Hz, 1H), 3.62-3.59 (m, 1H), 3.47 (bs, 1H), 3.39-3.35 (m, 1H), 2.71 (d, J=6.4 Hz, 2H), 2.58-2.54 (m, 2H), 1.54 (d, J=12.9 Hz, 1H), 1.47 (d, J=11.8 Hz, 1H), 1.32 (s, 9H), 1.03 (m, 1H), 0.88 (bs, 1H).

Step 6

Synthesis of (S)-3-(4-chlorobenzyl)-4-(piperidin-4-yl)-2,3,4,5-tetrahydrobenzo[f][1,4]oxazepine dihydrochloride (59f)

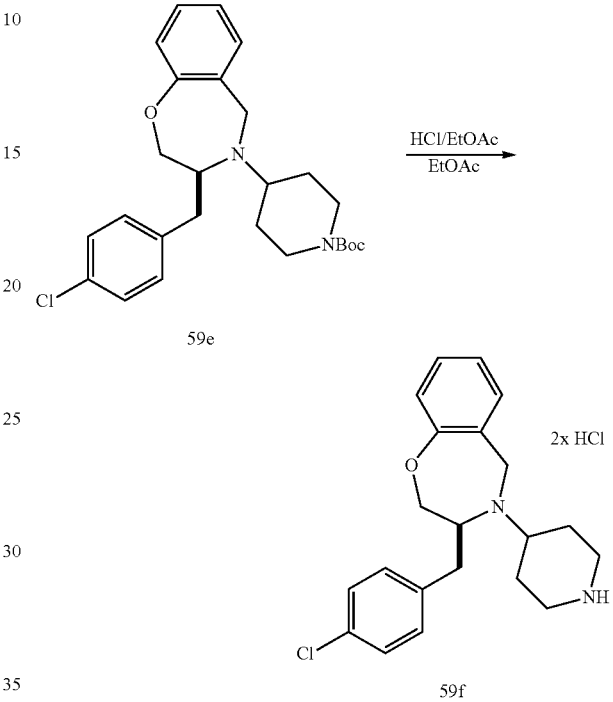

The title compound 59f was synthesized from compound 59e (46 mg; 0.10 mmol) according to the General Procedure VII and was obtained as a white powder (43 mg; 0.10 mmol; 99% yield).

ESI-MS m/z for $C_{21}H_{25}ClN_2O$ found 357.1 $(M+1)^+$.

Step 7

Synthesis of (S)-3-(4-(3-(4-chlorobenzyl)-2,3-dihydrobenzo[f][1,4]oxazepin-4(5H)-yl)piperidin-1-yl)-1H-1,2,4-triazol-5-amine (59)

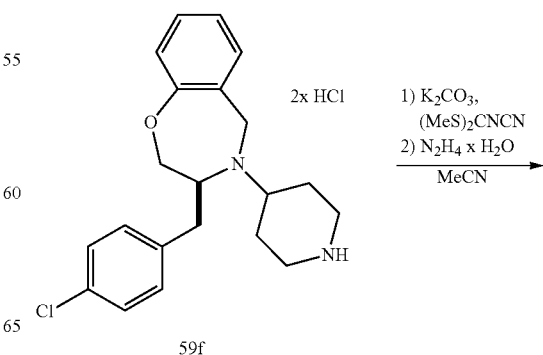

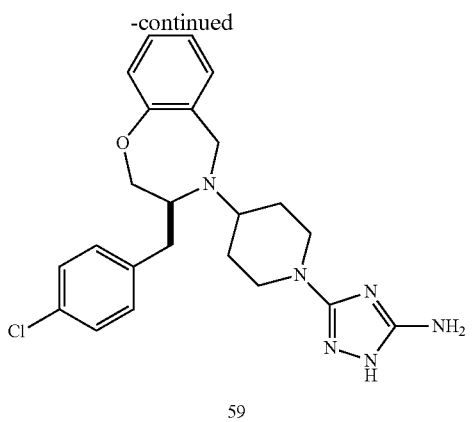

59

The title compound 59 was synthesized from compound 59f (43 mg; 0.10 mmol) according the to the General Procedure VIII. It was purified by reversed-phase chromatography and was obtained as TFA-salt (28 mg; 0.06 mmol; 63% yield).

ESI-MS m/z for $C_{23}H_{27}ClN_6O$ found 439.0 (M+1)$^+$.

$^1$H NMR (DMSO-d$_6$+D$_2$O, 700 MHz) δ 7.34 (m, 3H), 7.29-7.27 (m, 3H), 7.02 (t, J=7.2 Hz, 1H), 6.97 (d, J=8.0 Hz, 1H), 4.57-4.51 (m, 2H), 4.28 (bs, 1H), 3.91-3.87 (m, 2H), 3.74-3.72 (m, 2H), 3.46 (bs, 1H), 3.21 (bs, 1H), 3.10-3.06 (m, 1H), 2.81 (t, J=12.2 Hz, 1H), 2.72 (s, 1H), 2.08-1.94 (m, 2H), 1.70-1.62 (m, 2H).

Example 60

(S)-5-(4-(3-(4-chlorobenzyl)-7-fluoro-2,3-dihydrobenzo[f][1,4]oxazepin-4(5H)-yl)piperidin-1-yl)-4H-1,2,4-triazol-3-amine (60)

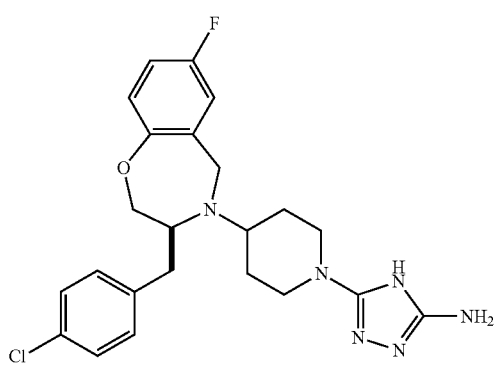

The title compound 60 was prepared in the same manner as Example 59 with the exception that 5-fluorosalicylic acid instead of salicylic acid was used in the first synthetic step.

ESI-MS m/z for $C_{23}H_{26}ClFN_6O$ found 457.1/459.1 (M+1)$^+$.

$^1$H NMR (MeOH-d$_4$, 400 MHz) δ: 7.27 (AA'BB', J=8.7 Hz, 2H), 7.24 (AA'BB', J=8.7 Hz, 2H), 6.90 (dd, J=8.5, 2.2 Hz, 1H), 6.87-6.80 (m, 2H), 4.49 (d, J=16.6 Hz, 1H), 4.16-4.07 (m, 2H), 3.81 (d, J=16.7 Hz, 1H), 3.67-3.59 (m, 1H), 3.58-3.50 (m, 1H), 3.48-3.40 (m, 1H), 2.86 (dd, J=13.4, 6.5 Hz, 1H), 2.81 (dd, J=13.3, 7.7 Hz, 1H), 2.73-2.55 (m, 3H), 1.78-1.70 (m, 1H), 1.68-1.60 (m, 1H), 1.44-1.21 (m, 2H).

Example 61

(S)-5-(4-(7-chloro-3-(4-chlorobenzyl)-2,3-dihydrobenzo[f][1,4]oxazepin-4(5H)-yl)piperidin-1-yl)-4H-1,2,4-triazol-3-amine (61)

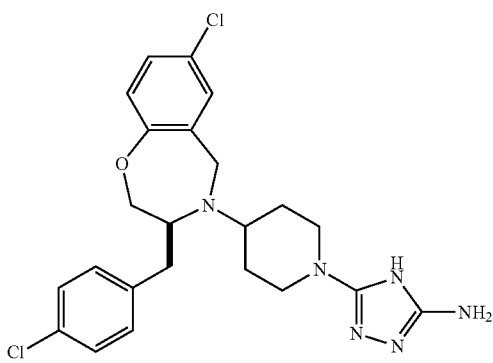

The title compound 59 was prepared in the same manner as Example 59 with the exception that 5-chlorosalicylic acid instead of salicylic acid was used in the first synthetic step.

ESI-MS m/z for $C_{23}H_{26}Cl_2N_6O$ found 473.1/475.1 (M+1)$^+$.

$^1$H NMR (MeOH-d$_4$, 400 MHz) δ: 7.26 (AA'BB', J=8.7 Hz, 2H), 7.22 (AA'BB', J=8.7 Hz, 2H), 7.13 (d, J=2.6 Hz, 1H), 7.08 (dd, J=8.5, 2.6 Hz, 1H), 6.82 (d, J=8.5 Hz, 1H), 4.47 (d, J=16.8 Hz, 1H), 4.20-4.12 (m, 2H), 3.81 (d, J=16.8 Hz, 1H), 3.66-3.58 (m, 1H), 3.58-3.51 (m, 1H), 3.50-3.42 (m, 1H), 2.80 (dd, J=13.4, 6.4 Hz, 1H), 2.76 (dd, J=13.4, 7.7 Hz, 1H), 2.71-2.53 (m, 3H), 1.74-1.66 (m, 1H), 1.66-1.58 (m, 1H), 1.44-1.19 (m, 2H).

Example 62

(S)-5-(4-(7,9-dichloro-3-(4-chlorobenzyl)-2,3-dihydrobenzo[f][1,4]oxazepin-4(5H)-yl)piperidin-1-yl)-4H-1,2,4-triazol-3-amine (62)

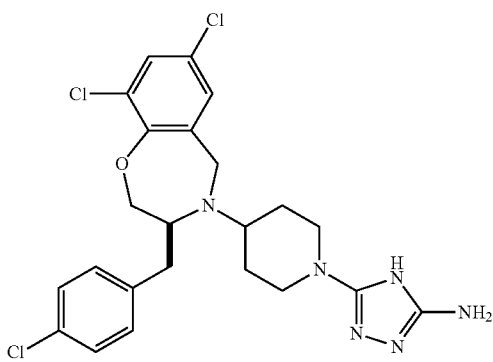

The title compound was prepared in the same manner as Example 59 with the exception that 3,5-dichlorosalicylic acid instead of salicylic acid was used in the first synthetic step.

ESI-LCMS: m/z for $C_{23}H_{25}Cl_3N_6O$ found 255.2 (M+2)$^{2+}$, 509.2 (M+1)$^+$.

$^1$H NMR (MeOH-d$_4$, 400 MHz) δ: 7.30-7.20 (m, 5H), 7.12 (d, J=2.5 Hz, 1H), 4.52 (d, J=16.7 Hz, 1H), 4.26 (dd,

J=13.1, 7.2 Hz, 1H), 4.21 (dd, J=13.2, 4.5 Hz, 1H), 3.85 (d, J=16.8 Hz, 1H), 3.67-3.44 (m, 3H), 2.81 (d, J=7.0 Hz, 2H), 2.75-2.48 (m, 3H), 1.70-1.63 (m, 1H), 1.63-1.55 (m, 1H), 1.38-1.22 (m, 2H).

Hz, 2H), 7.17 (AA'BB', J=6.8 Hz, 2H), 5.36 (d, J=7.8 Hz, 1H), 4.21-4.01 (m, 3H), 3.98 (s, 3H), 3.07-2.93 (m, 2H), 1.42 (s, 9H).

Example 63

(S)-5-(4-(3-(4-chlorobenzyl)-2,3-dihydropyrido[4,3-f][1,4]oxazepin-4(5H)-yl)piperidin-1-yl)-4H-1,2,4-triazol-3-amine (63)

Step 2

Synthesis of (S)-methyl 3-(2-amino-3-(4-chlorophenyl)propoxy)isonicotinate (63b)

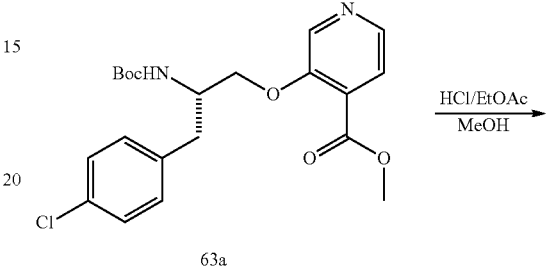

Step 1

Synthesis of (S)-methyl 3-(2-((tert-butoxycarbonyl)amino)-3-(4-chlorophenyl)propoxy)isonicotinate (63a)

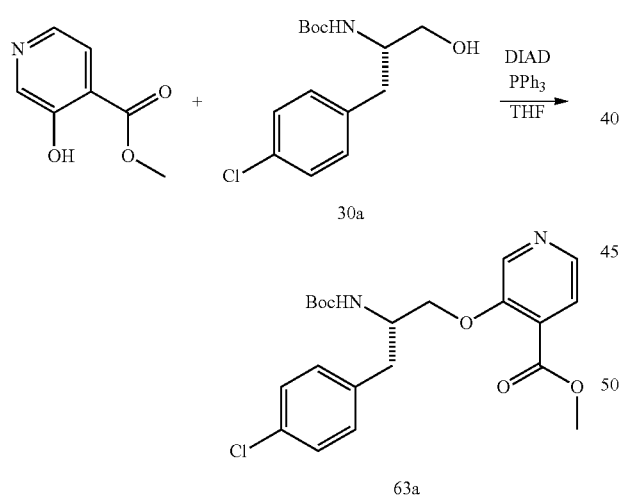

The title compound was prepared from methyl 3-hydroxy-4-pyridinecarboxylate (495 mg; 3.232 mmol) and compound 30a (967 mg; 3.394 mmol) according to the General Procedure XXII. In order to increase yield 2 equivalents of triphenylphosphine (1.98 g; 6.788 mmol) and DIAD (1.34 mL; 6.788 mmol) were used. Purification on silica-gel column chromatography (petroleum ether/AcOEt system) afforded the title product as a white solid (1.0 g; 2.375 mmol; 73% yield).

$^1$H NMR (CDCl$_3$, 400 MHz) δ: 8.37 (d, J=4.8 Hz, 1H), 8.34 (s, 1H), 7.66 (d, J=4.6 Hz, 1H), 7.25 (AA'BB', J=6.7

The title compound was synthesized from compound 63a (990 mg; 2.352 mmol) according to the General Procedure VII and was obtained as a solid (840 mg; 2.351 mmol; 99% yield) which was used in the next step without additional purification.

ESI-LCMS: m/z for $C_{16}H_{17}ClN_2O_3$ found 321.1 (M+1)$^+$.

Step 3

Synthesis of (S)-3-(4-chlorobenzyl)-3,4-dihydropyrido[4,3-f][1,4]oxazepin-5(2H)-one (63c)

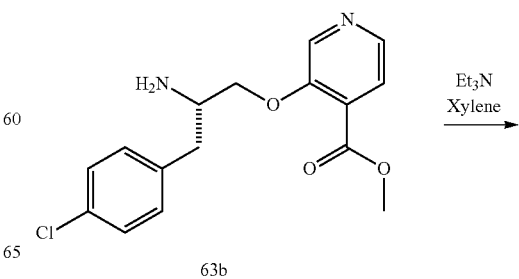

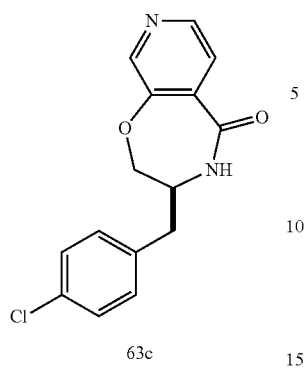

63c

To the suspension of the crude 63b (840 mg; 2.351 mmol) in xylene (23 mL) triethylamine (8 mL; 58.78 mmol) was added and the mixture was heated at reflux for 4 hours. After this time reaction was completed as indicated by TLC (DCM/MeOH 10:1). The mixture was concentrated and the product, after crystallization from MeOH, was obtained as a white solid (354 mg; 1.226 mmol). The filtrate was concentrated and subjected cyclization and crystallization in the same manner as described above to afford a second crop of the product (96 mg; 0.332 mmol) with total yield of 66% (440 mg; 1.558 mmol).

ESI-LCMS: m/z for $C_{15}H_{13}ClN_2O_2$ found 289.1 (M+1)$^+$.

$^1$H NMR (CDCl$_3$, 400 MHz) δ: 8.49 (s, 1H), 8.35 (d, J=5.2 Hz, 1H), 8.00 (d, J=5.2 Hz, 1H), 7.32 (d, J=8.3 Hz, 2H), 7.16 (d, J=8.2 Hz, 2H), 6.77 (bs, 1H), 4.40-4.29 (m, 2H), 3.89-3.78 (m, 1H), 2.94 (dd, J=13.8, 7.0 Hz, 1H), 2.84 (dd, J=13.9, 8.3 Hz, 1H).

Step 4

Synthesis of (S)-3-(4-chlorobenzyl)-2,3,4,5-tetrahydropyrido[4,3-f][1,4]oxazepine (63d)

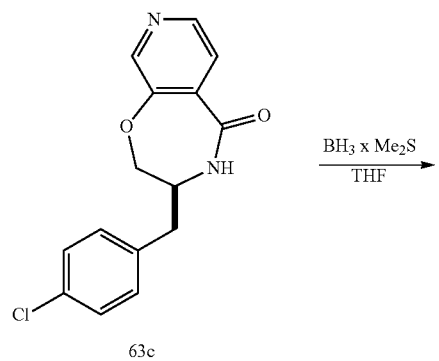

63c

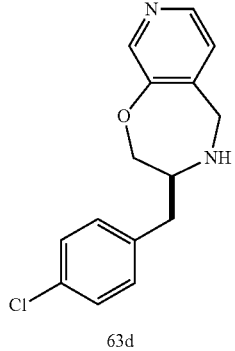

63d

The title compound was synthesized from compound 63c (441 mg; 1.527 mmol) according to the General Procedure V and was obtained as an oil (415 mg; 1.510 mmol; 99% yield).

ESI-LCMS: m/z for $C_{15}H_{15}ClN_2O$ found 275.1 (M+1)$^+$.

Step 5

Synthesis of (S)-tert-butyl 4-(3-(4-chlorobenzyl)-2,3-dihydropyrido[4,3-f][1,4]oxazepin-4(5H)-yl)piperidine-1-carboxylate (63e)

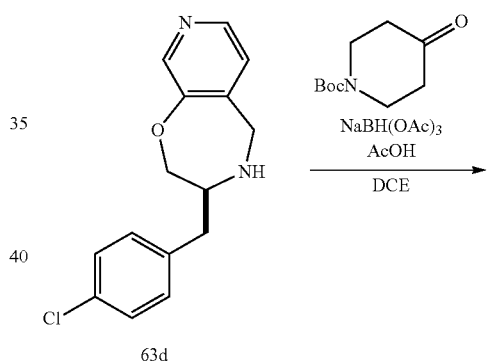

63d

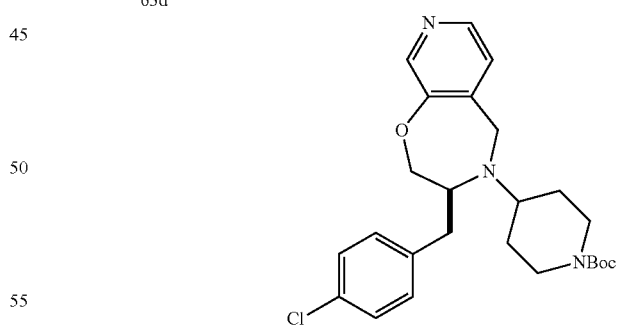

63e

The title compound was prepared from compound 63e (410 mg; 1.492 mmol) according to the General Procedure VI and was obtained as a glass (207 mg; 0.451 mmol; 29% yield).

ESI-LCMS: m/z for $C_{25}H_{32}ClN_3O_3$ found 402.2 (M+1$^t$Bu)$^+$, 458.3 (M+1)$^+$.

$^1$H NMR (CDCl$_3$, 400 MHz) δ: 8.21 (s, 1H), 8.16 (d, J=4.8 Hz, 1H), 7.27 (AA'BB', J=8.8 Hz, 2H), 7.14 (AA'BB',

J=8.4 Hz, 2H), 6.95 (d, J=4.8 Hz, 1H), 4.34 (d, J=17.1 Hz, 1H), 4.20-4.10 (m, 2H), 3.78 (d, J=17.2 Hz, 1H), 3.51-3.41 (m, 1H), 2.79 (dd, J=13.5, 6.8 Hz, 1H), 2.72 (dd, J=13.5, 7.0 Hz, 1H), 2.66-2.47 (m, 3H), 1.65-1.50 (m, 3H), 1.42 (s, 9H), 1.29-1.11 (m, 3H).

Step 6

Synthesis of (S)-3-(4-chlorobenzyl)-4-(piperidin-4-yl)-2,3,4,5-tetrahydropyrido[4,3-f][1,4]oxazepine (63f)

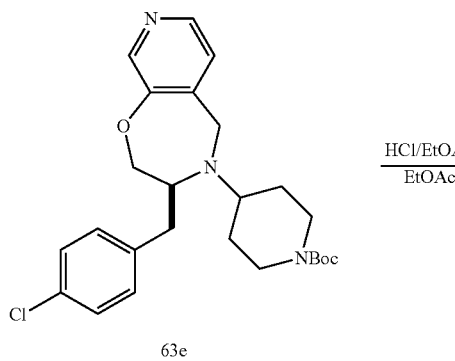

63e

HCl/EtOAc
———————→
EtOAc

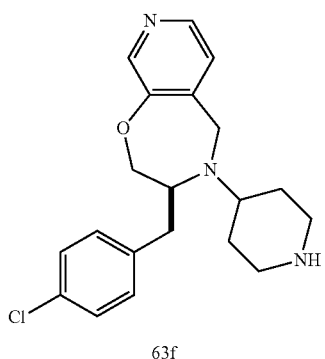

63f

To the solution of compound 63e (201 mg; 0.438 mmol) in MeOH (1 mL) 6 M HCl aqueous solution (2 mL) was added and the mixture was stirred for 16 hours. After this time TLC (DCM/MeOH 10:1) showed completion of the reaction. The mixture was alkalized with 4 N NaOH to adjust pH to ~14 and the product was extracted with DCM (4×10 mL). Combined organic solutions were dried over anhydrous MgSO$_4$ and concentrated. The crude product was obtained as an oil (154 mg; 0.430 mmol; 98% yield) and was used in the next step without additional purification.

Step 7

Synthesis of (S)-5-(4-(3-(4-chlorobenzyl)-2,3-dihydropyrido[4,3-f][1,4]oxazepin-4(5H)-yl)piperidin-1-yl)-4H-1,2,4-triazol-3-amine (63)

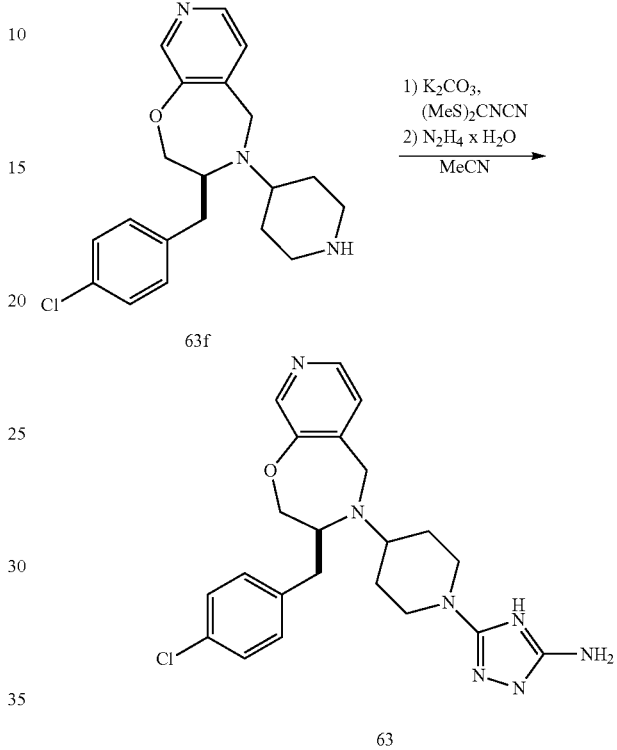

The title compound 63 was synthesized from compound 63f (154 mg; 0.430 mmol) according to the General Procedure VIII. It was purified by silica-gel chromatography in AcOEt/MeOH system and was obtained as a white solid (140 mg; 0.318 mmol; 72% yield).

ESI-LCMS: m/z for $C_{22}H_{26}ClN_7O$ found 220.7 (M+2)$^{2+}$, 440.2 (M+1)$^+$.

$^1$H NMR (MeOH-d$_4$, 400 MHz) δ: 8.07 (s, 1H), 8.06 (d, J=5.0 Hz, 1H), 7.27 (AA'BB', J=8.7 Hz, 2H), 7.24 (AA'BB', J=8.7 Hz, 2H), 7.19 (d, J=5.0 Hz, 1H), 4.52 (d, J=17.3 Hz, 1H), 4.29 (dd, J=13.1, 5.4 Hz, 1H), 4.25 (dd, J=13.1, 7.4 Hz, 1H), 3.92 (d, J=17.2 Hz, 1H), 3.67-3.49 (m, 3H), 2.78 (dd, J=13.4, 6.3 Hz, 1H), 2.74 (dd, J=13.4, 7.5 Hz, 1H), 2.70-2.44 (m, 3H), 1.69-1.55 (m, 2H), 1.35-1.19 (m, 2H).

INCORPORATION BY REFERENCE

All U.S. patents, U.S. published patent applications, and PCT published patent applications designating the U.S. mentioned herein are hereby incorporated by reference in their entirety as if each individual publication or patent was specifically and individually indicated to be incorporated by reference. In case of conflict, the present application, including any definitions herein, will control.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by formula (I),

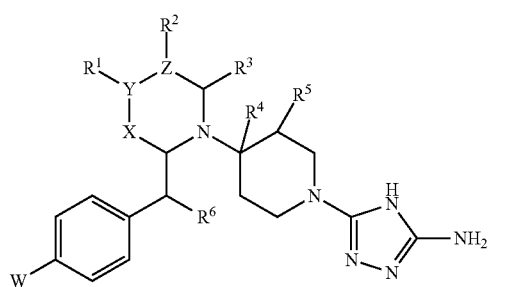

wherein:

W is halo, $(C_1-C_3)$alkyl, $(C_1-C_3)$alkoxy-, or $(C_1-C_3)$alkylthio-;

X is a single bond, —$CH_2$—, —$CH_2CH_2$—, —CH=CH—, —$C((C_1-C_3)$alkyl$)_2$-, or —C(O)—;

Y is a single bond, —CH—, —$CHCH_2$—, —$CH_2CH$—, —C=CH—, —CH=C—, —N—, —O—, —$OCH_2$—, —S(O)—, or —$S(O)_2$—;

if Y is a single bond, —O—, —$OCH_2$—, —S(O)—, or —$S(O)_2$—, then $R^1$ is absent;

$R^1$ is H, OH, $(C_1-C_6)$alkyl, $(C_1-C_6)$haloalkyl, $(C_1-C_6)$alkoxy, $(C_1-C_6)$hydroxyalkyl, $(C_1-C_6)$alkoxy$(C_1-C_6)$alkyl, aryl$(C_1-C_6)$alkyl, heteroaryl$(C_1-C_6)$alkyl, —C(O)$(C_1-C_6)$alkyl, —C(O)aryl, —C(O)heteroaryl, —C(O)aryl$(C_1-C_6)$alkyl, —C(O)heteroaryl$(C_1-C_6)$alkyl, —$S(O)_2(C_1-C_6)$alkyl, —$S(O)_2$aryl, —$S(O)_2$heteroaryl, —$S(O)_2$aryl$(C_1-C_6)$alkyl, —$S(O)_2$heteroaryl$(C_1-C_6)$alkyl, —$CO_2$H, —C(O)O$(C_1-C_6)$alkyl, —C(O)O(aryl), —C(O)O(heteroaryl), —C(O)O(aryl$(C_1-C_6)$alkyl), —C(O)O(heteroaryl$(C_1-C_6)$alkyl), —C(O)$NH_2$, —C(O)NHOH, —C(O)NHCN, —C(O)NH$((C_1-C_6)$alkyl), —C(O)N$((C_1-C_6)$alkyl$)_2$, —C(O)NH(aryl$(C_1-C_6)$alkyl), —C(O)N(aryl$(C_1-C_6)$alkyl$)_2$, —C(O)NH(aryl), —C(O)N(aryl)$((C_1-C_6)$alkyl), —C(O)N(aryl)$_2$, —C(O)N$(C_1-C_6)$alkyl)(aryl$(C_1-C_6)$alkyl), —C(O)N(aryl)(aryl$(C_1-C_6)$alkyl), —C(O)NH$((C_1-C_6)$haloalkyl), —C(O)N$((C_1-C_6)$haloalkyl$)_2$, —$S(O)_2NH_2$, —$S(O)_2$NH$((C_1-C_6)$alkyl), —$S(O)_2$NH$((C_1-C_6)$haloalkyl), —$S(O)_2$NH(aryl), —$S(O)_2$NH(heteroaryl$(C_1-C_6)$alkyl), —$S(O)_2$NH(heteroaryl), —$S(O)_2$N$((C_1-C_6)$alkyl$)_2$, —$S(O)_2$NHC(O)$(C_1-C_6)$alkyl, —$S(O)_2$NHC(O)$(C_1-C_6)$haloalkyl, —$S(O)_2$NHC(O)aryl, —$S(O)_2$NHC(O)aryl$(C_1-C_6)$alkyl, —$S(O)_2$NHC(O)heteroaryl, —$S(O)_2$NHC(O)heteroaryl$(C_1-C_6)$alkyl, —$NHS(O)_2(C_1-C_6)$alkyl, —$NHS(O)_2$aryl, $NHS(O)_2(C_1-C_6)$haloalkyl, —$NHS(O)_2$aryl$(C_1-C_6)$alkyl, —$NHS(O)_2$heteroaryl, —$NHS(O)_2$heteroaryl$(C_1-C_6)$alkyl, —NHC(O)$((C_1-C_6)$alkyl), —NHC(O)$((C_1-C_6)$haloalkyl), —NHC(O)(aryl), —NHC(O)(aryl$(C_1-C_6)$alkyl), —NHC(O)(heteroaryl), —NHC(O)(heteroaryl$(C_1-C_6)$alkyl), —NHC(O)NH$(C_1-C_6)$alkyl), —NHC(O)NH(aryl), —NHC(O)NH(aryl$(C_1-C_6)$alkyl), —NHC(O)NH(heteroaryl), —NHC(O)NH(heteroaryl$(C_1-C_6)$alkyl), —C(O)NHS$(O)_2(C_1-C_6)$alkyl, —C(O)NHS$(O)_2$aryl, C(O)NHS$(O)_2((C_1-C_6)$haloalkyl), —C(O)NHS$(O)_2$(aryl$(C_1-C_6)$alkyl), —C(O)NHS$(O)_2$heteroaryl, —C(O)NHS$(O)_2$(heteroaryl$(C_1-C_6)$alkyl), —P(O)(OH)$_2$, —$((C_1-C_6)$alkylene)C(O)OH, —$((C_1-C_6)$alkylene)C(O)O$(C_1-C_6)$alkyl, —$NH_2$, —NH$(C_1-C_6)$alkyl, —N$((C_1-C_6)$alkyl$)_2$, —NC, —CN, —C(S)$NH_2$, —NHC(O)$NH_2$, —C≡CH,$(C_1-C_6)$alkylthio-, $(C_1-C_6)$mercaptoalkyl-, or —C(O)heterocyclyl;

Z is —CH—, —C(O)—, —C$((C_1-C_3)$alkyl)-, or —C(=$CH_2$)—;

if Z is —C(O)—, then $R^2$ is absent, $R^2$ is H, OH, halo, $(C_1-C_6)$alkyl, $(C_1-C_6)$alkoxy, $(C_1-C_6)$hydroxyalkyl, $(C_1-C_6)$alkoxy$(C_1-C_6)$alkyl, —$CO_2$H, —C(O)O$(C_1-C_6)$alkyl, —C(O)O(aryl), —C(O)O(heteroaryl), —C(O)O(aryl$(C_1-C_6)$alkyl), —C(O)O(heteroaryl$(C_1-C_6)$alkyl), —C(O)NHOH, —C(O)NHCN, —C(O)$NH_2$, —C(O)NH$((C_1-C_6)$alkyl), —C(O)N$((C_1-C_6)$alkyl$)_2$, —C(O)NH(aryl$(C_1-C_6)$alkyl), —C(O)N(aryl$(C_1-C_6)$alkyl$)_2$, —C(O)NH(aryl), —C(O)N(aryl)$((C_1-C_6)$alkyl), —C(O)N(aryl)$_2$, —C(O)N$(C_1-C_6)$alkyl)(aryl$(C_1-C_6)$alkyl), —C(O)N(aryl)(aryl$(C_1-C_6)$alkyl), —C(O)NH$((C_1-C_6)$haloalkyl), —C(O)N$((C_1-C_6)$haloalkyl$)_2$, —$S(O)_2NH_2$, —$S(O)_2$NH$((C_1-C_6)$alkyl), —$S(O)_2$NH$((C_1-C_6)$haloalkyl), —$S(O)_2$NH(aryl), —$S(O)_2$NH(heteroaryl$(C_1-C_6)$alkyl), —$S(O)_2$NH(heteroaryl), —$S(O)_2$NH(heteroaryl$(C_1-C_6)$alkyl), —$S(O)_2$N$((C_1-C_6)$alkyl$)_2$, —$S(O)_2$NHC(O)$(C_1-C_6)$alkyl, —$S(O)_2$NHC(O)$(C_1-C_6)$haloalkyl, —$S(O)_2$NHC(O)aryl, —$S(O)_2$NHC(O)aryl$(C_1-C_6)$alkyl, —$S(O)_2$NHC(O)heteroaryl, —$S(O)_2$NHC(O)heteroaryl$(C_1-C_6)$alkyl, —$NHS(O)_2(C_1-C_6)$alkyl, —$NHS(O)_2$aryl, $NHS(O)_2(C_1-C_6)$haloalkyl, —$NHS(O)_2$aryl$(C_1-C_6)$alkyl, —$NHS(O)_2$heteroaryl, —$NHS(O)_2$heteroaryl$(C_1-C_6)$alkyl, —NHC(O)$((C_1-C_6)$alkyl), —NHC(O)$((C_1-C_6)$haloalkyl), —NHC(O)(aryl), —NHC(O)(aryl$(C_1-C_6)$alkyl), —NHC(O)(heteroaryl), —NHC(O)(heteroaryl$(C_1-C_6)$alkyl), —NHC(O)NH$(C_1-C_6)$alkyl, —NHC(O)NHaryl, —NHC(O)NH(aryl$(C_1-C_6)$alkyl), —NHC(O)NH(heteroaryl), —NHC(O)NH(heteroaryl$(C_1-C_6)$alkyl), —C(O)NHS$(O)_2(C_1-C_6)$alkyl, —C(O)NHS$(O)_2$aryl, C(O)NHS$(O)_2((C_1-C_6)$haloalkyl), —C(O)NHS$(O)_2$(aryl$(C_1-C_6)$alkyl), —C(O)NHS$(O)_2$heteroaryl, —C(O)NHS$(O)_2$(heteroaryl$(C_1-C_6)$alkyl), —P(O)(OH)$_2$, aryl$(C_1-C_6)$alkyl, $(C_3-C_7)$cycloalkyl$(C_1-C_6)$alkyl-, —NC, —CN, —C(S)$NH_2$, —NHC(O)$NH_2$,—C≡CH, $(C_1-C_6)$alkylthio-, $(C_1-C_6)$mercaptoalkyl-, or —C(O)heterocyclyl;

or $R^1$ and $R^2$, taken together with the intervening atoms, form a carbocyclic or heterocyclic ring;

$R^3$ is H, $(C_1-C_3)$alkyl, $(C_1-C_3)$alkoxy$(C_1-C_3)$alkyl, $(C_1-C_3)$alkylthio$(C_1-C_3)$alkyl, $(C_1-C_6)$haloalkyl, —NC, —CN, —C(S)$NH_2$, —NHC(O)$NH_2$, or —C≡CH;

$R^4$ is H, $(C_1-C_3)$alkyl, $(C_1-C_3)$alkylthio$(C_1-C_3)$alkyl, $(C_1-C_6)$haloalkyl, $(C_1-C_3)$alkoxy$(C_1-C_3)$alkyl-, or $(C_1-C_4)$hydroxyalkyl;

$R^5$ is H, halo, —$NO_2$, —CN, $(C_1-C_6)$alkyl, $(C_1-C_6)$haloalkyl, —$NH_2$, —NH$((C_1-C_6)$alkyl), —N$((C_1-C_6)$alkyl$)_2$, —OH, $(C_1-C_6)$alkoxy, hydroxy$(C_1-C_6)$alkyl, $(C_1-C_6)$alkoxy$(C_1-C_6)$alkyl, $(C_1-C_6)$haloalkoxy, —SH, $(C_1-C_3)$alkylthio$(C_1-C_3)$alkyl, —NC, —C(S)$NH_2$, —NHC(O)$NH_2$, or —C≡CH; and $R^6$ is H, halo, —OH, —$NH_2$, or —SH; or $R^6$, taken together with the carbon atom bearing it, represents —C(O)—;
wherein:
  any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of —OH, halo, —NH$_2$, —NH(($C_1$-$C_6$)alkyl), —N(($C_1$-$C_6$)alkyl)$_2$, —CN, —NO$_2$, ($C_1$-$C_6$)alkyl, ($C_1$-$C_6$)haloalkyl, ($C_1$-$C_6$)alkoxy, aryl, heteroaryl, aryl($C_1$-$C_6$)alkyl, heteroaryl($C_1$-$C_6$)alkyl, ($C_3$-$C_7$)cycloalkyl, heterocyclyl, —C(O)OH, —C(O)O($C_1$-$C_6$)alkyl, —C(O)NH$_2$, —C(O)NH($C_1$-$C_6$)alkyl, and —C(O)N(($C_1$-$C_6$)alkyl)$_2$;
or a pharmaceutically acceptable salt, solvate, tautomer, stereoisomer, or polymorph thereof.

2. The compound of claim 1, wherein:
W is halo, ($C_1$-$C_3$)alkyl, ($C_1$-$C_3$)alkoxy-, or ($C_1$-$C_3$)alkylthio-;
X is a single bond, —CH$_2$—, —CH$_2$CH$_2$—, —CH=CH—, or —C(O)—;
Y is a single bond, —CH—, —CHCH$_2$—, —CH$_2$CH—, —C=CH—, —CH=C—, —N—, —O—, —S(O)—, or —S(O)$_2$—;
  if Y is a single bond, —O—, —S(O)—, or —S(O)$_2$—, then $R^1$ is absent;
$R^1$ is H, ($C_1$-$C_6$)alkyl, ($C_1$-$C_6$)haloalkyl, ($C_1$-$C_6$)alkoxy, ($C_1$-$C_6$)hydroxyalkyl, ($C_1$-$C_6$)alkoxy($C_1$-$C_6$)alkyl, aryl($C_1$-$C_6$)alkyl, heteroaryl($C_1$-$C_6$)alkyl, —C(O)($C_1$-$C_6$)alkyl, —C(O)aryl, —C(O)heteroaryl, —C(O)aryl($C_1$-$C_6$)alkyl, —C(O)heteroaryl($C_1$-$C_6$)alkyl, —S(O)$_2$($C_1$-$C_6$)alkyl, —S(O)$_2$aryl, —S(O)$_2$heteroaryl, —S(O)$_2$aryl($C_1$-$C_6$)alkyl, —S(O)$_2$heteroaryl($C_1$-$C_6$)alkyl, —CO$_2$H, —C(O)O($C_1$-$C_6$)alkyl, —C(O)O(aryl), —C(O)O(heteroaryl), —C(O)O(aryl($C_1$-$C_6$)alkyl), —C(O)O(heteroaryl($C_1$-$C_6$)alkyl), —C(O)NH$_2$, —C(O)NHOH, —C(O)NHCN, —C(O)NH(($C_1$-$C_6$)alkyl), —C(O)N(($C_1$-$C_6$)alkyl)$_2$, —C(O)NH(aryl($C_1$-$C_6$)alkyl), —C(O)N(aryl($C_1$-$C_6$)alkyl)$_2$, —C(O)NH(aryl), —C(O)N(aryl)(($C_1$-$C_6$)alkyl), —C(O)N(aryl)$_2$, —C(O)N($C_1$-$C_6$)alkyl)(aryl($C_1$-$C_6$)alkyl), —C(O)NH(($C_1$-$C_6$)haloalkyl), —C(O)N(($C_1$-$C_6$)haloalkyl)$_2$, —S(O)$_2$NH$_2$, —S(O)$_2$NH(($C_1$-$C_6$)alkyl), —S(O)$_2$NH(($C_1$-$C_6$)haloalkyl), —S(O)$_2$NH(aryl), —S(O)$_2$NH(heteroaryl($C_1$-$C_6$)alkyl), —S(O)$_2$NH(heteroaryl), —S(O)$_2$N(($C_1$-$C_6$)alkyl)$_2$, —S(O)$_2$NHC(O)($C_1$-$C_6$)alkyl, —S(O)$_2$NHC(O)($C_1$-$C_6$)haloalkyl, —S(O)$_2$NHC(O)aryl, —S(O)$_2$NHC(O)aryl($C_1$-$C_6$)alkyl, —S(O)$_2$NHC(O)heteroaryl, —S(O)$_2$NHC(O)heteroaryl($C_1$-$C_6$)alkyl, —NHS(O)$_2$($C_1$-$C_6$)alkyl, —NHS(O)$_2$aryl, —NHS(O)$_2$($C_1$-$C_6$)haloalkyl, —NHS(O)$_2$aryl($C_1$-$C_6$)alkyl, —NHS(O)$_2$heteroaryl, —NHS(O)$_2$heteroaryl($C_1$-$C_6$)alkyl, —NHC(O)(($C_1$-$C_6$)alkyl), —NHC(O)(($C_1$-$C_6$)haloalkyl), —NHC(O)(aryl), —NHC(O)(aryl($C_1$-$C_6$)alkyl), —NHC(O)(heteroaryl), —NHC(O)(heteroaryl($C_1$-$C_6$)alkyl), —NHC(O)NH($C_1$-$C_6$)alkyl, —NHC(O)NH(aryl), —NHC(O)NH(aryl($C_1$-$C_6$)alkyl), —NHC(O)NH(heteroaryl), —NHC(O)NH(heteroaryl($C_1$-$C_6$)alkyl), —C(O)NHS(O)$_2$($C_1$-$C_6$)alkyl, —C(O)NHS(O)$_2$aryl, C(O)NHS(O)$_2$(($C_1$-$C_6$)haloalkyl), —C(O)NHS(O)$_2$(aryl($C_1$-$C_6$)alkyl), —C(O)NHS(O)$_2$heteroaryl, —C(O)NHS(O)$_2$(heteroaryl($C_1$-$C_6$)alkyl), —P(O)(OH)$_2$, —(($C_1$-$C_6$)alkylene)C(O)OH, —(($C_1$-$C_6$)alkylene)C(O)O($C_1$-$C_6$)alkyl, —NH$_2$, —NH($C_1$-$C_6$)alkyl, —N(($C_1$-$C_6$)alkyl)$_2$, —NC, —CN, —C(S)NH$_2$, —NHC(O)NH$_2$, —C≡CH,($C_1$-$C_6$)alkylthio-, ($C_1$-$C_6$)mercaptoalkyl-, or —C(O)heterocyclyl;
Z is —CH—, —C(O)—, or —C(($C_1$-$C_3$)alkyl)-;
  if Z is —C(O)—, then $R^2$ is absent,
$R^2$ is H, halo, ($C_1$-$C_6$)alkyl, ($C_1$-$C_6$)alkoxy, ($C_1$-$C_6$)hydroxyalkyl, ($C_1$-$C_6$)alkoxy($C_1$-$C_6$)alkyl, —CO$_2$H, —C(O)O($C_1$-$C_6$)alkyl, —C(O)O(aryl), —C(O)O(heteroaryl), —C(O)O(aryl($C_1$-$C_6$)alkyl), —C(O)O(heteroaryl($C_1$-$C_6$)alkyl), —C(O)NHOH, —C(O)NHCN, —C(O)NH$_2$, —C(O)NH(($C_1$-$C_6$)alkyl), —C(O)N(($C_1$-$C_6$)alkyl)$_2$, —C(O)NH(aryl($C_1$-$C_6$)alkyl), —C(O)N(aryl($C_1$-$C_6$)alkyl)$_2$, —C(O)NH(aryl), —C(O)N(aryl)(($C_1$-$C_6$)alkyl), —C(O)N(aryl)$_2$, —C(O)N(($C_1$-$C_6$)alkyl)(aryl($C_1$-$C_6$)alkyl), —C(O)N(aryl)(aryl($C_1$-$C_6$)alkyl), —C(O)NH(($C_1$-$C_6$)haloalkyl), —C(O)N(($C_1$-$C_6$)haloalkyl)$_2$, —S(O)$_2$NH$_2$, —S(O)$_2$NH(($C_1$-$C_6$)alkyl), —S(O)$_2$NH(($C_1$-$C_6$)haloalkyl), —S(O)$_2$NH(aryl), —S(O)$_2$NH(heteroaryl($C_1$-$C_6$)alkyl), —S(O)$_2$NH(heteroaryl), —S(O)$_2$NH(heteroaryl($C_1$-$C_6$) alkyl), —S(O)$_2$N(($C_1$-$C_6$)alkyl)$_2$, —S(O)$_2$NHC(O)($C_1$-$C_6$)alkyl, —S(O)$_2$NHC(O)($C_1$-$C_6$)haloalkyl, —S(O)$_2$NHC(O)aryl, —S(O)$_2$NHC(O)aryl($C_1$-$C_6$)alkyl, —S(O)$_2$NHC(O)heteroaryl, —S(O)$_2$NHC(O)heteroaryl($C_1$-$C_6$)alkyl, —NHS(O)$_2$($C_1$-$C_6$)alkyl, —NHS(O)$_2$aryl, NHS(O)$_2$($C_1$-$C_6$)haloalkyl, —NHS(O)$_2$aryl($C_1$-$C_6$)alkyl, —NHS(O)$_2$heteroaryl, —NHS(O)$_2$heteroaryl($C_1$-$C_6$)alkyl, —NHC(O)(($C_1$-$C_6$)alkyl), —NHC(O)(($C_1$-$C_6$)haloalkyl), —NHC(O)(aryl), —NHC(O)(aryl($C_1$-$C_6$)alkyl), —NHC(O)(heteroaryl), —NHC(O)(heteroaryl($C_1$-$C_6$)alkyl), —NHC(O)NH($C_1$-$C_6$)alkyl, —NHC(O)NHaryl, —NHC(O)NH(aryl($C_1$-$C_6$)alkyl), —NHC(O)NH(heteroaryl), —NHC(O)NH(heteroaryl($C_1$-$C_6$)alkyl), —C(O)NHS(O)$_2$($C_1$-$C_6$)alkyl, —C(O)NHS(O)$_2$aryl, C(O)NHS(O)$_2$(($C_1$-$C_6$)haloalkyl), —C(O)NHS(O)$_2$(aryl($C_1$-$C_6$)alkyl), —C(O)NHS(O)$_2$heteroaryl, —C(O)NHS(O)$_2$(heteroaryl($C_1$-$C_6$)alkyl), —P(O)(OH)$_2$, aryl($C_1$-$C_6$)alkyl, ($C_3$-$C_7$)cycloalkyl($C_1$-$C_6$)alkyl-, —NC, —CN, —C(S)NH$_2$, —NHC(O)NH$_2$, —C≡CH, ($C_1$-$C_6$)alkylthio-, ($C_1$-$C_6$)mercaptoalkyl-, or —C(O)heterocyclyl;
$R^3$ is H, ($C_1$-$C_3$)alkyl, ($C_1$-$C_3$)alkoxy($C_1$-$C_3$)alkyl, ($C_1$-$C_3$)alkylthio($C_1$-$C_3$)alkyl, ($C_1$-$C_6$)haloalkyl, —NC, —CN, —C(S)NH$_2$, —NHC(O)NH$_2$, or —C≡CH;
$R^4$ is H, ($C_1$-$C_3$)alkyl, ($C_1$-$C_3$)alkylthio($C_1$-$C_3$)alkyl, ($C_1$-$C_6$)haloalkyl, ($C_1$-$C_3$)alkoxy($C_1$-$C_3$)alkyl-, or ($C_1$-$C_4$)hydroxyalkyl;
$R^5$ is H, halo, —NO$_2$, —CN, ($C_1$-$C_6$)alkyl, ($C_1$-$C_6$)haloalkyl, —NH$_2$, —NH(($C_1$-$C_6$)alkyl), —N(($C_1$-$C_6$)alkyl)$_2$, —OH, ($C_1$-$C_6$)alkoxy, hydroxy($C_1$-$C_6$)alkyl, ($C_1$-$C_6$)alkoxy($C_1$-$C_6$)alkyl, ($C_1$-$C_6$)haloalkoxy, —SH, ($C_1$-$C_3$)alkylthio($C_1$-$C_3$)alkyl, —NC, —C(S)NH$_2$, —NHC(O)NH$_2$, or —C≡CH; and
$R^6$ is H, halo, —OH, —NH$_2$, or —SH; or
$R^6$, taken together with the carbon atom bearing it, represents —C(O)—;
wherein:
  any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more sub stituents independently selected from the group consisting of —OH, halo, —NH$_2$, —NH(($C_1$-$C_6$)alkyl), —N(($C_1$-$C_6$)alkyl)$_2$, —CN, —NO$_2$, ($C_1$-$C_6$)alkyl, ($C_1$-$C_6$)haloalkyl, ($C_1$-$C_6$)alkoxy, aryl, heteroaryl, aryl($C_1$-$C_6$)alkyl, heteroaryl($C_1$-$C_6$)alkyl, ($C_3$-$C_7$)cycloalkyl, heterocyclyl, —C(O)OH, —C(O)O($C_1$-$C_6$)alkyl, —C(O)$NH_2$, —C(O)NH($C_1$-$C_6$)alkyl, and —C(O)N(($C_1$-$C_6$)alkyl)$_2$.

3. The compound of claim 1, wherein W is fluoro, chloro, bromo, methyl, or methoxy.

4. The compound of claim 1, wherein $R^6$ is H or —OH.

5. The compound of claim 1, wherein X is a single bond, —$CH_2$—, or —C(O)—.

6. The compound of claim 1, wherein Y is a single bond, —CH—, —N—, —O—, or —S(O)$_2$—.

7. The compound of claim 1, wherein Y is —CH— or —N—.

8. The compound of claim 7, wherein $R^1$ is H or ($C_1$-$C_6$) alkyl.

9. The compound of claim 7, wherein $R^1$ is —C(O) heterocyclyl selected from the group consisting

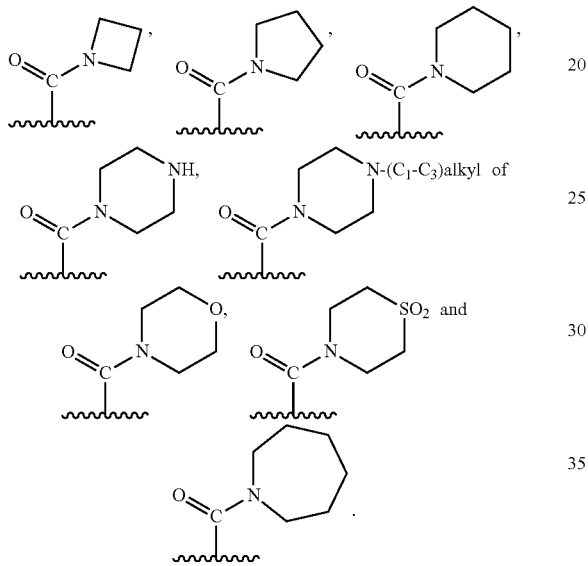

10. The compound of claim 7, wherein $R^1$ is —$CH_2CO_2H$ or —$CH_2C(O)O(C_1$-$C_6)$alkyl.

11. The compound of claim 1, wherein Z is —CH—.

12. The compound of claim 11, wherein $R^2$ is H, halo, ($C_1$-$C_6$)alkyl, ($C_1$-$C_6$)alkoxy, ($C_1$-$C_6$)hydroxyalkyl, ($C_1$-$C_6$) alkoxy($C_1$-$C_6$)alkyl, —$CO_2H$, —C(O)O($C_1$-$C_6$)alkyl, —C(O)O(aryl), —C(O)O(heteroaryl), —C(O)O(aryl($C_1$-$C_6$)alkyl), —C(O)O(heteroaryl($C_1$-$C_6$)alkyl), —C(O)$NH_2$, —C(O)NH(($C_1$-$C_6$)alkyl), —C(O)N(($C_1$-$C_6$)alkyl)$_2$, —C(O)NH(aryl($C_1$-$C_6$)alkyl), —C(O)N(aryl($C_1$-$C_6$) alkyl)$_2$, —C(O)NH(aryl), —C(O)N(aryl)(($C_1$-$C_6$)alkyl), —C(O)N(aryl)$_2$, —C(O)N($C_1$-$C_6$)alkyl)(aryl($C_1$-$C_6$)alkyl), —C(O)N(aryl)(aryl($C_1$-$C_6$)alkyl), —C(O)NH(($C_1$-$C_6$)haloalkyl), —C(O)N(($C_1$-$C_6$)haloalkyl)$_2$, aryl($C_1$-$C_6$)alkyl, ($C_3$-$C_7$)cycloalkyl($C_1$-$C_6$)alkyl-, or —C(O)heterocyclyl.

13. The compound of claim 11, wherein $R^2$ is H, ($C_1$-$C_6$) alkyl, or ($C_1$-$C_6$)alkoxy($C_1$-$C_6$)alkyl.

14. The compound of claim 11, wherein $R^2$ is —C(O) heterocyclyl selected from the group consisting

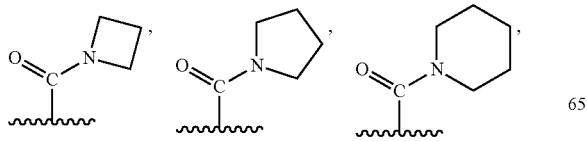

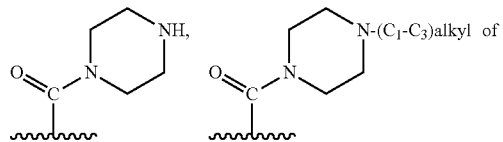

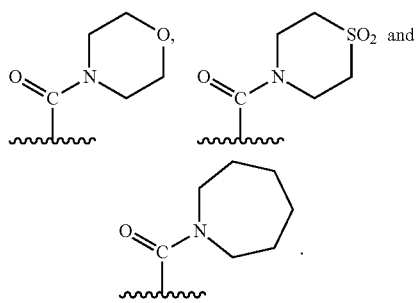

15. The compound of claim 1 represented by formula (I'):

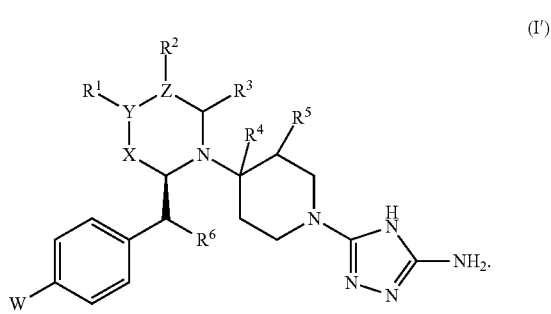

(I')

16. The compound of claim 1, wherein:

W is bromo or chloro;

X is a single bond, —$CH_2$—, or —C(O)—;

Y is a single bond, —CH—, —N—, —O—, or —S(O)$_2$—;

if Y is a single bond, —O—, or —S(O)$_2$—, then $R^1$ is absent;

$R^1$ is H, methyl, isobutyl, methoxy, acetyl, methoxycarbonyl, methanesulfonyl, p-toluenesulfonyl, methoxycarbonylmethyl, or carboxymethyl;

Z is —CH—, —C(O)—, or —C(CH$_3$)—;

if Z is —C(O)—, then $R^2$ is absent;

$R^2$ is H, methyl, ethyl, isopropyl, isobutyl, —C(O)$NH_2$, —C(O)NHMe, —$CH_2OH$, —$CH_2OCH_3$, —$CH_2OCH_2CH_3$, —C(CH$_3$)$_2$OH, —C(CH$_3$)$_2$OCH$_3$, —$CO_2H$, —$CO_2CH_2CH_3$, —$OCH_3$, —F, —$CH_2$-(p-chlorophenyl), or —$CH_2$-cyclohexyl;

$R^3$, $R^4$, and $R^5$ are each H; and $R^6$ is H or OH.

17. A compound represented by formula (II),

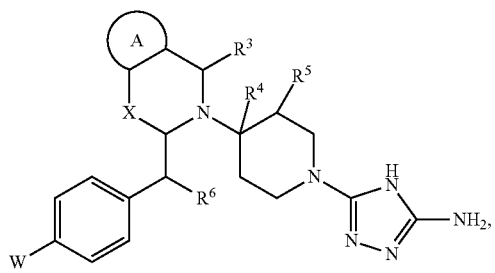

wherein:
W is halo, $(C_1-C_3)$alkyl, $(C_1-C_3)$alkoxy-, or $(C_1-C_3)$alkylthio-;
X is a single bond, —$CH_2$—, —$CH_2CH_2$—, —CH=CH—, —C($(C_1-C_3)$alkyl)$_2$-, —C(O)—, —$CH_2$O—, —$CH_2$NH—, or —$CH_2$N($(C_1-C_3)$alkyl)-, wherein when X is —$CH_2$O—, —$CH_2$NH—, or —$CH_2$N($(C_1-C_3)$alkyl)-, then the O or N atom is covalently bonded to Ring A;
Ring A represents an optionally substituted aryl or heteroaryl ring;
$R^3$ is H, $(C_1-C_3)$alkyl, $(C_1-C_3)$alkoxy$(C_1-C_3)$alkyl, $(C_1-C_3)$alkylthio$(C_1-C_3)$alkyl, $(C_1-C_6)$haloalkyl, —NC, —CN, —C(S)$NH_2$, —NHC(O)$NH_2$, or —C≡CH;
$R^4$ is H, $(C_1-C_3)$alkyl, $(C_1-C_3)$alkylthio$(C_1-C_3)$alkyl, $(C_1-C_6)$haloalkyl, $(C_1-C_3)$alkoxy$(C_1-C_3)$alkyl-, or $(C_1-C_4)$hydroxyalkyl;
$R^5$ is H, halo, —$NO_2$, —CN, $(C_1-C_6)$alkyl, $(C_1-C_6)$haloalkyl, —$NH_2$, —NH$((C_1-C_6)$alkyl), —N$((C_1-C_6)$alkyl)$_2$, —OH, $(C_1-C_6)$alkoxy, hydroxy$(C_1-C_6)$alkyl, $(C_1-C_6)$alkoxy$(C_1-C_6)$alkyl, $(C_1-C_6)$haloalkoxy, —SH, $(C_1-C_3)$alkylthio$(C_1-C_3)$alkyl, —NC, —C(S)$NH_2$, —NHC(O)$NH_2$, or —C≡CH; and
$R^6$ is H, halo, —OH, —$NH_2$, or —SH; or
$R^6$, taken together with the carbon atom bearing it, represents —C(O)—;
wherein:
any occurrence of alkyl, aryl, arylalkyl, heteroaryl, heteroarylalkyl, alkylene, heterocyclyl, cycloalkyl, alkoxy, alkylthio, haloalkyl, or hydroxyalkyl is optionally substituted with one or more substituents independently selected from the group consisting of —OH, halo, —$NH_2$, —NH$((C_1-C_6)$alkyl), —N$((C_1-C_6)$alkyl)$_2$, —CN, —$NO_2$, $(C_1-C_6)$alkyl, $(C_1-C_6)$haloalkyl, $(C_1-C_6)$alkoxy, aryl, heteroaryl, aryl$(C_1-C_6)$alkyl, heteroaryl$(C_1-C_6)$alkyl, $(C_3-C_7)$cycloalkyl, heterocyclyl, —C(O)OH, —C(O)O$(C_1-C_6)$alkyl, —C(O)$NH_2$, —C(O)NH$(C_1-C_6)$alkyl, and —C(O)N$((C_1-C_6)$alkyl)$_2$;
or a pharmaceutically acceptable salt, solvate, tautomer, stereoisomer, or polymorph thereof.

18. The compound of claim 17, wherein W is fluoro, chloro, bromo, methyl, or methoxy.

19. The compound of claim 17, wherein X is —$CH_2$O—, —$CH_2$NH—, or —$CH_2$N($(C_1-C_3)$alkyl)-.

20. The compound of claim 17, wherein Ring A represents a heteroaryl ring.

21. The compound of claim 17, wherein Ring A represents an optionally substituted phenyl ring.

22. The compound of claim 1 selected from the group consisting of the following structural formulae:

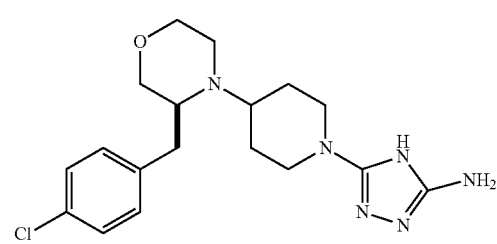

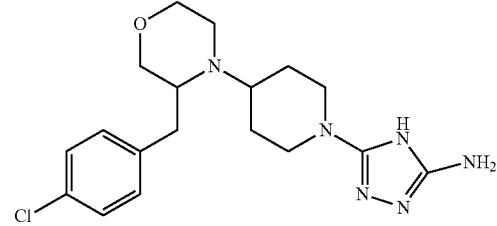

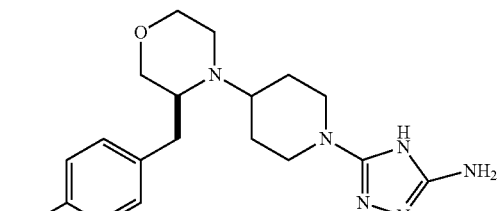

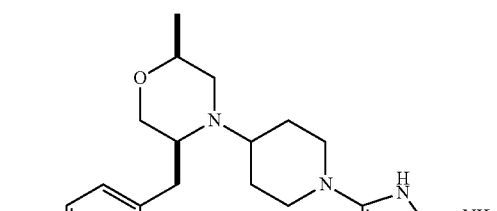

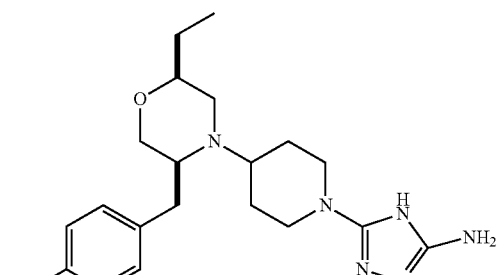

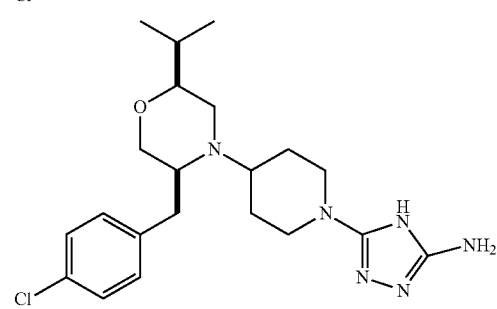

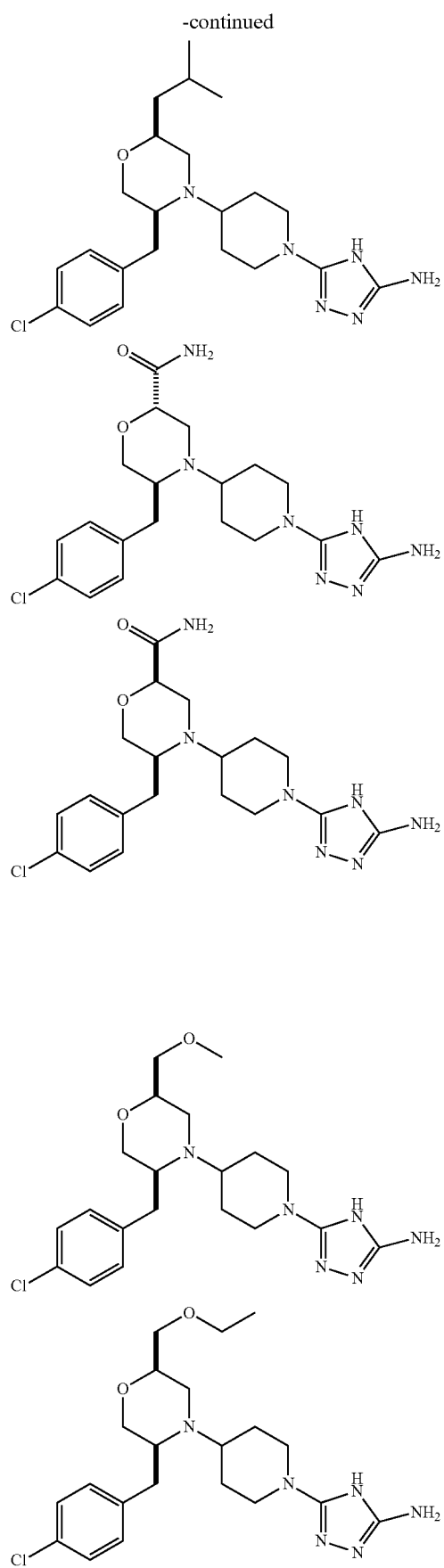
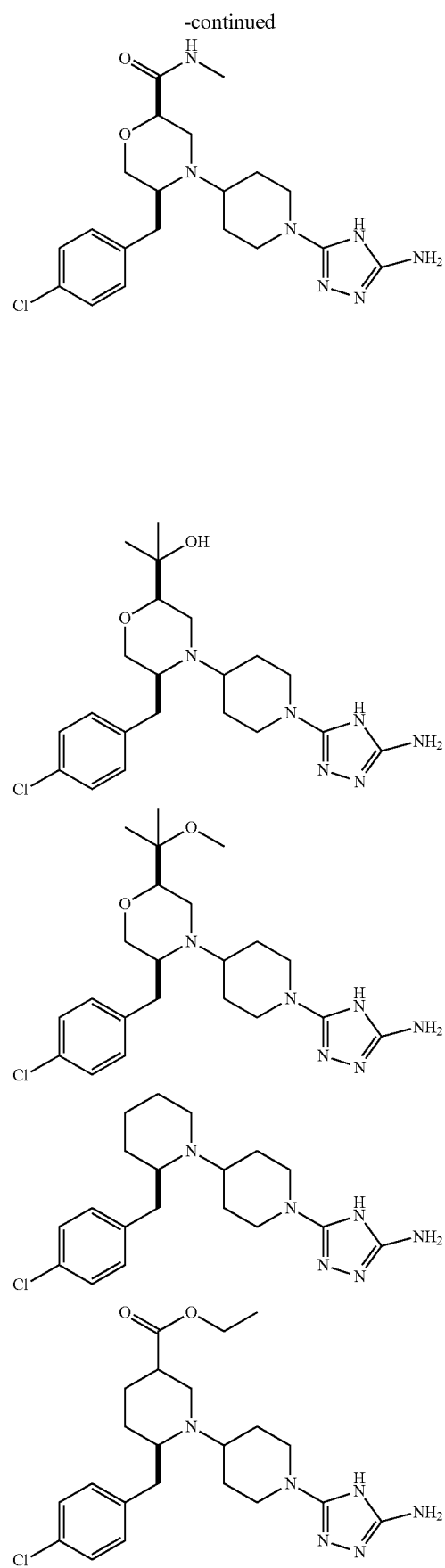

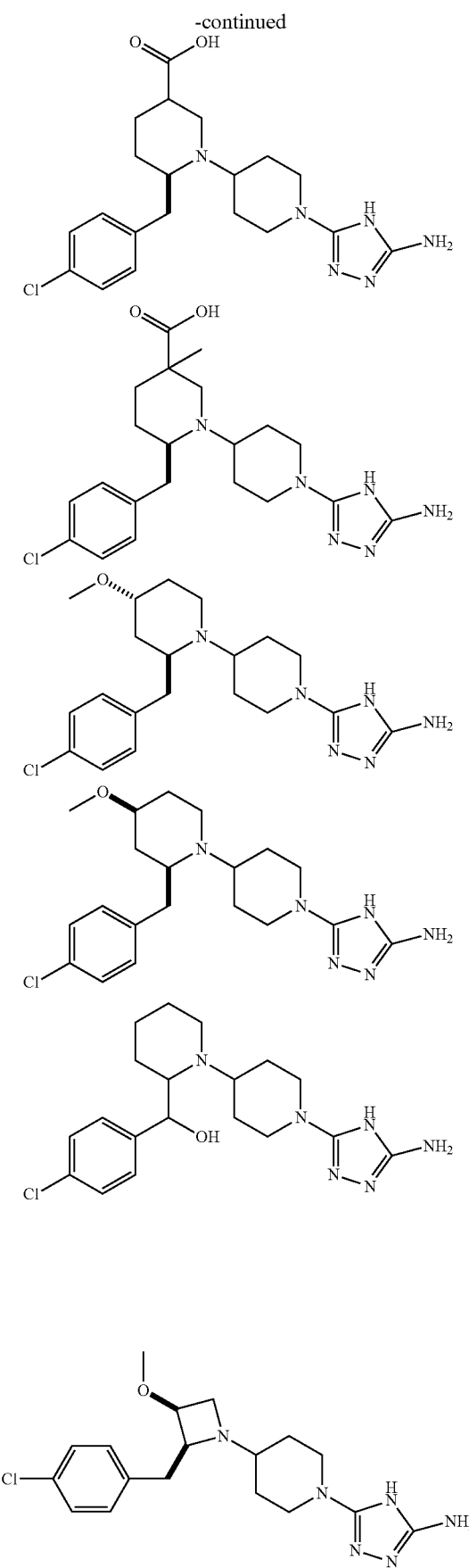
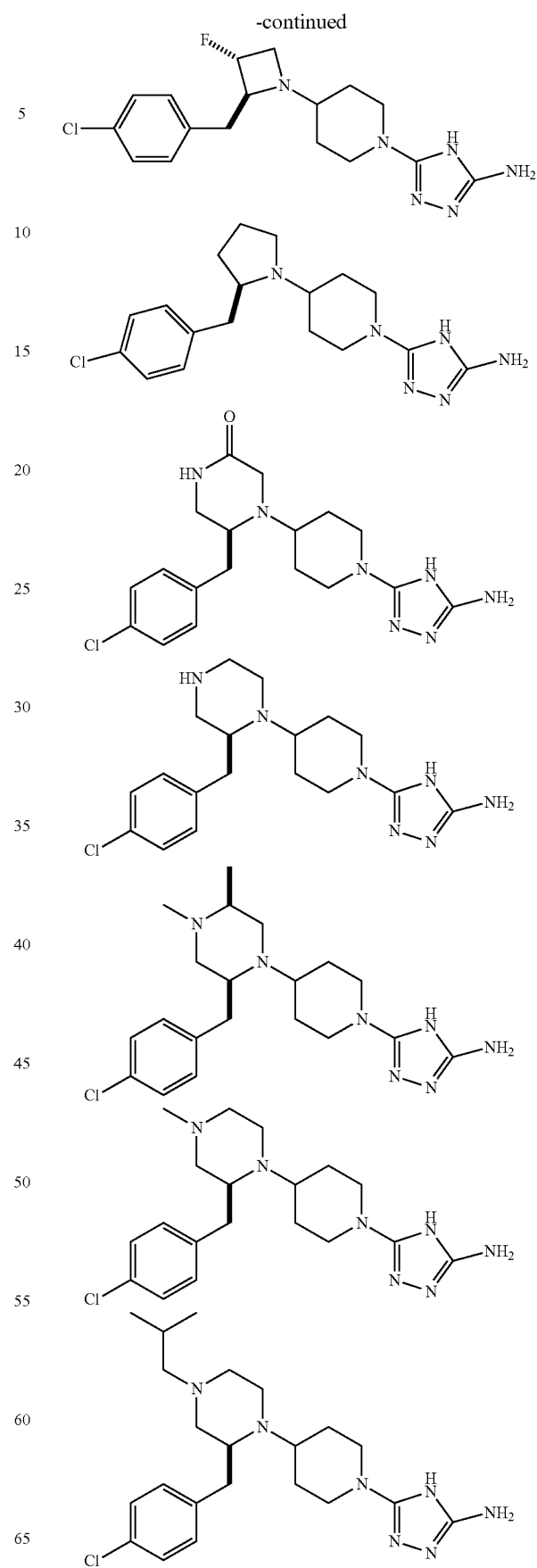

297
-continued
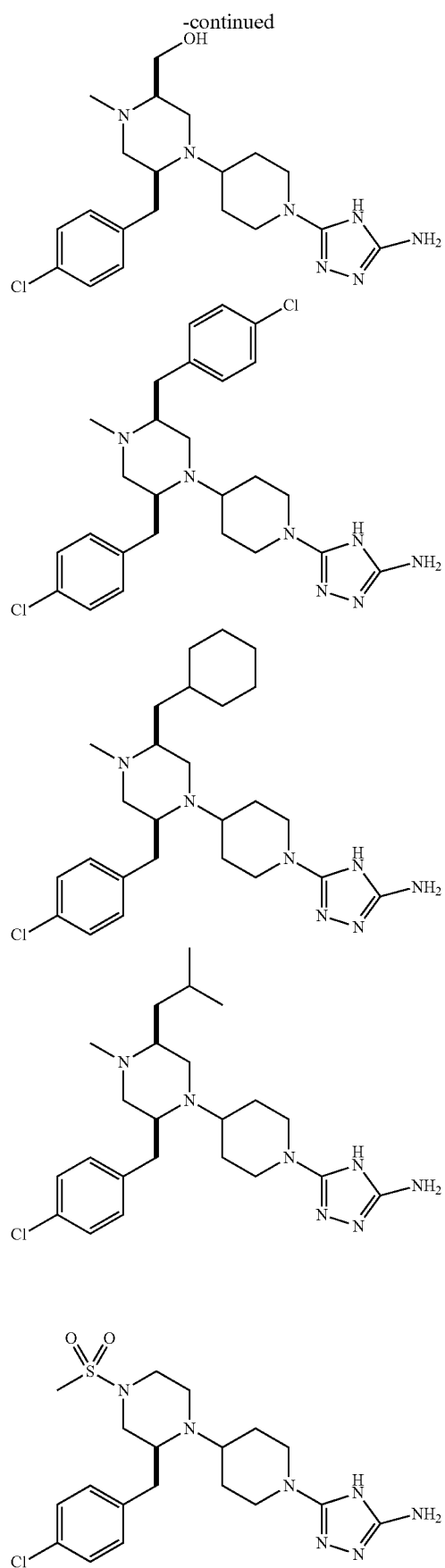
298
-continued
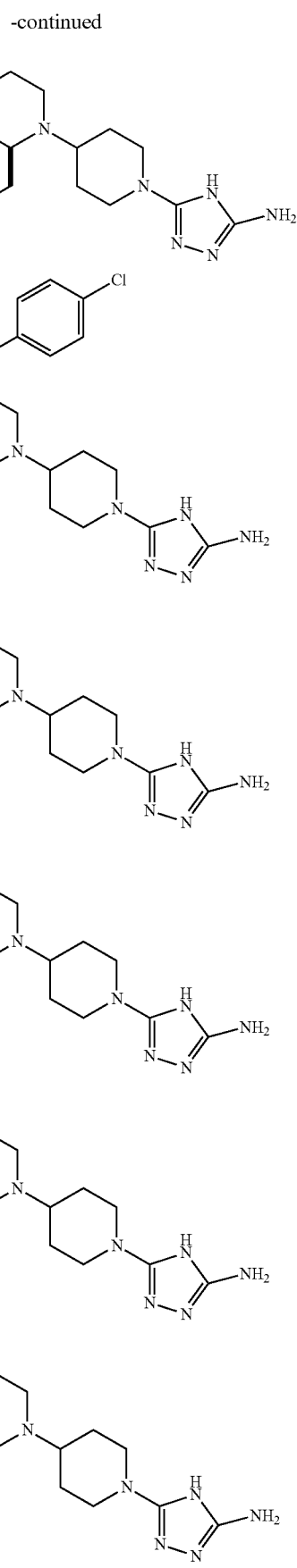

299
-continued
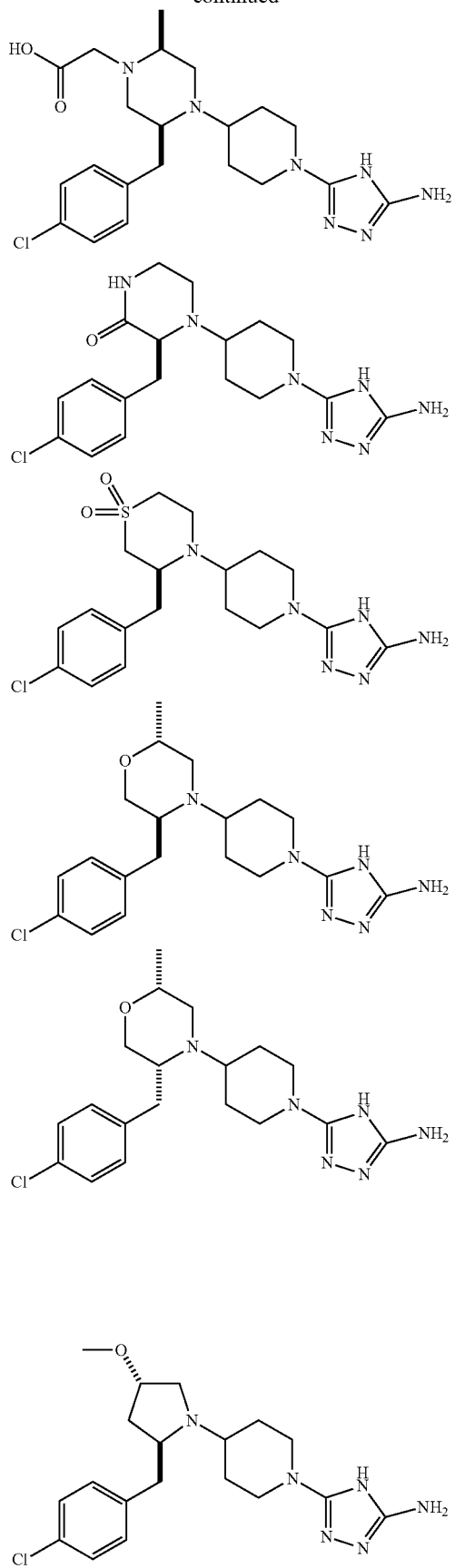
300
-continued
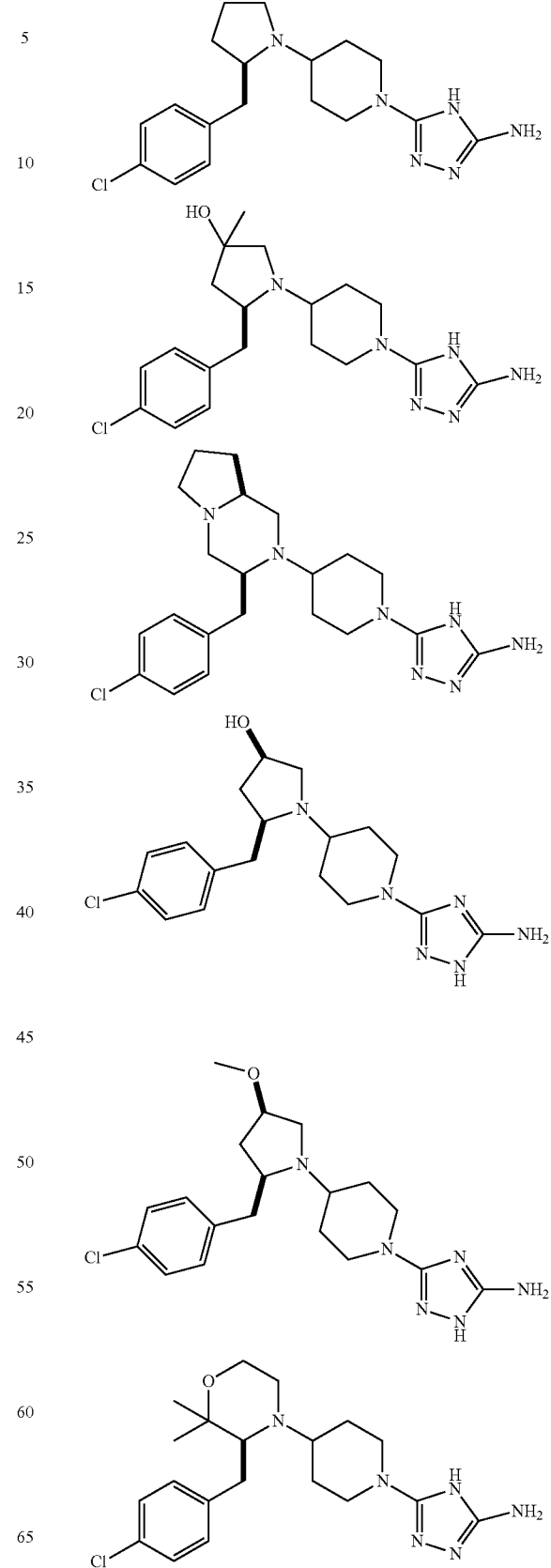

301
-continued
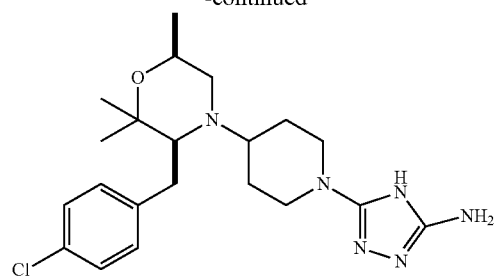
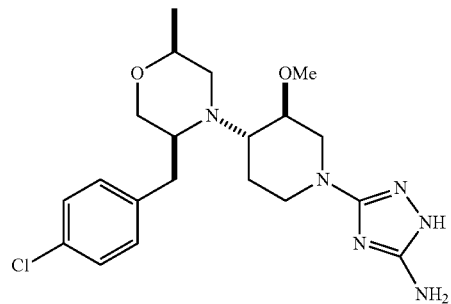
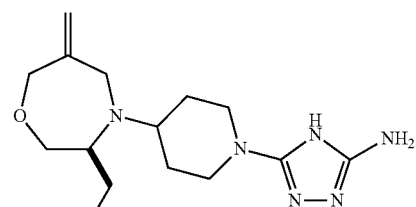
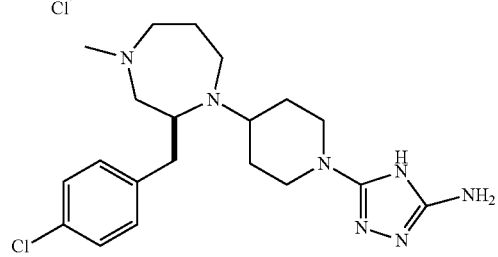
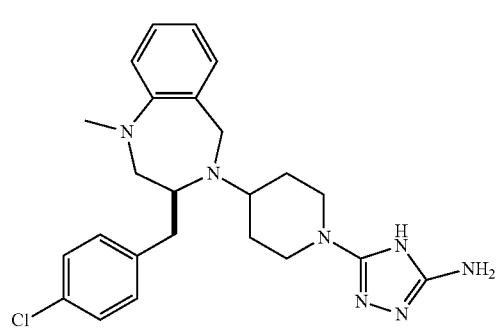
302
-continued
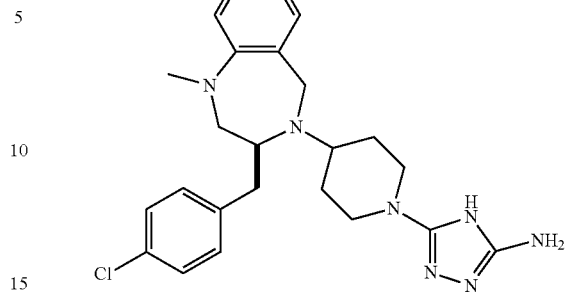
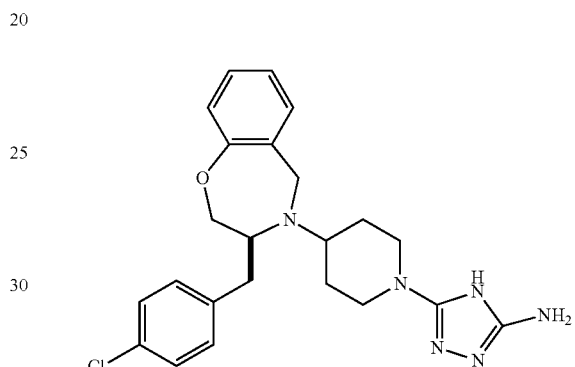
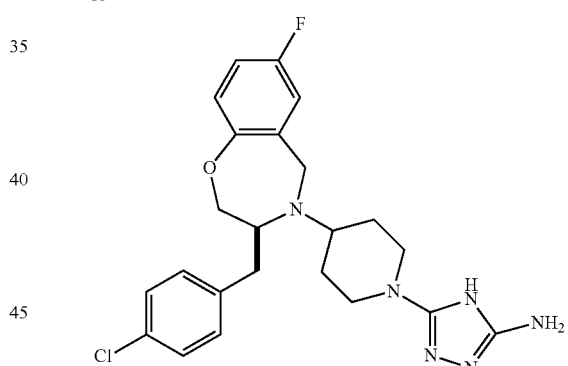
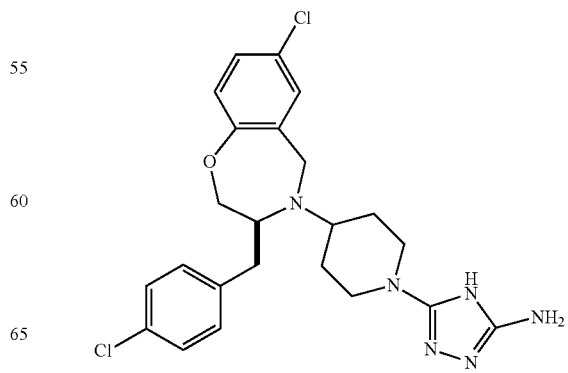

-continued

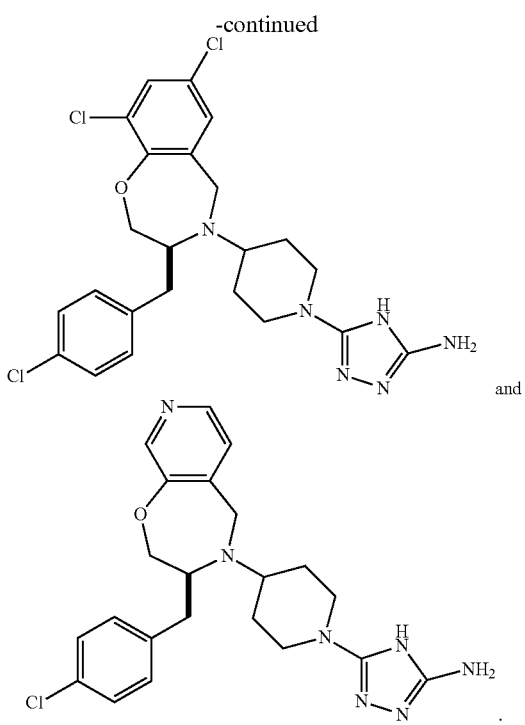

and

23. A pharmaceutical composition comprising a therapeutically effective amount of a compound of claim 1; and a pharmaceutically acceptable carrier.

24. A method for the therapeutic treatment of a disease, disorder, or condition associated with aberrant expression or activity of acidic mammalian chitinase, comprising administering to a subject in need thereof a therapeutically effective amount of at least one compound according to claim 1.

25. A method for the therapeutic treatment of a disease, disorder, or condition associated with aberrant expression or activity of chitotriosidase, comprising administering to a subject in need thereof a therapeutically effective amount of at least one compound according to claim 1.

26. The method of claim 24, wherein the disease, disorder, or condition is selected from the group consisting of allergic diseases, acute and chronic inflammatory diseases, autoimmune diseases, dental diseases, neurologic diseases, metabolic diseases, liver diseases, kidney diseases, skin diseases, polycystic ovary syndrome, endometriosis, fibrotic disorders, storage diseases, and cancer.

27. The compound of claim 1 of the following structural formulae:

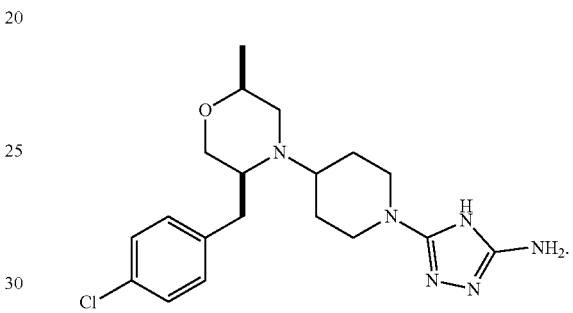

* * * * *

UNITED STATES PATENT AND TRADEMARK OFFICE
CERTIFICATE OF CORRECTION

| | | |
|---|---|---|
| PATENT NO. | : 9,944,624 B2 | Page 1 of 1 |
| APPLICATION NO. | : 15/255226 | |
| DATED | : April 17, 2018 | |
| INVENTOR(S) | : Marzena Mazur et al. | |

It is certified that error appears in the above-identified patent and that said Letters Patent is hereby corrected as shown below:

In the Specification

At Column 172, Line 27, please replace:
"The title compound (25) was obtained from the Boc-L-"
With:
-- The title compound (25a) was obtained from the Boc-L- --.

At Column 192, Line 39, please replace:
"according to the General Procedure VI. 0.29 g (1.0 mmol) of"
With:
-- according to the General Procedure V. 0.29 g (1.0 mmol) of --.

At Column 193, Line 20, please replace:
"34d according to the General Procedure VII. 0.36 g (0.76)"
With:
-- 34d according to the General Procedure VI. 0.36 g (0.76) --.

At Column 197, Line 36, please replace:
"according to the General Procedure VI. 0.20 g (0.48 mmol)"
With:
-- according to the General Procedure V. 0.20 g (0.48 mmol) --.

At Column 198, Line 19, please replace:
"according to the General Procedure VII. 0.30 g (0.50 mmol)"
With:
-- according to the General Procedure VI. 0.30 g (0.50 mmol) --.

Signed and Sealed this
Tenth Day of March, 2020

Andrei Iancu
*Director of the United States Patent and Trademark Office*